United States Patent
Gelfand et al.

(10) Patent No.: US 9,757,180 B2
(45) Date of Patent: Sep. 12, 2017

(54) ENDOVASCULAR CATHETERS AND METHODS FOR CAROTID BODY ABLATION

(71) Applicant: CIBIEM, INC., Los Altos, CA (US)

(72) Inventors: Mark Gelfand, New York, NY (US); Howard Levin, Teaneck, NJ (US); Charles Lennox, Hudson, NH (US)

(73) Assignee: Cibiem, Inc., Los Altos, CA (US)

( * ) Notice: Subject to any disclaimer, the term of this patent is extended or adjusted under 35 U.S.C. 154(b) by 0 days.

(21) Appl. No.: 15/214,222

(22) Filed: Jul. 19, 2016

(65) Prior Publication Data

US 2016/0324563 A1 Nov. 10, 2016

Related U.S. Application Data

(63) Continuation of application No. 13/869,765, filed on Apr. 24, 2013, now Pat. No. 9,393,070.

(Continued)

(51) Int. Cl.
*A61B 18/02* (2006.01)
*A61B 18/14* (2006.01)
(Continued)

(52) U.S. Cl.
CPC ...... *A61B 18/0218* (2013.01); *A61B 18/1492* (2013.01); *A61B 18/18* (2013.01);
(Continued)

(58) Field of Classification Search
CPC .............. A61B 18/1492; A61B 18/148; A61B 18/1477; A61B 18/1487; A61B 2018/1472; A61B 2018/1861; A61B 2018/1869; A61B 2018/00273; A61B 2018/00279; A61B 2018/00285; A61B 2018/00577; A61B 2018/1425; A61B 2018/1427; A61B 2018/1432; A61B 2018/00404;
(Continued)

(56) References Cited

U.S. PATENT DOCUMENTS

| | | |
|---|---|---|
| 3,650,277 A | 3/1972 | Sjostrand et al. |
| 4,011,872 A | 3/1977 | Komiya |

(Continued)

FOREIGN PATENT DOCUMENTS

| | | |
|---|---|---|
| CN | 1440256 A | 9/2003 |
| CN | 1905841 A | 1/2007 |

(Continued)

OTHER PUBLICATIONS

Abboud, F.; In search of autonomic balance: the good, the bad, and the ugly; Am J Physiol Regul Integr Comp Physiol; 298; pp. R1449-R1467; Jun. 2010.

(Continued)

*Primary Examiner* — Thomas Giuliani
(74) *Attorney, Agent, or Firm* — Shay Glenn LLP

(57) ABSTRACT

Systems, devices, and methods for treating a patient having a sympathetically mediated disease associated at least in part with augmented peripheral chemoreflex or heightened sympathetic activation. The treatments include ablating one or more peripheral chemoreceptors or associated afferent nerves to reduce or remove afferent neural signals from the peripheral chemoreceptor.

10 Claims, 65 Drawing Sheets

Related U.S. Application Data

(60) Provisional application No. 61/637,582, filed on Apr. 24, 2012, provisional application No. 61/643,243, filed on May 5, 2012, provisional application No. 61/644,620, filed on May 9, 2012, provisional application No. 61/794,667, filed on Mar. 15, 2013.

(51) Int. Cl.
  *A61B 18/18* (2006.01)
  *A61M 25/00* (2006.01)
  *A61B 18/00* (2006.01)
  *A61B 90/00* (2016.01)

(52) U.S. Cl.
  CPC . *A61M 25/0082* (2013.01); *A61B 2018/0022* (2013.01); *A61B 2018/00267* (2013.01); *A61B 2018/00279* (2013.01); *A61B 2018/00285* (2013.01); *A61B 2018/00291* (2013.01); *A61B 2018/00404* (2013.01); *A61B 2018/00577* (2013.01); *A61B 2018/00589* (2013.01); *A61B 2018/00714* (2013.01); *A61B 2018/00791* (2013.01); *A61B 2018/0212* (2013.01); *A61B 2018/0225* (2013.01); *A61B 2018/0293* (2013.01); *A61B 2018/1407* (2013.01); *A61B 2018/1425* (2013.01); *A61B 2018/1475* (2013.01); *A61B 2090/3784* (2016.02)

(58) Field of Classification Search
  CPC .. A61B 2018/00291; A61B 2018/1475; A61B 2018/0293; A61B 2018/0212
  USPC .............................. 606/21, 41; 607/9, 99, 116
  See application file for complete search history.

(56) References Cited

U.S. PATENT DOCUMENTS

| | | | |
|---|---|---|---|
| 4,201,219 A | 5/1980 | Gonzalez | |
| 4,791,931 A | 12/1988 | Slate | |
| 4,960,133 A | 10/1990 | Hewson | |
| 5,125,928 A | 6/1992 | Parins et al. | |
| 5,139,496 A | 8/1992 | Hed et al. | |
| 5,147,294 A * | 9/1992 | Smith | A61K 31/165 |
| | | | 128/898 |
| 5,354,271 A | 10/1994 | Voda | |
| 5,431,621 A | 7/1995 | Dory | |
| 5,435,311 A | 7/1995 | Umemura et al. | |
| 5,476,495 A | 12/1995 | Kordis et al. | |
| 5,492,126 A | 2/1996 | Hennige et al. | |
| 5,500,012 A | 3/1996 | Brucker et al. | |
| 5,588,432 A | 12/1996 | Crowley | |
| 5,735,280 A | 4/1998 | Sherman et al. | |
| 5,800,486 A | 9/1998 | Thome et al. | |
| 5,826,588 A | 10/1998 | Forman | |
| 5,879,295 A | 3/1999 | Li et al. | |
| 5,893,863 A | 4/1999 | Yoon | |
| 5,906,580 A | 5/1999 | Kline-Schoder et al. | |
| 5,916,213 A | 6/1999 | Haissaguerre et al. | |
| 5,919,187 A | 7/1999 | Guglielmi et al. | |
| 5,957,882 A | 9/1999 | Nita et al. | |
| 6,004,269 A | 12/1999 | Crowley et al. | |
| 6,068,629 A | 5/2000 | Haissaguerre et al. | |
| 6,071,279 A | 6/2000 | Whayne et al. | |
| 6,071,281 A | 6/2000 | Burnside et al. | |
| 6,125,857 A | 10/2000 | Silber | |
| 6,129,359 A | 10/2000 | Haas et al. | |
| 6,182,666 B1 | 2/2001 | Dobak, III | |
| 6,217,576 B1 | 4/2001 | Tu et al. | |
| 6,228,082 B1 | 5/2001 | Baker et al. | |
| 6,235,024 B1 | 5/2001 | Tu | |
| 6,306,133 B1 | 10/2001 | Tu et al. | |
| 6,355,029 B1 | 3/2002 | Joye et al. | |
| 6,379,348 B1 | 4/2002 | Onik | |
| 6,402,746 B1 | 6/2002 | Whayne et al. | |
| 6,411,852 B1 | 6/2002 | Danek et al. | |
| 6,425,867 B1 | 7/2002 | Vaezy et al. | |
| 6,454,713 B1 | 9/2002 | Ishibashi et al. | |
| 6,497,705 B2 | 12/2002 | Comben | |
| 6,522,926 B1 | 2/2003 | Kieval et al. | |
| 6,533,784 B2 | 3/2003 | Truckai et al. | |
| 6,544,187 B2 | 4/2003 | Seward | |
| 6,656,136 B1 | 12/2003 | Weng et al. | |
| 6,660,013 B2 | 12/2003 | Rabiner et al. | |
| 6,673,066 B2 | 1/2004 | Werneth | |
| 6,776,763 B2 | 8/2004 | Nix et al. | |
| 6,802,843 B2 | 10/2004 | Truckai et al. | |
| 6,905,497 B2 | 6/2005 | Truckai et al. | |
| 6,937,903 B2 | 8/2005 | Schuler et al. | |
| 7,097,641 B1 | 8/2006 | Arless et al. | |
| 7,137,963 B2 | 11/2006 | Nita et al. | |
| 7,149,574 B2 | 12/2006 | Yun et al. | |
| 7,155,284 B1 | 12/2006 | Whitehurst et al. | |
| 7,162,303 B2 | 1/2007 | Levin et al. | |
| 7,207,989 B2 | 4/2007 | Pike et al. | |
| 7,363,076 B2 | 4/2008 | Yun et al. | |
| 7,617,005 B2 | 11/2009 | Demarais et al. | |
| 7,628,785 B2 | 12/2009 | Hadjicostis et al. | |
| 7,736,360 B2 | 6/2010 | Mody et al. | |
| 7,738,952 B2 | 6/2010 | Yun et al. | |
| 7,766,961 B2 | 8/2010 | Patel et al. | |
| 7,853,333 B2 | 12/2010 | Demarais | |
| 7,901,450 B2 | 3/2011 | Johnson et al. | |
| 7,922,663 B2 | 4/2011 | Tran et al. | |
| 7,925,352 B2 | 4/2011 | Stack et al. | |
| 7,959,628 B2 | 6/2011 | Schaer et al. | |
| 8,002,728 B2 | 8/2011 | Chang | |
| 8,060,206 B2 | 11/2011 | Kieval et al. | |
| 8,075,554 B2 | 12/2011 | Malecki et al. | |
| 8,116,883 B2 | 2/2012 | Williams et al. | |
| 8,157,760 B2 | 4/2012 | Criado et al. | |
| 8,167,805 B2 | 5/2012 | Emery et al. | |
| 8,192,425 B2 | 6/2012 | Mirza et al. | |
| 8,192,760 B2 | 6/2012 | Hossainy et al. | |
| 8,292,879 B2 | 10/2012 | Manwaring et al. | |
| 8,295,912 B2 | 10/2012 | Gertner | |
| 8,308,709 B2 | 11/2012 | Chang | |
| 8,326,429 B2 | 12/2012 | Wenzel et al. | |
| 8,364,237 B2 | 1/2013 | Stone et al. | |
| 8,374,674 B2 | 2/2013 | Gertner | |
| 8,396,548 B2 | 3/2013 | Perry et al. | |
| 8,409,200 B2 | 4/2013 | Holcomb et al. | |
| 8,433,423 B2 | 4/2013 | Demarais | |
| 8,465,752 B2 | 6/2013 | Seward | |
| 8,469,904 B2 | 6/2013 | Gertner | |
| 8,568,399 B2 | 10/2013 | Azamian et al. | |
| 8,620,423 B2 | 12/2013 | Demarais et al. | |
| 9,060,784 B2 | 6/2015 | Coe et al. | |
| 9,089,541 B2 | 7/2015 | Azamian | |
| 9,089,700 B2 | 7/2015 | Hlavka | |
| 9,283,033 B2 | 3/2016 | Gelfand et al. | |
| 9,393,070 B2 | 7/2016 | Gelfand et al. | |
| 9,398,930 B2 | 7/2016 | Leung et al. | |
| 9,402,677 B2 | 8/2016 | Leung et al. | |
| 2001/0027333 A1 | 10/2001 | Schwartz | |
| 2001/0041890 A1 | 11/2001 | Hassett et al. | |
| 2002/0002372 A1 | 1/2002 | Jahns et al. | |
| 2002/0087151 A1 | 7/2002 | Mody et al. | |
| 2002/0128639 A1 | 9/2002 | Pless et al. | |
| 2003/0009125 A1 | 1/2003 | Nita et al. | |
| 2003/0153907 A1 | 8/2003 | Suorsa et al. | |
| 2004/0054347 A1 | 3/2004 | Zadno Azizi et al. | |
| 2004/0116921 A1 | 6/2004 | Sherman et al. | |
| 2004/0210214 A1 | 10/2004 | Knowlton | |
| 2004/0210239 A1 | 10/2004 | Nash et al. | |
| 2005/0096642 A1 | 5/2005 | Appling et al. | |
| 2005/0096710 A1 | 5/2005 | Kieval | |
| 2005/0143378 A1 | 6/2005 | Yun et al. | |
| 2005/0153885 A1 | 7/2005 | Yun et al. | |
| 2005/0245894 A1 | 11/2005 | Zadno Azizi | |
| 2005/0251122 A1 | 11/2005 | Swanson | |
| 2005/0288656 A1 | 12/2005 | Koerner et al. | |
| 2005/0288730 A1 | 12/2005 | Deem et al. | |
| 2006/0025756 A1 | 2/2006 | Francischelli et al. | |

(56) References Cited

U.S. PATENT DOCUMENTS

| | | | |
|---|---|---|---|
| 2006/0064137 A1 | 3/2006 | Stone | |
| 2006/0069385 A1 | 3/2006 | Lafontaine et al. | |
| 2006/0111754 A1 | 5/2006 | Rezai et al. | |
| 2006/0135962 A1 | 6/2006 | Kick et al. | |
| 2006/0165667 A1* | 7/2006 | Laughlin | A61K 35/28 424/93.21 |
| 2006/0178621 A1 | 8/2006 | Constantz et al. | |
| 2006/0195149 A1 | 8/2006 | Hopper et al. | |
| 2006/0224110 A1 | 10/2006 | Scott et al. | |
| 2006/0253161 A1 | 11/2006 | Libbus et al. | |
| 2006/0259084 A1 | 11/2006 | Zhang et al. | |
| 2006/0282131 A1 | 12/2006 | Caparso et al. | |
| 2006/0287679 A1 | 12/2006 | Stone | |
| 2007/0015006 A1 | 1/2007 | Lee et al. | |
| 2007/0112327 A1 | 5/2007 | Yun et al. | |
| 2007/0129633 A1 | 6/2007 | Lee et al. | |
| 2007/0135875 A1 | 6/2007 | Demarais et al. | |
| 2007/0142879 A1 | 6/2007 | Greenberg et al. | |
| 2007/0150006 A1 | 6/2007 | Libbus et al. | |
| 2007/0156179 A1 | 7/2007 | S.E. | |
| 2007/0208388 A1 | 9/2007 | Jahns et al. | |
| 2007/0265609 A1 | 11/2007 | Thapliyal et al. | |
| 2007/0299476 A1 | 12/2007 | Park et al. | |
| 2008/0009916 A1 | 1/2008 | Rossing et al. | |
| 2008/0009917 A1 | 1/2008 | Rossing et al. | |
| 2008/0027346 A1 | 1/2008 | Litt et al. | |
| 2008/0039727 A1 | 2/2008 | Babaev | |
| 2008/0045936 A1 | 2/2008 | Vaska et al. | |
| 2008/0058871 A1 | 3/2008 | Libbus et al. | |
| 2008/0086181 A1 | 4/2008 | Amurthur et al. | |
| 2008/0294158 A1 | 11/2008 | Pappone et al. | |
| 2009/0043186 A1 | 2/2009 | Jung et al. | |
| 2009/0131798 A1 | 5/2009 | Minar et al. | |
| 2009/0299362 A1 | 12/2009 | Long et al. | |
| 2010/0049031 A1 | 2/2010 | Fruland et al. | |
| 2010/0063564 A1 | 3/2010 | Libbus et al. | |
| 2010/0152590 A1 | 6/2010 | Moore et al. | |
| 2010/0160781 A1 | 6/2010 | Carter et al. | |
| 2010/0168731 A1 | 7/2010 | Wu et al. | |
| 2010/0168739 A1 | 7/2010 | Wu et al. | |
| 2010/0179424 A1 | 7/2010 | Warnking et al. | |
| 2010/0217151 A1 | 8/2010 | Gostout et al. | |
| 2010/0262013 A1 | 10/2010 | Smith et al. | |
| 2010/0268307 A1 | 10/2010 | Demarais et al. | |
| 2010/0274219 A1 | 10/2010 | Wenzel et al. | |
| 2011/0009854 A1 | 1/2011 | Babkin et al. | |
| 2011/0040297 A1 | 2/2011 | Babkin et al. | |
| 2011/0066085 A1 | 3/2011 | Weng et al. | |
| 2011/0098699 A1 | 4/2011 | Mateos et al. | |
| 2011/0104060 A1 | 5/2011 | Seward | |
| 2011/0112400 A1 | 5/2011 | Emery et al. | |
| 2011/0118600 A1* | 5/2011 | Gertner | A61B 8/06 600/439 |
| 2011/0130708 A1 | 6/2011 | Perry et al. | |
| 2011/0144631 A1 | 6/2011 | Elkins et al. | |
| 2011/0172529 A1 | 7/2011 | Gertner | |
| 2011/0208096 A1 | 8/2011 | Demarais et al. | |
| 2011/0208174 A1 | 8/2011 | Baust | |
| 2011/0208175 A1 | 8/2011 | Sobotka et al. | |
| 2011/0224667 A1 | 9/2011 | Koblish et al. | |
| 2011/0251487 A1 | 10/2011 | Magnin et al. | |
| 2011/0251607 A1 | 10/2011 | Kruecker et al. | |
| 2011/0257561 A1 | 10/2011 | Gertner et al. | |
| 2011/0257562 A1 | 10/2011 | Schaer | |
| 2011/0301587 A1 | 12/2011 | Deem et al. | |
| 2012/0016226 A1 | 1/2012 | Gertner | |
| 2012/0059437 A1* | 3/2012 | Shalev | A61N 1/05 607/62 |
| 2012/0065492 A1 | 3/2012 | Gertner et al. | |
| 2012/0065494 A1 | 3/2012 | Gertner et al. | |
| 2012/0065554 A1 | 3/2012 | Pikus | |
| 2012/0078248 A1 | 3/2012 | Worrell et al. | |
| 2012/0095335 A1 | 4/2012 | Sverdlik et al. | |
| 2012/0095371 A1 | 4/2012 | Sverdlik et al. | |
| 2012/0095372 A1 | 4/2012 | Sverdlik et al. | |
| 2012/0095461 A1 | 4/2012 | Herscher et al. | |
| 2012/0101018 A1 | 4/2012 | Miracle et al. | |
| 2012/0109018 A1 | 5/2012 | Gertner et al. | |
| 2012/0130368 A1 | 5/2012 | Jenson | |
| 2012/0157992 A1 | 6/2012 | Smith et al. | |
| 2012/0157993 A1 | 6/2012 | Jenson et al. | |
| 2012/0172680 A1 | 7/2012 | Gelfand et al. | |
| 2012/0172723 A1 | 7/2012 | Gertner | |
| 2012/0184952 A1 | 7/2012 | Jenson et al. | |
| 2012/0199616 A1 | 8/2012 | Lamb et al. | |
| 2012/0232436 A1 | 9/2012 | Warnking | |
| 2012/0238918 A1 | 9/2012 | Gertner | |
| 2012/0245494 A1 | 9/2012 | Gertner | |
| 2012/0265227 A1 | 10/2012 | Sverdlik et al. | |
| 2012/0277763 A1 | 11/2012 | Greenblatt et al. | |
| 2013/0006228 A1 | 1/2013 | Johnson et al. | |
| 2013/0066316 A1 | 3/2013 | Steinke et al. | |
| 2013/0123778 A1 | 5/2013 | Richardson et al. | |
| 2013/0131668 A1 | 5/2013 | Schaer | |
| 2013/0197555 A1 | 8/2013 | Schaer | |
| 2013/0197614 A1 | 8/2013 | Gustus et al. | |
| 2013/0199019 A1 | 8/2013 | Garbini et al. | |
| 2013/0303876 A1* | 11/2013 | Gelfand | A61B 18/12 600/407 |
| 2014/0018788 A1 | 1/2014 | Engelman et al. | |
| 2014/0039450 A1 | 2/2014 | Green et al. | |
| 2014/0135661 A1 | 5/2014 | Garrison et al. | |
| 2014/0180273 A1 | 6/2014 | Nair | |
| 2014/0243809 A1 | 8/2014 | Gelfand et al. | |
| 2014/0288015 A1 | 9/2014 | Venkateswara-Rao et al. | |
| 2014/0350401 A1 | 11/2014 | Sinelnikov | |
| 2015/0018725 A1 | 1/2015 | Sommer et al. | |
| 2015/0045675 A1 | 2/2015 | Chernomorsky | |
| 2015/0257779 A1 | 9/2015 | Sinelnikov | |
| 2015/0289929 A1 | 10/2015 | Toth et al. | |
| 2015/0328452 A1 | 11/2015 | Hlavka et al. | |
| 2016/0000499 A1 | 1/2016 | Lennox et al. | |
| 2016/0338753 A1 | 11/2016 | Ryba et al. | |
| 2016/0374710 A1 | 12/2016 | Sinelnikov et al. | |
| 2016/0375241 A1 | 12/2016 | Hlavka et al. | |

FOREIGN PATENT DOCUMENTS

| | | |
|---|---|---|
| CN | 101027097 A | 8/2007 |
| DE | 10151797 A1 | 5/2003 |
| EP | 0472368 A2 | 2/1992 |
| EP | 0819014 B1 | 2/2003 |
| EP | 2008600 A2 | 12/2008 |
| EP | 2488250 A | 8/2012 |
| EP | 1299035 B1 | 2/2013 |
| EP | 2783651 A1 | 10/2014 |
| EP | 2635348 B1 | 3/2016 |
| WO | WO97/25916 A1 | 7/1997 |
| WO | WO98/43701 A1 | 10/1998 |
| WO | WO00/25685 A1 | 5/2000 |
| WO | WO01/64123 A2 | 9/2001 |
| WO | WO02/069862 A1 | 9/2002 |
| WO | WO03/076008 A1 | 9/2003 |
| WO | WO2004/086936 A2 | 10/2004 |
| WO | WO2004/105807 A2 | 12/2004 |
| WO | WO2005/065563 A1 | 7/2005 |
| WO | WO2007/092330 A1 | 8/2007 |
| WO | WO2007/146834 A2 | 12/2007 |
| WO | WO2008/025855 A2 | 3/2008 |
| WO | WO2009/120953 A2 | 10/2009 |
| WO | WO2010/093603 A1 | 8/2010 |
| WO | WO2010/121738 A1 | 10/2010 |
| WO | WO2010/124120 A1 | 10/2010 |
| WO | WO2010/132703 A1 | 11/2010 |
| WO | WO2011/082278 A1 | 7/2011 |
| WO | WO2011/130531 A2 | 10/2011 |
| WO | WO2012/015720 A1 | 2/2012 |
| WO | WO2012/015721 A1 | 2/2012 |
| WO | WO2012/015722 A1 | 2/2012 |
| WO | WO2012/016135 A1 | 2/2012 |
| WO | WO2012/057916 A1 | 5/2012 |
| WO | WO2012/112165 A1 | 8/2012 |
| WO | WO2012/125172 A1 | 9/2012 |

(56) References Cited

FOREIGN PATENT DOCUMENTS

| WO | WO2013/018083 A2 | 2/2013 |
|---|---|---|
| WO | WO2013/074813 A1 | 5/2013 |
| WO | WO2013/157011 A2 | 10/2013 |

OTHER PUBLICATIONS

Abdala et al; Hypertension is critically dependent on the carotid body input in the spontaneously hypertensive rat; J Physiol; 590(17); pp. 4269-4277; Sep. 2012.
Abdala et al; Peripheral chemoreceptor inputs contribute to the development of high blood pressure in spontaneously hypertensive rats(proceeding abstract); Proc Physiol Soc 23; PC22; Oxford, England; Jul. 2011 (printed Sep. 24, 2013 from: http://www.physoc.org/proceedings/abstract/Proc%20Physiol%20Soc%2023PC22).
Al-Rawi et al.; Effect of lignocaine injection in carotid sinus on baroreceptor sensitivity during carotid endarterectomy; J Vasc Surg; 39(6); pp. 1288-1294; Jun. 2004.
Anand et al.; Management of the internal carotid artery during carotid body tumor surgery; Laryngoscope; 105; pp. 231-235; Mar. 1995.
Anderson et al. (executive committee); Carotid body resection; J. Allergy Clin. Immunol.; 78(2); pp. 273-275; Aug. 1986.
Arena et al.; Prognostic value of resting end-tidal carbon dioxide in patients with heart failure; Int J Cardiol; 109(3); pp. 351-358; May 2006.
Banzett et al.; Dyspnea and pain: similarities and contrasts between two very unpleasant sensations; APS Bulletin; 11(1); 6 pgs.; Mar./Apr. 2001.
Bencini et al.; The carotid bodies in bronchial asthma; Histopathology; 18; pp. 195-200; Mar. 1991.
Bencini, A.; Reduction of reflex bronchotropic impulses as a result of carotid body surgery; International Surgery; 54(6); pp. 415-423; Dec. 1970.
Bernstein et al.; Current status of glomectomy; (The Amer. Acad. of Allergy, Abstracts of papers given at Ann. Meeting, Feb. 3-7, 1978, Boston MA; J. Allergy; 41(2); pp. 88-89; Feb. 1968.
Bishop, Jr. et al.; Paragangliomas of the neck; Arch Surg.; 127; pp. 1441-1445; Dec. 1992.
Braunwald et al.; Carotid sinus nerve stimulation for the treatment of intractable angina pectoris: surgical technic; Annals of Surgery; 172(5); pp. 870-876; Nov. 1970.
Braunwald et al.; Carotid sinus nerve stimulation in the treatment of angina pectoris and supraventricular tachycardia; The Western Journal of Medicine; 112(3); pp. 41-50; Mar. 1970.
Capps et al.; The late effects of bilateral carotid sinus denervation in man; J Clin Invest; 17(4); pp. 385-389; Jul. 1938.
Chang et al.; Impaired response to hypoxia after bilateral carotid body resection for treatment of bronchial asthma; Chest; 73; pp. 667-669; May 1978.
Curran et al.; Glomectomy for severe bronchial asthma. A double-blind study; Am Rev Respir Dis; 93(1); pp. 84-89; Jan. 1966.
Davidson et al.; Role of the carotid bodies in breath-holding; N Engl J Med; 290(15); pp. 819-822; Apr. 1974.
de Weerd et al.; Prevalence of asymptomatic carotid artery stenosis according to age and sex: Systematic review and metaregression analysis; Stroke; 40(4); pp. 1105-1113; Apr. 2009.
Dickinson et al.; Carotid body tumour: 30 years experience; Br. J. Surg.; 73(1); pp. 14-16; Jan. 1986.
Ding et al.; Role of blood flow in carotid body chemoreflex function in heart failure; J Physiol; 589(1); pp. 245-258; Jan. 2011.
Doumas et al.; Benefits from treatment and control of patients with resistant hypertension; Int. J Hypertension; 8 pgs; Dec. 2011.
Fletcher, Jr. et al.; The surgical treatment of bronchial asthma by excision of the carotid body; J Christ Med Assoc India; 38; pp. 492-496; Sep. 1963.
Gain et al.; Anaesthesia for glomectomy in the asthmatic patient; Can Aneas Soc J; 11(4); pp. 417-424; Jul. 1964.

Giannoni et al.; Combined increased chemosensitiviy to hypoxia and hypercapnia as a prognosticator in heart failure; JACC; 53(21); pp. 1975-1980; May 2009.
Giannoni et al.; Clinical significance of chemosensitivity in chronic heart failure: influence on neurohormonal derangement, cheyne-strokes respiration and arrhythmias; Clinical Science (London); 114(7); pp. 489-497; Apr. 2008.
Grassi, G.; Renal denervation in cardiometabolic disease: Concepts, achievements and perspectives; Nutr Metab Cardiovasc Dis; 23(2); pp. 77-83; Feb. 2013 (Epub Nov. 10, 2012).
Green, M.; Observations on glomectomized asthmatic patients; Annals of Allergy; 23(5); pp. 213-219; May 1965.
Gudovsky et al.; Surgical treatment of bronchial asthma (with translation); Khirurgiia; 7; pp. 14-18; (year of pub. sufficiently earlier than effective US filing date and any foreign priority date) 2002.
Guz et al.; Peripheral chemoreceptor block in man; Respiration Physiology; 1; pp. 38-40; (year of pub. sufficiently earlier than effective US filing date and any foreign priority date) 1966.
Gwon et al.; Risk factors for stroke during surgery for carotid body tumors; World J Surg; 35(9); pp. 2154-2158; Sep. 2011.
Handelsman, H.; Bilateral carotid body resection as a treatment for chronic intractable bronchospastic diseases; Health Technology Assessment Series: Health Technology Assessment Report; No. 12; 13 pgs.; (year of pub. sufficiently earlier than effective US filing date and any foreign priority date) 1985.
Hickey et al.; Bilateral carotid endarterectomy with attempted preservation of the carotid body function; Ann. Surg.; 175(2); pp. 268-273; Feb. 1972.
Holton et al.; The effects of bilateral removal of the carotid bodies and denervation of the carotid sinuses in two human subjects; J. Physiol.; 181(2); pp. 365-378; Nov. 1965.
Honda et al.; Hypoxic chemosensitivity in asthmatic patients two decades after carotid body resection; J Appl Physiol.; 46(4); pp. 632-638; Apr. 1979.
Honda, Y.; Respiratory and circulatory activities in carotid body-resected humans; J Appl Physiol; 73(1); pp. 1-8; Jul. 1992.
Karashurov et al.; Radiofrequency electrostimulation of synocarotid for the treatment of bronchial asthma (with translation); Khirurgiia (Mosk); 12; pp. 4-6; (year of pub. sufficiently earlier than effective US filing date and any foreign priority date)1999.
Keim, W. F.; Carotid glomectomy in bronchial asthma; Archives of Otolaryngology; 79; pp. 225-228; Mar. 1964.
Khan et al.; Anatomical variations in human carotid bodies; J. Clin. Pathol.; 41(11); pp. 1196-1199; Nov. 1988.
Kim et al.; Carotid artery-hypoglossal nerve relationships in the neck: an anatomical work; Neurol Res; 31; pp. 895-899; Nov. 2009.
Kline et al.; Cervical glomectomy for bronchial asthma; Journal of the Medical Society of New Jersey; 61(5); pp. 176-178; May 1964.
Leggate, J. M.; Treatment of asthma by excision of the carotid body; Postgraduate Med. Journal; 26(292)pp. 71-77; Feb. 1950.
Lesske et al.; Hypertension caused by chronic intermittent hypoxia—influence of chemoreceptors and sympathetic nervous system; J Hypertens; 15(12); pp. 1593-1603; Dec. 1997.
Lo et al.; Anatomical variations of the common carotid artery bifurcation; ANZ J. Surg.; 76(11); pp. 970-972; Nov. 2006.
Lugliani et al.; A role for the carotid body in cardiovascular control in man; Chest; 63(5); pp. 744-750; May 1973.
Lugliani et al.; Effect of bilateral carotid-body resection on ventilatory control at rest and during exercise in man; New England J Med; 285(20); pp. 1105-1111; Nov. 1971.
Lusiani et al.; Prevalence of atherosclerotic involvement of the internal carotid artery in hypertensive patients; Int J Cardiol; 17; pp. 51-56; Oct. 1987.
Lyons et al.; Anatomical variants of the cervical sympathetic chain to be considered during neck dissection; Br J Oral Maxillofac Surg; 36(3); pp. 180-182; Jun. 1998.
Ma et al.; A retrospective study in management of carotid body tumour; Br J Oral Maxillofac Surg; 47(6); pp. 461-465; Sep. 2009.
MacGowan, W.; Removal of the carotid body for asthma: A report of 19 treated patients; Dis Chest; 51(3); pp. 278-281; Mar. 1967.
Marschke et al.; Carotid-body removal in asthma; JAMA; 191(5); p. 397; Feb. 1965.

(56) References Cited

OTHER PUBLICATIONS

Marshall, J.; Peripheral chemoreceptors and cardiovascular regulation; Physiological Reviews; 74(3); pp. 543-594; Jul. 1994.
Meyerson, Sheldon; A histological study of the morphology of the cervical carotid bifurcation, including descriptions of intramural neural elements (Thesis); Ohio State University; 47 pgs.; (year of pub. sufficiently earlier than effective US filing date and any foreign priority date) 1968.
Myers et al.; End-tidal CO2 pressure and cardiac performance during exercise in heart failure; Med Sci Sports Exerc; 41(1); pp. 18-24; Jan. 2009.
Nadel et al.; Effect of changes in blood gas tensions and carotid sinus pressure on tracheal volume and total lung resistance to airflow; J Physiol; 163(1); pp. 13-33; Aug. 1962.
Nakayama, K.; Surgical removal of the carotid body for bronchial asthma; Chest; 40(6); pp. 595-604; Dec. 1961.
Nakayama, K.; Surgical removal of the carotid body for bronchial asthma; The Australian and the New Zealand Journal of Surgery; 31(3); pp. 214-221; Feb. 1962.
Nakayama, K.; The surgical significance of the carotid body in relation to bronchial asthma; Thoracic Surgery; Journal of the International College of Surgeons; 39(4); pp. 374-389; Apr. 1963.
Nespoulet et al.; Altitude illness is related to low hypoxic chemoresponse and low oxygenation during sleep; Eur Respir J; 40(3); pp. 673-680; Sep. 2012 (ERJ Express; epub Apr. 20, 2012).
Nguyen et al.; Carotid body detection on CT angiography; Am J Neuroradiol; 32; pp. 1096-1099; Jun.-Jul. 2011.
O'Donnell et al.; Pathophysiology of dyspnea in chronic obstructive pulmonary disease: a rountable; Proc Am Thorac Soc; 4(2); pp. 145-168; May 2007.
O'Rourke et al.; Removal of the carotid body for asthma: A preliminary report of 40 cases; The Medical Journal of Australia; 2; pp. 1040-1043; Dec. 1963.
O'Rourke et al.; Removal of the carotid body for asthma: An appraisal of results; The Medical Journal of Australia; 2; pp. 869-870; Nov. 1964.
Overholt et al.; Hidden or unsuspected brochiectasis in the asthmatic patient; JAMA; 150(5); pp. 438-441; Oct. 1952.
Overholt, R.; Glomectomy for asthma; Chest; 40; pp. 605-610; Dec. 1961.
Paliwoda et al.; Surgical removal of the carotid body and denervation of the carotid sinus for bronchial asthma; East African Medical Journal; 44(7); pp. 285-287; Jul. 1967.
Paton et al.; The carotid body as a therapeutic target for the treatment of sympathetically mediated diseases; Hypertension; 61; pp. 5-13; Jan. 2013.
Pennes; Analysis of tissue and arterial blood temperatures in the resting human forearm; J. Appl. Physiol.; 1(2); pp. 93-122; Aug. 1948.
Perret et al.; High prevalence of peripheral atherosclerosis in a rapidly developing country; Atherosclerosis; 153(1); pp. 9-21; Nov. 2000.
Petersen et al.; Lesion dimensions during temperature-controlled radiofrequency catheter ablation of left ventricular porcine myocardium impact of ablation site; electrode size, and convective cooling; Circulation; 99(2); pp. 319-325; Jan. 1999.
Phillips et al.; Results of glomectomy in chronic obstructive pulmonary disease: A four year follow-up report of 57 cases; Chest; 58(4); pp. 358-362; Oct. 1970.
Phillips, J.; Removal of the carotid body for asthma and emphysema; Southern Medical Journal; 57; pp. 1278-1281; Nov. 1964.
Phillips, J.; Treatment of obstructive bronchial diseases; Geriatrics; 21(7); pp. 137-143; Jul. 1966.
Ponikowski et al.; Peripheral chemoreceptor hypersensitivity; Circulation; 101; pp. 544-549; Jul. 2001.
Rabl et al.; Diagnosis and treatment of carotid body tumors; Thorac Cardiovasc Surg.; 41(6); pp. 340-343; Dec. 1993.
Sanghvi et al.; Carotid body tumors; Journal of Surgical Oncology; 54(3); pp. 190-192; Nov. 1993.

Sapareto et al.; Thermal dose determination in cancer therapy; Int. J. Radiat. Biol. Phys.; 10(6); pp. 787-800; Jun. 1984.
Sedwitz et al.; Should the carotid body be removed in the treatment of asthma and emphysema?; International Surgery; 57(6); pp. 467-469; Jun. 1972.
Sedwitz et al.; Unilateral excision of the carotid body in the treatment of 500 asthma patients; Vascular Diseases; 2; pp. 91-98; Mar. 1965.
Sedwitz, J.; Unilateral carotid body resectin for asthma; Jounal of the National Medical Association; 55(5); pp. 384-388; Sep. 1963.
Segal et al.; Glomectomy in the treatment of chronic bronchial asthma; NEJM; 272(2); pp. 57-63; Jan. 1965.
Segal, M.; Glomectomy for chronic bronchial asthma: A three phase study; Annals of Allergy; 23; pp. 377-384; Aug. 1965.
Sehirli et al.; The diameters of common carotid artery and its branches in newborns; Surg. Radiol. Anat.; 27(4); pp. 292-296; Nov. 2005.
Severinghaus, J.; Carotid body resection for COPD?; Chest; 95(5); pp. 1128-1129; May 1989.
Shalev, Alon; U.S. Appl. No. 61/178,049 entitled "Endovascular systems for performing interventions during ischemic conditions of the CNS by utilizing the carotid baroreceptors and chemoreceptors and methods for using same," filed May 14, 2009.
Shamblin et al.; Carotid Body Tumor; Am J Surg; 122; pp. 732-739; Dec. 1971.
Shek, J.; Excision of carotid body for advanced emphysema; Michigan State Medical Society Journal; 63; pp. 211-212; Mar. 1964.
Silva et al.; Welcome the carotid chemoreflex to the 'neural control of the circulation during exercise' club; J Physiol; 590(Pt 12) ; pp. 2835-2836; Jun. 2012.
Somfay et al.; Dose-response effect of oxygen on hyperinflation and exercise endurance in non-hypoxaemic COPD patients; European Respiratory Journal 18; pp. 77-84; Jul. 2001.
Somfay et al.; Effect of hyperoxia on gas exchange and lactate kinetics following exercise on set in nonhypoxemic COPD patients; Chest; 121(2); pp. 393-400; Feb. 2002.
Stickland et al.; Distribution during exercise in health and chronic heart failure; Circ Res; 100; pp. 1371-1378; May 2007.
Streian et al.; Glomectomy in carotid sinus syncope and associated arrythmias: Symptomatic bradycardia, atrial flutter and atrial fibrillation; Rom J Intern Med; 44(2); pp. 153-163; (year of pub. sufficiently earlier than effective US filing date and any foreign priority date) 2006.
Streian et al.; Glomectomy in carotid sinus syncope; Rev. Roum. Med.—Med. Int.; 26(1); pp. 47-52; Jan.-Mar. 1988.
Syed et al.; Percutaneous superficial temporal artery access for carotid artery stenting in patients with a hostile aortic arch; J Endovasc Ther; 18(5); pp. 729-733; Oct. 2011.
Tamura et al.; A morphometric study of the carotid sinus nerve in patients with diabetes mellitus and chronic alchoholism; Journal of the Autonomic Nervous System; 23; pp. 9-15; Jun. 1988.
Tchibukmacher, N.; Surgical anatomy of carotid sinus nerve and intercarotid ganglion; Surgery, Gynecology and Obstetrics; 67; pp. 740-745; (year of pub. sufficiently earlier than effective US filing date and any foreign priority date)1938.
Timmers et al.; Denervation of carotid baro- and chemoreceptors in humans; J Physiol; 553(1); pp. 3-11; Nov. 2003.
Toorop et al.; Anatomy of the carotid sinus nerve and surgical implications in carotid sinus syndrome; J Vasc Surg; 50; pp. 177-182; Jul. 2009.
Toorop et al.; Effective surgical treatment of the carotid sinus syndrome; J Cardiovasc Surg.; 50; pp. 683-686; Oct. 2009.
Tubbs et al.; Anatomic landmarks for nerves of the neck: a vade mecum for neurosurgeons; Operative Neurosurgery; 56(ONS Suppl 2); pp. ONS256-ONS260; Apr. 2005.
Van Der Mey et al.; Management of carotid body tumors; Otolaryngol Clin North Am.; 34(5); pp. 907-924; Oct. 2001.
Vermeire et al.; Carotid body resection in patients with severe chronic airflow limitation; Bull Eur Physiopathol Respir; 23 Suppl 11; pp. 165s-166s; Aug. 1987.
Ward et al.; Embolization: An adjunctive measure for removal of carotid body tumors; Laryngoscope; 98; pp. 1287-1291; Dec. 1988.

(56) References Cited

OTHER PUBLICATIONS

Wasserman et al.; Effect of carotid body resection on ventilatory and acid-base control during exercise; Journal of Applied Physiology; 39(3); pp. 354-358; Aug. 1975.

Wasserman et al.; Ventilation during exercise in chronic heart failure; Basic Res Cardiol; 91(suppl. 1); pp. 1-11; (year of pub. sufficiently earlier than effective US filing date and any foreign priority date) 1996.

Whipp et al.; Physiologic changes following bilateral carotid-body resection in patients with chronic obstructive pulmonary disease; Chest; 101(3); pp. 656-661; Mar. 1992.

Whipp, B.J.; Carotid bodies and breathing in humans; Thorax; 49(11); pp. 1081-1084; Nov. 1994.

Williams et al.; Carotid body tumor; Arch Surg.; 127; pp. 963-968; Aug. 1992.

Winter et al.; Immediate effects of bilateral carotid body resection on total respiratory resistance and compliance in humans; Adv Exp Med Biol; 551; pp. 15-21; (year of pub. sufficiently earlier than effective US filing date and any foreign priority date) 2005.

Winter, B.; Bilateral carotid body resection for asthma and emphysema; International Surgery; 57(6); pp. 458-466; Jun. 1972.

Winter, B.; Carotid body resection in chronic obstructive pulmonary disease; Chest; 100(3); p. 883; Sep. 1991.

Winter, B.; Carotid body resection: Controversy—confusion—conflict; Ann thorac Surg.; 16(6); pp. 648-659; Dec. 1973.

Wittkampf et al.; Control of radiofrequency lesion size by power regulation; Circulation; 80(4); pp. 962-968; Oct. 1989.

Wood et al.; Bilateral removal of carotid bodies for asthma; thorax; 20(6); pp. 570-573; Nov. 1965.

Sinelnikov et al.; U.S. Appl. No. 15/069,531 entitled "Carotid septum ablation with ultrasound imaging and ablation catheters," filed Mar. 14, 2016.

Martin et al.; U.S. Appl. No. 15/105,599 entitled "Methods, devices and systems for carotid body ablation via a transradial or transbrachial approach," filed Jun. 17, 2016.

Ivancev et al.; Novel access technique facilitating carotid artery stenting, Vascular; 14(4); pp. 219-222; Jul. 1, 2006.

\* cited by examiner

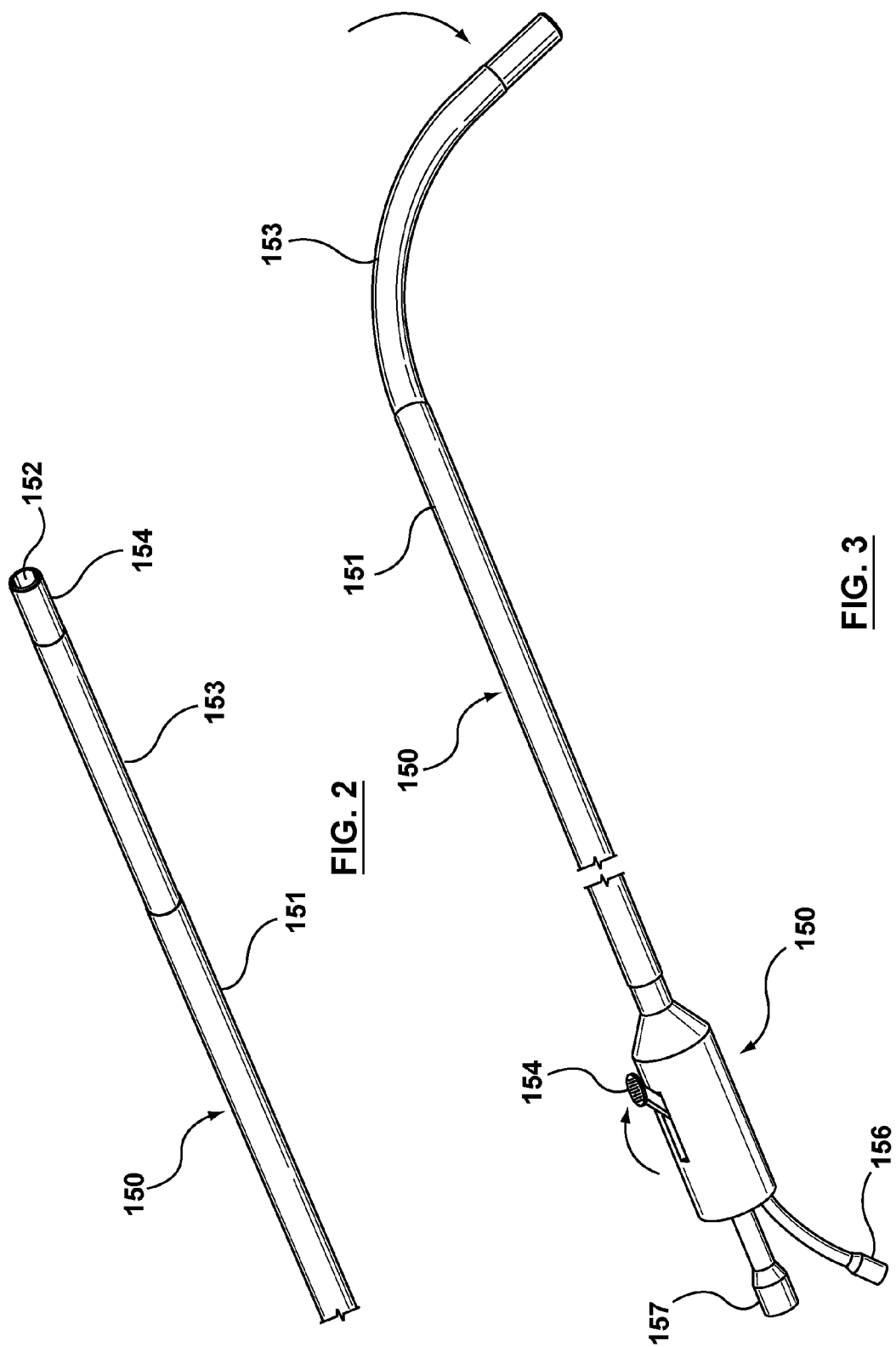

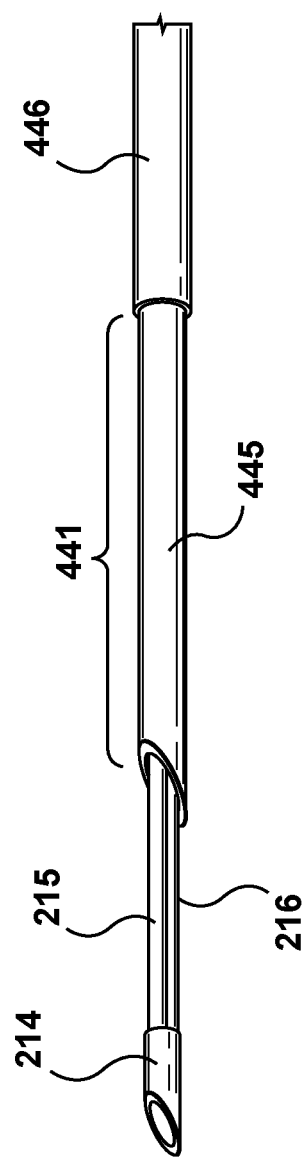

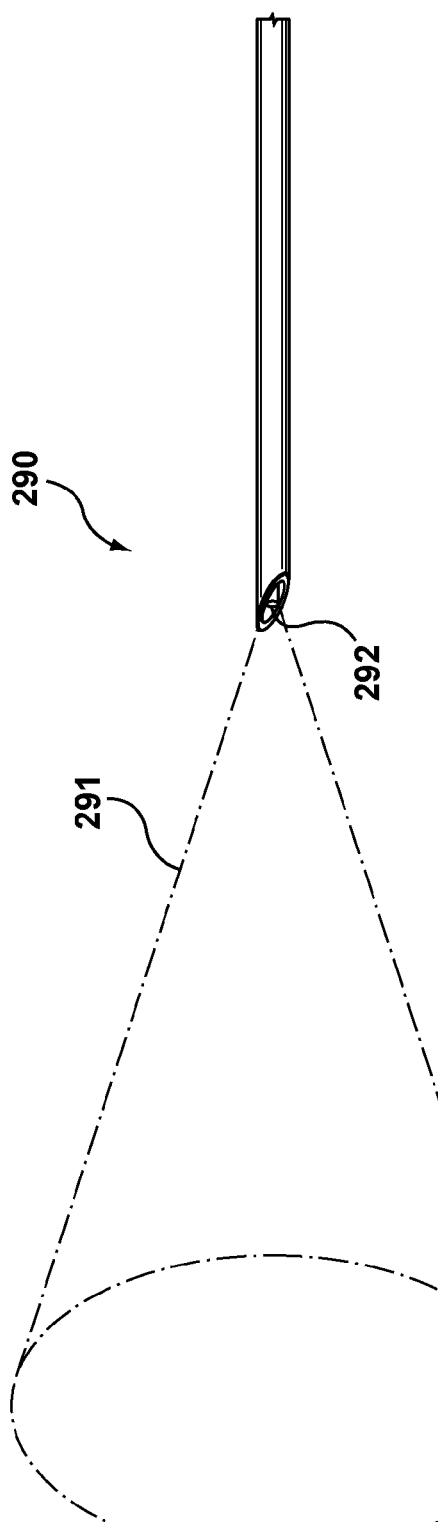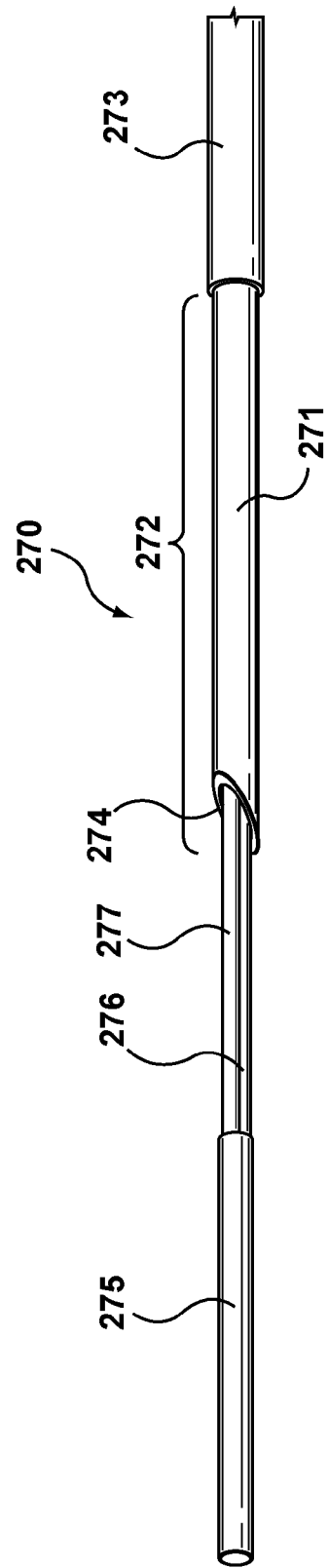

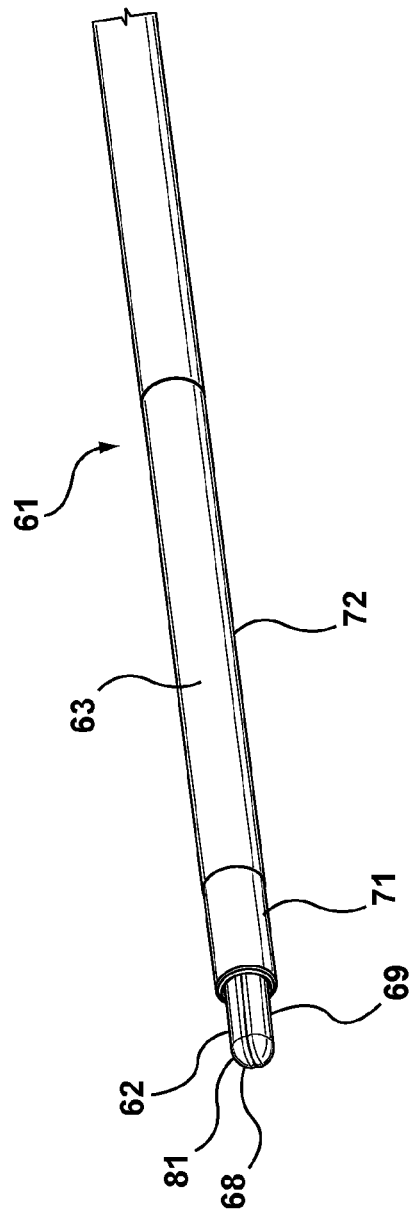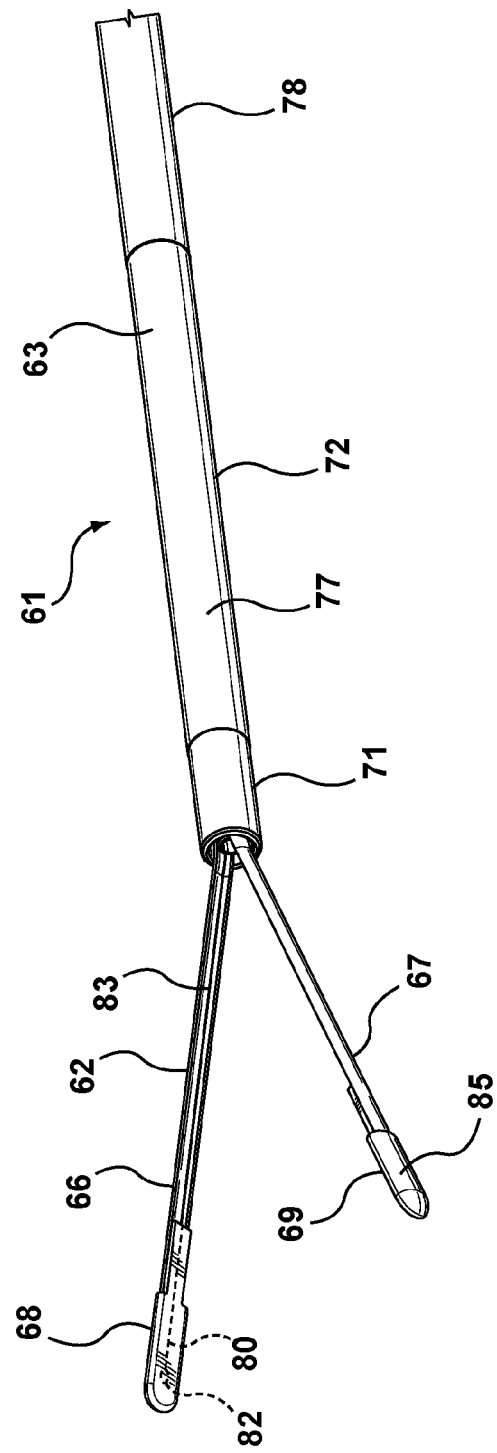

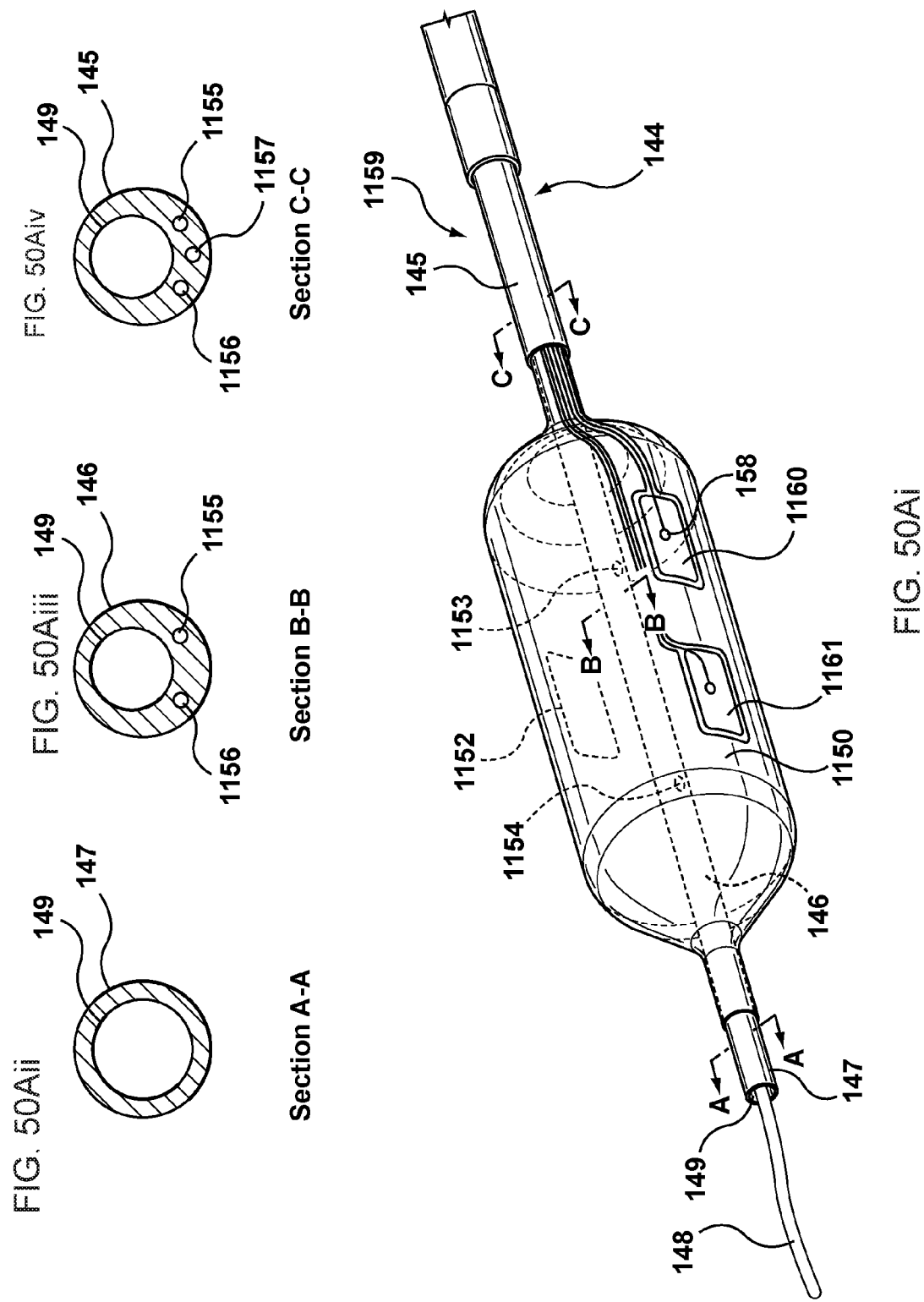

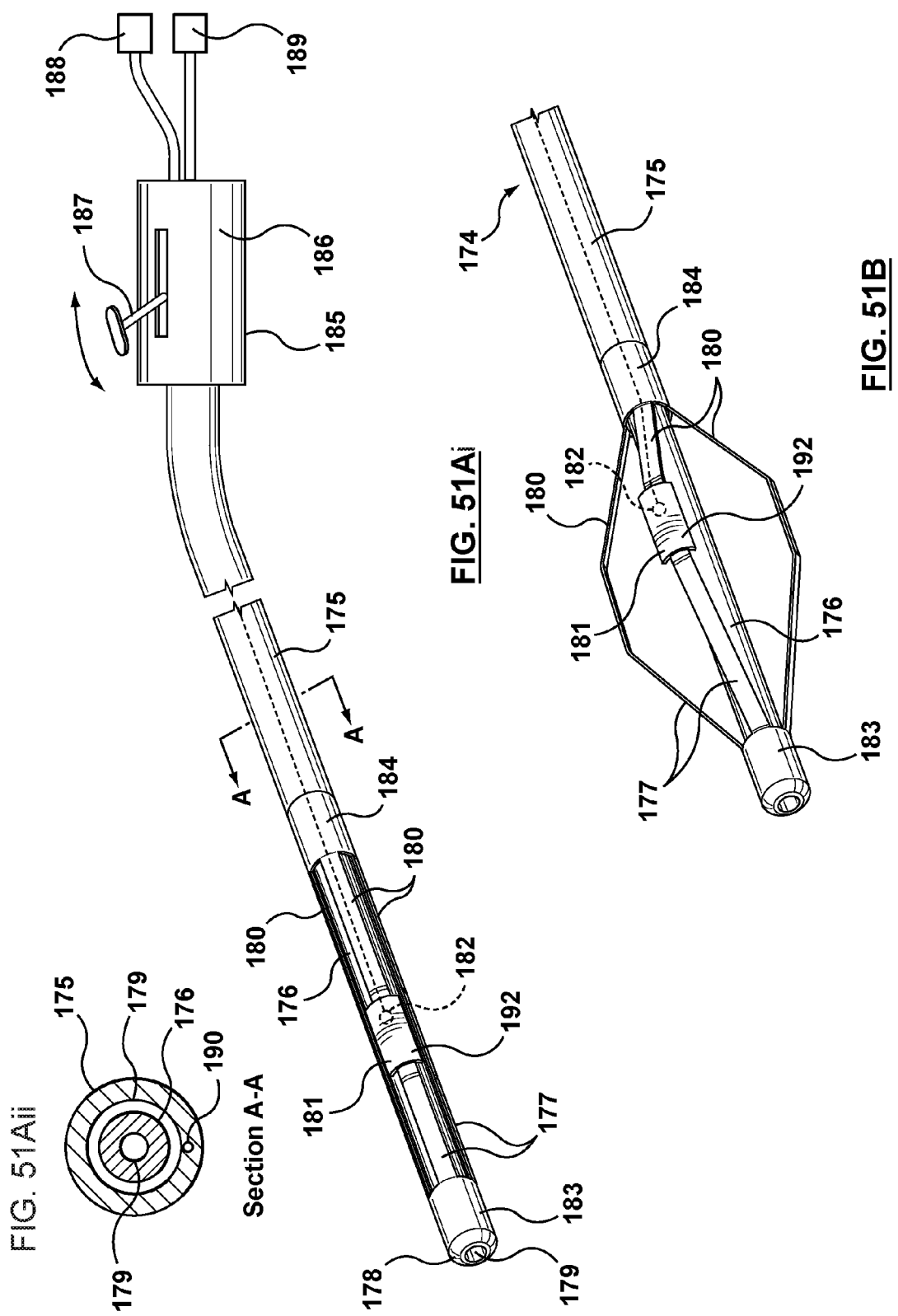

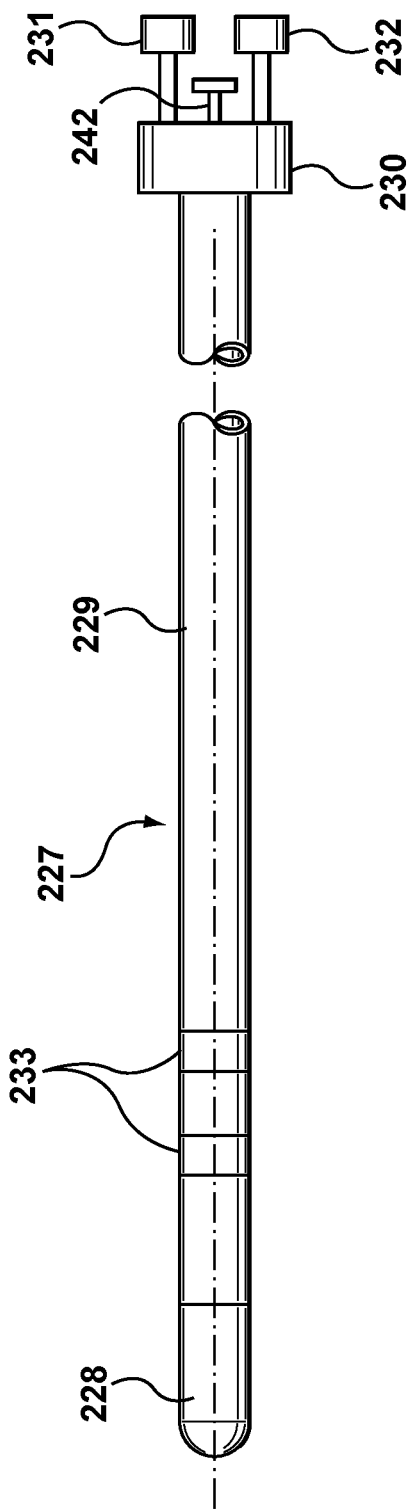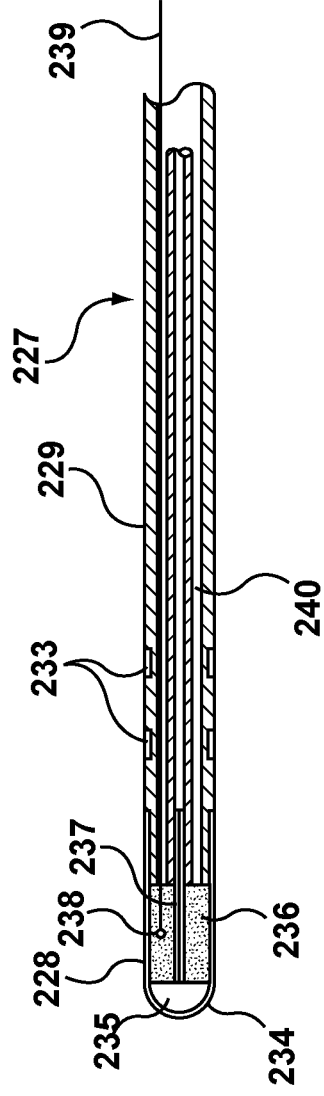
FIG. 57A
FIG. 57B

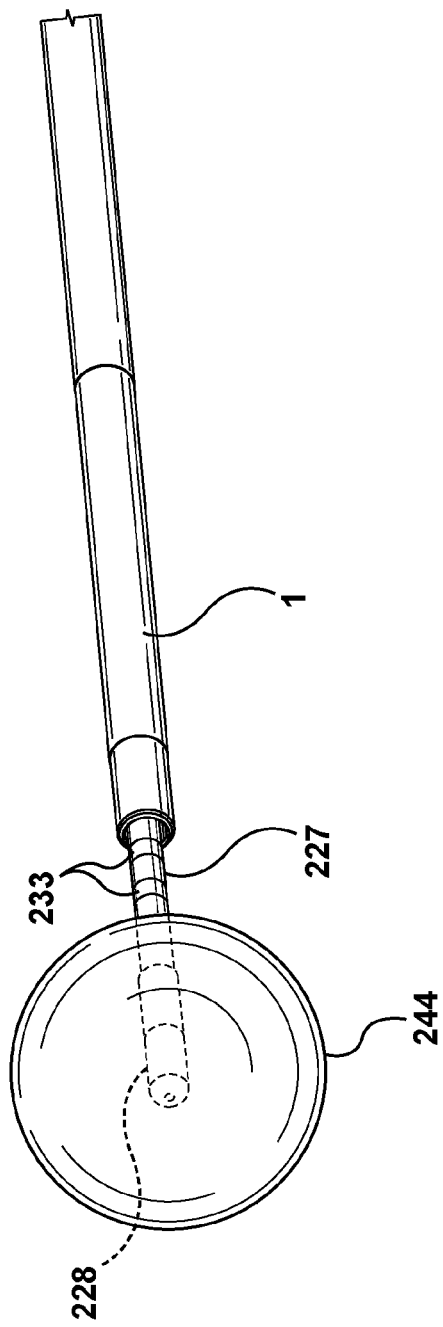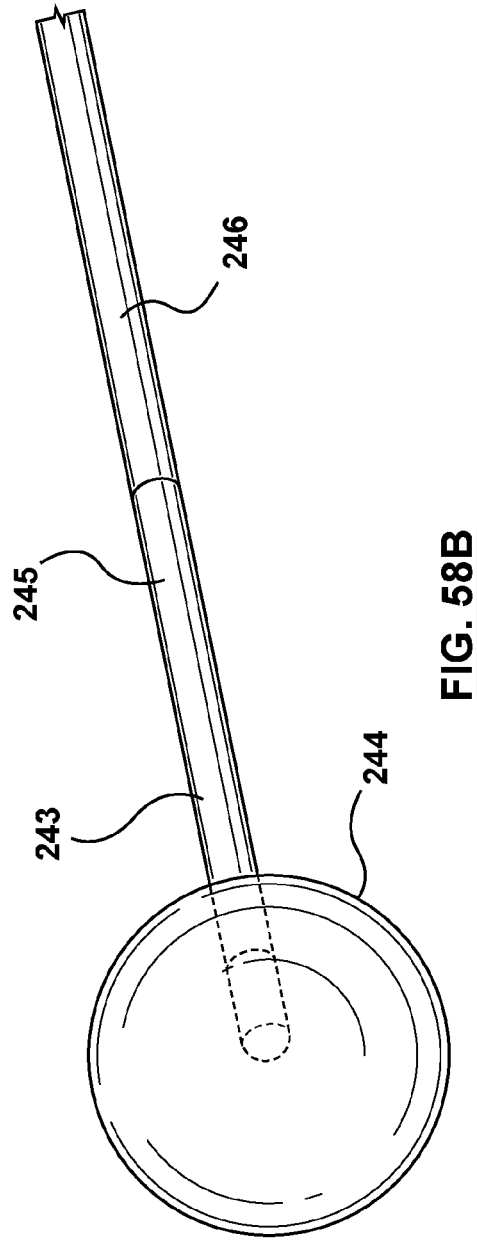
FIG. 58A
FIG. 58B

ENDOVASCULAR CATHETERS AND METHODS FOR CAROTID BODY ABLATION

CROSS REFERENCE TO RELATED APPLICATIONS

This application is a continuation of U.S. patent application Ser. No. 13/869,765, filed Apr. 24, 2013, now U.S. Pat. No. 9,393,070, which application claims priority to the following U.S. Provisional Patent Applications, the disclosures of which are incorporated by reference herein in their entireties: U.S. Provisional Application No. 61/637,582, filed Apr. 24, 2012; U.S. Provisional Application No. 61/643,243, filed May 5, 2012; U.S. Provisional Application No. 61/644,620, filed May 9, 2012; and U.S. Provisional Application No. 61/794,667, filed Mar. 15, 2013.

INCORPORATION BY REFERENCE

All publications and patent applications mentioned in this specification are herein incorporated by reference to the same extent as if each individual publication or patent application was specifically and individually indicated to be incorporated by reference.

BACKGROUND

An imbalance of the autonomic nervous system is associated with several disease states. Restoration of autonomic balance has been a target of several medical treatments including modalities such as pharmacological, device-based, and electrical stimulation. For example, beta blockers are a class of drugs used to reduce sympathetic activity to treat cardiac arrhythmias and hypertension; Gelfand and Levin (U.S. Pat. No. 7,162,303) describe a device-based treatment used to decrease renal sympathetic activity to treat heart failure, hypertension, and renal failure; Yun and Yuarn-Bor (U.S. Pat. No. 7,149,574; U.S. Pat. No. 7,363,076; U.S. Pat. No. 7,738,952) describe a method of restoring autonomic balance by increasing parasympathetic activity to treat disease associated with parasympathetic attrition; Kieval, Burns and Serdar (U.S. Pat. No. 8,060,206) describe an electrical pulse generator that stimulates a baroreceptor, increasing parasympathetic activity, in response to high blood pressure; Hlavka and Elliott (US 2010/0070004) describe an implantable electrical stimulator in communication with an afferent neural pathway of a carotid body chemoreceptor to control dyspnea via electrical neuromodulation.

Devices are needed that are configured to be positioned in the vicinity of a carotid body and are adapted to ablate the carotid body or related structure to treat one or more sympathetically mediated diseases.

SUMMARY OF THE DISCLOSURE

The disclosure includes methods, devices, and systems for endovascular interstitial ablation of a carotid body. Endovascular interstitial ablation of a carotid body generally refers to delivering a device through a patient's vasculature to a vessel proximate a peripheral chemosensor (e.g., carotid body) or an associated nerve of the patient, and passing an ablation element from the device through the vessel wall into interstitial space (e.g., intercarotid septum) to ablate the peripheral chemosensor.

A carotid body may be ablated by placing an ablation needle into a lumen of a carotid artery adjacent to the carotid body of interest, inserting the ablation needle into the periarterial space containing the carotid body, delivering an ablation agent into the periarterial space by means of the needle, withdrawing the needle from the periarterial space back into the carotid artery.

A carotid body may also be ablated by placing an ablation needle into a lumen of a carotid artery adjacent to the carotid body of interest, inserting the needle into periarterial space containing the carotid body, delivering an ablation agent into the periarterial space by the needle, withdrawing the needle from the periarterial space back into the carotid artery, whereby electrosurgical current is provided at a tip region of the needle to facilitate insertion, and heat is applied to the needle tract prior to or during withdrawal to reduce or prevent bleeding.

In another exemplary procedure a location of periarterial space associated with a carotid body is identified, and ablation parameters are selected, an ablation needle is placed into a lumen of a carotid artery in proximity of the carotid body of interest, the ablation needle is inserted into the periarterial space containing the carotid body, an ablation agent is delivered into the periarterial space by means of the needle, the needle is withdrawn from the periarterial space back into the carotid artery, whereby position of the ablation needle within the periarterial space and selection of ablation parameters provides for ablation of the carotid body without substantial collateral damage to adjacent functional structures.

In a further exemplary procedure a location of periarterial space associated with a carotid body is identified, as well as location of vital structures not associated with the carotid body, and based on these locations ablation parameters are selected, an ablation needle is placed into a lumen of a carotid artery in proximity of the carotid body of interest, the needle is inserted into the periarterial space containing the carotid body, an ablation agent is delivered into the periarterial space by means of the needle, the needle is withdrawn from the periarterial space back into the carotid artery, whereby the position of the ablation needle within the periarterial space and the selection of ablation parameters provides for ablation of the carotid body or a nerve associated with carotid body located in the periarterial space without substantial collateral damage to adjacent functional structures.

In a further example, ablation agents for needle delivery into periarterial space comprising a carotid body include chemicals selected for thrombogenic properties, chemicals selected for sympathetic neural toxicity, chemicals selected for glomus cell toxicity, tissue heating energies including radiofrequency energy, microwave energy, ultrasonic energy, laser energy, or resistive element heating.

Selectable carotid body ablation parameters may include ablation needle temperature, duration of ablation agent delivery, ablation energy power, ablation needle position within periarterial space, ablation needle size, type of ablation agent delivered, volume of ablation agent delivered, or ablation needle insertion tract.

The location of periarterial space associated with a carotid body may be determined by means of a non-fluoroscopic imaging procedure prior to carotid body ablation, where the non-fluoroscopic location information is translated to a coordinate system based on fluoroscopically identifiable anatomical and/or artificial landmarks.

The function of a carotid body may be stimulated and at least one physiological parameter recorded prior to and during the stimulation, the carotid body is ablated, and the stimulation is repeated, whereby a change in recorded physiological parameter(s) prior to and after ablation is an indication of the effectiveness of the ablation.

A function of a carotid body may be blocked and at least one physiological parameter(s) recorded prior to and during the blockade, the carotid body is ablated, and the blockade is repeated, whereby a change in recorded physiological parameter(s) prior to and after ablation is an indication of the effectiveness of the ablation.

In an exemplary method, a device configured to prevent embolic debris from entering the brain is deployed in an internal carotid artery associated with a carotid body, an ablation needle is inserted into periarterial space containing the carotid body, an ablation agent is delivered into periarterial space with the ablation needle, the ablation needle is then withdrawn from the periarterial space, the embolic prevention device is withdrawn from the internal carotid artery, whereby the device in the internal carotid artery prevents debris resulting from use of the ablation needle from entering the brain.

In an exemplary method the location of the periarterial space associated with a carotid body is identified, then an ablation needle is inserted into a predetermined location within the periarterial space from a carotid artery, ablation parameters are selected and an ablation agent is delivered into the periarterial space with the needle in accordance with the selected parameters, the ablation needle is withdrawn into the carotid artery and reinserted into the periarterial space in at least one additional predetermined location, an ablation agent is delivered using the same or different ablation parameters, whereby the positions of the ablation needle within the periarterial space and the selection of ablation parameters provides for ablation of the carotid body without substantial collateral damage to adjacent functional structures.

In an exemplary embodiment a system comprises a catheter device configured with an ablation needle positioned in a vicinity of a distal end of the catheter device, and a connection between the ablation needle to a source of an ablation agent at a proximal end of the catheter device, whereby the distal end of the catheter is constructed to be inserted into a peripheral artery of a patient and maneuvered into a carotid artery using standard fluoroscopic guidance techniques.

In an exemplary embodiment a system includes a carotid artery catheter configured with an ablation needle in a vicinity of a distal end of the catheter configured for carotid body ablation and further configured for at least one of the following: neural stimulation, neural blockade, carotid body stimulation or carotid body blockade; and a connection between the ablation needle to a source of an ablation agent, stimulation agent or blockade agent located in a vicinity of a proximal end of the catheter.

Stimulation agents may include chemicals that stimulate nerves, chemicals that stimulate carotid body function, electrical energy configured for nerve stimulation, or electrical energy configured for carotid body stimulation.

Blockade agents may include chemicals that blockade nerve function, chemicals that blockade carotid body function, electrical energy configured for blockade of nerve function, or electrical energy configured for blockade of carotid body function.

In some embodiments a system comprises a carotid artery catheter configured with an ablation needle and at least one electrode positioned proximate a distal region of the catheter, configured for at least one of the following: neural stimulation, neural blockade, carotid body stimulation, and carotid body blockade; and at a proximal region of the catheter a connection between the ablation needle to a source of an ablation agent, and a connection between the ablation needle or electrode(s) to a source of stimulation energy or blockade energy.

In some embodiments a carotid artery catheter includes an ablation needle mounted in a vicinity of a distal end of the catheter configured for tissue heating, whereby, the ablation needle comprises at least one ablation electrode and at least one temperature sensor, and a connection between the ablation needle electrode(s) and temperature sensor(s) to an ablation energy source mounted in a vicinity of a proximal end of the catheter, with the ablation energy source being configured to maintain the ablation needle electrode at a temperature in a range of 40 to 100 degrees centigrade during ablation using signals received from the temperature sensor(s).

In some embodiments a system includes a carotid artery catheter with an ablation element needle in a vicinity of a distal end of the catheter configured for tissue heating, whereby, the ablation needle comprises at least one ablation electrode and at least one temperature sensor and at least one irrigation channel, and a connection between the ablation needle electrode(s) and temperature sensor(s) and irrigation channel(s) to an ablation energy source mounted in a vicinity of a proximal end of the catheter, with the ablation energy source being configured to maintain the ablation needle electrode at a temperature in the range of 40 to 100 degrees centigrade during ablation using signals received from the temperature sensor(s) and by providing irrigation to the vicinity of the ablation needle electrode.

In some embodiments a carotid artery catheter includes a deflection mechanism comprising a user deflectable segment in a vicinity of a distal end of the catheter and a non-deflectable segment proximal to the deflectable segment, where deflection of the deflectable segment is facilitated by a pull wire within the catheter in communication between the distal segment and a handle containing a deflection actuator at a proximal end of the catheter, and an ablation needle mounted in vicinity of the distal end, whereby the deflection mechanism is configured to provide the user with a means for placing and holding the ablation needle against the wall of a carotid artery for insertion of the needle through the artery wall into periarterial space.

A system may include a carotid artery sheath with a user deflectable segment in vicinity of a distal end of the sheath and a non-deflectable segment proximal to the deflectable segment, where deflection of the deflectable segment is facilitated by a pull wire within the sheath in communication between the deflectable segment and a handle containing a deflection actuator at a proximal end of the catheter, whereby the sheath is configured for positioning an ablation needle catheter for needle insertion into the periarterial space containing a carotid body.

In some embodiments a carotid artery catheter comprises a forceps structure and an ablation needle mounted in vicinity of a distal end of the catheter, and a means for actuating the forceps structure and a connection between the ablation needle to an ablation agent source, and a device located in vicinity of a proximal end of the catheter that inserts the ablation needle into a periarterial space proximate a carotid bifurcation saddle containing a carotid body, whereby the forceps are configured to grasp and hold the carotid bifurcation saddle at a position suited for ablation needle insertion into the periarterial space, and to facilitate the needle insertion.

In some embodiments a carotid artery catheter comprises a suction cup structure and an ablation needle mounted in a vicinity of a distal end of the catheter, and a suction device which applies suction to the suction cup structure and a connection between the ablation needle to an ablation agent source, and an insertion device in a vicinity of a proximal end of the catheter for inserting the ablation needle into a periarterial space containing a carotid body from within a carotid artery, whereby the suction cup and suction device are configured to attach and hold the ablation needle catheter to a carotid artery at a position suited for ablation needle insertion into the periarterial space, and to facilitate the needle insertion.

In some embodiments a carotid artery catheter includes a deployable structure configured for user actuated radial expansion in vicinity of a distal end of the catheter, a radiopaque ablation needle mounted on one side of the deployable structure and at least one radiopaque element mounted on an opposite side of the deployable structure, whereby the deployable structure provides the user with a means for positioning the ablation needle for insertion into periarterial space comprising a carotid body, where a combination of the radiopaque ablation needle and the radiopaque element provide the user with a substantially unambiguous fluoroscopic determination of location of the ablation needle within the carotid artery.

In some embodiments a system adapted for endovascular interstitial ablation of a carotid body includes comprising a carotid artery catheter with an ablation needle mounted in a vicinity of a distal end of the catheter, a means for positioning the ablation needle within a carotid artery at a specific location, a means to provide a user with a substantially unambiguous fluoroscopic determination of position of the ablation needle within a carotid artery, a means for inserting the ablation needle into a periarterial space containing a carotid body to predetermined depth, a means for connecting the ablation needle to a source of an ablation agent mounted in vicinity of a proximal end of the catheter, and a console comprising a source of an ablation agent, a means for controlling delivery of the ablation agent, a user interface configured to provide the user with a selection of ablation parameters, indications of status of the console and status of ablation activity, a means to activate and deactivate an ablation, and an umbilical to provide a means for connecting the catheter to the console.

In some embodiments a method reduces or inhibit chemoreflex function generated by a carotid body in a mammalian patient, to reduce afferent nerve sympathetic activity of carotid body nerves to treat a sympathetically mediated disease, the method comprising: positioning a catheter in a vascular system of the patient such that a distal section of the catheter is in a lumen proximate to the carotid body of the patient; advancing an ablation element from the lumen into an intercarotid septum the carotid body or at least a portion of a carotid body; supplying energy to the ablation element wherein the energy is supplied by an energy supply apparatus outside of the patient; applying the energy from the energy supply to the ablation element to ablate tissue proximate to or included in the carotid body; and removing the ablation device from the patient; wherein a carotid body chemoreflex function is inhibited or sympathetic afferent nerve activity of carotid body nerves is reduced due to the ablation.

In some embodiments a method to treat a patient having a sympathetically mediated disease by reducing or inhibiting chemoreflex function generated by a carotid body includes the steps of inserting a catheter into the patient's vasculature, positioning a portion of the catheter proximate a carotid body (e.g., in a carotid artery, pointing a trajectory of a deployable interstitial ablation needle toward a target ablation site (e.g., carotid body, intercarotid septum, carotid plexus, carotid sinus nerve), holding position of the catheter, inserting a deployable interstitial ablation needle into tissue, piercing a vessel wall with the interstitial ablation needle, applying ablative energy to the target ablation site via the interstitial ablation needle, retracting the interstitial ablation needle from tissue, applying heat to tissue from the interstitial ablation needle while retracting it from tissue to seal a puncture in the vessel, and removing the catheter from the patient's vasculature.

The disclosure also includes methods, devices, and systems for endovascular transmural ablation of a carotid body. Endovascular transmural ablation of a carotid body generally refers to delivering a device through a patient's vasculature to a blood vessel proximate to a peripheral chemosensor (e.g., carotid body) or an associated nerve or nerve plexus of the patient and placing an ablation element associated with the device against the internal wall of the vessel adjacent to the peripheral chemosensor and activating the ablation element to ablate the peripheral chemosensor.

A carotid body may be ablated by placing an ablation element within and against the wall of a carotid artery adjacent to the carotid body of interest, then activating the ablation element causing a change in the temperature of the periarterial space containing the carotid body to an extent and duration sufficient to ablate the carotid body.

A carotid body may also be ablated by placing an ablation element within and against the wall of an internal jugular vein adjacent to the carotid body of interest, then activating the ablation element causing a change in the temperature of the perivenous space containing the carotid body to an extent and duration sufficient to ablate the carotid body.

In another exemplary procedure a location of periarterial space associated with a carotid body is identified, then an ablation element is placed against the interior wall of a carotid artery adjacent to the identified location, then ablation parameters are selected and the ablation element is activated thereby ablating the carotid body, whereby the position of the ablation element and the selection of ablation parameters provides for ablation of the carotid body without substantial collateral damage to adjacent functional structures.

In a further exemplary procedure a location of perivenous space associated with a carotid body is identified, then an ablation element is placed against the interior wall of an internal jugular vein adjacent to the identified location, then ablation parameters are selected and the ablation element is activated thereby ablating the carotid body, whereby the position of the ablation element and the selection of ablation parameters provides for ablation of the carotid body without substantial collateral damage to adjacent functional structures.

In further example the location of the periarterial space associated with a carotid body is identified, as well as the location of vital structures not associated with the carotid body, then an ablation element is placed against the interior wall of a carotid artery adjacent to the identified location, ablation parameters are selected and the ablation element is then activated thereby ablating the carotid body, whereby the position of the ablation element and the selection of ablation parameters provides for ablation of the target carotid body without substantial collateral damage to vital structures in the vicinity of the carotid body.

In another example the location of the perivenous space associated with a carotid body is identified, as well as the location of vital structures not associated with the carotid body, then an ablation element is placed against the interior wall of an internal jugular vein adjacent to the identified location, ablation parameters are selected and the ablation element is then activated thereby ablating the carotid body, whereby the position of the ablation element and the selection of ablation parameters provides for ablation of the target carotid body without substantial collateral damage to vital structures in the vicinity of the carotid body.

Selectable carotid body ablation parameters include ablation element temperature, duration of ablation element activation, ablation power, ablation element force of contact with a vessel wall, ablation element size, ablation modality, and ablation element position within a vessel.

The location of the perivascular space associated with a carotid body can be determined by means of a non-fluoroscopic imaging procedure prior to carotid body ablation, where the non-fluoroscopic location information is translated to a coordinate system based on fluoroscopically identifiable anatomical and/or artificial landmarks.

A function of a carotid body can be stimulated and at least one physiological parameter is recorded prior to and during the stimulation, then the carotid body is ablated, and the stimulation is repeated, whereby the change in recorded physiological parameter(s) prior to and after ablation is an indication of the effectiveness of the ablation.

A function of a carotid body can be temporarily blocked and at least one physiological parameter(s) is recorded prior to and during the blockade, then the carotid body is ablated, and the blockade is repeated, whereby the change in recorded physiological parameter(s) prior to and after ablation is an indication of the effectiveness of the ablation.

In some embodiments a device configured to prevent embolic debris from entering the brain is deployed in an internal carotid artery associated with a carotid body, then an ablation element is placed within and against the wall of the external carotid artery associated with the carotid body, the ablation element is activated resulting in carotid body ablation, the ablation element is then withdrawn from the external carotid artery, then the embolic prevention device is withdrawn from the internal carotid artery, whereby the device in the internal carotid artery prevents debris resulting from the use of the ablation element form entering the brain.

In some embodiments a method includes identifying a location of the perivascular space associated with a carotid body, then an ablation element is placed in a predetermined location against the interior wall of vessel adjacent to the identified location, then ablation parameters are selected and the ablation element is activated and then deactivated, the ablation element is then repositioned in at least one additional predetermine location against the same interior wall and the ablation element is then reactivated using the same or different ablation parameters, whereby the positions of the ablation element and the selection of ablation parameters provides for ablation of the carotid body without substantial collateral damage to adjacent functional structures.

In some embodiments the location of the perivascular space associated with a carotid body is identified, an ablation element configured for tissue freezing is placed against the interior wall of a vessel adjacent to the identified location, ablation parameters are selected for reversible cryo-ablation and the ablation element is activated, the effectiveness of the ablation is then determined by at least one physiological response to the ablation, and if the determination is that the physiological response is favorable, then the ablation element is reactivated using the ablation parameters selected for permanent carotid body ablation.

Some embodiments includes a system that comprises a vascular catheter configured with an ablation element in the vicinity of the distal end, and a connection between the ablation element and a source of ablation energy at the proximal end, whereby the distal end of the catheter is constructed to be inserted into a peripheral artery of a patient and then maneuvered into an internal or external carotid artery using standard fluoroscopic guidance techniques.

Some embodiments includes a device that comprises a catheter configured with an ablation element in the vicinity of the distal end, and a means to connect the ablation element to a source of ablation energy at the proximal end, whereby the distal end of the catheter is constructed to be inserted into a peripheral vein of a patient and then maneuvered into an internal jugular vein using standard fluoroscopic guidance techniques.

Some embodiments includes a system comprising a vascular catheter configured with an ablation element in the vicinity of the distal end configured for carotid body ablation and further configured for at least one of the following: neural stimulation, neural blockade, carotid body stimulation and carotid body blockade; and a connection between the ablation element and a source of ablation energy, stimulation energy and/or blockade energy.

Some embodiments includes a system comprising a vascular catheter configured with an ablation element and at least one electrode configured for at least one of the following: neural stimulation, neural blockade, carotid body stimulation and carotid body blockade; and a connection between the ablation element to a source of ablation energy, and a connection between the ablation element and/or electrode(s) to a source of stimulation energy and/or blockade energy.

Some embodiments includes a system comprising a vascular catheter with an ablation element mounted in the vicinity of the distal end configured for tissue heating, whereby, the ablation element comprises at least one electrode and at least one temperature sensor, a connection between the ablation element electrode(s) and temperature sensor(s) to an ablation energy source, with the ablation energy source being configured to maintain the ablation element at a temperature in the range of 40 to 100 degrees centigrade during ablation using signals received from the temperature sensor(s).

Some embodiments includes a system comprising a vascular catheter with an ablation element mounted in the vicinity of the distal end configured for tissue heating, whereby, the ablation element comprises at least one electrode and at least one temperature sensor and at least one irrigation channel, and a connection between the ablation element electrode(s) and temperature sensor(s) and irrigation channel(s) to an ablation energy source, with the ablation energy source being configured to maintain the ablation element at a temperature in the range of 40 to 100 degrees centigrade during ablation using signals received from the temperature sensor(s) and by providing irrigation to the vicinity of the ablation element.

Some embodiments includes a system comprising a vascular catheter with an ablation element mounted in the vicinity of the distal end configured for tissue freezing, whereby, the ablation element comprises at least one cryogenic expansion chamber and at least one temperature sensor, and a connection between the ablation element expansion chamber and temperature sensor(s) to a cryogenic agent source, with the cryogenic agent source being configured to maintain the ablation element at a predetermined temperature in the range of −20 to −160 degrees centigrade during ablation using signals received from the temperature sensor(s).

Some embodiments includes a system comprising a vascular catheter with an ablation element mounted in the vicinity of the distal end configured to freeze tissue, and to heat tissue, whereby, the ablation element comprises at least one cryogenic expansion chamber constructed of an electrically conductive material and configured as an electrode, and at least one temperature sensor, and a connection between the ablation element expansion chamber/electrode and temperature sensor(s) to an ablation source consisting of cryogenic agent source and an electrical heating energy source.

Some embodiments include a carotid artery catheter with a user deflectable segment in the vicinity of the distal end and a non-deflectable segment proximal to the deflectable segment, where the deflection of the distal segment is facilitated by a pull wire within the catheter in communication between the distal segment and a handle containing a deflection actuator at the proximal end, and an ablation element mounted in the vicinity of the distal end, whereby the deflection mechanism is configured to provide the user with a means for placing the ablation element against the wall of a carotid artery.

Some embodiments include a jugular vein catheter a user deflectable segment in the vicinity of the distal end and a non-deflectable segment proximal to the deflectable segment, where the deflection of the distal segment is facilitated by a pull wire within the catheter in communication between the distal segment and a handle containing a deflection actuator at the proximal end, and an ablation element mounted in the vicinity of the distal end, whereby the deflection mechanism is configured to provide the user with a means for placing the ablation element against the wall of a jugular vein.

Some embodiments include a carotid artery sheath with a user deflectable segment in the vicinity of the distal end and a non-deflectable segment proximal to the deflectable segment, where the deflection of the distal segment is facilitated by a pull wire within the sheath in communication between the distal segment and a handle containing a deflection actuator at the proximal end, and an ablation element mounted in the vicinity of the distal end, whereby the deflection mechanism is configured to provide the user with a means for placing the ablation element against the wall of a carotid artery.

Some embodiments include a jugular vein sheath with a user deflectable segment in the vicinity of the distal end and a non-deflectable segment proximal to the deflectable segment, where the deflection of the distal segment is facilitated by a pull wire within the sheath in communication between the distal segment and a handle containing a deflection actuator at the proximal end, and an ablation element mounted in the vicinity of the distal end, whereby the deflection mechanism is configured to provide the user with a means for placing the ablation element against the wall of a jugular vein.

Some embodiments include a procedural kit for ablation of a carotid body comprising a carotid artery sheath with a user deflectable distal section, an ablation element mounted in the vicinity of the distal end, and a carotid artery catheter constructed for use through the sheath configured to prevent debris caused by use of the sheath from entering the brain through the internal carotid artery associated with the carotid body.

Some embodiments include a procedural kit for ablation of a carotid body comprising a vascular sheath with a user deflectable distal section, an ablation element mounted in the vicinity of the distal end, and an ultrasonic imaging catheter constructed for use through the sheath and configured to image the carotid body and surrounding anatomy as a means for guiding the user in the placement of the ablation element as well as image a change in the carotid body and surrounding anatomy as a result of the ablation in real time as a means for providing the user with an indication of the progress and/or effectiveness of the ablation.

Some embodiments include an vascular ultrasonic imaging catheter comprises an imaging element in the vicinity of the distal end configured for circumferential ultrasonic imaging at an angle between −15 degrees and −50 degrees from normal, and further configured for imaging: a carotid body from within a vessel proximate to the carotid body, vital and non-vital anatomical structures in the vicinity of the carotid body, and a change in a carotid body in real time due to an ablation of the carotid body.

Another aspect of this disclosure is a vascular catheter with a structure configured for user actuated radial expansion in the vicinity of the distal end, a radiopaque ablation element mounted on one side of the structure and at least one radiopaque element mounted on the opposite side of the structure, whereby the structure provides the user with a means for pressing the ablation element against the wall of a vessel, and the combination of the radiopaque ablation element and the radiopaque element provide the user with a substantially unambiguous fluoroscopic determination of the location of the ablation element within the vessel.

Some embodiments include a carotid artery catheter with a forceps structure comprising at least two arms configured for user actuation in the vicinity of the distal end, a radiopaque ablation element mounted on at least one arm of the structure and at least one radiopaque element on the opposite arm of the structure, whereby the structure provides the user with a means for pressing the ablation element against the wall of a carotid artery, and the combination of the radiopaque ablation element and the radiopaque element provide the user with a substantially unambiguous fluoroscopic determination of the location of the ablation element within a carotid artery.

Some embodiments include a system for endovascular transmural ablation of a carotid body comprising a carotid artery catheter with an ablation element mounted in the vicinity of the distal end, a means for pressing the ablation element against the wall of a carotid artery at a specific location, a means for providing the user with a substantially unambiguous fluoroscopic determination of the position of the ablation element in a carotid artery, a means for connecting the ablation element to a source of ablation energy mounted in the vicinity of the proximal end, and a console comprising a source of ablation energy, a means for controlling the ablation energy, a user interface configured to provide the user with a selection of ablation parameters, indications of the status of the console and the status of the ablation activity, a means to activate and deactivate an ablation, and an umbilical to provide a means for connecting the catheter to the console.

Some embodiments include a method to reduce or inhibit chemoreflex function generated by a carotid body in a mammalian patient, to reduce afferent nerve sympathetic activity of carotid body nerves to treat a sympathetically mediated disease, the method comprising: positioning a catheter in a vascular system of the patient such that a distal section of the catheter is in a lumen proximate to the carotid body of the patient; pressing an ablation element against the wall of the lumen adjacent to the carotid body, supplying energy to the ablation element wherein the energy is supplied by an energy supply apparatus outside of the patient; applying the energy from the energy supply to the ablation element to ablate tissue proximate to or included in the Carotid body; and removing the ablation device from the patient; wherein a carotid body chemoreflex function is inhibited or sympathetic afferent nerve activity of carotid body nerves is reduced due to the ablation.

Some embodiments include a method to treat a patient having a sympathetically mediated disease by reducing or inhibiting chemoreflex function generated by a carotid body including steps of inserting a catheter into the patient's vasculature, positioning a portion of the catheter proximate a carotid body (e.g., in a carotid artery), positioning an ablation element toward a target ablation site (e.g., carotid body, intercarotid septum, carotid plexus, carotid sinus nerve), holding position of the catheter, applying ablative energy to the target ablation site via the ablation element, and removing the catheter from the patient's vasculature.

The methods and systems disclosed herein may be applied to satisfy clinical needs related to treating cardiac, metabolic, and pulmonary diseases associated, at least in part, with enhanced chemoreflex (e.g., high chemosensor sensitivity or high chemosensor activity) and related sympathetic activation. The treatments disclosed herein may be used to restore autonomic balance by reducing sympathetic activity, as opposed to increasing parasympathetic activity. It is understood that parasympathetic activity can increase as a result of the reduction of sympathetic activity (e.g., sympathetic withdrawal) and normalization of autonomic balance. Furthermore, the treatments may be used to reduce sympathetic activity by modulating a peripheral chemoreflex. Furthermore, the treatments may be used to reduce afferent neural stimulus, conducted via afferent carotid body nerves, from a carotid body to the central nervous system. Enhanced peripheral and central chemoreflex is implicated in several pathologies including hypertension, cardiac tachyarrhythmias, sleep apnea, dyspnea, chronic obstructive pulmonary disease (COPD), diabetes and insulin resistance, and CHF. Mechanisms by which these diseases progress may be different, but they can commonly include contribution from increased afferent neural signals from a carotid body. Central sympathetic nervous system activation is common to all these progressive and debilitating diseases. Peripheral chemoreflex may be modulated, for example, by modulating carotid body activity. The carotid body is the sensing element of the afferent limb of the peripheral chemoreflex. Carotid body activity may be modulated, for example, by ablating a carotid body or afferent nerves emerging from the carotid body. Such nerves can be found in a carotid body itself, in a carotid plexus, in an intercarotid septum, in periarterial space of a carotid bifurcation and internal and external carotid arteries, and internal jugular vein. Therefore, a therapeutic method has been conceived that comprises a goal of restoring or partially restoring autonomic balance by reducing or removing carotid body input into the central nervous system.

One aspect of the disclosure is an ablation catheter adapted to be advanced endovascularly to a bifurcation of an internal carotid artery and an external carotid artery comprising: a forceps structure comprising at least two arms configured for user actuation, the first arm configured to engage with a wall of the internal carotid artery delimiting a carotid septum and the second arm configured to be simultaneously engaged with a wall of the external carotid artery delimiting the carotid septum; and an ablation element mounted on at least one arm of the structure, the ablation element configured to ablate at least a portion of the carotid septum.

In some embodiments the forceps structure includes means for pressing the ablation element against a wall of a carotid artery at a specific location adjacent the carotid septum. The first and second arms can be configured so that a force of contact distends the ablation element about 1 mm to 3 mm into a wall of a carotid artery. In some embodiments the forceps structure includes means for pressing the ablation element against a wall of a carotid artery. In some embodiments the ablation element is positioned on the arm such that it engages a wall of the internal or external carotid artery delimiting a carotid septum. In some embodiments the ablation element comprises a surface adapted to contact a vessel wall adjacent the carotid septum.

In some embodiments the ablation element is an electrode disposed on the first or the second arm. In some embodiments the first and second arms are adapted to compress the carotid septum. In some embodiments the catheter comprises an arm actuator adapted to move the first and second arms towards each other. In some embodiments the first and second arms are further adapted to move away from each other toward a preset position.

In some embodiments the ablation element comprises a first electrode disposed on the first arm and a second electrode disposed on the second arm. In some embodiments the first and second arms are adapted to move from an undeployed configuration to a deployed configuration in which the first and second arms are further apart than in the undeployed configuration. In some embodiments the catheter includes a sheath adapted to contain the first and second arms during endovascular advancement. A functional sheath diameter can be between 3 French and 12 French. In some embodiments the first and second arms are adapted to move toward the deployed configuration as they emerge from the sheath. In some embodiments the sheath is adapted to be advanced toward the first and second arms to move the first and second arms toward each other.

In some embodiments the ablation element is configured to heat the target tissue to a temperature above 37° C., and in some embodiments the ablation element is configured to heat the target tissue to, a temperature above 45° C.

In some embodiments the catheter further comprises one or more temperature sensors positioned at the first and/or second arms.

In some embodiments the catheter is configured to be positioned against the carotid bifurcation saddle to position the ablation element at a predetermined distance distal of the carotid bifurcation saddle. In some embodiments the catheter is configured to place the ablation element against the wall of a carotid artery at a position no more than 15 mm distal to the carotid bifurcation saddle.

In some embodiments a system includes an ablation catheter, an ablation source operably connected to the ablation element of the ablation catheter, and a user control comprising an ablation actuator operative to deliver an ablation agent from the ablation source to the ablation element to ablate the target tissue. The ablation source can comprise an RF generator. The ablation element can comprise a first electrode disposed on the first arm and a second electrode disposed on the second arm, and wherein the first and second electrodes are connected to opposite poles of the RF generator or to the same poles of the RF generator. The user control can be configured to specify or calculate treatment parameters to control a desired ablation.

One aspect of the disclosure is an ablation catheter adapted to be advanced endovascularly to a bifurcation of an internal carotid artery and an external carotid artery adjacent a carotid septum, the catheter supporting an ablation element for ablating target tissue and first and second arms, the first arm being adapted to engage with a wall of the external carotid artery adjacent the carotid septum, and the second arm being adapted to simultaneously engage with a wall of the internal carotid artery adjacent the carotid septum, to support the ablation element in a position to ablate target tissue within the carotid septum, wherein the catheter is connectable to an ablation source.

The first and second arms can be further adapted to press the ablation element into contact with a carotid artery wall. The first and second arms can be configured so that a force of contact distends the ablation element about 1 mm to 3 mm into a wall of a carotid artery. The catheter can includes means for pressing the ablation element into contact with a wall of a carotid artery. The ablation element can comprise a surface adapted to contact a vessel wall adjacent the carotid septum.

The ablation element can be an electrode disposed on the first or the second arm. The first and second arms can be further adapted to position the ablation element into contact with the vessel wall at a bifurcation between the external carotid artery and the internal carotid artery.

The ablation element can comprise a sharp distal point adapted to penetrate through the vessel wall into the carotid septum.

The first and second arms can be further adapted to compress the carotid septum. The catheter can further comprise an arm actuator adapted to move the first and second arms towards each other. The first and second arms can be further adapted to move away from each other toward a preset position.

The ablation element can comprise a first electrode disposed on the first arm and a second electrode disposed on the second arm.

The first and second arms can be further adapted to move from an undeployed configuration to a deployed configuration in which the first and second arms are further apart than in the undeployed configuration. The catheter can also include a sheath adapted to contain the first and second arms during endovascular advancement. A functional sheath diameter can be between 3 French and 12 French. The first and second arms can be adapted to move toward the deployed configuration as they emerge from the sheath. The sheath can be adapted to be advanced toward the first and second arms to move the first and second arms toward each other.

In some embodiments the ablation element is configured to heat the target tissue to a temperature above 37° C., and in some embodiments the ablation element is configured to heat the target tissue to a temperature above 45° C.

The catheter can include one or more temperature sensors positioned at the first and/or second arms.

The catheter can be configured to be positioned against the carotid bifurcation saddle to position the ablation element at a predetermined distance distal of the carotid bifurcation saddle. The catheter can be configured to place the ablation element against the wall of a carotid artery at a position no more than 15 mm distal to the carotid bifurcation saddle.

One aspect of the disclosure is an ablation catheter adapted to be advanced endovascularly to a bifurcation of an internal carotid artery and an external carotid artery comprising: an ablation device comprising at least two arms configured for user actuation, the first arm configured to engage with a wall of the internal carotid artery delimiting a carotid septum and the second arm configured to be simultaneously engaged with a wall of the external carotid artery delimiting the carotid septum; and an ablation element mounted on at least one arm, the ablation element configured to ablate at least a portion of the carotid septum. Exemplary embodiments of this aspect are described above.

One aspect of the disclosure is an ablation method for ablating target tissue within a carotid septum of a patient, the method comprising: advancing an ablation device into an artery of a patient, the ablation device comprising first and second arms and an ablation element; passing the first arm into an external carotid artery of the patient and into engagement with a wall of the external carotid artery adjacent a carotid septum; passing the second arm into an internal carotid artery of the patient and into engagement with a wall of the internal carotid artery adjacent the carotid septum; and actuating the ablation element to ablate target tissue within the carotid septum.

The method can further comprise contacting the ablation element with a vessel wall adjacent the carotid septum. Contacting the ablation element with a vessel wall adjacent the carotid septum can comprise contacting the ablation element with a vessel wall no more than 15 mm distal to a carotid bifurcation saddle.

The method can further comprise inserting the ablation element into the carotid septum. The contacting step can comprise contacting the vessel wall at a bifurcation between the external carotid artery and the internal carotid artery.

The first and second arms can support the ablation element in contact with the vessel wall.

The method can include grasping the carotid septum with the first and second arms. The method can include compressing the carotid septum with the first and second arms.

The actuating step can be performed during the compressing step.

The method can also include moving the first and second arms away from each other. The advancing step can comprise advancing the ablation device with the first and second arms in an undeployed configuration, the moving step comprising moving the first and second arms away from each other from the undeployed configuration to a deployed configuration. The advancing step can comprise advancing the first and second arms within a sheath. The moving step can comprise permitting the first and second arms to return toward a preset position.

The method can also include moving the first and second arms toward each other. The moving step can include operating an arm actuator.

The actuating step can comprise actuating the ablation element to ablate the target tissue while the first and second arms are engaged with the artery walls.

In some embodiments at least part of the ablation element is disposed on the first arm or the second arm. The ablation element can comprise first and second electrodes, the first electrode being disposed on the first arm and the second electrode being disposed on the second arm, the actuating step comprising using the first and second electrodes to ablate the target tissue with RF energy. The first and second electrodes can be connected to the same pole of an RF generator, or they can be connected to opposite poles of an RF generator. The ablation element can comprise a pair of bipolar electrodes.

The actuating step can comprise heating the target tissue to a temperature above 37° C. The actuating step can comprise heating the target tissue to a temperature above 45°

C. The actuating step can comprise delivering ablation energy from the ablation element to the target tissue for 30-120 seconds.

BRIEF DESCRIPTION OF THE DRAWINGS

FIG. 2 is a schematic view of a steerable sheath.

FIG. 3 is a schematic view of a steerable sheath in a deflected state.

FIG. 6 is an exploded view of a radiofrequency electrode needle.

FIG. 20 is a schematic view of an interstitial laser ablation needle.

FIG. 21 is a schematic view of an interstitial microwave ablation needle.

FIGS. 34A, 34B, 34C and 34D are schematic views of an endovascular ablation catheter having deployable arms with ablation elements.

FIGS. 51Ai and 51Aii are schematic views of an endovascular catheter having a deployable wire basket and an ablation element, in an undeployed state.

FIG. 51B is a schematic view of an endovascular catheter having a deployable wire basket and an ablation element, in a deployed state.

FIGS. 57A and 57B are schematic views of an endovascular ablation catheter configured for transmural cooled radiofrequency ablation of a carotid body.

FIG. 58A is a schematic view of an endovascular ablation catheter having a point-ablate cryogenic ablation element, contained in a steerable sheath, showing an ice ball formed around the cryogenic ablation element.

FIG. 58B is a schematic view of a steerable endovascular ablation catheter having a point-ablate cryogenic ablation element showing an ice ball formed around the cryogenic ablation element.

DETAILED DESCRIPTION

Figure 1:
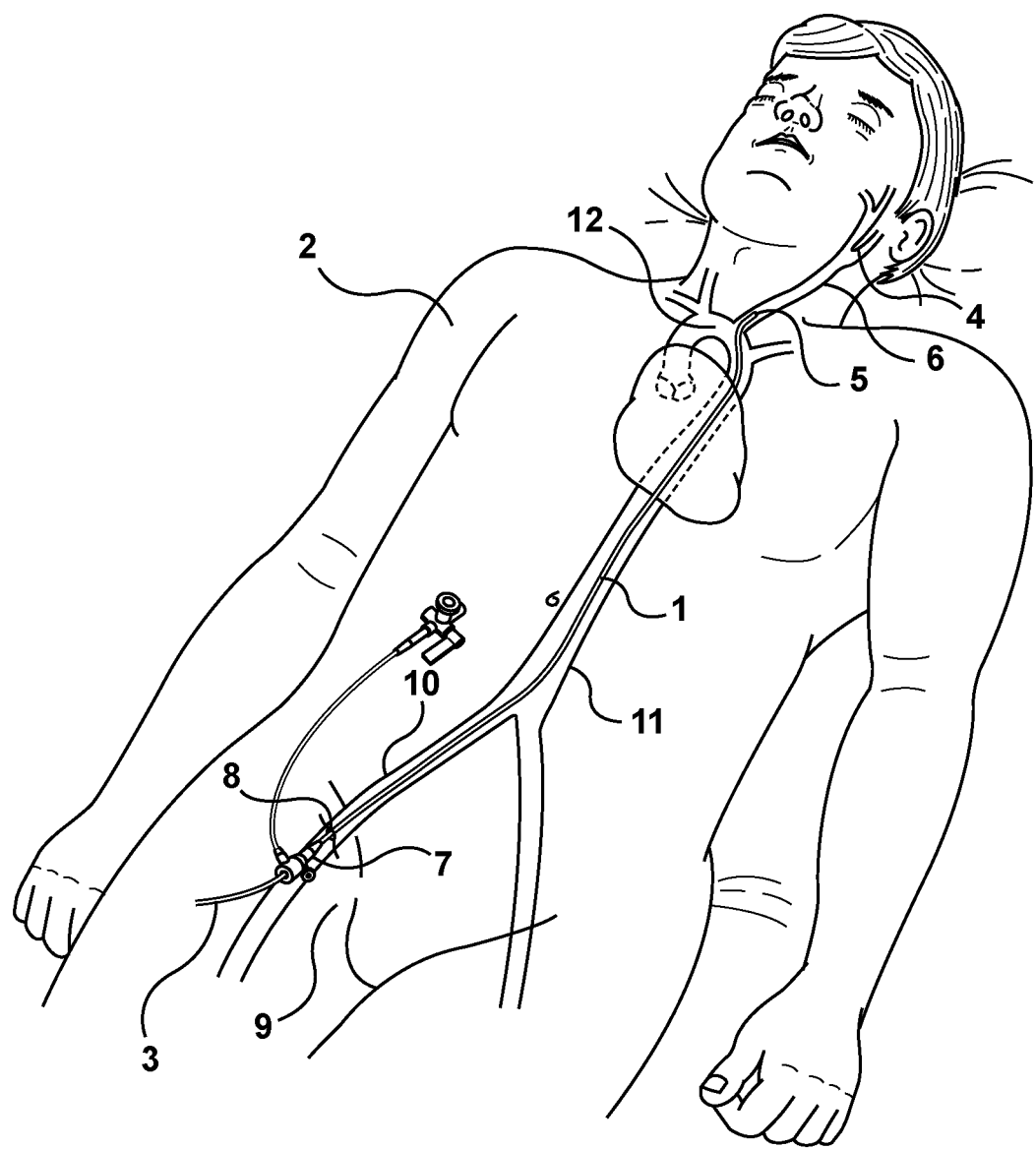
FIG. 1 is a schematic view showing endovascular access of a catheter to a left common carotid artery of a patient.

The present disclosure is directed generally to systems and methods for treating patients having a sympathetically mediated disease associated at least in part with augmented peripheral chemoreflex or heightened sympathetic activation. The treatments include ablating one or more peripheral chemoreceptors or associated afferent nerves to reduce or remove afferent neural signals from the peripheral chemoreceptor. When the disclosure indicates that the peripheral chemoreceptor is ablated, it may be referring to the chemoreceptor and/or the associated afferent nerves.

The carotid body is a small cluster of chemoreceptors (also known as glomus cells) and supporting cells located near, and in most cases directly at, the medial side of the bifurcation (fork) of the carotid artery, which runs along both sides of the throat.

These organs act as sensors detecting different chemical stimuli from arterial blood and triggering an action potential in the afferent fibers that communicate this information to the Central Nervous System ("CNS"). In response, the CNS activates reflexes that control heart rate (FIR), renal function and peripheral blood circulation to maintain the desired homeostasis of blood gases, $O_2$ and $CO_2$, and blood pH. This closed loop control function that involves blood gas chemoreceptors is known as the carotid body chemoreflex ("CBC"). The CBC is integrated in the CNS with the carotid sinus baroreflex (CSB) that maintains arterial blood pressure. In a healthy organism these two reflexes maintain blood pressure and blood gases within a narrow physiologic range. Chemosensors and barosensors in the aortic arch contribute redundancy and fine-tuning function to the closed loop chemoreflex and baroreflex. In addition to sensing blood gasses, the carotid body is now understood to be sensitive to blood flow and velocity, blood pH and glucose concentration. Thus it is understood that in conditions such as hypertension, congestive heart failure ("CHF"), insulin resistance, diabetes and other metabolic derangements, afferent signaling of carotid body nerves may be elevated. Carotid body hyperactivity may be present even in the absence of detectable hypersensitivity to hypoxia and hypercapnia that are traditionally used to index carotid body function.

Some exemplary methods of treatment include ablating one or both carotid bodies or associated afferent nerves via endovascular access to remove or reduce afferent neural signals from a carotid body and reduce carotid body contribution to central sympathetic tone. The disclosure herein focuses on ablating carotid bodies and associated afferent nerves, but it is not intended to be so limiting.

The expected reduction of chemoreflex activity and sensitivity to hypoxia and other stimuli such as blood flow, blood $CO_2$, glucose concentration or blood pH can directly reduce afferent signals from chemoreceptors and produce at least one beneficial effect such as the reduction of central sympathetic activation, reduction of the sensation of breathlessness (dyspnea), vasodilation, increase of exercise capacity, reduction of blood pressure, reduction of sodium and water retention, redistribution of blood volume to skeletal muscle, reduction of insulin resistance, reduction of hyperventilation, reduction of tachypnea, reduction of hypocapnia, increase of baroreflex and barosensitivity of baroreceptors, increase of vagal tone, or improve symptoms of a sympathetically mediated disease and may ultimately slow down the disease progression and extend life. It is understood that a sympathetically mediated disease that may be treated with carotid body ablation may comprise elevated sympathetic tone, an elevated sympathetic/parasympathetic activity ratio, autonomic imbalance primarily attributable to central sympathetic tone being abnormally or undesirably high, or heightened sympathetic tone at least partially attributable to afferent excitation traceable to hypersensitivity or hyperactivity of a peripheral chemoreceptor (e.g., carotid body). In some important clinical cases where baseline hypocapnia or tachypnea is present, reduction of hyperventilation and breathing rate may be expected. It is understood that hyperventilation in the context herein means respiration in excess of metabolic needs on the individual that generally leads to slight but significant hypocapnea (blood $CO_2$ partial pressure below normal of approximately 40 mmHg, for example in the range of 33 to 38 mmHg).

Sympathetically mediated diseases that can be treated using the devices, systems, and methods herein include, without limitation, cardiac, renal, metabolic, and pulmonary diseases such as, for example, hypertension, congestive heart failure ("CHF"), sleep apnea, sleep disordered breathing, diabetes or insulin resistance).

To inhibit or suppress a peripheral chemoreflex, anatomical targets for ablation (also referred to herein as targeted tissue, target ablation sites, target sites, or derivatives thereof) may include at least a portion of at least one carotid body, an aortic body, nerves associated with a peripheral chemoreceptor (e.g., carotid body nerves, carotid sinus nerve, carotid plexus), small blood vessels feeding a peripheral chemoreceptor, carotid body parenchyma, chemosensitive cells (e.g., glomus cells), tissue in a location where a carotid body is suspected to reside (e.g., based on preoperative imaging or anatomical likelihood), an intercarotid septum, a substantial part of an intercarotid septum, or any combination thereof.

As used herein, "interstitial space" includes, without limitation, an intercarotid septum, periarterial space, perivenous space, and extravascular space.

Figure 4:
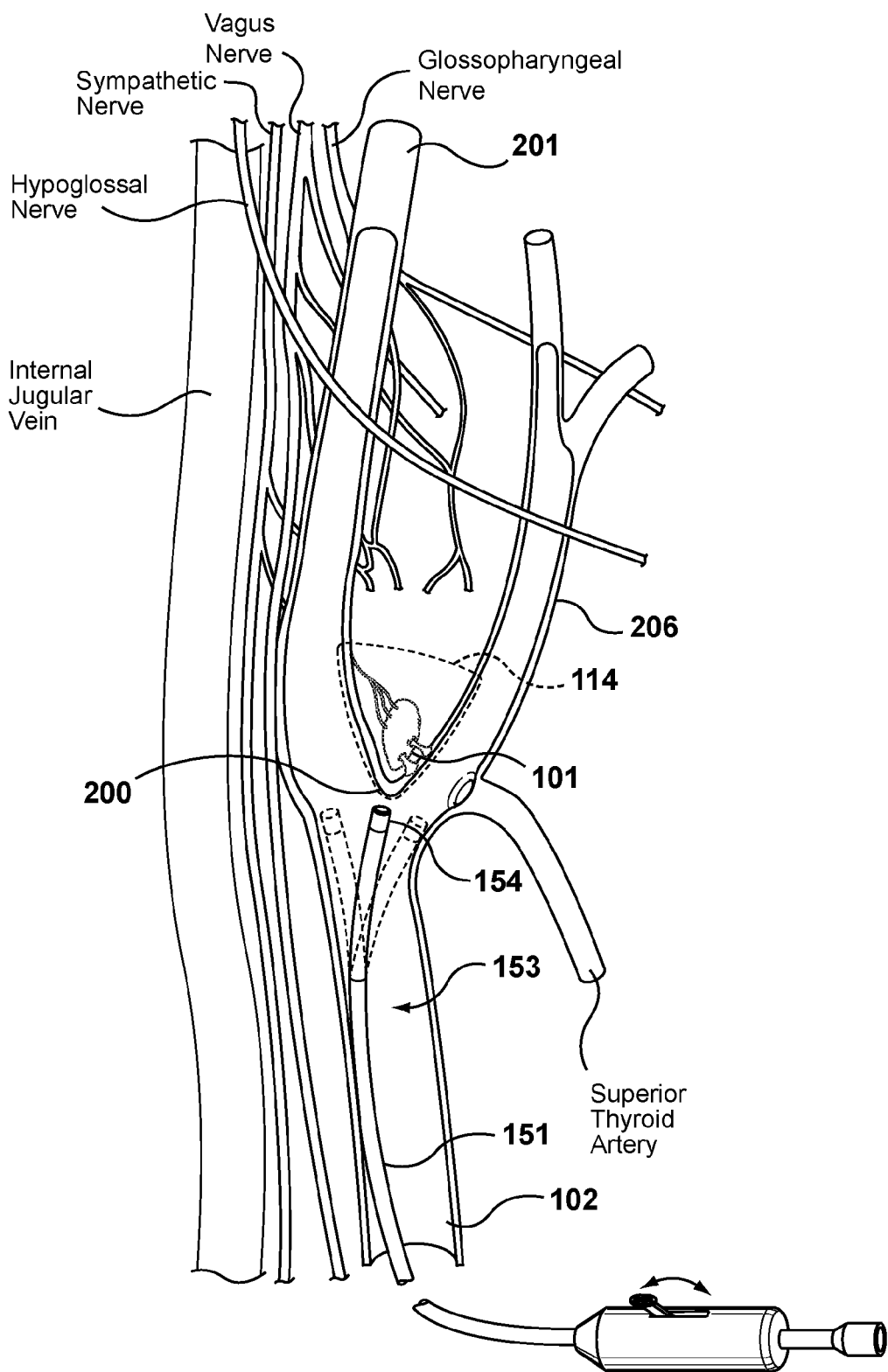
FIG. 4 is a cutaway illustration of a lateral view a patient's right carotid artery system with a schematic view of a steerable sheath positioning a distal region proximate a target penetration site.

An intercarotid septum (also referred to herein as a carotid septum) is a wedge or triangular segment of tissue with the following boundaries: 1) the saddle of the carotid bifurcation defines the caudal aspect (an apex) of the carotid septum; the facing walls of the internal and external carotid arteries define two of the sides of the carotid septum; a cranial boundary of the carotid septum extends between these arteries and is 10 mm-15 mm from the saddle of the carotid bifurcation; and the medial and lateral walls of the carotid septum are generally defined by two-dimensional planes tangent to the internal and external carotid arteries. One of the planes is tangent to the lateral wall of the internal and external carotid arteries and the other plane is tangent to the medial walls of these arteries. The carotid septum is between the medial and lateral walls. As shown in FIG. 4, an intercarotid septum 114 may contain a carotid body and may be absent of vital structures such as a vagus nerve or hypoglossal nerve. An intercarotid septum may additionally include some baroreceptors and baroreceptor nerves.

Carotid body nerves are anatomically defined herein as carotid plexus nerves and carotid sinus nerves. Carotid body nerves are functionally defined herein as nerves that conduct information from a carotid body to a central nervous system.

An ablation may be focused exclusively on targeted tissue, or be focused on the targeted tissue while safely ablating tissue proximate to the targeted tissue (e.g., to ensure the targeted tissue is ablated or as an approach to gain access to the targeted tissue). An ablation may be as big as the peripheral chemoreceptor (e.g., carotid body or aortic body) itself, somewhat smaller, or bigger and can include tissue surrounding the chemoreceptor such as, for example, blood vessels, adventitia, fascia, small blood vessels perfusing the chemoreceptor, or nerves connected to and innervating the glomus cells. An intercarotid plexus or carotid sinus nerve may be a target of ablation with an understanding that some baroreceptor nerves will be ablated together with carotid body nerves. Baroreceptors are distributed in the human arteries and have high degree of redundancy.

An embodiment of a therapy may substantially reduce chemoreflex without excessively reducing the baroreflex of the patient. The proposed ablation procedure may be targeted to substantially spare the carotid sinus, baroreceptors distributed in the walls of carotid arteries (specifically internal carotid artery), and at least some of the carotid sinus nerves that conduct signals from said baroreceptors. For example, the baroreflex may be substantially spared by targeting a limited volume of ablated tissue possibly enclosing the carotid body, tissues containing a substantial number of carotid body nerves, tissues located in periadventitial space of a medial segment of a carotid bifurcation, tissue located at the attachment of a carotid body to an artery, or extending to tissues located on the medial side of a carotid artery bifurcation saddle and avoiding damage to the lateral side. The carotid sinus baroreflex is accomplished by negative feedback systems incorporating pressure sensors (e.g., baroreceptors) that sense the arterial pressure. Baroreceptors also exist in other places, such as the aorta and coronary arteries. Important arterial baroreceptors are located in the carotid sinus, a slight dilatation of the internal carotid artery at its origin from the common carotid. The carotid sinus baroreceptors are close to but anatomically separate from the carotid body. Baroreceptors respond to stretching of the arterial wall and communicate blood pressure information to CNS. Baroreceptors are distributed in the arterial walls of the carotid sinus while the chemoreceptors (glomus cells) are clustered inside the carotid body. This makes the selective reduction of chemoreflex described in this application possible while substantially sparing the baroreflex. In the ablation therapies herein, however, sparing the baroreflex may not be a necessary feature of the therapy because the carotid baroreflex is quite forgiving and can return quickly if injured.

In some embodiments tissue may be ablated to inhibit or suppress a chemoreflex of only one of a patient's two carotid bodies. Other embodiments involve ablating tissue to inhibit or suppress a chemoreflex of both of a patient's carotid bodies. For example a therapeutic method may include ablation of one carotid body, measurement of resulting chemosensitivity, sympathetic activity, respiration or other parameter related to carotid body hyperactivity and ablation of the second carotid body if needed to further reduce chemosensitivity following unilateral ablation.

Said targeted ablation is enabled by visualization of the area or carotid body itself, for example by CT, CT angiography, MRI, ultrasound sonography, fluoroscopy, blood flow visualization, or injection of contrast, and positioning of an instrument in the carotid body or in close proximity while avoiding excessive damage (e.g., perforation, stenosis, thrombosis) to carotid arteries, baroreceptors or carotid sinus nerves. Thus imaging a carotid body before ablation may be instrumental in (a) selecting candidates if a carotid body is present, large enough and identified and (b) guiding therapy by providing a landmark map for an operator to guide an ablation instrument to carotid body nerves, the area of a blood vessel proximate to a carotid body, or to an area where carotid body nerves may be anticipated. It may also help exclude patients in whom the carotid body is located in a position close to a vagus nerve, hypoglossal nerve, jugular vein or some other structure that can be endangered by ablation. In one embodiment only patients with carotid body substantially located within the intercarotid septum are selected for ablation therapy.

Once a carotid body is ablated, removed or denervated, the carotid body chemoreflex does not substantially return in humans (in humans aortic chemoreceptors are considered undeveloped). To the contrary, once a carotid sinus baroreflex is removed it is generally compensated, after weeks or months, by the aortic baroreceptor baroreflex. Thus, if both the carotid chemoreflex and baroreflex are removed or substantially reduced, for example by interruption of the carotid sinus nerve or intercarotid plexus nerves, baroreflex may eventually be restored while the chemoreflex may not. The consequences of temporary removal or reduction of the baroreflex can be relatively severe and require hospitalization and management with drugs, but they generally are not life threatening, terminal or permanent. Thus, it is understood that while selective removal of carotid body chemoreflex with baroreflex preservation may be desired, it may not be absolutely necessary in some cases.

As used herein, "ablate," "ablation"," or "ablating" (generally referred to as "ablation") refers to an intervention that alters a tissue to suppress or inhibit its biological function or ability to respond to stimulation permanently or for an extended period of time, such as greater than 3 weeks, greater than 6 months, greater than a year, for several years, or for the remainder of the patient's life. In some embodiments ablation refers to an intervention that is intended to permanently suppress or inhibit natural chemoreceptor or afferent nerve functioning. Ablation is used herein in contrast to neuromodulation, which reversibly deactivates and reactivates chemoreceptor functioning. Ablation may involve, but is not limited to, thermal necrosis (e.g., using energy such as thermal energy, radiofrequency electrical current, direct current, microwave, ultrasound, high intensity focused ultrasound, and laser), cryogenic ablation, electroporation, selective denervation, embolization (e.g., occlusion of blood vessels feeding the gland), artificial sclerosing of blood vessels, mechanical impingement or crushing, surgical removal, chemical ablation, or application of radiation causing controlled necrosis (e.g., brachytherapy). Selective denervation may involve, for example, interruption of afferent nerves from a carotid body while preserving nerves from a carotid sinus, which conduct baroreceptor signals. Another example of selective denervation may involve interruption of a carotid sinus nerve, or intercarotid plexus which is in communication with both a carotid body and baroreceptors wherein chemoreflex from the carotid body is reduced permanently or for an extended period of time and baroreflex is substantially restored.

Carotid Body Ablation ("CBA") herein refers to ablation of a target tissue wherein the desired effect is to reduce or remove the afferent neural signaling from a chemosensor (e.g., a carotid body) or reducing a chemoreflex. Chemoreflex or afferent nerve activity cannot be directly measured in a practical way, thus indexes of chemoreflex such as chemosensitivity can sometimes be uses instead. Chemoreflex reduction is generally indicated by a reduction of an increase of ventilation and ventilation effort per unit of blood gas change or by a reduction of central sympathetic nerve activity that can be measured indirectly. Sympathetic nerve activity can be assessed by measuring activity of peripheral nerves leading to muscles (MSNA), heart rate (HR), heart rate variability (HRV), production of hormones such as renin, epinephrine and angiotensin, and peripheral vascular resistance. All these parameters are measurable and can lead directly to the health improvements. In the case of CHF patients, blood pH, blood $PCO_2$, degree of hyperventilation and metabolic exercise test parameters such as peak $VO_2$, and $VE/VCO_2$ slope are equally important. It is believed that patients with heightened chemoreflex have low $VO_2$ and high $VE/VCO_2$ slope (index of respiratory efficiency) as a result of tachypnea and low blood $CO_2$. These parameters are also firmly related exercise limitations that further speed up patient's status deterioration towards morbidity and death. It is understood that all these indexes are indirect and imperfect and intended to direct therapy to patients that are most likely to benefit or to acquire an indication of technical success of ablation rather than to provide an exact measurement of effect or guarantee a success.

CBA may include methods and systems for the thermal ablation of tissue via thermal heating or cooling mechanisms. Thermal ablation may be achieved due to a direct effect on tissues and structures that are induced by the thermal stress. Additionally or alternatively, the thermal disruption may at least in part be due to alteration of vascular or peri-vascular structures (e.g., arteries, arterioles, capillaries or veins), which perfuse the carotid body and neural fibers surrounding the carotid body (e.g., nerves that transmit afferent information from carotid body chemoreceptors to the brain). Additionally or alternatively thermal disruption may be due to a healing process, fibrosis, or scarring of tissue following thermal injury, particularly when prevention of regrowth and regeneration of active tissue is desired. As used herein, thermal mechanisms for ablation may include both thermal necrosis or thermal injury or damage (e.g., via sustained heating, convective heating or resistive heating or combination). Thermal heating mechanisms may include raising the temperature of target neural fibers above a desired threshold, for example, above a body temperature of about 37° C. e.g., to achieve thermal injury or damage, or above a temperature of about 45° C. (e.g., above about 60° C.) to achieve thermal necrosis. Thermal-cooling mechanisms for ablation may include reducing the temperature of target neural fibers below a desired threshold (e.g., to achieve freezing thermal injury). It is generally accepted that temperatures below −40° C. applied over a minute or two results in irreversible necrosis of tissue and scar formation. It is recognized that tissue ablation by cold involves mechanisms of necrosis and apoptosis. At a low cooling rate freeze, tissue is destroyed by cellular dehydration and at high cooling rate freeze by intracellular ice formation and lethal rupture of plasma membrane.

In addition to raising or lowering temperature during thermal ablation, a length of exposure to thermal stimuli may be specified to affect an extent or degree of efficacy of the thermal ablation. For example, the length of exposure to thermal stimuli may be for example, longer than or equal to about 30 seconds, or even longer than or equal to about 2 minutes. Furthermore, the length of exposure can be less than or equal to about 10 minutes, though this should not be construed as the upper limit of the exposure period. A temperature threshold, or thermal dosage, may be determined as a function of the duration of exposure to thermal stimuli. Additionally or alternatively, the length of exposure may be determined as a function of the desired temperature threshold. These and other parameters may be specified or calculated to achieve and control desired thermal ablation.

In some embodiments, thermally-induced ablation of carotid body or carotid body nerves may be achieved via direct application of thermal cooling or heating energy to the target tissue. For example, a chilled or heated fluid can be applied at least proximate to the target, or heated or cooled elements (e.g., thermoelectric element, resistive heating element, cryogenic tip or balloon) can be placed in the vicinity of a chemosensor (e.g., carotid body). In other embodiments, thermally-induced ablation may be achieved via indirect generation or application of thermal energy to the target neural fibers, such as through application of an electric field (e.g., radiofrequency, alternating current, and direct current), high-intensity focused ultrasound (HIFU), laser irradiation, or microwave radiation, to the target neural fibers. For example, thermally induced ablation may be achieved via delivery of a pulsed or continuous thermal electric field to the target tissue such as RF and pulsed RF, the electric field being of sufficient magnitude or duration to thermally induce ablation of the target tissue (e.g., to heat or thermally ablate or cause necrosis of the targeted tissue). Additional and alternative methods and apparatuses may be utilized to achieve thermally induced ablation, as described hereinafter.

An ablated tissue lesion at or near the carotid body may be created by the application of thermal energy from an energy delivery element proximate to the distal end of the carotid body ablation device. The ablated tissue lesion may disable the carotid body or may suppress the activity of the carotid body or interrupt conduction of afferent nerve signals from a carotid body to sympathetic nervous system. The disabling or suppression of the carotid body reduces the responsiveness of the glomus cells to changes of blood gas composition and effectively reduces the chemoreflex gain of the patient.

Endovascular Access:

The disclosure herein includes positioning an ablation catheter in position within a patient's vasculature. An endovascular catheter for carotid body ablation may be delivered into a patient's vasculature via percutaneous introduction into a blood vessel, for example a femoral, radial, brachial artery or vein, or even via a cervical approach into a carotid artery. FIG. 1 illustrates an exemplary placement of a carotid access sheath 1 into a patient 2 via femoral artery percutaneous access. Sheath 1 is depicted in position for insertion of an endovascular ablation catheter 3 into the vicinity of the patient's left carotid artery bifurcation 4 through central lumen 41 of carotid access sheath 1. The distal end 5 of sheath 1 is shown residing in the patient's left common carotid artery 6. The proximal end 7 of sheath 1 is shown residing outside of the patient 2, with the sheath's entry point into the patient 8 being in the vicinity of the groin 9. From the sheath's entry point 8, the sheath enters a peripheral artery 10 (in this embodiment a femoral artery), and traverses the abdominal aorta 11, the aortic arch 12, and into the left common carotid artery 6. The carotid access sheath 1 may be commercially available, or may be configured specifically for endovascular transmural ablation of a carotid body. Techniques for placing a carotid access sheath 1 into the position as depicted are known. An endovascular procedure may also involve the use of a guide wire, delivery sheath, guide catheter, introducer catheter, or introducer. Furthermore, these devices may be steerable and torquable (i.e., able to conduct rotation from proximal to distal end).

Steerable sheath 150, as shown in FIG. 2 may be used to facilitate an endovascular carotid body ablation procedure. The steerable sheath 150 may comprise an elongate tube 151 with a lumen 152 and a distal region 153 that is controllably deflectable or deformable, as shown in FIG. 3. Deflection of a distal region (e.g., bending on a plane, deforming into a helical configuration, selective bending toward multiple directions, or other configurations deviating from a substantially linear configuration) may be controlled by a user-actuated mechanism 154 at a proximal region of the steerable sheath (e.g., a lever on a handle). A steerable sheath may facilitate navigation through tortuous vessels or branching vessels by allowing a user to direct the distal region toward a desired vessel branch or along a vessel's tortuous path. Once the sheath is navigated to a target region a steerable sheath may be used to introduce instruments to the vicinity of the target region (e.g., the carotid bifurcation) to facilitate carotid body ablation, as shown in FIG. 4. Controlled deflection of the distal region may allow a user to position said instruments at a precise target location (e.g., inner surface of a vessel wall at a carotid bifurcation, internal carotid artery, or external carotid artery). Multiple instruments may be delivered through a steerable sheath simultaneously. For example, a distal protection catheter may first be positioned in an internal carotid artery via delivery through a steerable sheath, and the sheath may be retracted to a carotid bifurcation to deliver an ablation catheter while containing a shaft of the distal protection catheter. Multiple instruments may be delivered consecutively while the steerable sheath maintains position of the distal tip.

A steerable sheath may comprise a temperature sensor (e.g., thermocouple, thermistor, microwave or fluoroptic sensor) on an outer surface intended to be in contact with tissue of a distal region that can measure and control ablation temperature created by an ablation catheter delivered through a steerable catheter. In another embodiment a steerable catheter may comprise an electrode configured to measure impedance, which may be used to monitor ablation formation or detect tissue contact, tissue composition, presence of plaque, or position with relatively least amount of plaque to assist in locating a suitable position to create an ablation. Impedance is measures by passing low non-excitatory level of alternating current through tissue and measuring current and voltage. In another embodiment a steerable sheath may provide electrical nerve stimulation or blockade via an electrode positioned at a distal region of the steerable sheath. Evidence of proximity to certain nerve structures (e.g., chemoreceptors, baroreceptors, vagus nerve, hypoglossal nerve) may be provided if stimulation current is delivered and a concomitant physiological response is elicited. A steerable sheath 150 may have an outer diameter of about 8 F to 10 F and a length of about 120 cm to 140 cm and may be made from commonly used catheter materials such as polyurethane or Pebax. The sheath may be made of layers of different materials with desired properties (strength, lubriciousness) for jacket and liner (e.g., PTFE, FEP, PE, PEBA, Polyurethane, Nylon, customized engineering polymers.)

The sheath may optionally have braided reinforcement (e.g., Stainless Steel, Polyester, Nylon, Nitinol) to improve torque transmission while maintaining flexibility. The sheath may comprise a lumen (e.g., about 6 F to 9 F diameter) to accommodate an ablation catheter and a lumen containing a control wire used to apply a force to deflect the distal region. A distal deflectable region of the steerable sheath may be about 3 cm to 6 cm long. The distal deflectable region may comprise a deflectable structure, such as a laser cut stainless steel or Nitinol tube that is biased to bend in a desired direction when a compressive force is applied by the control wire. A distal tip 154 of a steerable sheath may be configured to provide atraumatic contact with vasculature as it is passed through. For example, the distal tip may have a rounded surface. The distal tip may further comprise an anchor for a control wire, a stimulation electrode, or a sensor (e.g., temperature sensor, impedance sensor). A distal tip may have about the same diameter of the shaft (e.g., 8 F-10 F) and a length suitable to carry its components. For example, a distal tip may be between or including about 1 mm to 10 mm long. The distal tip may be constructed from stainless steel. The distal tip may have an atraumatic rim or extension made of softer material. For embodiments having sensors a distal tip may further comprise a dielectric coating such as ceramic partially covering the stainless steel such that the sensor is exposed to a desired side of the steerable sheath, for example on the side that the sheath deflects towards, or at the distal face of the sheath. A dielectric coating may further provide abrasion resistance so it slides easily through vasculature and reduces a risk of dislodging atheromatous plaque. A control wire may be anchored (e.g., welded, soldered, bonded) distal to a deflectable structure, for example it may be anchored to a distal tip 154 or a distal portion of the deflectable structure 153 itself or a separate anchor. A control wire may be made from stainless steel or other high strength wire and it may continue through a shaft 151 to a proximal region 155 of a steerable sheath where it may be connected to an actuator 154 (e.g., lever) on a handle. When a user actuates the actuator the control wire is pulled creating a compressive force to the deflectable structure, which deflects to a compressibly biased direction. Optionally, a control wire that is electrically conductive may also be used to conduct electrical current for impedance measurement, or sensor input. A proximal region 155 of a steerable sheath may comprise an electrical connector 156 to connect conductors in a steerable sheath to a connector cable or to an electrical source (e.g., RF generator). A proximal region of a steerable sheath may also have a proximal exit port 157 of a lumen 152 which may terminate with a fitting such as a Touhy Borst fitting or luer fitting.

One aspect of the disclosure is a method of ablating target tissue within a carotid septum of a patient. In some embodiments of this aspect ablating the target tissue includes performing an endovascular interstitial carotid body ablation. Interstitial carotid body ablation includes advancing an ablation element through a wall of a carotid artery and proximate target tissue in the carotid septum, and delivering an ablation agent from the ablation element to the target tissue. An exemplary interstitial ablation method includes inserting a catheter in the patient's vascular system, positioning a distal region of the catheter in a vessel proximate a carotid body (e.g., in a common carotid artery, internal carotid artery, external carotid artery, or at a carotid bifurcation), advancing an ablation element from the distal region of the catheter through a wall of the carotid vessel, positioning the ablation element proximate to a target site (e.g., a carotid body, an afferent nerve associated with a carotid body, or a peripheral chemosensor), and delivering an ablation agent from the ablation element to ablate the target site. In interstitial carotid body ablation the ablation element resides within the intercarotid septum at the time of ablation.

Figures 5A, 5B:
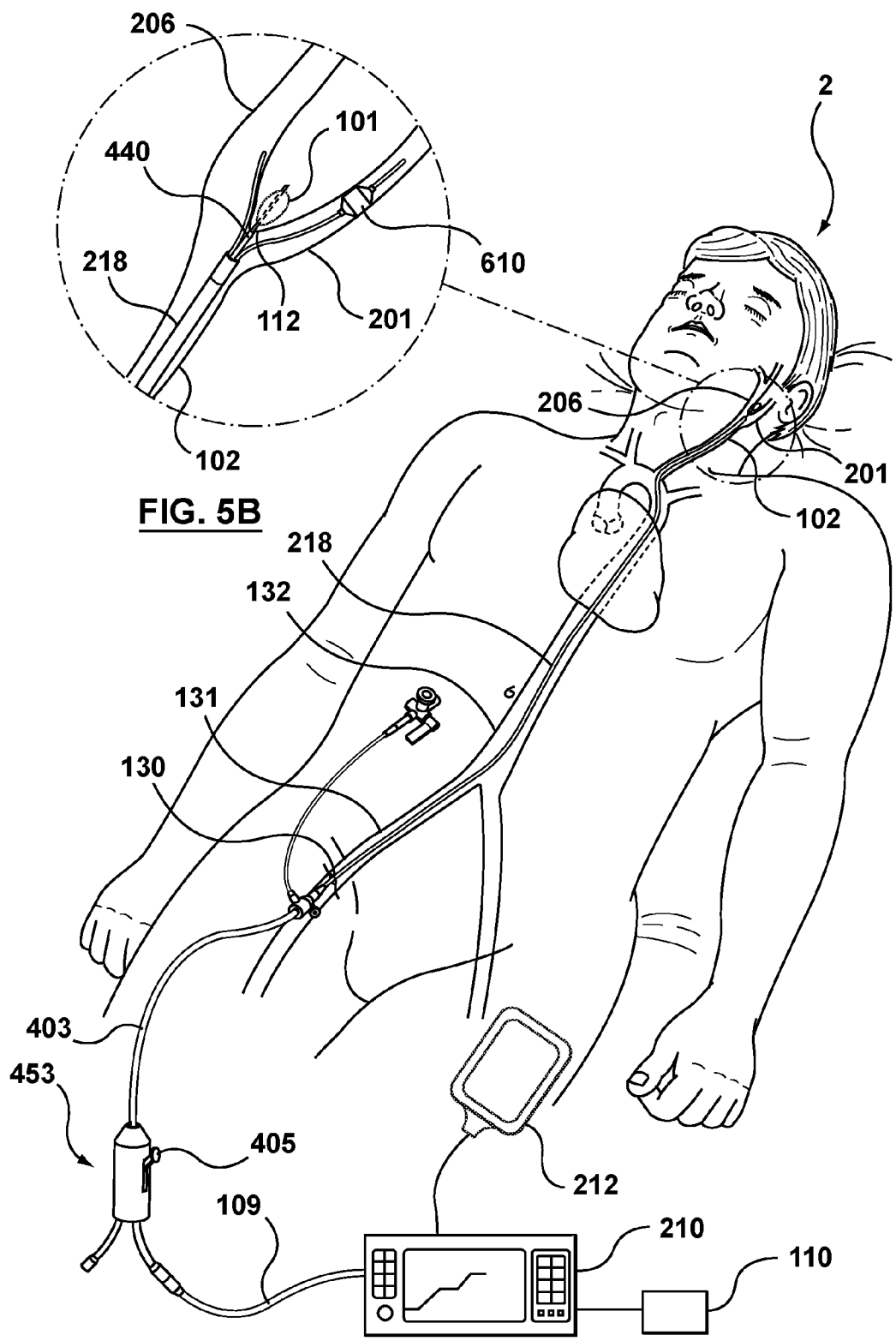
FIGS. 5A and 5B are schematic views showing endovascular access of a catheter to a left common carotid artery of a patient.

FIGS. 5A and 5B illustrate an exemplary method of endovascular interstitial carotid body ablation. Exemplary endovascular catheter 403 is used to deliver ablation element 440 across a vessel wall 112 to affect target tissue in interstitial space (e.g., intercarotid septum, periarterial space, extravascular space) as shown in FIGS. 5A and 5B. The ablation element can be, for example without limitation, a radiofrequency electrode, a laser fiber, a microwave antenna, an ultrasound transducer, a cryoablation element, an electroporation electrode, or a fluid delivery needle. The ablation element may be made from radiopaque material or comprise a radiopaque marker and when deployed through a vessel wall it may be visualized using fluoroscopy to confirm position. Alternatively, a contrast solution may be injected through a lumen in the ablation element to verify position in a target tissue. The ablation element may have a sharp tip capable of piercing the elastic and strong tissue of an arterial wall or even a calcified arterial wall.

Interstitial RF Ablation Electrode:

In some embodiments an endovascular catheter adapted for interstitial carotid body ablation ("CBA") comprises an ablation element in the form of a radiofrequency ("RF") ablation electrode. The RF ablation electrode may be in the form of a needle with a sharp tip that pierces through tissue. In some embodiments the electrode is delivered through a vessel wall through a separate sharp delivery needle. The ablation electrode can also be configured for RF perforation of tissue as well as RF ablation.

RF is a rapidly alternating current that ablates tissue by generating heat in the tissue through ionic agitation, which is typically proportional to current density. Other factors that influence temperature generated in tissue include heat sinks (e.g., thermal convection due to blood flow) and tissue impedance. The volume of heated tissue is dependent on factors such as electrode size, electrode shape, RF power, duration of RF delivery, and waveform characteristics such as pulsing. In an embodiment shown in FIGS. 5A and 5B, carotid body ablation catheter 403 is connected by wires 109 to RF energy generator 210. Generator 210 may include computer controller 110 that controls the application of energy to electrode 440. Reference electrode 212 is placed on the surface of the body of patient 2. Reference electrode 212 establishes a current return path to RF generator 210 for current flowing from electrode 440, through the body of the patient and to reference electrode 212. The arrangement in which current flows through reference electrode 212 and active electrode 440 is generally referred to as a monopolar arrangement. Reference electrode 212 has a relatively large surface area to minimize current density and avoid skin burns.

An energy field generator 210 may be located external to the patient. Various types of energy generators or supplies, such as electrical frequency generators, ultrasonic generators, microwave generators, laser consoles, and heating or cryogenic fluid supplies, may be used to provide energy to the energy delivery element at the distal tip of the catheter. An electrode or other energy applicator at the distal tip of the catheter should conform to the type of energy generator coupled to the catheter. The generator may include computer controls to automatically or manually adjust frequency and strength of the energy applied to the catheter, timing and period during which energy is applied, and safety limits to the application of energy. It should be understood that embodiments of energy delivery electrodes described hereinafter may be electrically connected to the generator even though the generator is not explicitly shown or described with each embodiment.

Figure 7:
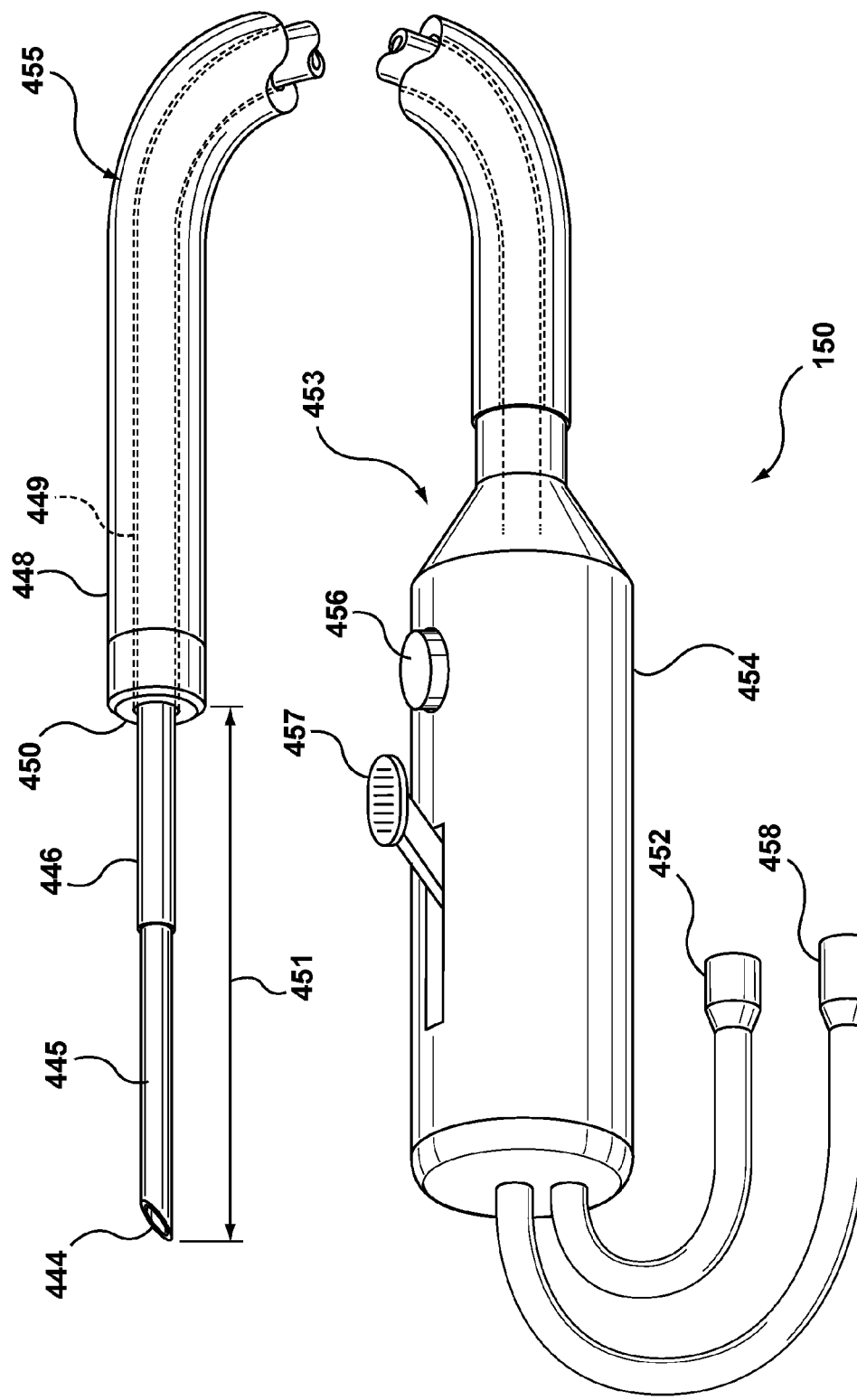
FIG. 7 is a schematic view of an endovascular catheter having a radiofrequency electrode needle.

FIG. 6 illustrates RF electrode needle 441, which may be made from an electrically conductive material (e.g., stainless steel, gold, platinum-iridium, Nitinol) and may be constructed from a hypotube with a sharpened needle point 444 (see FIG. 7). The sharp point 444 of needle 441 may be of a shape that creates a puncture in tissue by piercing and spreading rather than coring or cutting of tissue (e.g., cone-shape, trocar, pencil point), which may facilitate closure of the puncture after needle retraction. The RF needle caliber may be between and including about 18 gauge to 28 gauge (e.g., having an outer diameter between and including about 1.270 mm and 0.362 mm). In one embodiment, a RF electrode is an exposed portion on a distal end of hypotube 445 that extends about a length of a catheter and the unexposed region of the hypotube is electrically insulated with a dielectric material 446 (e.g., polymer, PET, PEEK, Teflon). The RF electrode needle 441 may have an exposed length of between or including about 2 mm to 10 mm (e.g., about 5 mm). A temperature sensor (e.g., thermocouple, thermistor, fluoroptic thermometry sensor) may be located in, near, or at the surface of the RF electrode 441. FIG. 6 is an exploded view of a RF electrode needle showing thermocouple 214 connected to two conductors 215 and 216. The conductors extend through the catheter body (e.g., through a lumen in hypotube 445) from the distal to proximal end and are connected to wires 109 (see FIG. 5A) allowing the thermocouple to communicate with RF generator 210. Conductors 215 and 216 may be, for example a copper and constantan conductor, respectively, such that joining conductors 215 and 216 via solder, laser welding or the like creates a thermocouple junction. Copper conductor 215 may be used to carry both a thermocouple signal and deliver RF energy to the electrode 441. Alternatively, a separate conductor (not shown) may deliver RF energy to the electrode. The temperature sensor can be thermally insulated (e.g., surrounded or imbedded in plastic) from the electrode in order to better reflect temperature of tissue where it is in contact with tissue.

Alternatively, two electrodes may be arranged at or near the distal tip of a carotid body ablation catheter such that current flows from an active electrode to a return electrode to create an energy field, (e.g., an electric field) in the region adjacent the electrodes and that ablates tissue. Such an arrangement is generally referred to as a bipolar configuration. Active and return electrodes may be located on the interstitial ablation element so they are both inserted into a target site. For example, the electrodes may be about the same size and shape and be distanced between about 0.5 mm and 4 mm apart from one another. Alternatively, the electrodes may be different sizes so current density is greater around the smaller electrode creating a greater thermal effect. In a bipolar arrangement a reference electrode (e.g., the reference electrode 212 shown in FIG. 5A) is not required. The bipolar configuration has certain advantages in shaping and directing and containing the lesion and RF energy is concentrated in a region around or between the two electrodes. In the bipolar configuration the reference electrode can be incorporated into the design of the needle 441, catheter, sheath, or guide wire.

In another embodiment a return path for RF energy may be provided by a return electrode that is positioned within a vessel. For example, the return electrode may be on a distal region of an endovascular catheter such as on a deployable structure in contact with an inner surface of a vessel lumen, or the return electrode may be on a distal region of a delivery sheath. The return electrode may be similar in size to the active interstitial electrode so that a bipolar RF ablation is created. Alternatively, the return electrode may be substantially larger than the active interstitial electrode so current density is dispersed and a monopolar RF ablation is created only at the active electrode. Formation of an ablation may be controlled and shaped by position of a reference electrode even if high current density is present only at one electrode (e.g., interstitial electrode).

A RF ablation electrode may additionally be configured to provide cooled RF energy delivery. For example, a catheter may contain a lumen in fluid communication with an RF electrode to irrigate a cooling fluid (e.g., room temperature or chilled saline) to the RF electrode. The cooling fluid may exit the RF electrode through irrigation ports. Alternatively, cooling fluid may be circulated through a cavity or lumen in a cooled RF electrode and then circulate back through a lumen in the catheter shaft to be deposited elsewhere in the patient's vasculature or outside the body. A cooled RF system may additionally comprise a cooling fluid source and pump. The benefit of cooling a RF electrode may be reduction of the risk of heating blood, which may create a clot or emboli. Furthermore, cooled RF may produce ablations deeper in the tissue or may heat the contact layers of the tissue less.

Figure 8:
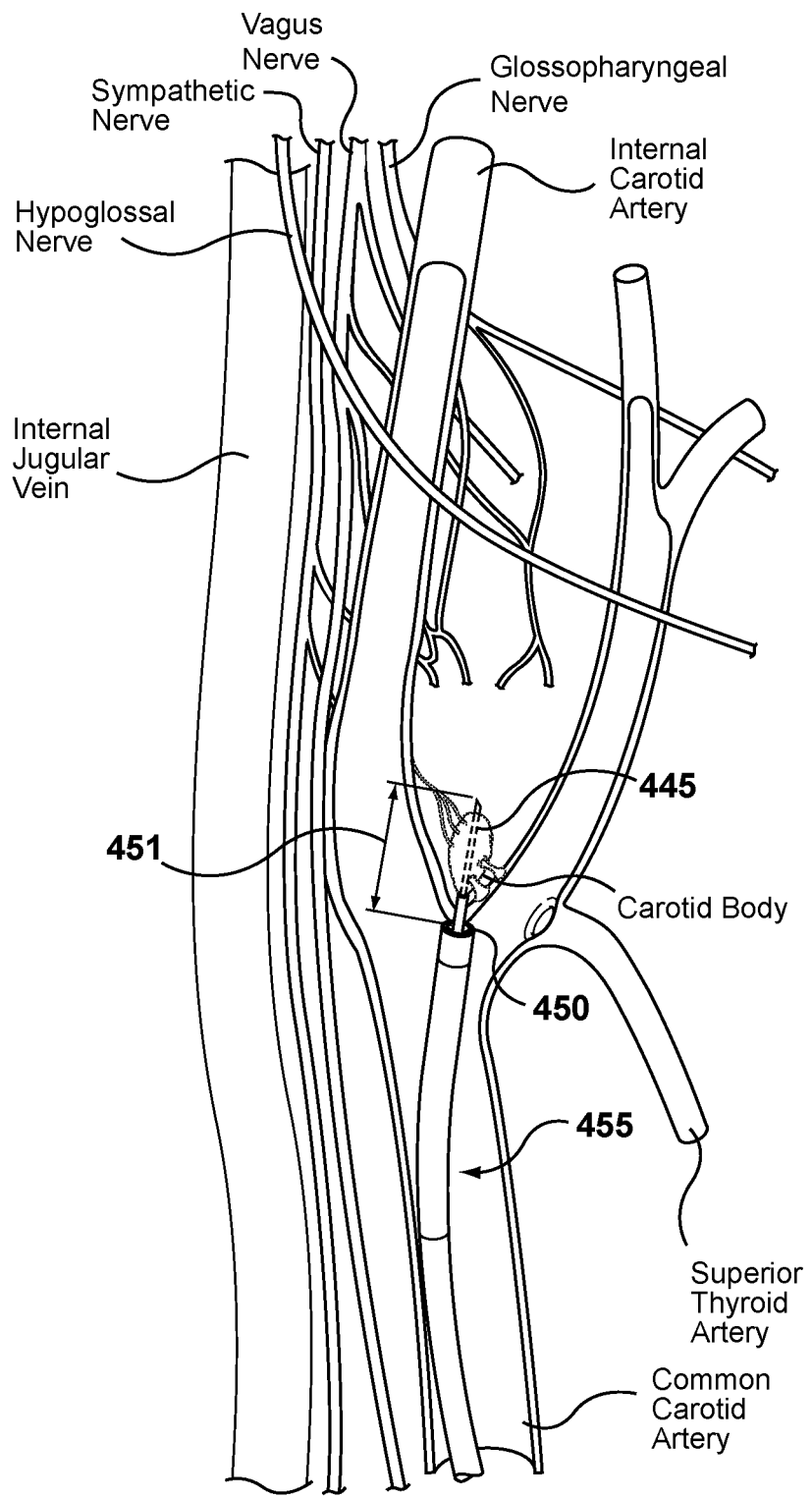
FIG. 8 is a cutaway illustration of a lateral view a patient's right carotid artery system with a schematic view of an endovascular catheter having a radiofrequency electrode needle inserted into a target site.

FIG. 7 illustrates an exemplary endovascular catheter for interstitial CBA, with the needle 445 shown in a deployed configuration. The catheter includes sheath 448. While the endovascular catheter is advanced into placement at a region of needle deployment (e.g., near a carotid bifurcation) ablation element needle 445 is positioned inside sheath 448, which protects the needle, as well as vascular structures and a user. Once the sheath 448 is in the target position, a user deploys the ablation element needle from sheath 448 and into the artery wall using a needle deployment mechanism. Sheath 448 may have a lumen 449 for containing the needle that is about 0.004" to 0.010" larger than the outer diameter of insulation 446. Sheath 448 may have a wall thickness of about 0.004" to 0.030". Sheath 448 may be constructed from a polymer with a lubricious liner (e.g., PTFE) on the inner lumen surface and outer surface to facilitate delivery through a vessel or a delivery sheath, and to facilitate movement of the ablation element within the lumen 449. Sheath 448 may further comprise a stainless steel wire coil or braid in its wall for additional strength. FIG. 8 illustrates the catheter shown in FIG. 7 in an exemplary method of CBA. As shown in FIG. 8, the catheter may be configured such that the interstitial RF ablation electrode 445, when deployed, has an extension length 451 beyond a distal tip 450 of the sheath a distance sufficient to reach a target site. For example, a catheter used to deliver an interstitial ablation element through a carotid bifurcation to a carotid body, as labeled, may have an extension length 451 between and including about 2 mm to 15 mm (e.g., about 10 mm).

A proximal region 453 (see FIG. 7) of the endovascular catheter for interstitial ablation may comprise a handle 454. Optionally, handle 454 may have a needle deployment mechanism that is actuated by trigger 456 and can be spring loaded. Once the distal tip 450 of the sheath is positioned and stabilized in a desired location (e.g., at a carotid bifurcation) and confirmed visually with fluoroscopy a user may actuate the trigger 456 releasing the spring-loaded deployment mechanism which thrusts the ablation element needle 445 from the sheath and through tissue to a target site. The trigger may further comprise a safety means (e.g., a cover or safety latch) so the trigger is not accidentally actuated. Alternatively a needle may be deployed by an operator by manually pushing a proximal end of a needle hypotube, pulling a control wire, or applying hydraulic pressure. Optionally, a handle may further comprise a deflection actuator 457 connected to a pull wire that deflects a deflectable region at a distal end of a catheter. Deflection may facilitate positioning of the distal tip 450 at a desired location. Optionally, a handle 454 may comprise a fluid injection port 452 in communication with the lumen 449. The fluid injection port may be used for injecting contrast from the distal opening of the lumen 449 into a vessel so the catheter's position on the vessel can be seen on fluoroscopy. The handle 454 may further comprise an electrical connector 458 to connect the RF ablation electrode 445 and temperature sensor 214 to an RF generator 210 (see FIG. 5A). An electrical connector 458 may also be used to connect a chemosensor electrical stimulation/blockage electrode to a signal generator.

Figure 9:
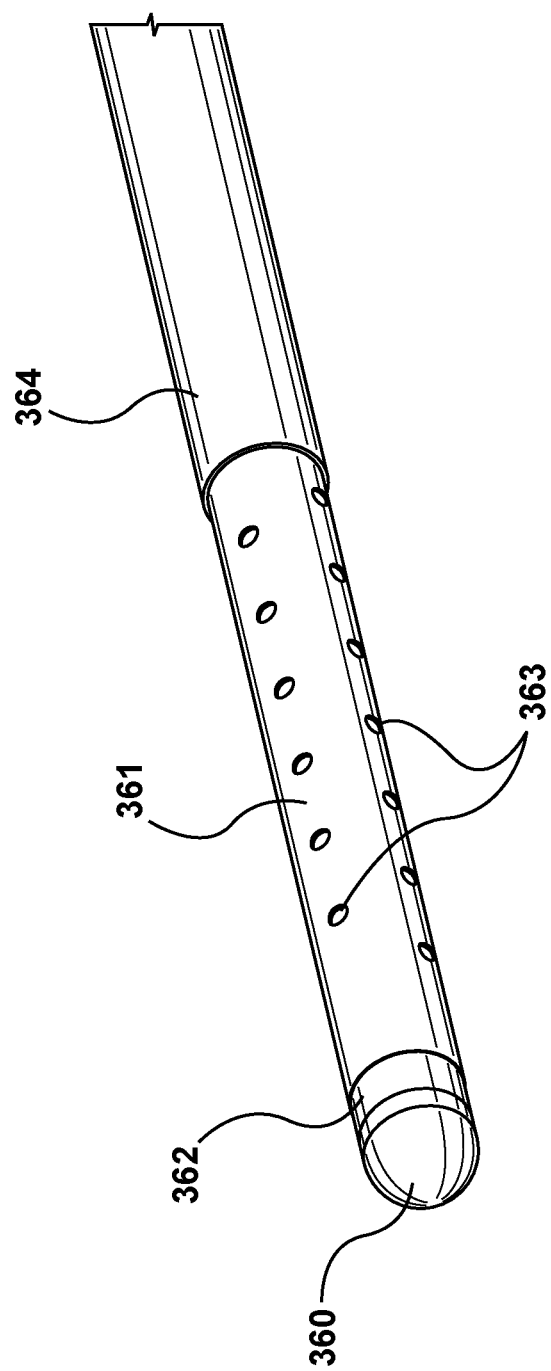
FIG. 9 is a schematic view of an interstitial RF perforation, ablation and sealing device.
Figure 10:
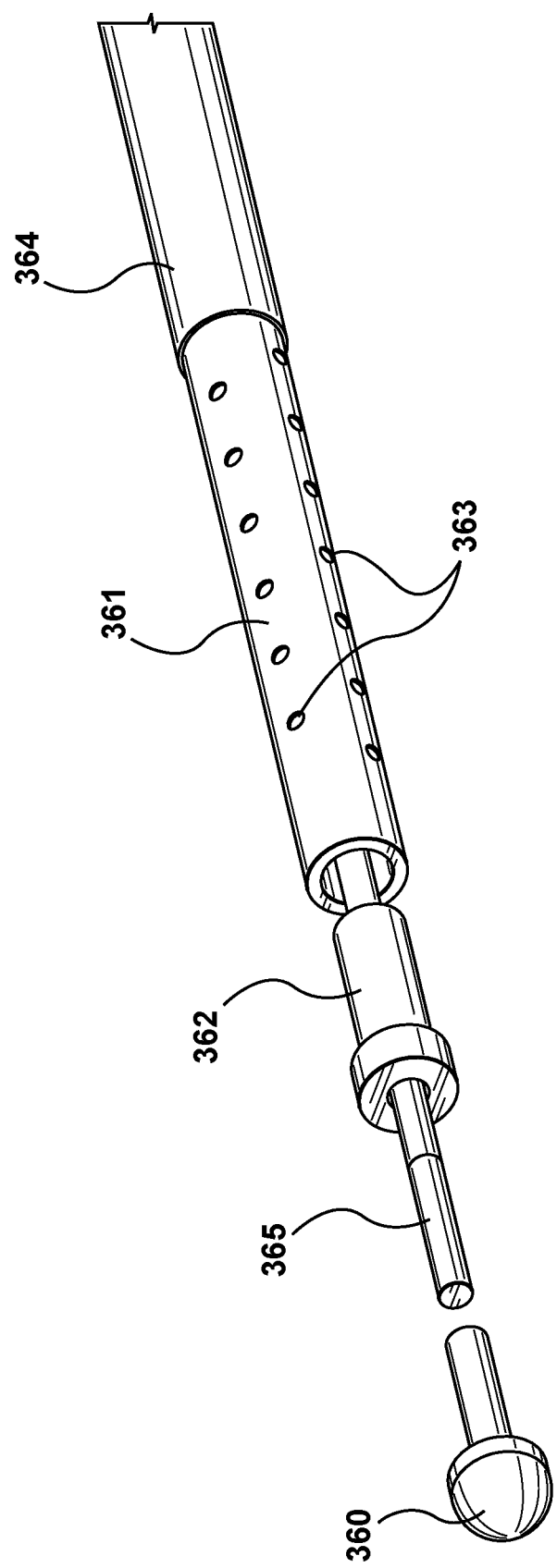
FIG. 10 is an exploded view of an interstitial RF perforation, ablation and sealing device.
Figure 11:
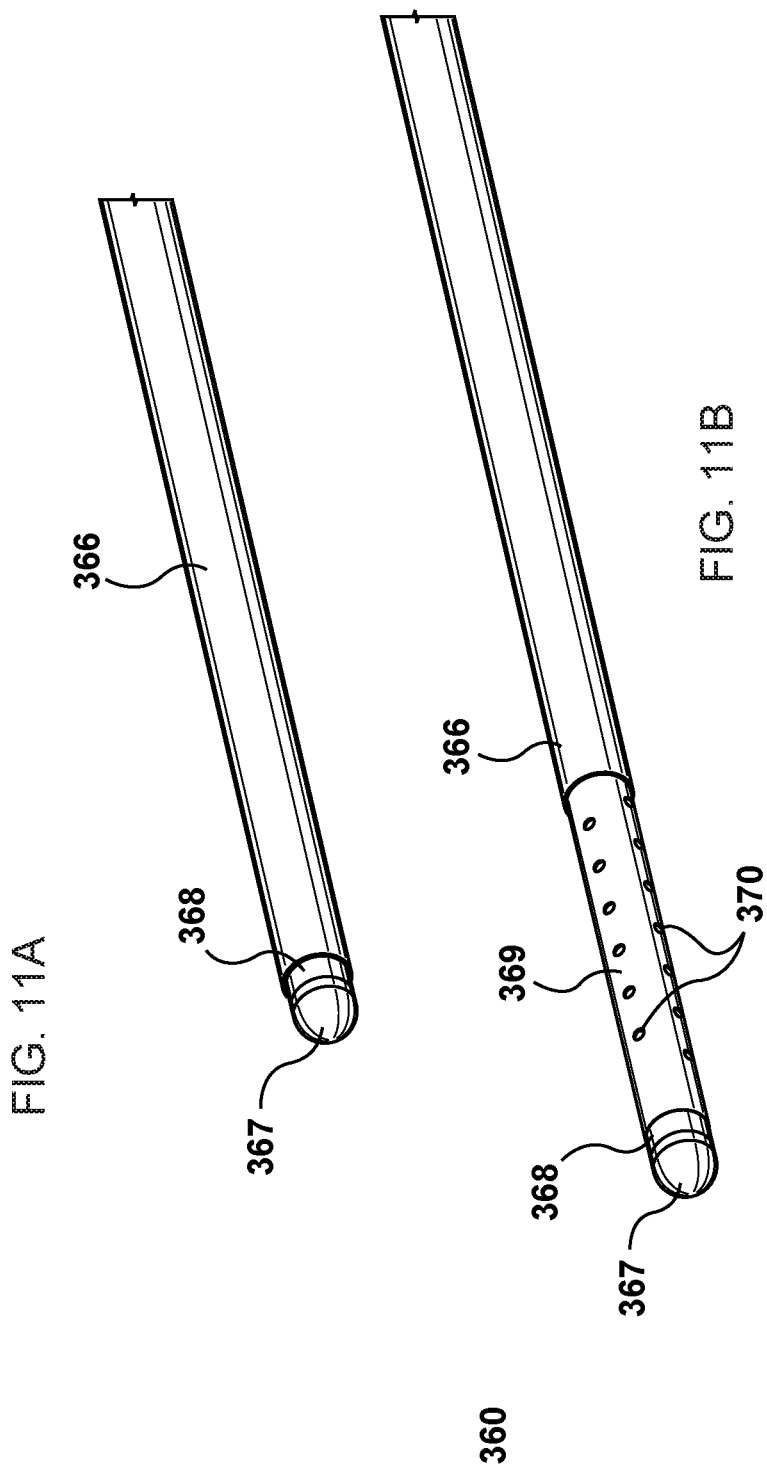
FIGS. 11A and 11B are schematic views of an interstitial RF perforation, ablation and sealing device.

Interstitial RF Perforation, Ablation and Sealing Electrode:

FIGS. 9, 10, and 11 illustrate an exemplary embodiment of an interstitial RF ablation electrode that is configured for radiofrequency perforation to perforate a vessel wall and advance to a target ablation site, radiofrequency ablation to ablate a target site (e.g., carotid body), radiofrequency collagen shrinking or coagulation as the electrode is removed from the tissue to seal the perforation. RF perforation energy, RF ablation energy, and RF coagulation energy are similar in that they comprise electrical current in the radiofrequency range (e.g., about 300 to 500 kHz) that is delivered from an electrode through tissue to a return electrode. However, RF perforation energy differs from RF ablation energy in that it uses a high voltage (e.g., 150-180V) applied to a higher impedance (e.g., 2000 to 6000 Ohms) for very short durations (e.g., 1 to 3 s) raising cellular temperature above 100 degrees C. and causing intracellular expansion and rupture. RF ablation energy is applied to a lower tissue impedance (e.g., 150 to 300 Ohms) with a lower power (e.g., 4 to 10 W) and a voltage of about 35 to 50V over a longer duration (e.g., 60 to 120 s) raising tissue temperature (e.g., between about 50 and 90 degrees C.) to cause cellular death (e.g., protein denaturation or desiccation) but not rupture. RF ablation is generally used to affect a relatively larger volume of tissue on the order of several mm radius from the electrode. RF coagulation is aimed at raising tissue temperature to approximately 60 degrees C. to denature protein, particularly collagen fibers but not necessarily killing cells, in order to seal tissue.

Radiofrequency perforation may comprise passing a tip of an electrode through a vessel wall by delivering a radiofrequency current that lyses vessel wall cells. The perforation may lyse cells only in very close proximity (e.g., a couple cells deep) of the perforation electrode rendering a controlled perforation that may cause little to no damage to surrounding tissue. Very little mechanical force may be required and the perforation electrode may be blunt. RF perforation may facilitate the delivery of an ablation electrode through a carotid artery wall by eliminating a need to apply mechanical force that could cause tissue tenting or the electrode to miss an intended positioning. Use of a blunt tipped perforation electrode increases safety compared to a sharp tip. A blunt tip could be delivered through a sheath without a risk of cutting the sheath. Furthermore, it could be manipulated in a carotid artery until a desired position is obtained, and then RF perforation energy may be delivered to gently advance the electrode through the vessel wall. RF perforation energy may further be applied to advance the electrode beyond the vessel wall through tissue until it is in close proximity or within a target ablation site such as a carotid body or its nerves. For example an RF electrode may be advanced through a carina of a carotid bifurcation and into a carotid septum. Once positioned proximate a target site RF ablation energy may be delivered from the same electrode or a different electrode to ablate target tissue. RF ablation energy may be applied to ablate tissue within a radius of about 2 to 4 mm of the electrode to effectively ablate a target carotid body or its nerves while avoiding thermal injury of important non-target tissues or internal or external carotid arteries. Following ablation the electrode may be removed from the carotid septum. Optionally, RF coagulation energy may be applied while removing the electrode in order to seal the perforation in the vessel to reduce risk of bleeding.

FIG. 9 shows an interstitial perforation/ablation portion of an embodiment comprised for RF perforation, ablation and coagulation. A distal tip of the interstitial perforation/ablation portion comprises a RF perforation electrode 360, which may have blunt or domed shape and a diameter of approximately 20 to 25 gauge. The RF perforation electrode 360 may be separated from an RF ablation electrode 361 by an electrical insulator 362 made, for example, from ceramic. The RF ablation electrode may have a length of about 3 to 6 mm and a diameter of about 20 to 25 gauge. The RF ablation electrode may further comprise irrigation ports 363 through which saline may be irrigated to cool the electrode which may facilitate creation of a larger ablation. Proximal to the RF ablation electrode the shaft may have an electrical insulation coating 364 on its outer surface.

FIG. 10 is an exploded view of the embodiment shown in FIG. 9. An electrical conductor 365 may be connected to the RF perforation electrode 360 and pass through the shaft of the catheter to a proximal end where it may be connected to a radiofrequency console via an electrical connector. The length of the conductor 365 may be electrically insulated so RF perforation energy is delivered only to the RF perforation electrode and not the RF ablation electrode.

FIGS. 11A and 11B are an alternative embodiment of an interstitial perforation/ablation portion of a catheter wherein an outer insulative sheath 366 may be slidably advanced over a RF ablation electrode exposing only an RF perforation electrode 367 during the perforation step. To further isolate the ablation electrode 369. Once the interstitial perforation/ablation portion is positioned proximate a target tissue the sheath 366 may be retracted to expose the RF ablation electrode 369. As shown this embodiment also comprises an electrical insulator 368 separating the RF perforation electrode 367 and the RF ablation electrode 369. Alternatively, an RF perforation electrode may be the same component as an RF ablation electrode and an outer insulative sheath may be advanced to reduce the size of the electrode during perforation and retracted to increase the size of the electrode during ablation or coagulation.

Curved Interstitial RF Ablation Electrode:

In an alternative embodiment, an interstitial RF ablation electrode may be curved in a configuration that optimizes a needle deployment trajectory toward a target site. A carotid body may be positioned away from an axis of a catheter shaft such that advancing a straight RF ablation electrode will miss the carotid body. For example, a carotid body may be positioned toward a medial side of a carotid bifurcation and toward an external carotid artery. The position of the carotid body may be determined before the CBA procedure using a medical imaging modality such as CTA, computer tomography or magnetic resonance imaging. The curved RF ablation electrode may be made from Nitinol and be constrained to a substantially straight configuration when undeployed within a needle sheath. As the curved RF ablation electrode is advanced from the sheath the elastic properties of the Nitinol may cause it to assume its curved form so it is advanced away from the needle sheath axis and toward the target site.

An example of a curved interstitial RF ablation electrode includes a curvature configured for penetration through a vessel wall at a carotid bifurcation and a trajectory toward a carotid body. A suitable RF ablation electrode curvature may have a radius of curvature between and including about 5 mm to 20 mm (e.g., about 12 mm). Another example of a suitable curvature may place the tip of the RF electrode between about 10° and 40° from a central plane between the internal and external carotid arteries toward a medial side. The sheath may comprise two radiopaque markers on its distal region, which may be used to determine the alignment of the sheath with respect to the central plane between the internal and external carotid arteries prior to deploying the curved RF electrode.

Figure 12:
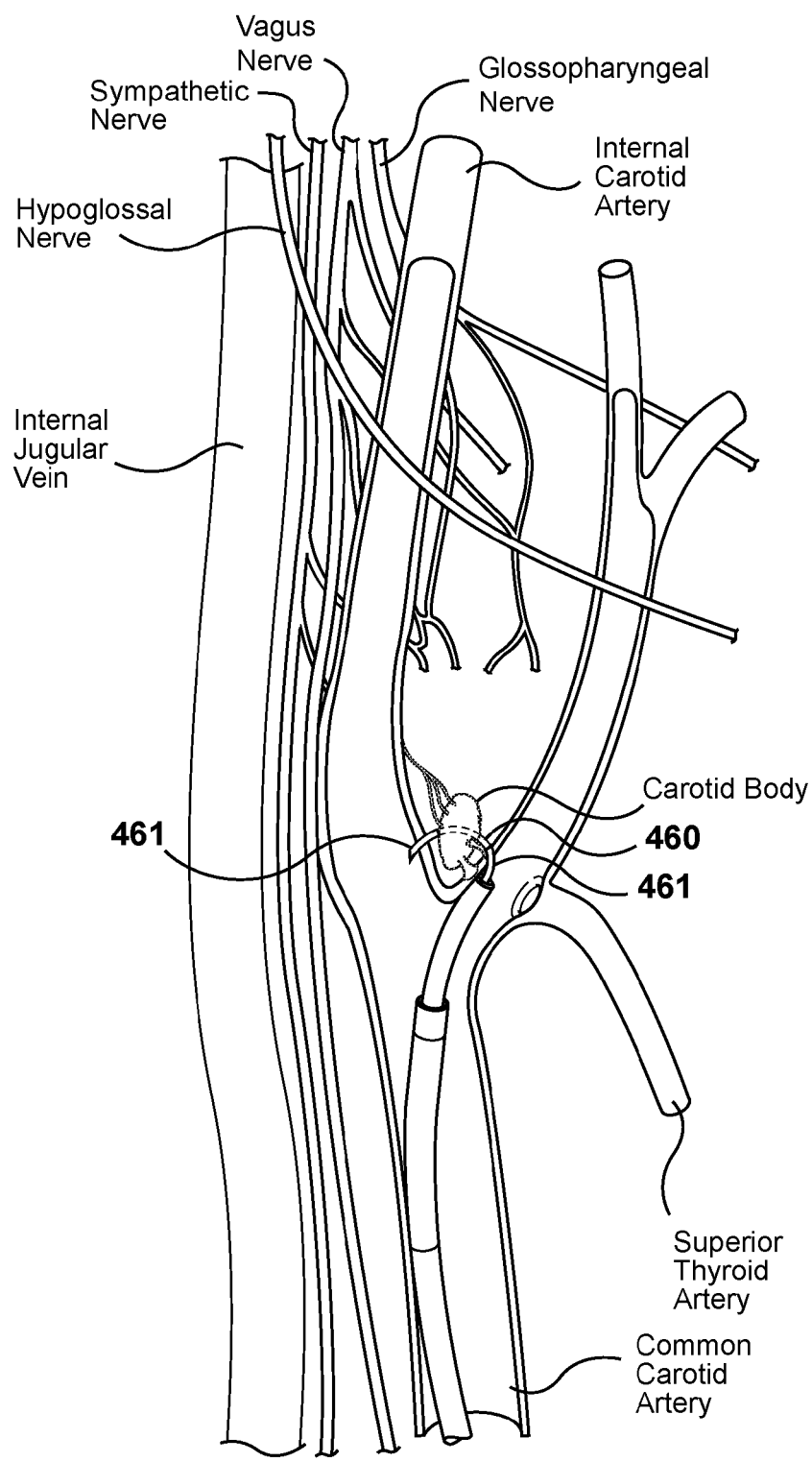
FIG. 12 is a cutaway illustration of a lateral view of a patient's right carotid artery system with a schematic view of an endovascular catheter having a curved radiofrequency electrode needle inserted into a target site.

FIG. 12 illustrates a deployed configuration and exemplary position of an exemplary curved interstitial RF ablation electrode 460 that includes a curvature configured for penetration through a vessel wall from within an external or internal carotid artery and a trajectory toward a carotid body. This configuration of electrode 460 acts like a hook to cross tissue of an intercarotid septum from an external to internal carotid artery. In this way fixation may be achieved and the electrode 460 may be retained in position during ablation. The catheter includes insulation coating 461 proximal to the exposed electrode 460, which is a conductive material.

Figure 13:
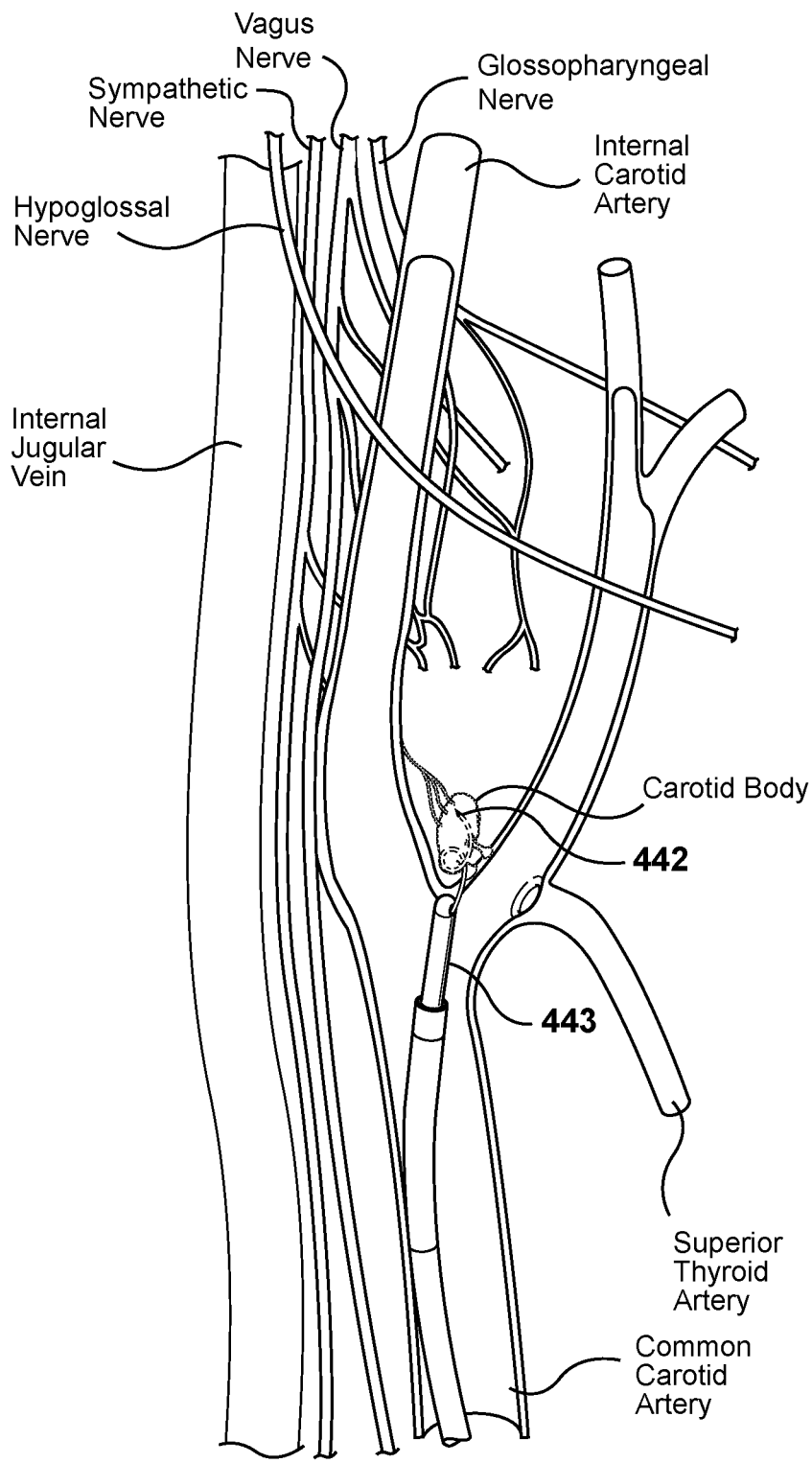
FIG. 13 is a cutaway illustration of a lateral view a patient's right carotid artery system with a schematic view of an endovascular catheter having a radiofrequency electrode needle with a helical curvature inserted into a target site.

Helical Interstitial RF Ablation Electrode:

FIG. 13 illustrates an exemplary embodiment of a CBA catheter in which the interstitial RF electrode has a preformed curvature, and in this embodiment has a helical curvature configuration. Helical RF electrode needle 442 may be made from Nitinol. A sheath lumen is in communication with a port at a distal end of the catheter, wherein the port is disposed on a side of the catheter such that the trajectory of the helical RF electrode needle is in a forward direction. The side port allows the axis of the helical-shaped RF electrode to be sufficiently aligned with the axis of sheath 443. In this embodiment, the helical RF electrode needle 442 may be advanced into tissue like a corkscrew, which may provide improved stability compared to a straight electrode so there is less risk of the electrode falling out of place. Furthermore, compared to a straight electrode, a helical RF electrode needle may allow for a greater amount of surface area of electrode to be placed within a target site, which may allow for a larger ablation and improved efficacy. This embodiment may have all of the other characteristics as the interstitial RF ablation electrode described herein.

In some embodiments ablating target tissue within a carotid septum of a patient includes advancing an ablation device into an artery of a patient, the ablation device comprising first and second arms and an ablation element, passing the first arm into an external carotid artery of the patient and into engagement with a wall of the external carotid artery adjacent a carotid septum, passing the second arm into an internal carotid artery of the patient and into engagement with a wall of the internal carotid artery adjacent the carotid septum, and actuating the ablation element to ablate target tissue within the carotid septum.

Figure 14:
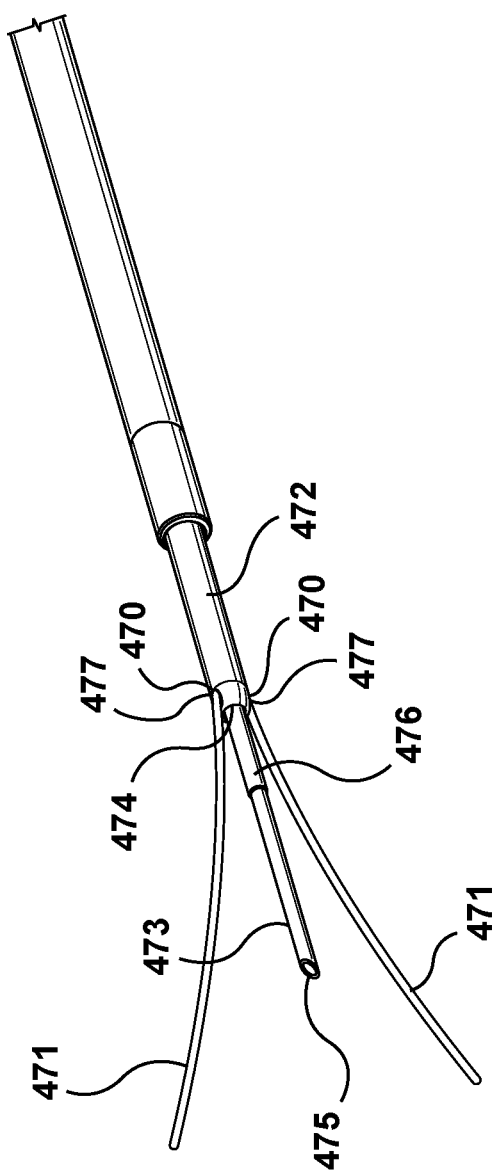
FIG. 14 is a schematic view of an interstitial RF ablation catheter with side exiting guide wires.

An exemplary embodiment of an ablation catheter that includes first and second arms and an ablation element is shown in FIG. 14. The ablation catheter comprises two side-exiting lumens 470 that provide passage for guide wires 471 (which are also described herein as "arms" and "positioning elements") used to assist the positioning of a distal tip of catheter shaft 472 at a target penetration site (e.g., inner wall of an internal carotid artery, external carotid artery or carotid bifurcation proximate a carotid body or carotid body nerves) and for maintaining stable position as interstitial ablation element 473 is advanced through tissue to a target ablation site, and during energy delivery. Lumens 470 are located within a longitudinal shaft of catheter 472 and exit the catheter at a proximal region and at a distal region such that guide wires 471 may be slidably engaged within the lumens from the proximal region of the shaft to the distal region of the shaft. Distal region exit ports 477 of the lumens are positioned off-axis allowing the guide wires to exit the lumen at a pre-determined angle (e.g., between or including an angle of about 5° to 90°) to the axis of the catheter shaft. The distal region exit ports may be positioned on approximately opposing sides of a catheter shaft. The guide wires diverge from the axis of the catheter shaft forming a "V-shape."

Figure 15:
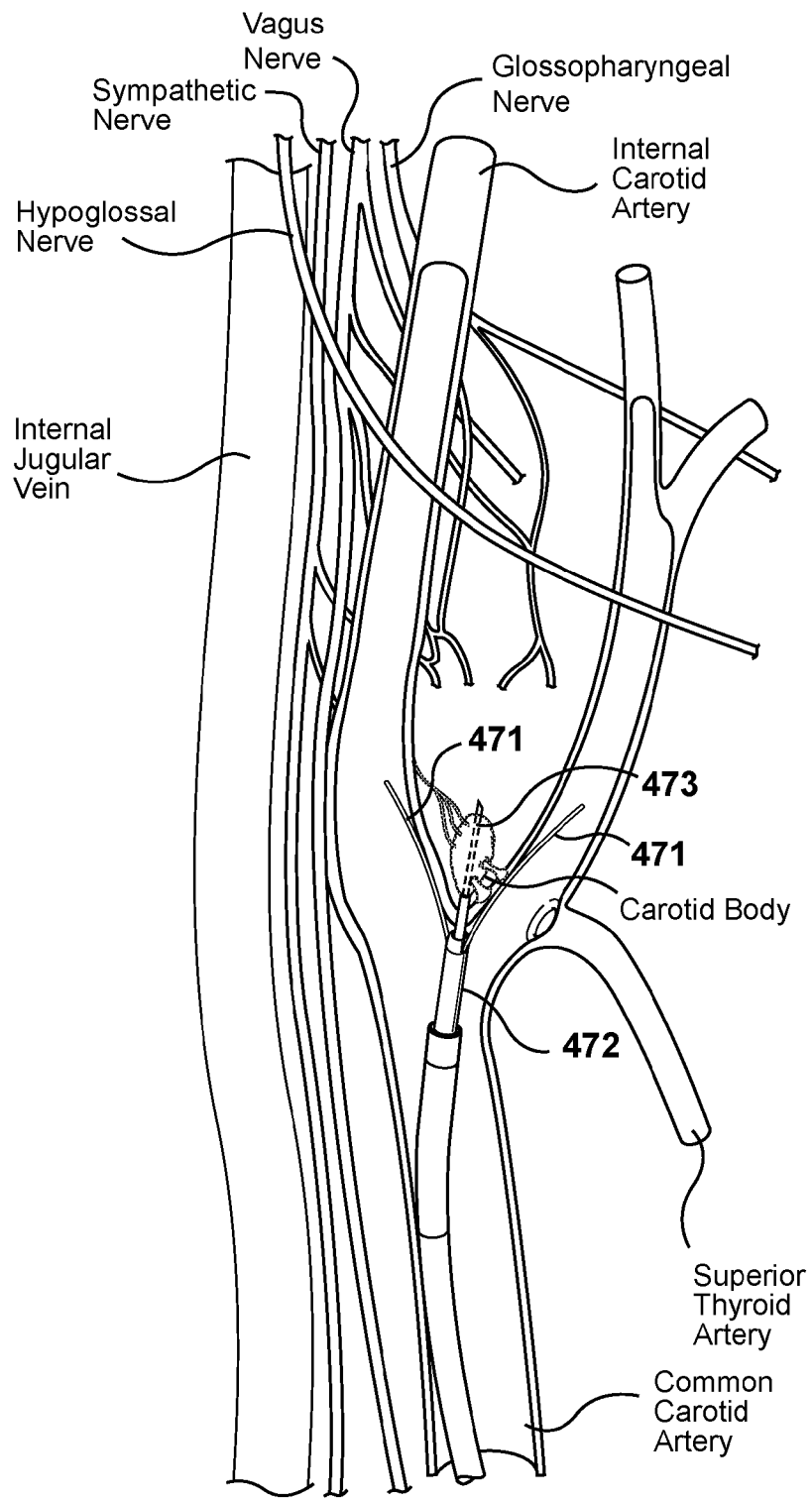
FIG. 15 is a cutaway illustration of a lateral view a patient's right carotid artery system with a schematic view of an ablation catheter, with side exiting guide wires, positioning an ablation element for interstitial ablation of a carotid body.

FIG. 15 illustrates an exemplary method of using the ablation catheter shown in FIG. 14. The catheter shown in FIG. 14 is first positioned in a common carotid artery labeled in FIG. 15, such as via a femoral approach, optionally through a steerable guide sheath or with an introducer catheter or guide wire. Guide wires 471 are then advanced from distal region exit ports 477, with a first guide wire being advanced into an internal carotid artery as shown and the second guide wire being advanced into an external carotid artery, as shown. The catheter shaft may be pushed forward such that the septum of the carotid bifurcation rests in the "V-shape" between the two guide wires. This wedging of the catheter into the carotid bifurcation septum facilitates ideal positioning of a distal tip of the catheter at a penetration target site and provides stability of the catheter. As shown in FIG. 15, the two guidewires are engaging the walls of the internal and external carotid arteries, respectively. A needle lumen in the catheter shaft 472 exits at the distal tip of the catheter at distal needle port 474. Interstitial ablation element 473 (e.g., RF electrode needle, microwave antenna, ultrasound transducer, fluid delivery needle, cryogenic applicator, or any other ablation element described herein) is deployed from distal needle port 474 and through tissue to a target ablation site in a carotid body, as shown in FIG. 15. Ablating element 473 is then actuated to ablate target tissue within the carotid body. Ablating the target tissue within the carotid body treats the sympathetically mediated disease.

In some embodiments shaft 472 has a diameter between or including about 5 F to 9 F (e.g., about 5 F to 7 F). The catheter may have a length between or including about 120 cm to 200 cm (e.g., about 120 cm to 140 cm) suitable to be delivered via femoral access. The catheter shaft 472 may be made from a polymer such as polyurethane or Pebax and the shaft may comprise braided reinforcement for additional strength or torque transmission. The shaft may also be coated with a hydrophilic or other lubricious coating for improved slidability through a sheath or introducer. The inner lumens of the shaft may also be coated with a lubricious coating to facilitate passage of guide wires or an interstitial ablation element. The shaft may comprise guide wire lumens, for example with a diameter between or including about 0.014" to 0.020". The catheter shaft 472 may further comprise a needle lumen with a diameter between or including about 0.004" to 0.010".

In the embodiment in FIG. 14 interstitial ablation element 473 is an RF electrode needle, and can be the same or similar to the needle electrode described in FIG. 6. The RF electrode needle may be made from an electrically conductive material (e.g., stainless steel, gold, platinum-iridium, or Nitinol) and may be constructed from a hypotube with a sharpened needle point 475. The RF needle may be straight or curved. The RF needle caliber may be between and including about 18 gauge to 28 gauge (e.g., having an outer diameter between and including about 1.270 mm and 0.362 mm). In one embodiment, a RF electrode is an exposed portion on a distal end of a hypotube that extends about a length of the catheter shaft 472 and the unexposed region of the hypotube is electrically insulated with a dielectric material 476, as shown in FIG. 14 (e.g., polymer, PET, PEEK, Teflon). The RF electrode needle may have an exposed length of between or including about 2 mm to 10 mm, and in some embodiments is about 5 mm. A temperature sensor (e.g., thermocouple, thermistor, or fluoroptic thermometry sensor) may be located in, near, or at the surface of the RF electrode needle. The RF electrode needle may further comprise a temperature sensor (e.g., thermocouple connected to two conductors). Alternatively, a temperature sensor may be in contact with tissue and insulated from direct thermal contact with an electrode to better reflect tissue ablation temperature. For example, a temperature sensor may protrude from an electrode. The conductors travel through the catheter body (e.g., through a lumen in a hypotube) from the distal to proximal end and are connected to wires allowing the temperature sensor to communicate with an RF generator 210, shown in FIG. 5A. The conductors may be, for example a copper and constantan conductor, respectively, such that joining the conductors via solder, laser welding or the like creates a thermocouple junction. The copper conductor may be used to carry both a thermocouple signal and deliver RF energy to electrode 473. Alternatively, a separate conductor (not shown) may deliver RF energy to the electrode.

A proximal region of a RF catheter with positioning guide wires may comprise an electrical connector containing terminals for temperature sensor conductors or a RF delivery conductor. Furthermore, the proximal region may comprise exit ports in communication with the guide wire lumens. The proximal region exit port may be configured with a guide wire lumen extension tube terminating with a fitting (e.g., Touhy Borst or Luer fitting).

Multiple catheters with varying distal region exit port configurations may be provided in a kit. For example, the varying configurations may comprise a range of port-to-tip distances (e.g., 3 mm, 5 mm, 7 mm, 9 mm) or port exit angles (e.g., 10°, 20°, 40°, 60°). A user may select an appropriate catheter configuration depending on carotid artery geometry or position of a carotid body relative to carotid arteries.

Some embodiments of the RF ablation catheter with positioning guide wires comprises more than two lumens with distal exit ports positioned at different distances from a distal tip of the catheter. When using such catheters a user may select a lumen and thus an exit port through which a positioning guide wire is advanced, depending on, for example, geometry of a carotid bifurcation (e.g., angle of divergence, thickness of septum, sharpness of bifurcation) or position of a carotid body relative to a carotid bifurcation (e.g., distance from bifurcation, proximity to an internal or external carotid artery). In these embodiments the user can thus select the most desired position for one or more guide positioning elements depending on, for example, the patient anatomy.

Yet another alternative embodiment of the RF catheter with positioning guide wires involves a sheath having one or more lumens for one or more positioning guide wires. An ablation catheter may be advanced through the sheath and thus the distance between an RF electrode on the ablation catheter and the guide wire exit port may be changed according to position of a carotid body relative to a carotid bifurcation.

A deployable balloon may be used as an alternative to one or more positioning guide wires. In a similar fashion, a positioning catheter with a balloon may be advanced through a lumen to diverge from an ablation catheter, which may facilitate stable placement of an energy delivery element (e.g., RF electrode) proximate a carotid bifurcation. The positioning catheter may be placed in an internal carotid artery and the balloon may be deployed in the internal carotid artery approximately 1 cm to 10 cm from a carotid bifurcation. The balloon may increase stability of the ablation catheter position and may further occlude the internal carotid artery so blood flow coming from a common carotid artery passes substantially through an external carotid artery. Occlusion of the internal carotid artery during placement of the ablation catheter and delivery of ablative energy may prevent debris such as dislodged plaque or thrombus from flowing into the internal carotid artery and divert it to the external carotid artery. This may protect the patient from potential brain embolism which otherwise may be caused by debris in the blood stream. Such occlusion of an internal carotid artery may also increase the size of a thermal ablation lesion for the same power delivered by decreasing cooling of tissue by blood flow.

Figure 16:
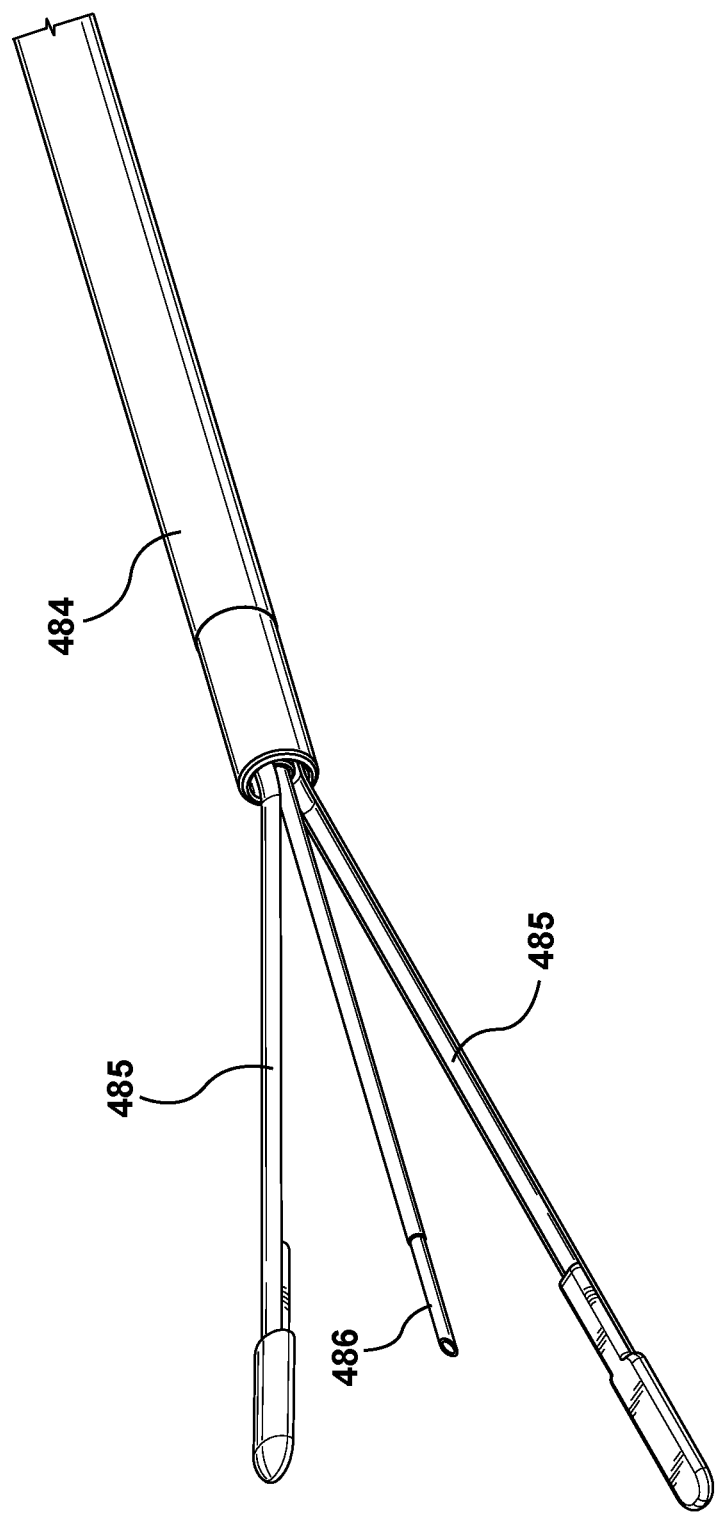
FIG. 16 is a schematic view of an endovascular ablation catheter having deployable arms.

FIG. 16 illustrates a portion of another exemplary ablation catheter. The catheter in FIG. 16, like the catheter in FIG. 14, is adapted to be used in a method of ablating target tissue within a carotid septum of a patient, wherein the method includes advancing an ablation device into an artery of a patient, the ablation device comprising first and second arms and an ablation element, passing the first arm into an external carotid artery of the patient and into engagement with a wall of the external carotid artery adjacent a carotid septum, passing the second arm into an internal carotid artery of the patient and into engagement with a wall of the internal carotid artery adjacent the carotid septum, and actuating the ablation element to ablate target tissue within the carotid septum.

The exemplary endovascular catheter for carotid body ablation ("CBA") shown in FIG. 16 comprises bifurcation forceps 485, which may also be referred to herein as "arms" or "positioning elements." The bifurcation forceps are adapted to be used for any and all of the following: grasping a carotid bifurcation septum to provide an anchor for interstitial ablation element (e.g., a needle electrode) deployment; stimulation of a carotid body by compressing the carotid body between each jaw of forceps 485; ablation of a carotid body with RF energy delivered from both jaws (i.e., an example of transmural ablation as described herein) while the carotid body and intervening tissue is being compressed by both jaws; alignment and fixation of the catheter for interstitial ablation needle deployment; providing electrical stimulation/blockade to a carotid body through electrodes on the forceps, which may be used for carotid body locating (e.g., maximum stimulation/blockade may be achieved when a carotid body is located between the two electrodes); and locating a carotid body by measurement of afferent signals through forceps electrodes.

Figure 17:
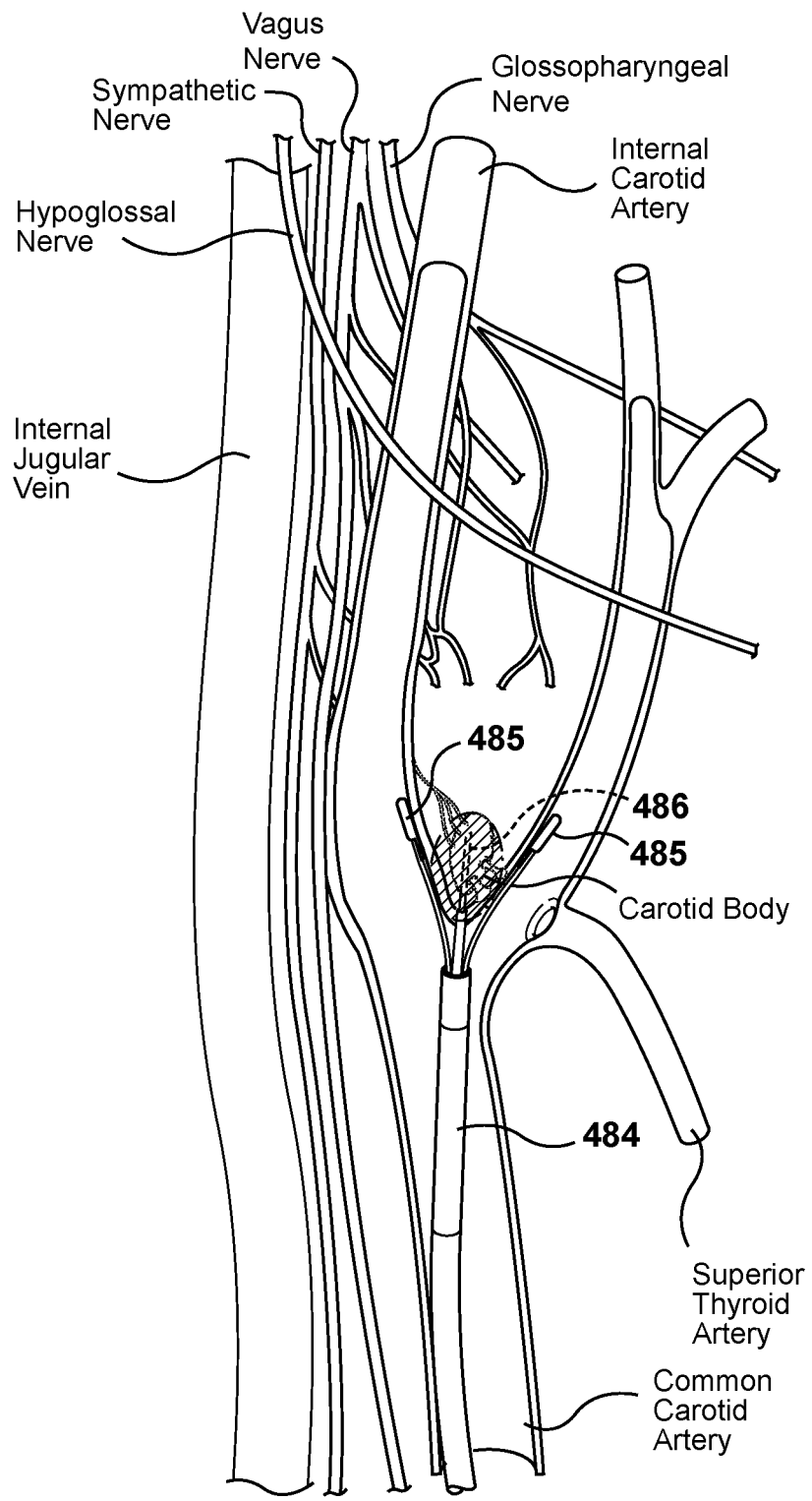
FIG. 17 is a cutaway illustration of a lateral view of a patient's right carotid artery system with a schematic view of an endovascular ablation catheter having deployable arms positioned in the patient's internal and external carotid arteries for interstitial ablation of a carotid body.

FIG. 17 illustrates the catheter from FIG. 16 in an exemplary method of use. In some embodiments the bifurcation forceps are delivered in an undeployed configuration with the forceps and interstitial ablation element 486 constrained within sheath 484. Once positioned in a vicinity of a carotid bifurcation, sheath 484 is retracted allowing forceps 485 to elastically deploy while ablation element 486 is maintained protected within the sheath. The catheter may be advanced against a carotid bifurcation with a first arm of the forceps in an internal carotid artery as shown, and the second arm of the forceps in an external carotid artery as shown. Sheath 484 may be advanced partially to apply pressure to the forceps such that they apply a squeezing force on the intercarotid septum. As shown in FIG. 17, the arms of forceps 485 are in engagement with the walls of the internal and external carotid arteries, respectively. The ablation element 486 may be advanced from the sheath and through tissue of the carotid bifurcation into a target ablation site in the carotid body, as shown in FIG. 17. Ablating element 486 is then actuated to ablate target tissue within the carotid body. As set forth above, the method can also include delivering RF energy through the jaws to ablate the carotid body.

Figure 18:
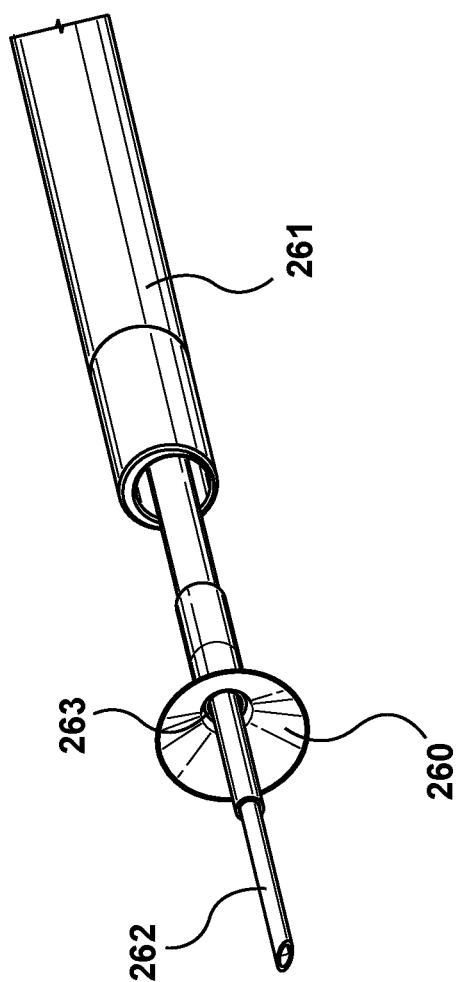
FIG. 18 is a schematic view of an endovascular ablation catheter having a suction element and an interstitial radiofrequency electrode.

Interstitial Catheter with a Suction Element:

FIG. 18 illustrates another embodiment of an endovascular catheter for interstitial CBA that comprises a suction element. Examples of functionality of the catheter with suction element 260 may include: providing an anchoring means at a carotid bifurcation in a vicinity of a carotid body artery using suction, stimulating a carotid body by applying suction to the ostium of the carotid body artery (e.g., suction applied to the carotid body artery may cause retrograde blood flow through the carotid body vascular bed, pulling hypoxic venous blood into the arterioles surrounding the carotid body causing an elevation in carotid body afferent signaling and corresponding physiological response); alignment and fixation for interstitial ablation needle deployment; alignment and fixation for cannulation of a carotid body artery with a guide wire, micro-catheter and/or ablation probe; providing electrical stimulation/blockade to a carotid body through electrodes mounted on a contact surface of the suction element, which may be used for carotid body locating (e.g., maximum stimulation/blockade achieved when the electrodes cover or are in close proximity to the carotid body artery); locating a carotid body by measurement of afferent signals through electrodes mounted on the surface of a suction element; RF ablation of a carotid body and artery ostium using an RF electrode mounted on a contact surface of a suction element; discrete infusion of contrast, stimulation, blockading or chemo-ablative fluids using the suction element as positive pressure seal. It is important to maintain an ablation element in place during ablative energy delivery, which may be for example between 30 to 120 seconds. Attempting to pierce an arterial wall that is resilient with a needle may push the needle away from the wall. Therefor affixing a catheter to a wall of an artery during puncture with a needle may benefit by maintaining position during ablation and while piercing an arterial wall.

Figure 19:
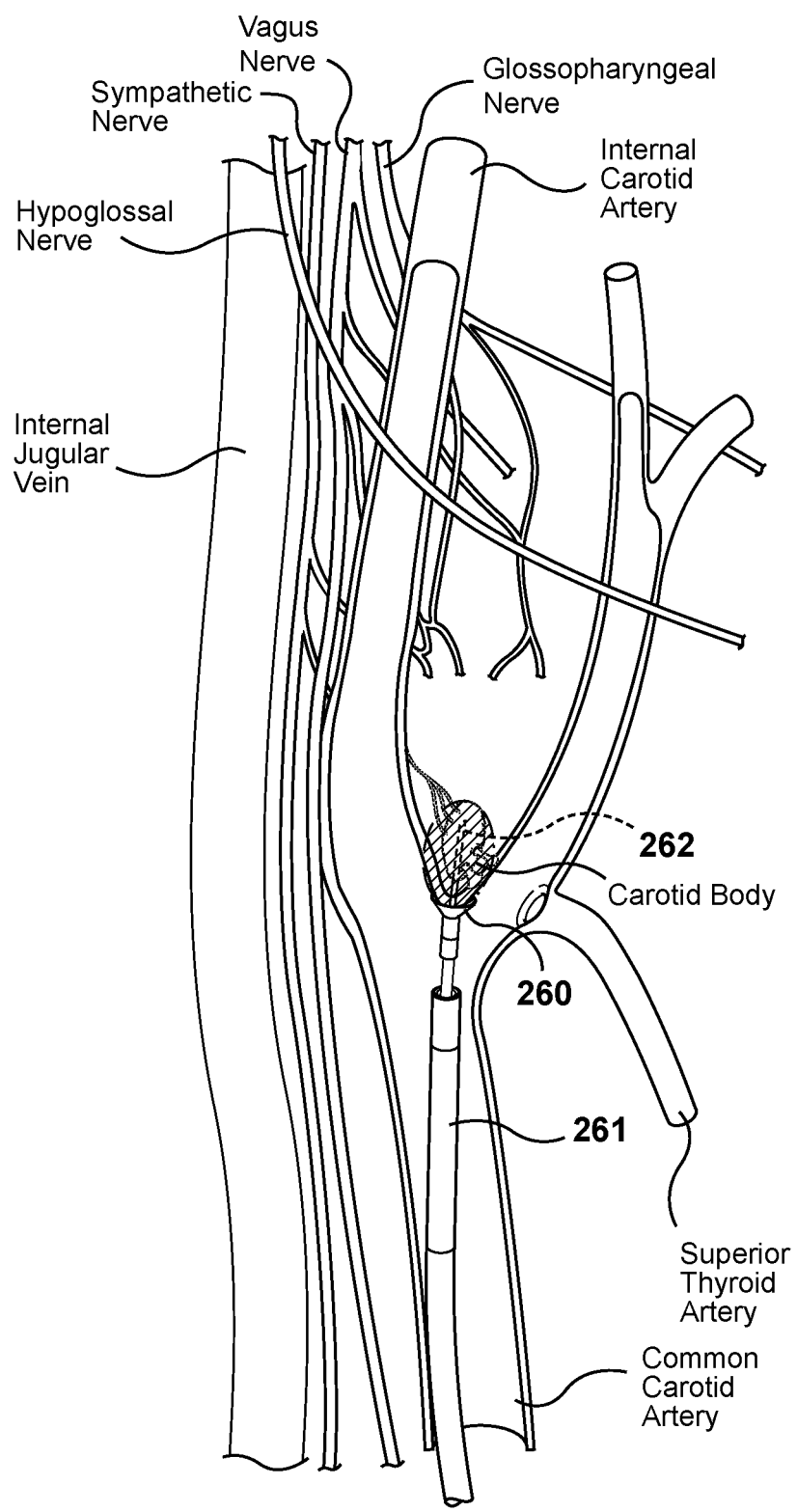
FIG. 19 is a cutaway illustration of a lateral view a patient's right carotid artery system with a schematic view of an endovascular ablation catheter having a suction element and an interstitial radiofrequency electrode positioned in a carotid septum for interstitial ablation of a carotid body.

Suction element 260 may be delivered in an undeployed configuration contained within sheath 261. Suction element 260 may be connected to an elongated tube having lumen 263. Interstitial ablation element 262 (e.g., an interstitial RF ablation needle) may be contained within lumen 263. Once the distal end of the catheter is positioned near a target penetration site (e.g., at a carotid bifurcation) sheath 261 may be retracted, allowing suction element 260 to reconfigure to the deployed configuration shown in FIG. 18. Suction element 260 may then be advanced into contact with the target penetration site with the interstitial ablation element maintained within the lumen 263. Negative pressure may be applied within the lumen 263, for example, by a syringe or suction pump at a proximal end of the lumen 263 causing the suction element 260 to adhere to the target penetration site. Interstitial ablation element 262 may then be advanced from the lumen 263 through the vessel wall to the target ablation site (e.g., carotid body) as shown in the exemplary method of use shown FIG. 19. Other aspects of the method of use of the catheter shown in FIG. 18 can be found in other methods of use described herein.

Interstitial Laser Ablation Needle:

As previously described, laser may be a suitable form of ablative energy for interstitial CBA. FIG. 20 illustrates an exemplary CBA catheter including an interstitial laser ablation needle, which can be incorporated into any of the embodiments for delivering an interstitial ablation element described herein, including the catheter having a needle sheath and a spring loaded trigger actuator shown in FIGS. 7 and 8, the catheter having positioning guide wires shown in FIGS. 14 and 15, the catheter having bifurcation forceps shown in FIGS. 16 and 17, and the catheter having a suction element shown in FIGS. 18 and 19. As shown, the catheter includes interstitial laser ablation needle 290 may be. However, when a laser ablation needle is incorporated into other embodiments described herein, the insertion depth is shorter than that of a radiofrequency ablation needle. Instead of inserting a needle through a target site, a laser needle may be inserted such that a distal tip of the needle is pointing at the target site so that as a laser propagation cone 291 is emitted from laser ablation needle 290, the tissue within the propagation cone is ablated. In this embodiment the system can include a laser console in addition to or instead of a radiofrequency generator. The laser console is adapted to deliver energy to the needle through optical fiber 292.

Potential functionality of an interstitial laser ablation needle may include one or more of the following: ablating a carotid body while minimizing collateral damage to a carotid artery by placement of a laser ablation needle into extra-vascular space in close or immediate proximity of the carotid body; accessing extra-vascular space in vicinity of a carotid body from within a carotid artery using a needle device with a caliber that is known to be safe for arterial puncture; precisely controlling a laser ablation process by having an optical temperature sensor within a laser source console that measures black body radiation from the ablation zone, which is used to modulate laser energy for optimum ablation formation; avoiding disruption of plaque, and eliminating plaque as an obstacle to carotid body ablation; using the electrically conductive needle as an electrode to facilitate direct electrical stimulation and/or blockade of carotid body function, or using the electrode to sense carotid body afferent signals that may be a measure of technical success.

Interstitial Microwave Ablation Needle:

As previously described, microwave may be a suitable form of ablative energy for interstitial carotid body ablation. An exemplary interstitial microwave ablation needle, as shown in an exploded view in FIG. 21, may be incorporated into any of the embodiments for delivering an interstitial ablation element described herein, including the catheter having a needle sheath and a spring loaded trigger actuator shown in FIGS. 7 and 8, the catheter having a curved interstitial ablation needle shown in FIGS. 12 and 13, the catheter having positioning guide wires shown in FIGS. 14 and 15, the catheter having bifurcation forceps shown in FIGS. 16 and 17, and the catheter having a suction element shown in FIGS. 18 and 19. Similar to an interstitial radiofrequency ablation needle (445 in FIG. 8, 442 in FIG. 13, 473 in FIG. 15, 486 in FIG. 17, and 262 in FIG. 19) an interstitial microwave ablation needle may be inserted into, near, or through an ablation target such as a carotid body. On a proximal region of a microwave catheter the microwave ablation needle may be connected to a microwave generator with a coaxial microwave connector. Conductors for a temperature sensor may be connected to the microwave generator. As shown in FIG. 21 interstitial microwave ablation needle 270 may be constructed from hypotube 271 made from a conductive material (e.g., Nitinol, stainless steel) and may have a gauge for example between and including about 18 Ga and 28 Ga (e.g., about 25 Ga). A distal tip 274 of hypotube 271 may be sharpened to facilitate insertion into tissue. An exposed region at a distal end of hypotube 271 forms microwave radiation emission zone 272. Optionally, the exposed distal tip may also be used as an electrode for electorally stimulation or blockade of nerves, or for sensing nerve activity prior to or after delivery of microwave energy. When microwave energy is delivered to the microwave radiation emission zone 272 surrounding tissue is heated. A microwave radiation emission zone length that is suitable for CBA may be between or including about 2 mm to 10 mm (e.g., 5 mm). The remaining length of the hypotube 271 may be shielded to contain microwave radiation emission. Shielding 273 may comprise an inner dielectric layer, a middle electrically conductive layer and an outer dielectric layer. A temperature sensor 275 (e.g., thermistor, thermocouple, optic sensor) may be positioned in a lumen of the hypotube 271 in the region of the microwave radiation emission zone 272. The exploded view of FIG. 21 shows a thermocouple 275 exploded from the lumen. Thermocouple 275 may be made by joining two dissimilar metal conductors such as copper conductor 276 and constantan conductor 277.

Potential functionality of an interstitial microwave ablation needle may include one or more of the following: ablating a carotid body while minimizing collateral damage to a carotid artery by placement of a microwave ablation electrode into extra-vascular space in close or immediate proximity of the carotid body; accessing extra-vascular space in vicinity of a carotid body from within a carotid artery using a needle device with a caliber that is known to be safe for arterial puncture; precisely controlling a microwave ablation process by having a temperature sensor within an ablation zone, which is used to modulate microwave energy for optimum lesion formation; avoiding disruption of plaque, and eliminating plaque as an obstacle to carotid body ablation; and facilitating direct electrical stimulation or blockade of carotid body function, or extra-vascular placement of an electrode for carotid body afferent signal detection, which may be used as a measure of technical success.

Interstitial Ultrasound Ablation Needle:

As previously described, ultrasound may be a suitable form of ablative energy for interstitial carotid body ablation. An interstitial ultrasound ablation needle, as shown in an exploded view in FIG. 22, may be incorporated into any of the embodiments for delivering an interstitial ablation element described herein, including the catheter having a needle sheath and a spring loaded trigger actuator shown in FIGS. 7 and 8, the catheter having a curved interstitial ablation needle shown in FIGS. 12 and 13, the catheter having positioning guide wires shown in FIGS. 14 and 15, the catheter having bifurcation forceps shown in FIGS. 16 and 17, and the catheter having a suction element shown in FIGS. 18 and 19. Similar to an interstitial radiofrequency ablation needle (445 in FIG. 8, 442 in FIG. 13, 473 in FIG. 15, 486 in FIG. 17, and 262 in FIG. 19) an interstitial ultrasound ablation needle may be inserted into, near, or through an ablation target such as a carotid body.

Figure 22:
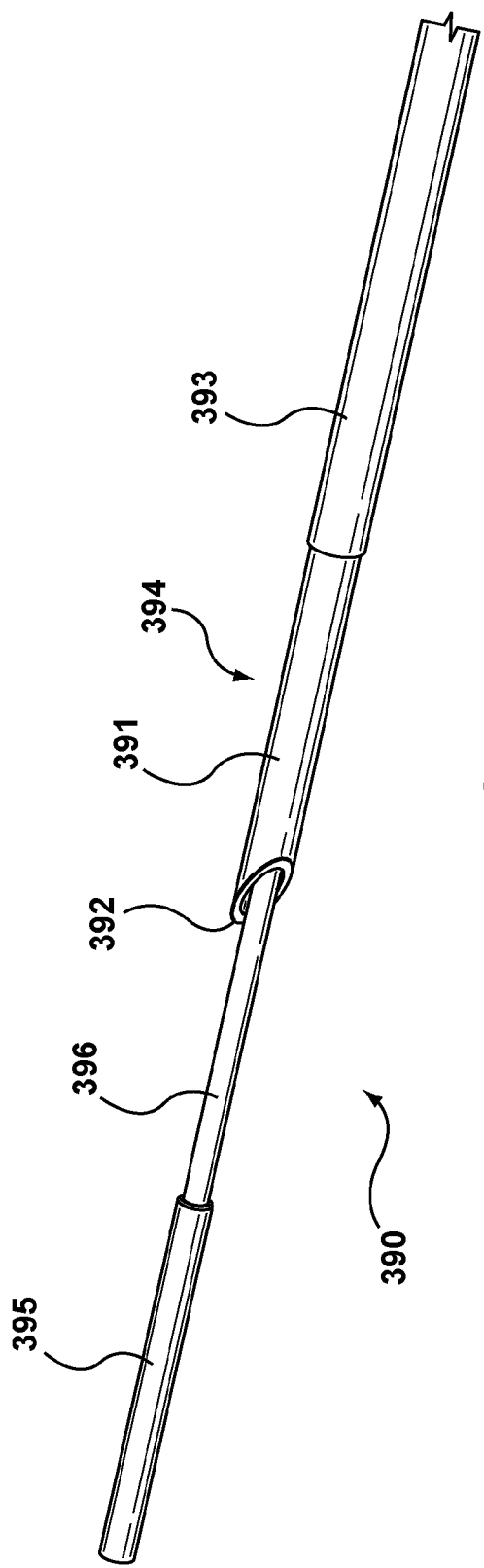
FIG. 22 is a schematic view of an interstitial ultrasound ablation needle.

As shown in an exploded view in FIG. 22, interstitial ultrasound ablation needle 390 may be made from a hypotube 391 (e.g., Nitinol, stainless steel) and may have a gauge for example between and including about 18 Ga and 28 Ga (e.g., about 25 Ga). A distal tip 392 of the hypotube 391 may be sharpened to facilitate insertion into tissue. Optionally, the hypotube may be electrically insulated with a dielectric material 393 along the length of the hypotube 391 leaving an exposed distal tip 394. The exposed distal tip may be used as an electrode for electorally stimulation or blockage of nerves, or for sensing nerve activity prior to or after delivery of microwave energy. Contained within a lumen of the hypotube 391 may be a piezoelectric crystal 395 connected to an insulated center conductor 396 that is connected to an electrical connector at a proximal region of the catheter for connection to an ultrasound power generator. For example, the piezoelectric crystal 395 may be a cylindrical shape with an outer diameter (e.g., about 0.014") that substantially matches and electrically connects with an inner diameter of the hypotube 391. The hypotube 391 may thus act as a conductor and be connected to the electrical connector at the proximal region of the catheter for connection to the ultrasound power generator. The crystal 395 may have a lumen (e.g., about 0.006") that fits and electrically connects with a stripped portion of the center conductor 396. The crystal 395 may have a length suitable for CBA (e.g., between or including about 2 mm to 10 mm, or about 5 mm). Heat is generated in a tissue zone surrounding the needle by ultrasonic kinetic energy absorption that is frequency dependent. The frequency, which may be controlled by the generator, can be tailored for maximum thermal effect, or limited thermal effect.

Potential functionality of an interstitial ultrasound ablation needle may include one or more of the following: ablating a carotid body while minimizing collateral damage to a carotid artery by placement of an ultrasound thermal ablation needle probe into extra-vascular space in close or immediate proximity of the carotid body; accessing extra-vascular space in vicinity of a carotid body from within a carotid artery using a needle device with a caliber that is known to be safe for arterial puncture; creating a larger ablation zone in relation to probe size using ultrasonic thermal ablation compared to RF energy; avoiding disruption of plaque, and eliminating plaque as an obstacle to carotid body ablation; and the electrode may be used to facilitate direct electrical stimulation or blockade of carotid body function, or sense carotid body afferent signals as a measure of technical success of ablation.

Figure 23:
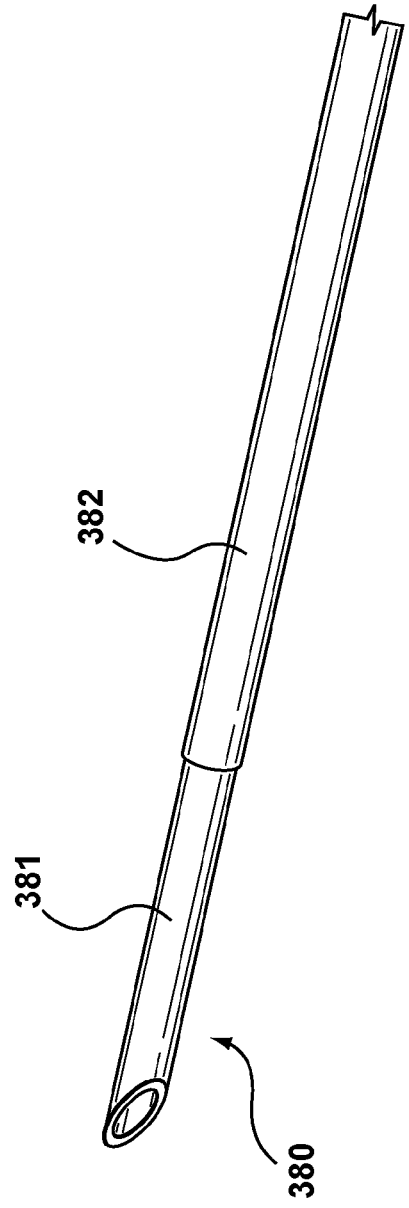
FIG. 23 is a schematic view of an interstitial chemical ablation needle.

Interstitial Chemical Ablation Needle:

As previously described, chemical ablation may be a suitable form of ablative energy for interstitial carotid body ablation. An exemplary interstitial chemical ablation needle, as shown in FIG. 23, may be incorporated into any of the embodiments for delivering an interstitial ablation element described herein, including the catheter having a needle sheath and a spring loaded trigger actuator shown in FIGS. 7 and 8, the catheter having a curved interstitial ablation needle shown in FIGS. 12 and 13, the catheter having positioning guide wires shown in FIGS. 14 and 15, the catheter having bifurcation forceps shown in FIGS. 16 and 17, and the catheter having a suction element shown in FIGS. 18 and 19. Similar to an interstitial radiofrequency ablation needle (445 in FIG. 8, 442 in FIG. 13, 473 in FIG. 15, 486 in FIG. 17, and 262 in FIG. 19) an interstitial chemical ablation needle may be inserted into, near, or through an ablation target such as a carotid body. A chemical ablation needle, as shown in FIG. 23, may be made from a hypotube 381 with a sharped tip that facilitates insertion through tissue. The hypotube may be, for example about 25 Ga and made from Nitinol or stainless steel. Optionally, the needle may be insulated with a polymer or dielectric coating 382 along the length of the hypotube with an exposed region or about 5 mm at a distal end of the needle. This exposed region may be used as an electrode.

Potential functionality of an interstitial chemical ablation needle may include one or more of the following: ablating a carotid body while minimizing collateral damage to a carotid artery by placement of an chemical ablation agent into extra-vascular space in close or immediate proximity of the carotid body; accessing extra-vascular space in vicinity of a carotid body from within a carotid artery using a needle device with a caliber that is known to be safe for arterial puncture; creating a larger ablation zone in relation to probe size using chemical ablation agent compared to RF energy; avoiding disruption of plaque, and eliminate plaque as an obstacle to carotid body ablation; and the electrode can be used to facilitate direct electrical stimulation or blockade of carotid body function, or to sense carotid body afferent signals as a measure of technical success of ablation.

An interstitial chemical ablation needle may be used to deliver an ablative agent (also referred to herein as an ablation agent), sclerosing agent or a neural disruptive agent into a target tissue. An example of an agent that may be used to disable sympathetic signaling from a carotid body is Guanethidine, which is known to cause sympathectomy, by inhibiting mitochondrial respiration, and induce an immune response.

As set forth above, an aspect of the disclosure is a method of ablating target tissue within a carotid septum of a patient. In some embodiments of this aspect ablating the target tissue includes performing an endovascular transmural carotid body ablation.

Transmural Ablation:

In general, transmural ablation as used herein refers to delivering an ablation agent from an ablation element, through a vessel wall and possibly other tissue, and to target ablation tissue to ablate the target tissue. An ablation element may be, for example, a radiofrequency electrode, a laser fiber, a microwave antenna, an ultrasound transducer, a cryoablation element, an electroporation electrode. The ablation element may be made from radiopaque material or comprise a radiopaque marker and it may be visualized using fluoroscopy to confirm position. Alternatively, a contrast solution may be injected through a lumen in the ablation element to verify position. Ablation energy may be delivered, for example from a source external to the patient such as a generator or console, to the ablation element and through the vessel wall and other tissue to the target ablation site.

Ablation Sheath

Figure 24A:
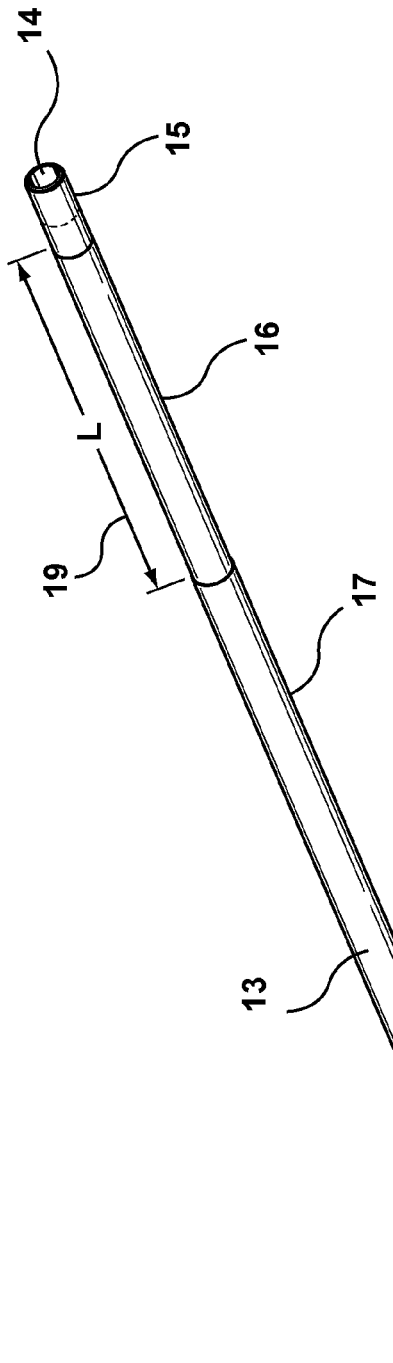
FIG. 24A is a schematic view of a steerable sheath.
Figure 24B:
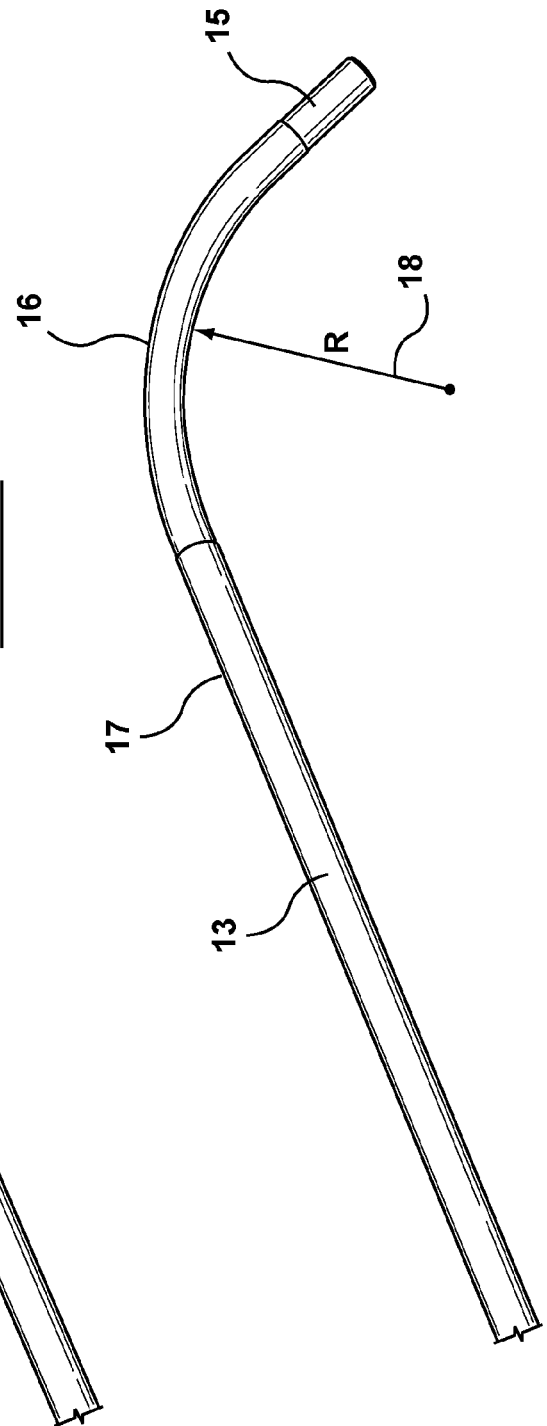
FIG. 24B is a schematic view of a steerable sheath in a deflected state.

FIG. 24A and FIG. 24B depict the distal end of an exemplary carotid access sheath 13 adapted for endovascular transmural ablation of a carotid body, which may be referred herein as an ETA Carotid Access Sheath. Sheath 13 comprises a central lumen 14 that traverses the length of the sheath from the distal end depicted in FIGS. 24A and 24B to the proximal end not shown. The central lumen is sized for use with an endovascular transmural ablation catheter, not shown, with a functional sheath diameter between 3 French and 12 French (e.g., about 6 French). Sheath 13 comprises a distal tip 15, a deflectable segment 16 proximal to the distal tip 15, and a non-deflectable segment 17 proximal to the deflectable segment 16. In addition, not shown, is a handle mounted at the proximal end of the catheter with an actuator configured for user-actuated deflection of the deflectable segment 16. A pull wire in communication between the distal tip 15 and the handle mounted actuator is configured to deflect the deflectable segment 16 in response to user actuation. The techniques for constructing a deflectable tipped sheath are known. Sheath 13 is adapted for endovascular transmural ablation of a carotid body in at least one of the following manners: the radius of curvature 18 and length 19 of the deflectable segment are configured for use in the vicinity of the carotid bifurcation with the radius of curvature 18 being between 5 mm and 20 mm, and the length of the deflectable segment 19 being between 10 mm and 25 mm. Additionally, distal tip 15 may comprise at least one electrode, not shown, configured for at least one of the following: transmural ablation of a carotid body, stimulation of a carotid body, blockade of a carotid body, stimulation of nervous function not associated with a carotid body, and blockade of nervous function not associated with the function of a carotid body. Central lumen 14 can be used to place into the region of the carotid bifurcation 4 an additional procedural instrument. A stimulation or blockade step can be used to locate a preferred position for transmural ablation of a carotid artery. Stimulation or blockade of nervous function not associated with a carotid body can be used to avoid damage to vital nervous structures such as a vagal nerve.

Figure 25:
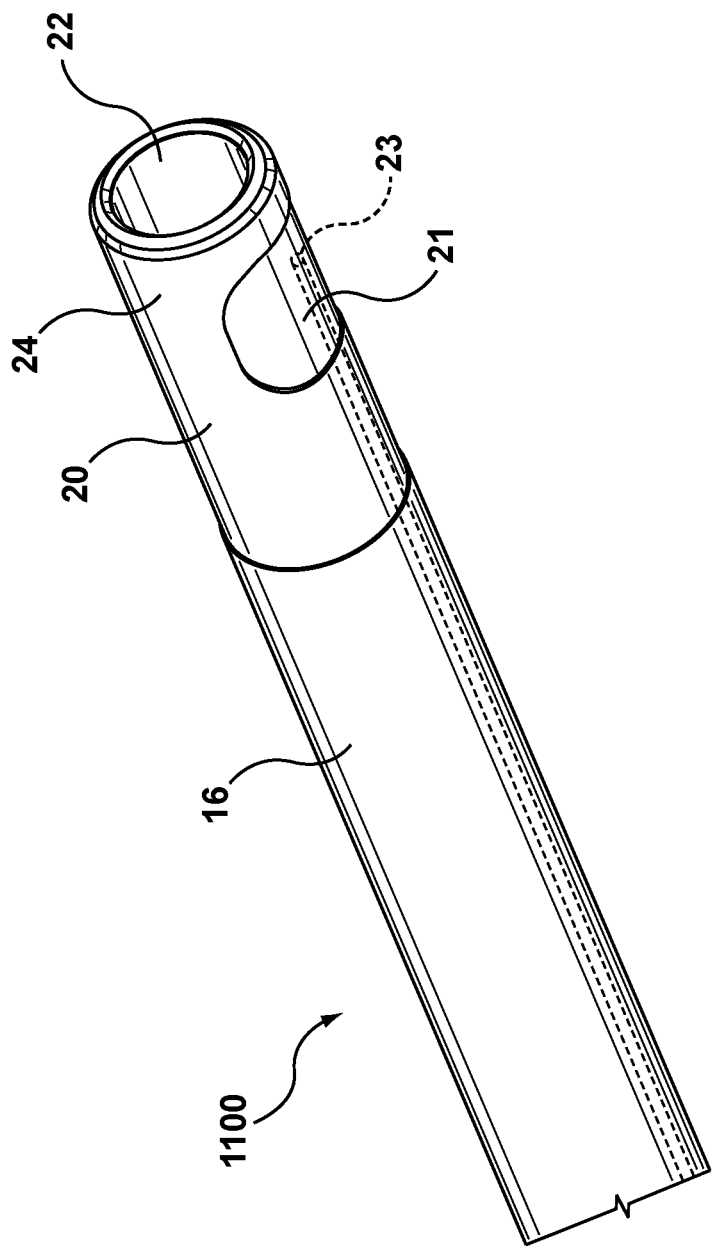
FIG. 25 is a schematic view of a steerable sheath with an ablation element.

FIG. 25 depicts the distal end of an arrangement of a sheath 1100 configured for transmural ablation of a carotid body. The distal ablation tip 20 comprises an electrode 21, a central lumen 22, a temperature sensor 23 mounted within the wall of the distal ablation tip 20 in the vicinity of the electrode 21, and a coating of electrically isolative material 24 disposed on the distal ablation tip 20 that defines the electrode surface 21 by its absence, as shown. The electrode 21 comprises a radial segment of the distal ablation tip between about 30 degrees and 180 degrees. The axial length of the electrode 21 is between about 4 mm and 8 mm. Proximal to the distal ablation tip 20 is a deflectable segment 16, as well as the following features not shown but described in the previous section: non-deflectable segment, handle, deflection actuator, and pull wire. The distal ablation tip is constructed of a biocompatible and radiopaque metal such as stainless steel or platinum. It has an outer diameter between 6 French and 12 French, an inner diameter between 5 French and 10 French defining the distal end of the sheath's central lumen 22, and a length between 5 mm and 10 mm. The distal ablation tip 20 also has a means for attaching a pull wire to the proximal end of the ablation tip 20, and a means for mounting a temperature sensor 23 within the wall of the ablation tip 20, and a means for attaching an electrical conductor, not shown to the distal tip. In addition to the features described in the in previous section, this arrangement of sheath 1100 comprises a means to connect the ablation tip 20, and the temperature sensor 23 to a source of ablation energy by means of an electrical connector mounted, not shown, in the vicinity of the handle, and electrical conductors, not shown, mounted in the wall of the sheath, in communication between the ablation tip 20, temperature sensor 23, and the electrical connector. In an alternate embodiment the sheath may comprise two electrodes disposed on distal tip 20 configured for bipolar RF ablation.

Figure 26:
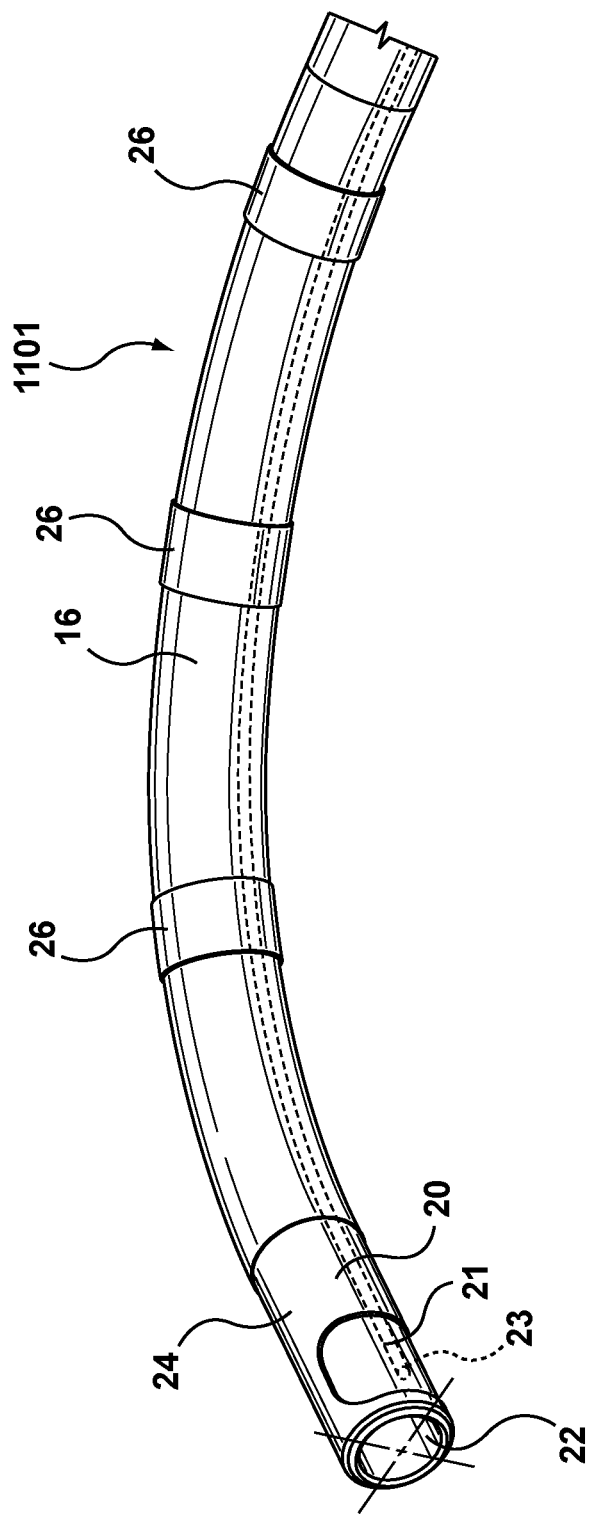
FIG. 26 is a schematic view of a steerable sheath with an ablation element in a deflected state.

FIG. 26 depicts the distal end of an optional arrangement of a sheath 1101, where the ablation electrode 21 is associated with the pull wire 25, shown in phantom, such that the electrode surface 21 is central to the radial position of the pull wire, and therefore the direction of the actuated deflection. This arrangement provides the user with a means to determine the position of the electrode within a carotid artery by fluoroscopically observing the direction of the deflection using the distal ablation tip, and the at least two radiopaque markers 26 mounted on the deflectable section 16 as visual references. In an alternative arrangement, the radiopaque markers 26 are also configured as electrodes for electrical nervous stimulation or blockade, more generally referred to as electrical neuro-modulation. In this arrangement, a means for connecting the at least two radiopaque electrodes 26 to a source of stimulation or blockade energy comprises electrical conductors in communication with the radiopaque electrodes 26, and an electrical connector mounted in the vicinity of the handle configured for connection to a source of stimulation or blockade energy.

Figure 27:
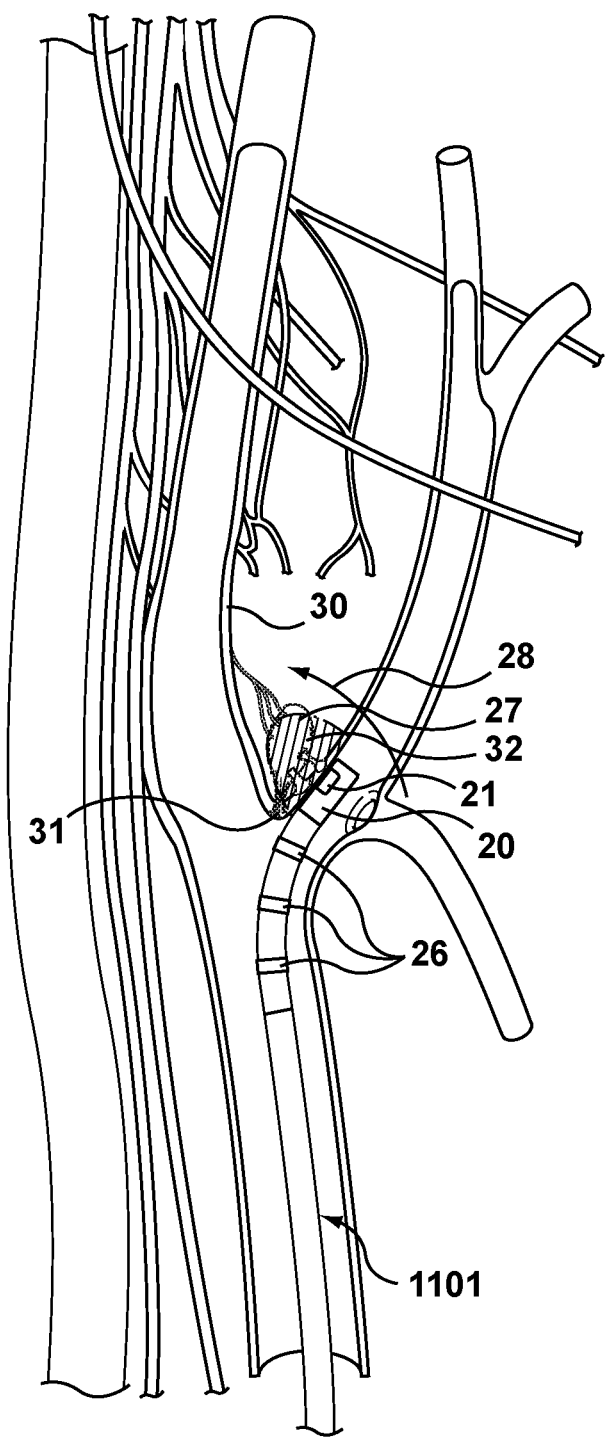
FIG. 27 is a cutaway illustration of a lateral view a patient's right carotid artery system with a schematic view of a steerable sheath positioning an ablation element proximate a target ablation site.

FIG. 27 depicts sheath 1101 from FIG. 26 in position for ablation of a carotid body 27 and illustrates the ablation agent delivered into the carotid septum. As depicted, the distal ablation tip electrode 21 has been radially oriented in the direction of the carotid body 27 by the user using fluoroscopic guidance with the distal tip 20 and the proximal radiopaque markers 26 serving a visual reference of the direction of an actuated deflection 28. In this depiction the carotid body 27 lies between the external carotid artery 29 and the internal carotid artery 30 just cranial to the carotid bifurcation 31. Since the location of a carotid body 27 within the region of a carotid bifurcation 31 substantially varies from patient to patient and from left side to right side in a single patient, and since the location of the carotid bifurcation is not determinable by fluoroscopic imaging techniques, the position and size of the carotid body is predetermined by other imaging modalities prior to positioning the sheath into the position shown in FIG. 27. The predetermined position and size of the carotid body provides the user with information necessary to select ablation parameters such that the zone of ablative effect 32 is substantially limited to the periarterial space comprising the carotid body 27. The user selectable ablation parameters for ablation with the sheath are radiofrequency power, electrode 21 temperature, duration of ablation activation and force of contact between the distal tip 21 and the wall of the external carotid artery 29 in this depiction. Note, that the user may also ablate the carotid body 27 from the internal carotid artery 30, or by placing the distal tip electrode 21 against the carotid bifurcation 31. In addition, if the anatomical circumstances of the patient dictate, carotid body 27 may be ablated by sheath 1101 from within an internal jugular vein 173 associated with a carotid body.

Distal Protection

Figure 28:
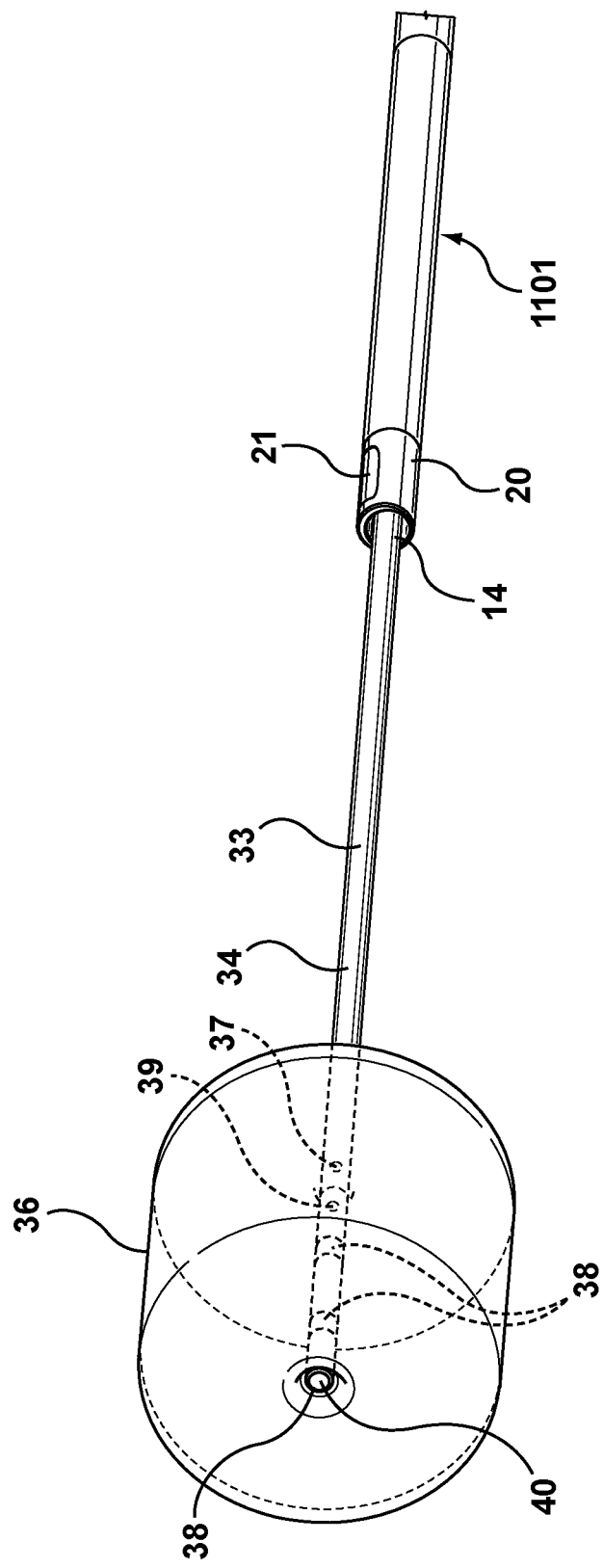
FIG. 28 is a schematic view of a distal protection balloon.

FIG. 28 depicts an embodiment showing a distal end of sheath 1101 with a distal embolic protection device ("DEPD") catheter 33 extending within central lumen 14 of sheath 1101. DEPD catheter 33 comprises a catheter shaft 34, with a central lumen 38 configured for use with a guide wire, not shown, an occlusion balloon 36 mounted in the vicinity of the distal end, at least one aspiration/irrigation fenestration 37 proximal to the occlusion balloon 36 and radiopaque markers 38 mounted within balloon 36, a balloon inflation port 39 in communication with a balloon inflation lumen, not shown, and a distal guide wire valve 40. The DEPD catheter shaft 34 may comprise at least a central lumen 38 and a balloon inflation lumen not shown. The central lumen 38 traverses the length of the DEPD catheter shaft 34 and is sized for use with a guide wire between 0.014" and 0.038" diameter. The central lumen 38 terminates at a proximal end, not shown with a female leur connection, or alternatively a Touy Borst connector. At the distal end of the catheter shaft 34 proximal to the occlusion balloon 36 is at least one aspiration/irrigation fenestration 37 in communication with the central lumen 38. At the distal end of the catheter shaft 34 distal to the occlusion balloon is a valve, not shown mounted in the central lumen 38. The valve is configured as a septum that fluidically isolates the central lumen 38 from blood surrounding the distal catheter shaft 34 when a guide wire is absent, but allows a guide wire to extend beyond the distal end of catheter shaft 34 when needed for guidance. This allows for the removal of the guide wire from the DEPD catheter 33 so that the central lumen 38 can then be dedicated for irrigation or aspiration of the proximal internal carotid artery 30 through the fenestration(s) 37.

Figure 29:
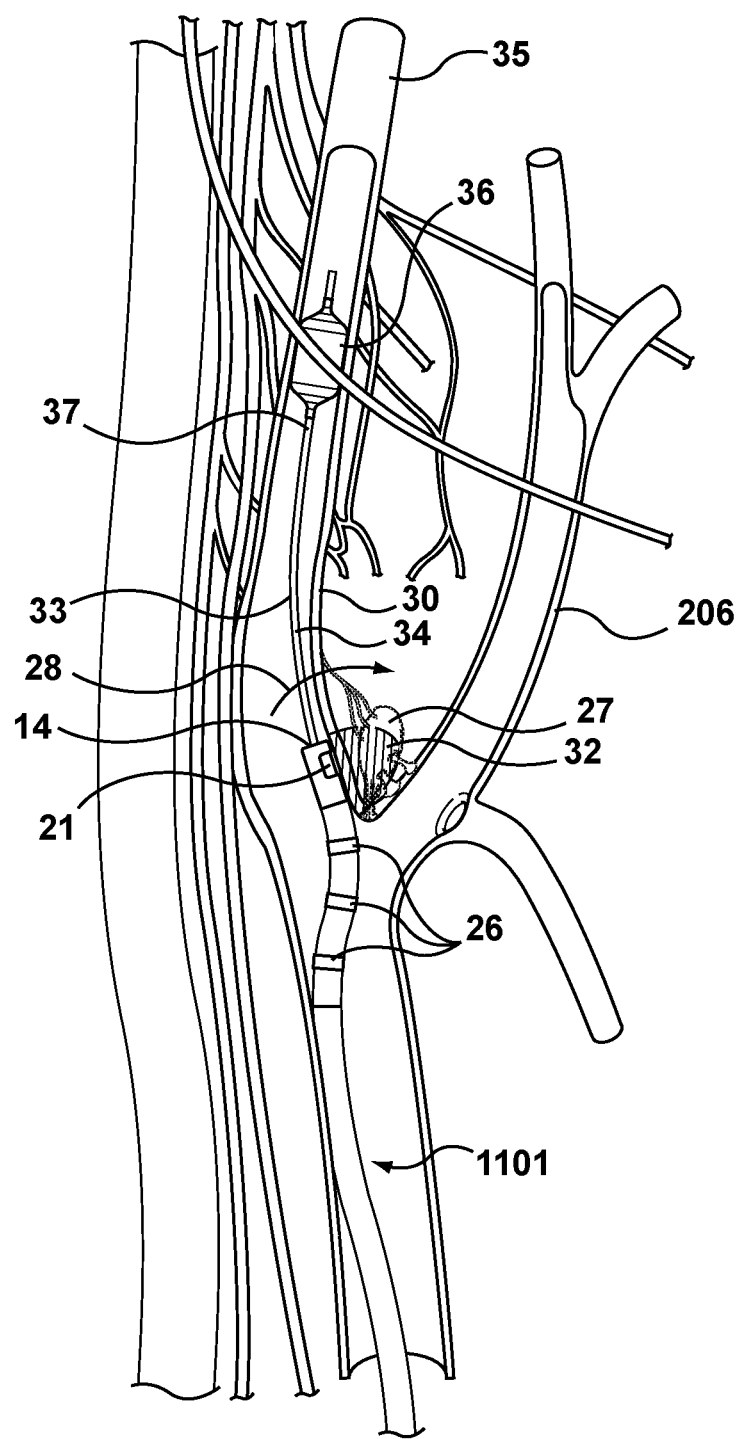
FIG. 29 is a cutaway illustration of a lateral view a patient's right carotid artery system with a schematic view of a steerable sheath positioning an ablation element on an inner wall of an internal carotid artery to transmurally ablate a carotid body, and a distal protection balloon delivered through the sheath.

FIG. 29 depicts sheath 1101 from FIG. 28 in position for ablation of a carotid body 27 and illustrates an ablation agent delivered to target tissue within the carotid septum immediately following an ablation. As depicted, the distal ablation tip electrode 21, residing in the internal carotid artery 30, has been radially oriented in the direction of the carotid body 27 by the user using fluoroscopic guidance with distal tip 20 and the proximal radiopaque markers 26 serving a visual reference of the direction of an actuated deflection 28. In addition DEPD catheter 33 is shown placed in the distal internal carotid artery 35 through the central lumen 14 of the sheath 1101. In this embodiment, the carotid body 27 is ablated with sheath 1101 while the brain is protected from embolic debris with the use of a DEPD catheter 33. An exemplary method of ablating the carotid body includes first determining the position and size of a target carotid body 27. The distal end of DEPD catheter 33 is then positioned into the distal internal carotid artery 35 associated with the carotid body 27 as shown using a guide wire and fluoroscopic imaging for guidance. The occlusion balloon 36 is then inflated using the balloon inflation means of the DEPD catheter 33. Sheath 1101 is advanced over the DEPD catheter shaft 34 into position in the proximal internal carotid artery 30 adjacent to the determined location of the carotid body 27. Using a combination of axial movement, rotational movement, and distal tip 20 deflection, the ablation electrode 21 is positioned against the wall of the internal carotid artery 30 at a location based at least in part on the determination of location and size of the carotid body 27. The ablation parameters are then selected, and the ablation is initiated. Next, either the proximal carotid artery 30 is irrigated with a physiological solution such as saline causing any debris resulting from the ablation trapped proximal to the occlusion balloon 36 to flow in a retrograde fashion from the proximal internal carotid artery 30 into and downstream in the external carotid artery 29 thereby preventing the debris from entering the patient's brain, or the proximal carotid artery 30 is aspirated, thereby removing any debris resulting from the ablation from the patient's body thereby preventing the debris from entering the patient's brain. The ablation is then ceased and sheath 1101 is withdrawn. The occlusion balloon 36 is deflated and the DEPD catheter 33 is withdrawn. Not all of the previous steps need to be performed, and the order of some steps can be changed as desired.

Bifurcation Coupling Guide Wires

Figure 30:
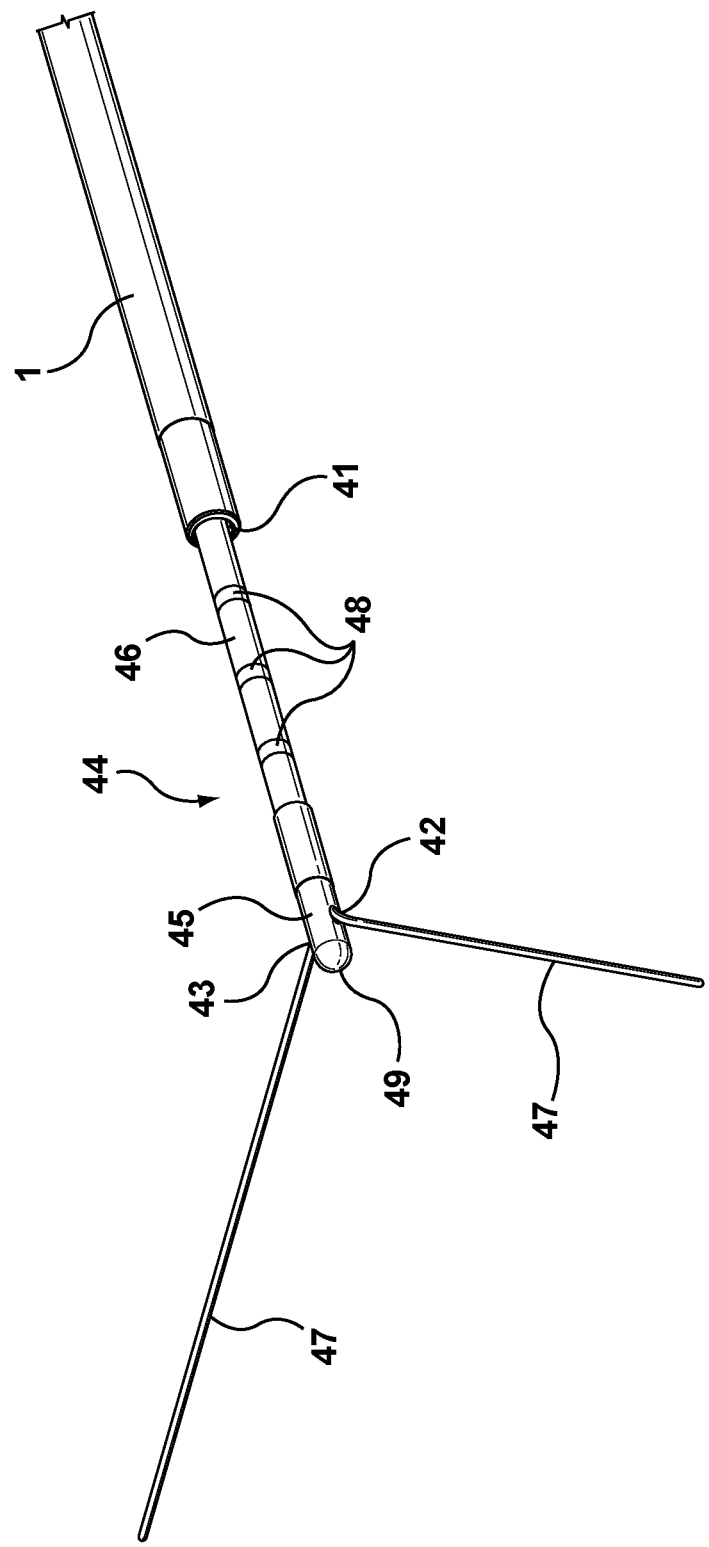
FIG. 30 is a schematic view of an ablation catheter with side exiting guide wires.

FIG. 30 depicts the distal end of carotid access sheath 1 with transmural ablation catheter 44 disposed within lumen 41 of sheath 1 and extending distally therefrom. Catheter 44 comprises two side exiting guide wire ports 42 and 43 (although catheter 44 may include more than two) and will herein be referred to as a 2-Wire catheter 44. The 2-Wire catheter includes an ablation element 45 mounted in the vicinity of the distal end. The two side exiting guide wire ports 43 and 42 are in substantial diametric opposition to each other in the vicinity of the distal end. Catheter 44 includes catheter shaft 46 comprising at least two guide wire lumens, not shown, in communication with guide wire ports 43 & 44, a connection that connects the ablation element 45 to an ablation energy source in the vicinity of the proximal end, not shown, and one or more guide wire fittings (not shown) for inserting a guide wire into the guide wire lumens at the proximal end, such as female leur fittings or Tuohy Borst fittings. The 2-Wire catheter is shown with first and second guide wires 47 exiting guide wire ports 42 and 43. Guide wire ports 42 and 43 may be configured such that guide wires 47 exit the guide wire ports 42 and 43 at an angle of approximately 45 degrees relative to each other as shown, or may be configured for a guide wire exit angle that is greater than or less than that depicted (e.g., between about 15 and 45 degrees). The guide wire port 42 and 43 and corresponding lumens may be configured for use with guide wire 47 between, for example, 0.014" and 0.018" diameter. The distance of the guide wire ports from the distal tip 49 may be fixed as depicted, or may be user selectable by a distance selection means, not shown. The distance between guide wire port 42 and the distal tip 49 may be the same or different than the distance between guide wire port 43 and distal tip 49. The distance between distal tip 49 and either of guide wire port 42 and 43 may be independently selectable by the user. The ablation element 45 may be configured as at least one radiofrequency ablation electrode, which may be associated with at least one temperature sensor, not shown. Ablation element 45 may be configured for monopolar or bipolar RF ablation. The ablation element may also be configured for cryo-ablation, and may be associated with at least one temperature sensor. Catheter shaft 46 may comprise at least one catheter shaft electrode 48 configured for electrical neuro-modulation. The ablation element 45 may be configured for electrical neuro-modulation independently or in conjunction with catheter shaft electrode(s) 40. The 2-Wire catheter 44 is configured for use with a carotid access sheath having a working length between about 100 cm and about 140 cm, and a diameter of 5 French to 8 French. The techniques for constructing the 2-Wire catheter as depicted are familiar to those skilled in the art of catheter making, and therefore are not further elaborated.

Figure 31:
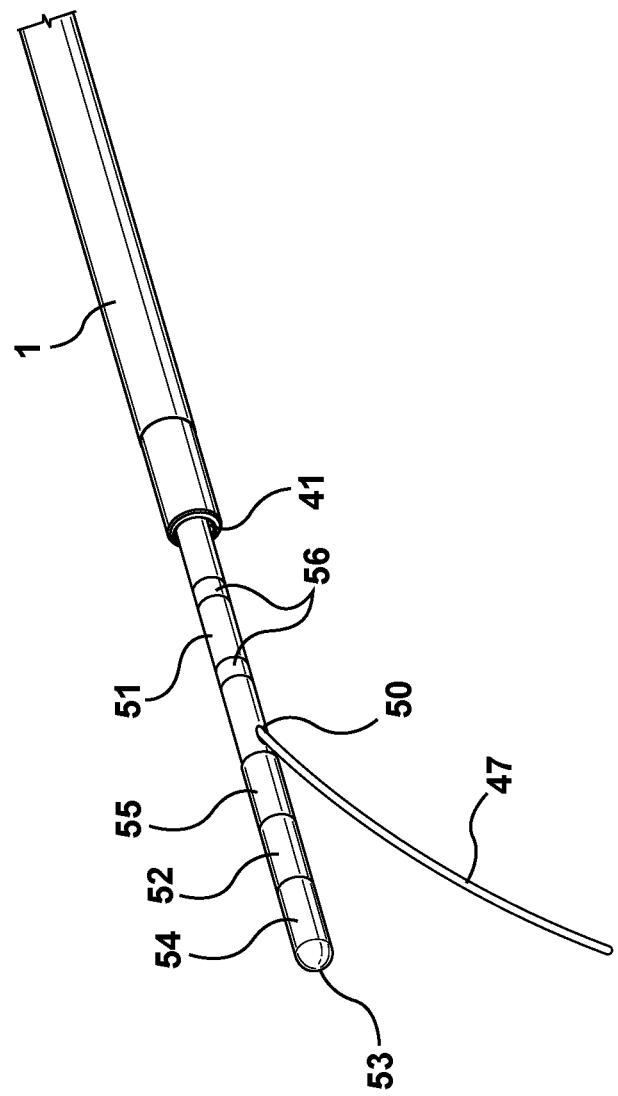
FIG. 31 is a schematic view of an ablation catheter with a side exiting guide wire

FIG. 31 depicts the distal end of carotid access sheath 1 with catheter 51 extending within lumen 41 of sheath and extending distally therefrom. Catheter 51 comprises a single side exiting guide wire port 50 and is herein referred to as a side-wire catheter 51. Port 50 extends from central lumen 41 of carotid access sheath 1. Catheter 51 comprises an ablation element 54 mounted in the vicinity of the distal end, and a side exiting guide wire port 50 in the vicinity of the distal end. Catheter 51 includes catheter shaft 52 comprising a guide wire lumen, not shown, in communication with guide wire port 50, a means to connect the ablation element 54 to an ablation energy source in the vicinity of the proximal end, not shown, and a means for inserting a guide wire into the guide wire lumen at the proximal end consisting of female leur fitting or Tuohy Borst fitting, not shown. Catheter 51 is shown with guide wire 47 exiting guide wire port 50. Guide wire port 50 may be configured such that guide wire 47 exits guide wire port 50 at an angle of approximately 45 degrees with respect to catheter shaft 52 as shown, or may be configured for a guide wire 47 exit angle that is greater than or less than that depicted (e.g., between about 15 and 45 degrees). Guide wire port 50 and corresponding lumen may be configured for use with a guide wire between 0.014" and 0.018" diameter. The distance of the guide wire port 50 from the distal tip 53 may be fixed as depicted, or may be user selectable by a distance selection means, not shown. Ablation element 54 may be configured as at least one radiofrequency ablation electrode, which may be associated with at least one temperature sensor, not shown. Ablation element 54 may be configured as one electrode and proximal ablation electrode is configured as one electrode in a bipolar radiofrequency ablation relationship. Alternatively, ablation element 54 may also be configured for cryo-ablation, and may be associated with at least one temperature sensor. Ablation element 54 may comprise an electrode configured for electrical neuro-modulation. Proximal ablation electrode 55 may also be configured for electrical neuro-modulation independently or in conjunction ablation element 54. The catheter shaft 46 may further comprise at least one catheter shaft electrode 56 configured for electrical neuro-modulation. Ablation element 54 or proximal ablation electrode 55 may be configured for electrical neuro-modulation independently or in conjunction with catheter shaft electrode(s) 56. Catheter 51 is configured for use with a carotid access sheath 1 having a working length between 100 cm and 140 cm, and a diameter of 5 French to 8 French. The techniques for constructing catheter 51 as shown are familiar to those skilled in the art of catheter making, and therefore are not further elaborated.

Figure 32:
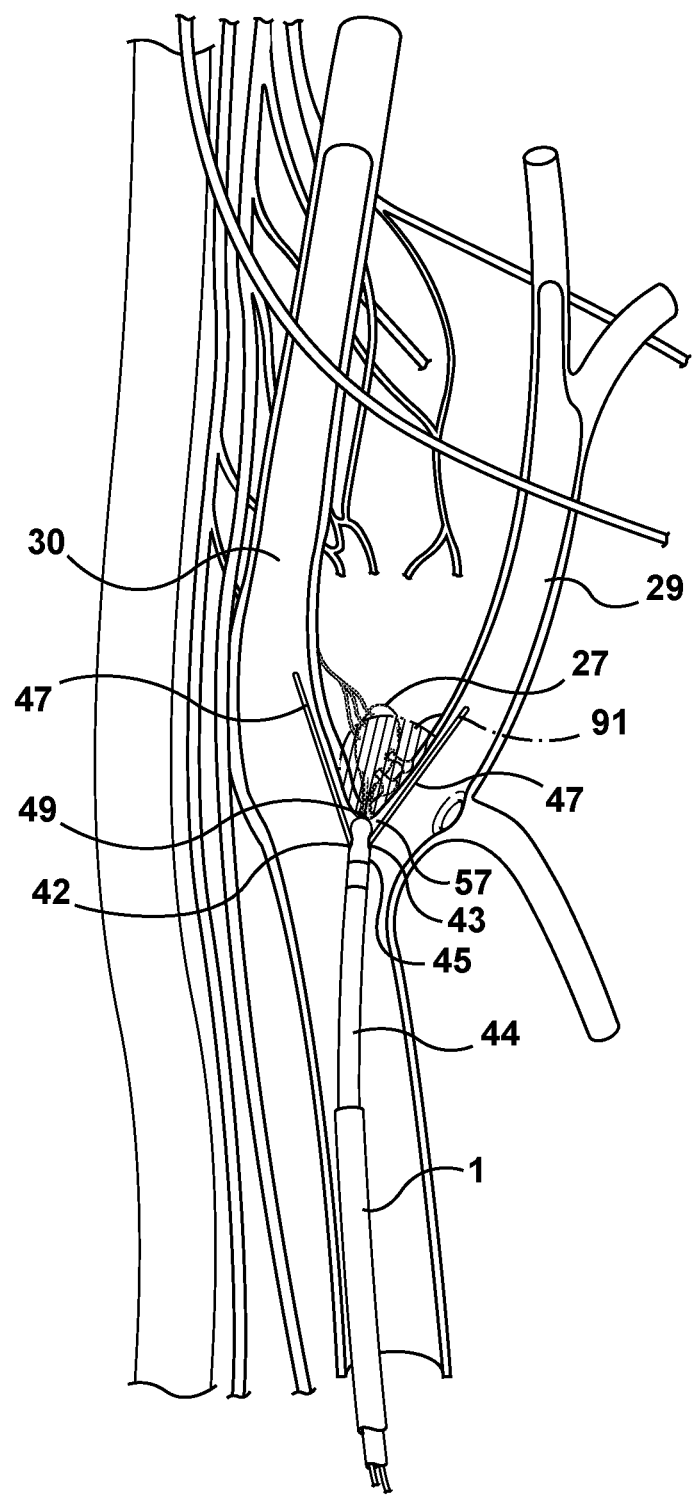
FIG. 32 is a cutaway illustration of a lateral view a patient's right carotid artery system with a schematic view of an ablation catheter, with side exiting guide wires, positioning an ablation element on an inner wall of a carotid bifurcation to transmurally ablate a carotid body.
Figure 33:
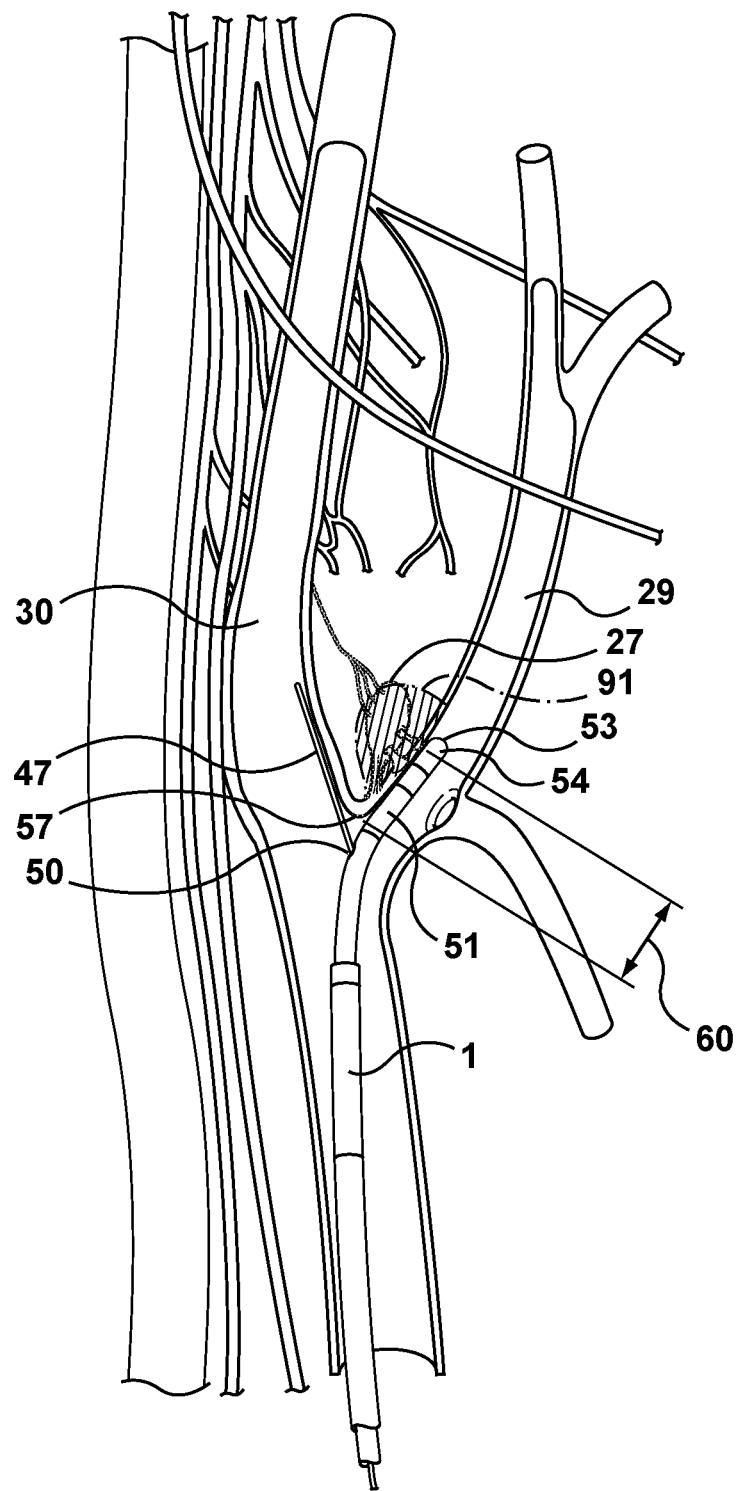
FIG. 33 is a cutaway illustration of a lateral view a patient's right carotid artery system with a schematic view of an ablation catheter, with side exiting guide wires, positioning an ablation element on an inner wall of an external carotid artery to transmurally ablate a carotid body.

FIG. 32 illustrates catheter 44 (shown in FIG. 30) in position for ablation of a carotid body 27 and ablation zone 58 immediately following an ablation. As depicted the distal tip 49 of ablation element 45 is positioned against the bifurcation carotid bifurcation saddle 57, with a guide wire 47 exiting side guide wire port 42 into the internal carotid artery 30, and a second guide wire 47 exiting side port 43 into the external carotid artery 29 as shown. The guide wires 47 provide a means for positioning and maintaining the distal tip 49 of ablation element 45 approximately centered at the bifurcation saddle 49 in a stable manner during ablation. The ablation zone 58 is depicted encompassing the periarterial space comprising the carotid body 27. Also depicted is the carotid access sheath 1 used for placement of catheter 44 into the common carotid artery 59.

FIG. 32 depicts catheter 51 (from FIG. 31) in position for ablation of a carotid body 27 and the ablation zone immediately following an ablation 91. As depicted, ablation element 54 is positioned against the wall of the external carotid artery 29 at a position distal to the carotid bifurcation saddle 57, which distance 60 as shown was predetermined prior to the placement of the catheter 51. A guide wire 47 exiting side guide wire port 50 is positioned into the internal carotid artery 30. The guide wire 47 in conjunction with guide wire port 50 provide a means for positioning the ablation element 54 against the wall of the external carotid artery 29 at a predetermined distance 60 based on the distance between the distal tip 53 and the guide wire port 50. The force of contact between the ablation element 54 and the wall of the external carotid artery 29 can be influenced by the selection of the stiffness or diameter of the guide wire 47, the angle of exit of the guide wire 47, as well as the distance between the distal tip 53 and the guide wire port 50. For example, a force of contact that distends an ablation element into a wall of an external carotid artery about 1 to 3 mm may facilitate production of a suitable ablation when delivering radiofrequency. The ablation zone 91 is depicted encompassing the periarterial space comprising the carotid body 27. Also depicted is the carotid access sheath 1 used for placement of catheter 51 into the common carotid artery. Alternatively, guide wire 47 may be positioned in external carotid artery 29, and ablation element 54 may be positioned into the internal carotid artery 30, an illustration of which is not shown.

Bipolar Assembly

Figure 34C:
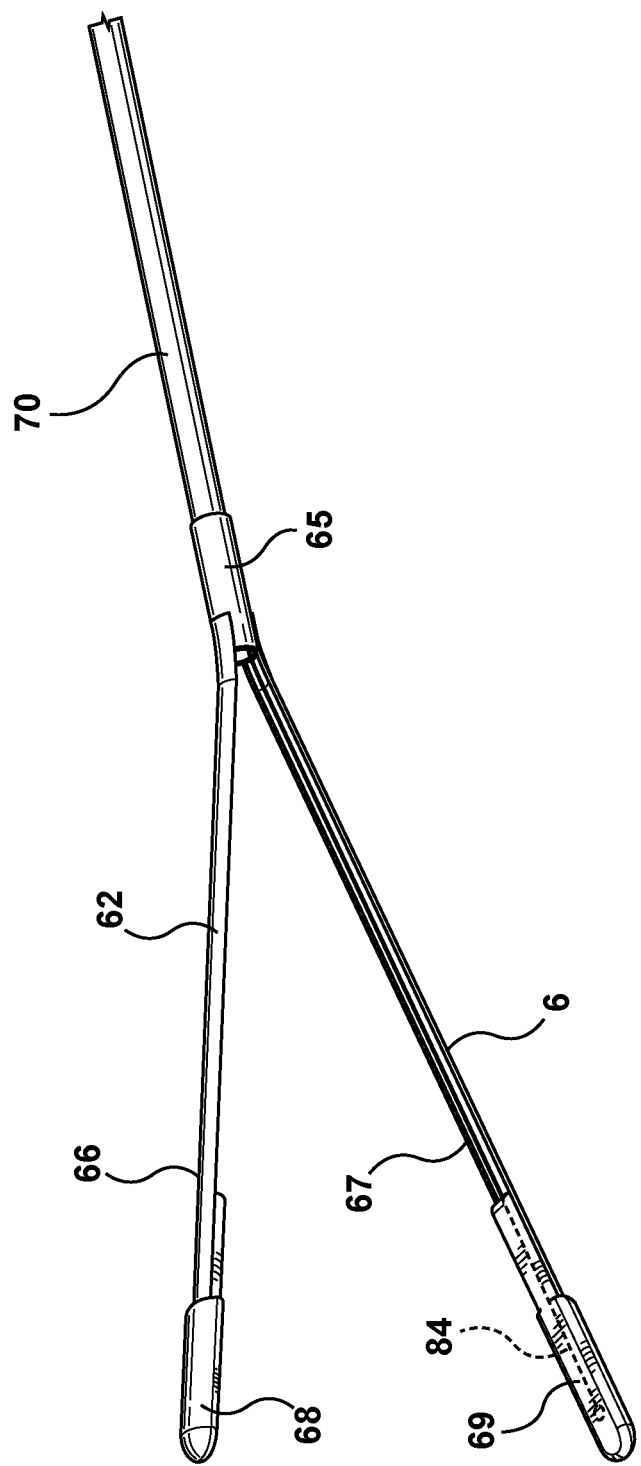
Figure 34D:
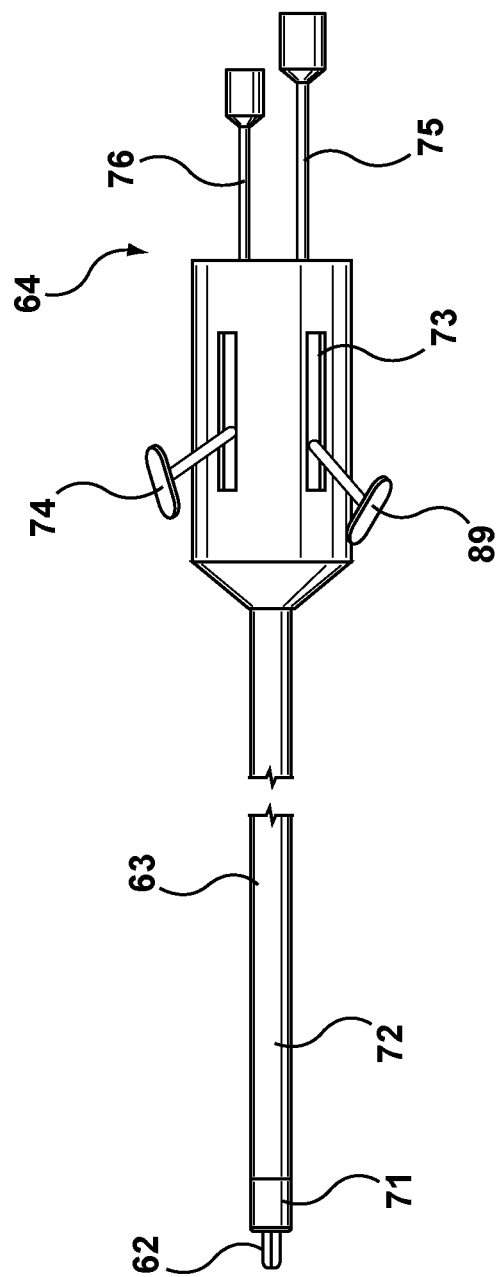

FIGS. 34A-34D depict an exemplary catheter 61 that includes forceps. Catheter 61 comprises forceps assembly 62, forceps sheath 63, and a proximal terminal 64. The forceps assembly 62 comprises jaw 65 and two jaw struts 66 and 67 extending therefrom (see FIG. 34C), and tube 70 to which jaw 65 is mounted at its distal end. A first jaw pad 68 is mounted at the end of jaw strut 66, and a second jaw pad 69 mounted on the end of jaw strut 67. The forceps sheath 63 comprises a distal tip 71 and a sheath shaft 72. Mounted on the proximal end of the sheath shaft 72 is proximal terminal 64 comprising handle 73, forceps actuator 74, electrical connector 75, and a hub and tube 76 in communication with tube 70. Optionally, forceps sheath 63 may be configured with a user deflectable segment 77 (FIG. 34B) proximal to the distal tip 71, and a non-deflectable segment 78 immediately proximal to the deflectable segment 77. Proximal terminal 64 may further comprise a deflectable segment actuator 89 which is in communication with deflectable segment 77 by means of a pull wire, not shown. The forceps assembly 62 is disposed within forceps sheath 63 in a slidable relationship. Forceps jaw struts 66 and 67 are constructed to be biased to an open configuration as depicted in FIG. 34B. When the forceps sheath 62 is advanced forward with respect to the forceps assembly, forceps jaw struts 66 and 67 are forced towards one another by distal tip 71 of sheath 62. When the forceps sheath 63 is fully advanced over forceps assembly 62 the forceps pads 68 and 69 are in a closed position as depicted in FIG. 12A. The advancement and retraction of the forceps sheath 63 over the forceps assembly 62 is controlled by actuator 74 mounted in proximal terminal handle 73. The pinching force of the forceps pads on tissue is also controlled by actuator 74. Actuator 74 may optionally provide means, not shown, for the user to select a forceps pad contact force, observe by means of a force gage a contact force, or to provide the user with a tactile feedback of the contact force. Forceps pad 68 may be configured as an electrode whereby inner surface 80 may be bare metal and outer surface 81 may be insulated. Forceps pad 68 may be configured as an electrode whereby a portion of outer surface 81 is bare metal and where inner surface 80 is may be insulated. Forceps pad 68 may be configured as an electrode with a temperature sensor 82 mounted within the walls of forceps pad 68. Temperature sensor lead wire(s) 83 connect temperature sensor 82 to electrical connector 75 of proximal terminal 64 through central tube 70. Forceps pad 69 may be configured as an electrode whereby inner surface 84 may be bare metal and outer surface 85 may be insulated. Forceps pad 69 may be configured as an electrode whereby a portion of outer surface 85 is bare metal and where inner surface 84 is may be insulated. Forceps pad 69 may be configured as an electrode with a temperature sensor 82 mounted within the walls of forceps pad 69. Temperature sensor lead wire(s) 83 connect temperature sensor 82 to electrical connector 75 of proximal terminal 64 through central tube 70. Forceps pad 68 may be solid metal, or a polymer/metal composite structure or a ceramic/metal composite structure. Forceps 69 may also be solid metal, or a polymer/metal composite structure or a ceramic/metal composite structure. Forceps jaw struts 66 & 67 may be fabricated from a super-elastic metallic alloy such as Nitinol, but may be fabricated from another metallic alloy, or may be a composite structure. Central tube 70 may be fabricated from a super-elastic alloy, or may be constructed from another metallic alloy, or may be composite structure. Central tube 70 is configured to work in conjunction with forceps actuator 74 a to apply a tensile force on the forceps assembly 62 for advancement of forceps sheath 63 over forceps assembly 62 to close forceps, and to apply a compressive force on the forceps assembly 62 to withdraw forceps sheath 63 from over forceps assembly 62 to open forceps. Central tube 70 can be configured as an electrical conduit between forceps pad 68 or forceps pad 69 and electrical connector 75. Alternatively, center tube 70 may be configured with wires to connect forceps pad 68 or forceps pad 69 to electrical connector 75. Electrical connector 75 is configured to connect an electrode surface on forceps pad 68 or an electrode surface of forceps pad 69 to one pole of an electrical generator. Electrical connector 75 may be configured to connect an electrode surface of forceps pad 68 to one pole of an electrical generator, and to connect an electrode surface of forceps pad 69 to the opposite pole of an electrical generator. An electrical generator may be configured for connection to electrical connector 75 and to supply RF ablation current to an electrode surface on forceps pad 68 or an electrode surface on forceps pad 69. The electrical generator may be further configured to provide an electrode surface on forceps pad 68 with neural stimulation current or neural blockade current or to provide an electrode surface on forceps pad 69 with neural stimulation current or neural blockade current. Forceps pads 68 and 69 may be constructed in a manner where their fluoroscopic appearance is distinct to provide the user with an ability to distinguish forceps pad 68 from forceps pad 69. The techniques for constructing the catheter 61 are familiar to those skilled in the art, and therefore are not further described.

Figure 35:
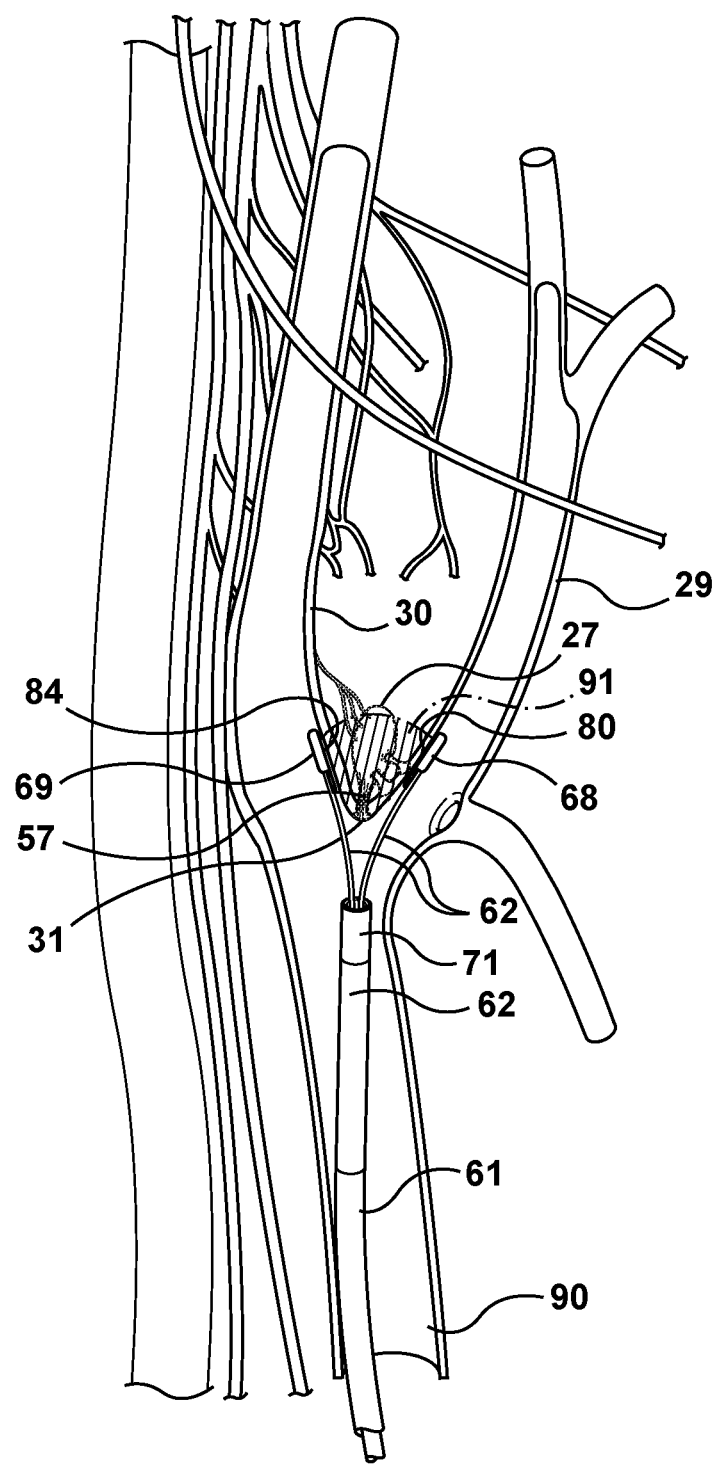
FIG. 35 is a cutaway illustration of a lateral view a patient's right carotid artery system with a schematic view of an endovascular ablation catheter having deployable arms with ablation elements positioned in the patient's internal and external carotid arteries for transmural ablation of a carotid body.

FIG. 35 depicts catheter 61 in position for ablation of a carotid body 27 and ablation zone 91 immediately following an ablation. Catheter 61 is positioned in the vicinity of the carotid bifurcation 31 with the distal sheath tip 71 just proximal to the carotid bifurcation 31, with forceps pad 68 positioned against the wall of the external carotid artery 29, and forceps pad 69 positioned against the wall of the internal carotid artery 30. Forceps sheath 63 has been advanced over forceps assembly 62 to apply a squeezing force on the carotid bifurcation saddle 57 within which lies the carotid body 27. In one embodiment depicted here, inner surface 80 of forceps pad 68 is configured as an electrode. In an additional embodiment, inner surface 84 of forceps pad 69 is configured as an electrode. In another embodiment inner surface 80 of forceps pad 68 and inner surface 84 of forceps pad 69 are configured as electrodes, where inner surface 80 and inner surface 84 are connected to the same pole, or opposite poles of an electric generator. The electrical generator may be configured to supply RF ablation current, or neural stimulation current or neural blockade current. During RF ablation the squeezing force of forceps 62 enhances ablation by compressing the bifurcation saddle 57 to reduce the distance of the carotid body 27 from the inner surfaces 80 and 84, and to substantially reduce the blood flow within the bifurcation saddle, and associated convective cooling normally associated with interstitial blood flow. In addition to the embodiment where catheter 61 is configured for electrical neural stimulation, the carotid body 27 may be located by squeezing the saddle as depicted. Since the carotid body is a chemoreceptor whose function is to signal hypoxia, squeezing results in ischemic hypoxia within the bifurcation saddle 57, which causes the carotid body to signal for a user detectable physiological response to ischemia induced by the forceps.

Figure 36:
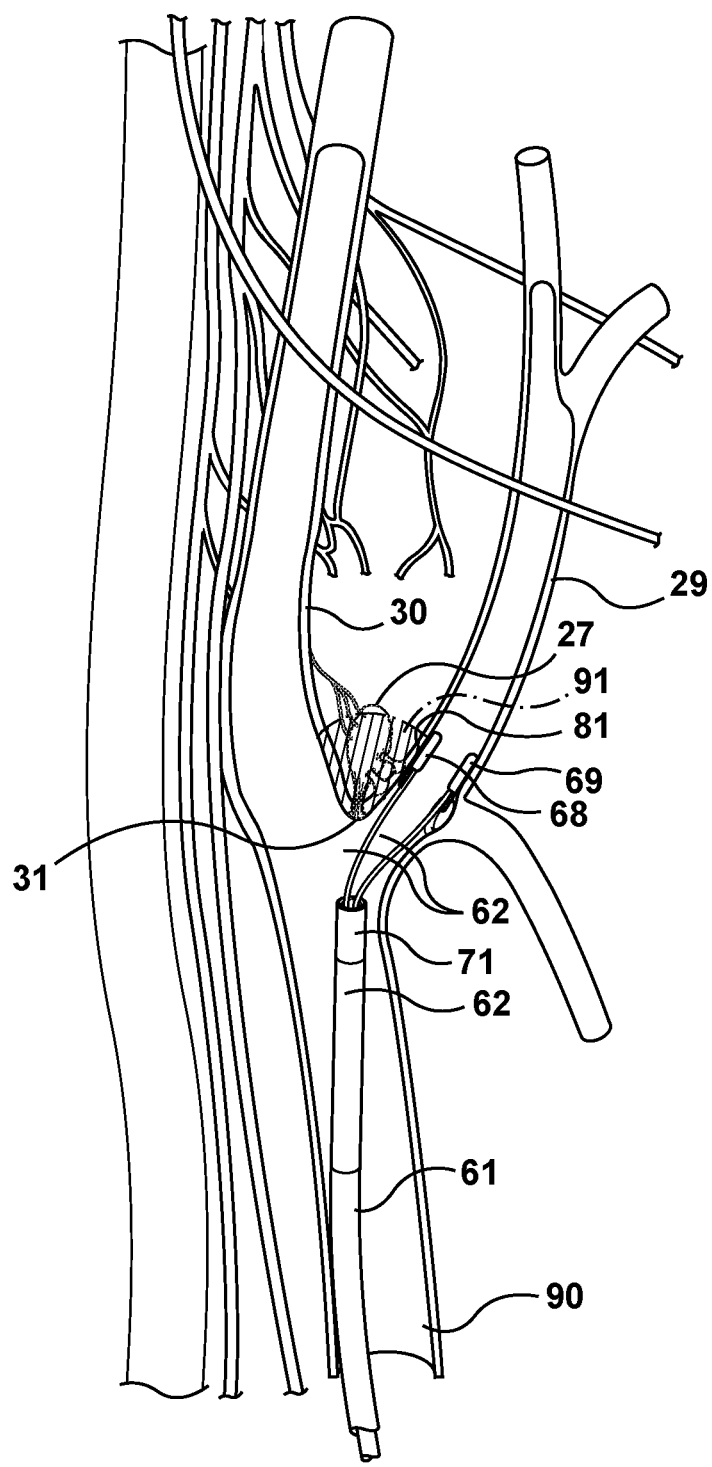
FIG. 36 is a cutaway illustration of a lateral view a patient's right carotid artery system with a schematic view of an endovascular ablation catheter having deployable arms with ablation elements positioned in the patient's external carotid artery for transmural ablation of a carotid body.

FIG. 36 depicts catheter 61 in position for ablation of a carotid body 27 and ablation zone 91 immediately following an ablation. Catheter 61 is positioned in the vicinity of carotid bifurcation 31 with the distal sheath tip 71 just proximal to the carotid bifurcation 31 with forceps pad 68 positioned against the wall of the external carotid artery 29 proximate to carotid body 27, and with forceps pad 69 against the wall of the external carotid artery 29 approximately in diametric opposition to forceps pad 68. In this embodiment, outer surface 81 of forceps pad 68 is configured as an electrode, which may be used for RF ablation, electrical neural stimulation, and electrical neural blockade. Forceps pad 69 is constructed to be fluoroscopically distinct from forceps pad 68 so that the user has a substantially unambiguous indication of the location of forceps pads 68 and 69 within the external carotid artery 29 (e.g., location along a length of the artery and rotational specification within the artery). Force of contact of forceps pad 68 against the wall of the external carotid artery 29 may be user adjusted by the degree of advancement of the ETAF sheath 61 over the forceps assembly 62 by the forceps actuator 74 not shown. It is noted that the ETAF catheter can be used in a similar manner with the forceps pads 68 & 69 positioned within the internal carotid artery 30. Carotid body 27 may also be ablated by ETAF catheter 61 from internal jugular vein 173 if warranted.

Endovascular Transmural Ablation Suction Catheter

Figure 37:
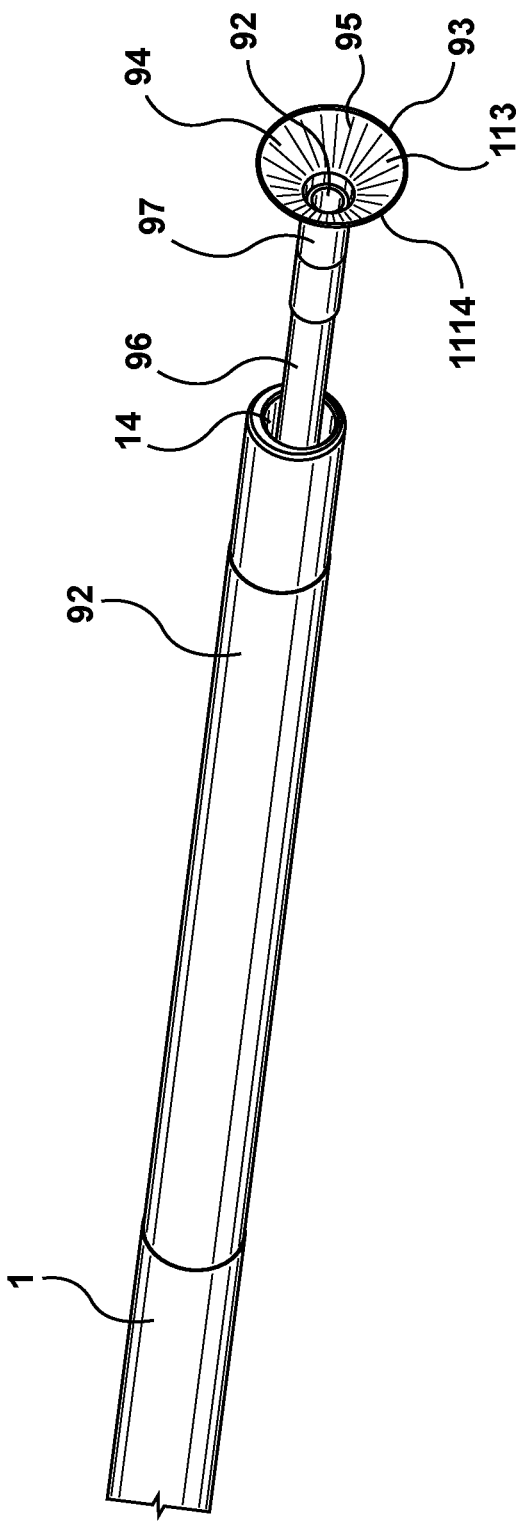
FIG. 37 is a schematic view of an endovascular ablation catheter having a suction element with a radiofrequency electrode on a contact surface of the suction element.

FIG. 37 depicts the end of an endovascular transmural ablation suction catheter 92 extended through a steerable carotid access sheath 1. The catheter comprises catheter shaft 96 with a central lumen 97, a suction cup 93 mounted on the distal end of catheter shaft 96, and a proximal terminal 100 disposed at the proximal end of catheter shaft 96. The catheter is configured for use through a steerable carotid access sheath 1, which has a similar arrangement to the carotid access sheath depicted in FIGS. 24A and 24B. The suction cup 93 comprises a conical structure with a tissue contact surface 113. Disposed on tissue contact surface 113 is at least one electrode wire 94, and optionally at least one temperature sensor 95. In this embodiment suction cup 93 is fabricated from an elastomeric material, which may be a silicone rubber. The diameter of suction cup 93 outer flange 1114 is between about 2 mm and about 10 mm when in an expanded position as shown. Suction cup 93 is configured to collapse within catheter 92 during insertion of the catheter through the central lumen 14 of carotid access sheath 1 and deploy into a use position, which is the position depicted in FIG. 37. The wall thickness of the conical section of suction cup 93 is between about 0.1 mm and about 0.5 mm, which may taper across the wall section. Electrode wire(s) 94 may be molded into the wall of suction cup 93 or may be bonded to contact surface 113. Electrode 94 may be at least one wire disposed in a radial manner as shown. Electrode 94 may be at least one wire disposed in a spiral manner, not shown. Electrode 94 may comprise a woven or knitted wire structure. Temperature sensor 95 may be molded into the wall of suction cup 93, or may be bonded to contact surface 113. Wires are configured to connect electrode 94 and temperature sensor 95 within catheter shaft 96 to a connector disposed in the vicinity of the proximal terminal 100 not shown. The central lumen 97 is in fluidic communication between the suction cup and fluid connector 108 disposed in the vicinity of proximal terminal 100, not shown. Catheter shaft 96 may be fabricated from a polymer material such as Pebax or polyurethane, of may be fabricated from a superelastic metal alloy such as Nitinol. Radiopaque marker 97 provides the user with a substantially unambiguous fluoroscopic indication of the position of the suction cup during use. In some embodiments the working length of the catheter is between about 100 cm and about 140 cm.

Figure 38:
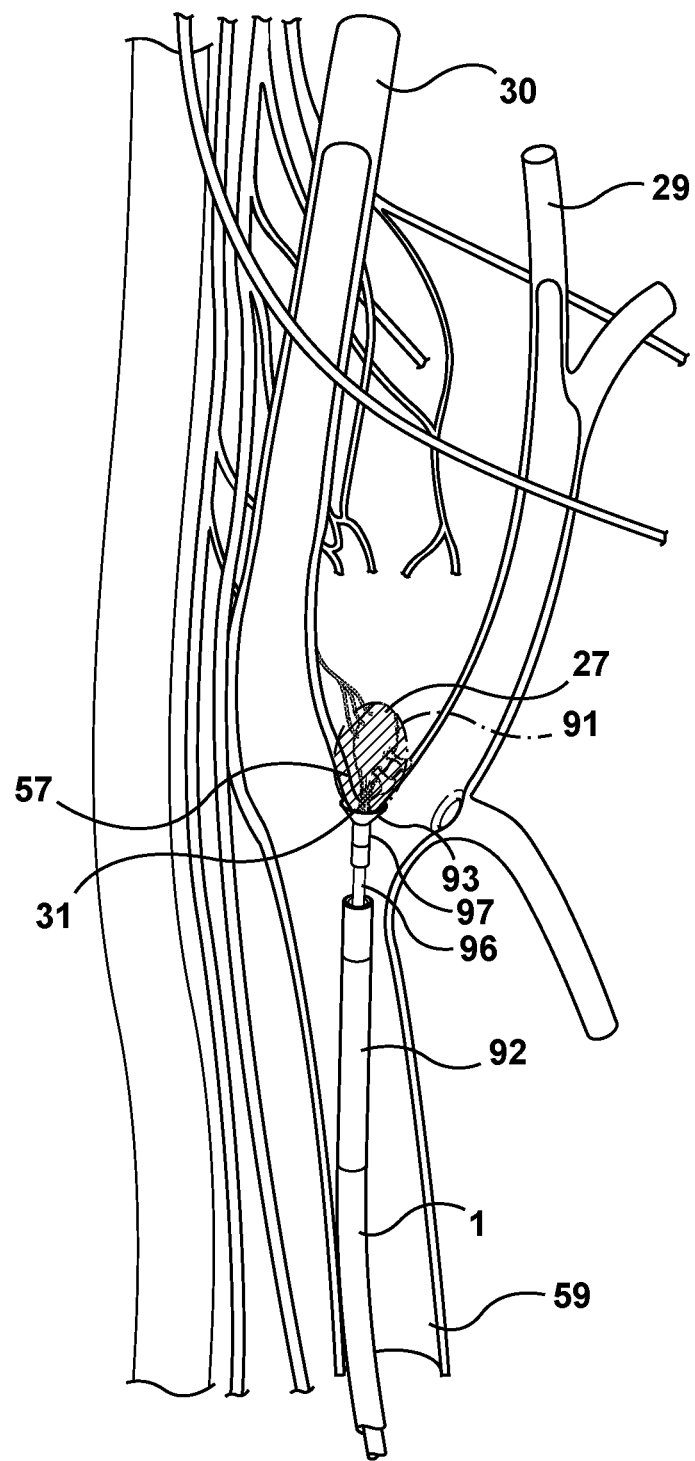
FIG. 38 is a cutaway illustration of a lateral view a patient's right carotid artery system with a schematic view of an endovascular ablation catheter having a suction element with a radiofrequency electrode on a contact surface of the suction element positioned on a carotid bifurcation for transmural ablation of a carotid body.

FIG. 38 depicts catheter 92 in position for ablation of a carotid body 27 and immediately following an ablation 91. Suction cup 93 is shown in position against the carotid bifurcation saddle 57 being held in place by applying suction to the inner contact surface 113 of suction cup 93 through central lumen 97. Suction maintains firm contact between the tissue and the electrode 94 while RF electrical energy is applied to electrode 94 at a sufficient level and duration to substantially ablate carotid body 27.

Figure 39:
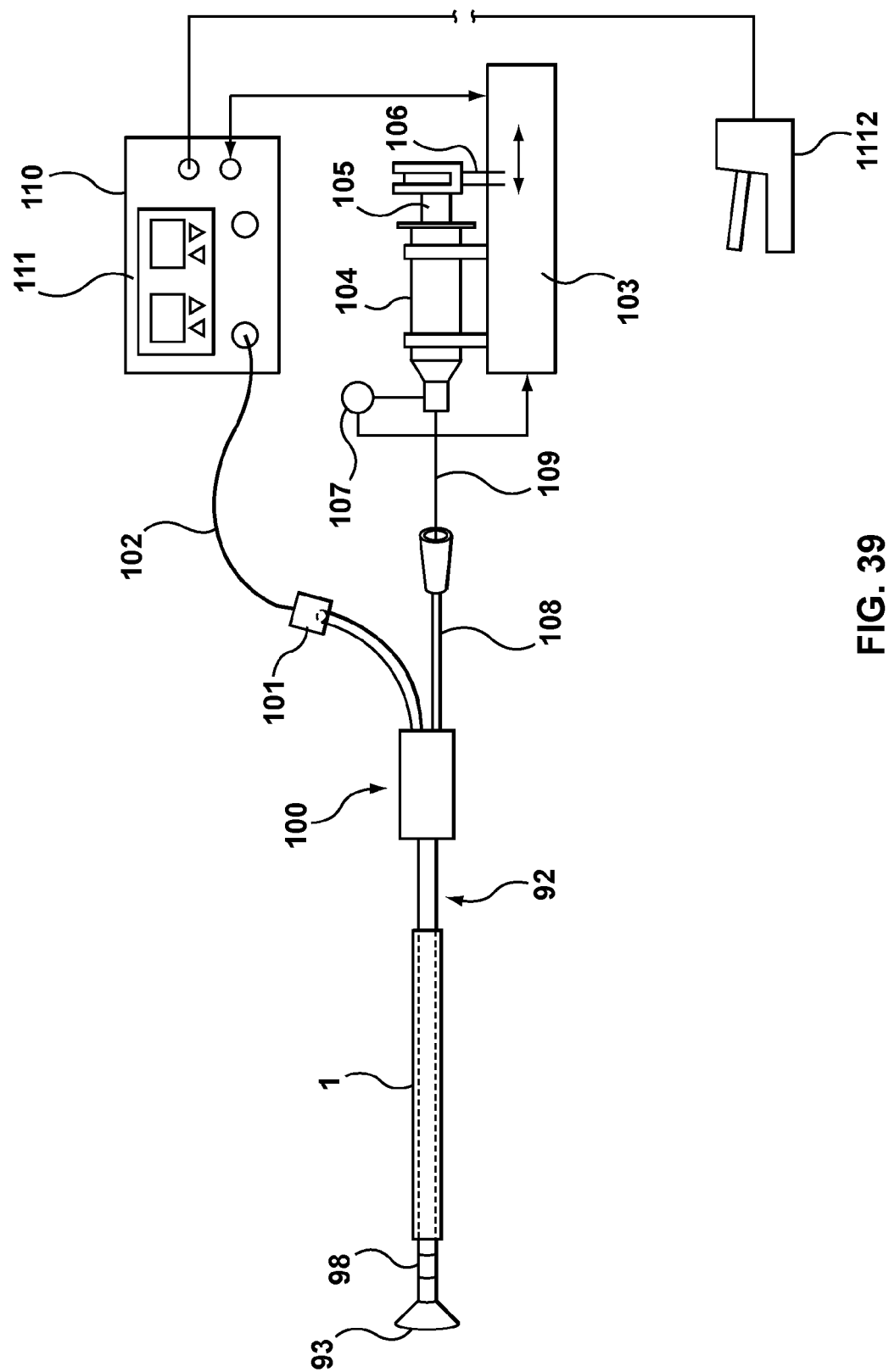
FIG. 39 is a schematic view of an endovascular ablation catheter having a suction element with a radiofrequency electrode on a contact surface of the suction element.

FIG. 39 depicts in schematic form an exemplary system for carotid body 27 ablation using catheter 92. The system comprises catheter 92, a carotid access sheath 1, control module 110, a suction module 103, a foot switch 1112, and cable 102 that connects the ETAS catheter 92 to the control module 110. The control module 110 comprises a source of RF ablation energy, a means to control the ablation energy based on user selection of power control algorithms, and or by means of temperature control algorithms based signals from temperature sensor(s) 95, a suction module controller that responds to vacuum sensor 107, and foot switch 1112, a user interface 111 that provides the selection of ablation parameters, an indication of the status of the system, an actuator for initiating an ablation and terminating an ablation. Suction module 103 may comprise a syringe 104, a syringe actuator 106, and a vacuum sensor 107. An actuator (e.g., a foot switch 1112) is configured to actuate suction by switch depression, and deactivate suction upon removal of said depression. In an exemplary method, the system is used as follows. Carotid access sheath 1 is inserted into a patient and the distal end is positioned within a common carotid artery 59. The catheter is inserted into the proximal central lumen 41 of carotid access sheath 1 and advanced through central lumen until the suction cup 93 extends beyond the carotid access sheath 1. Suction cup 93 is maneuvered using fluoroscopic guidance into contact with the carotid bifurcation saddle 57. Foot switch 1112 is depressed, thus activating suction module 103 in the following manner: syringe actuator 106 is moved to the right resulting in suction; vacuum pressure is continuously monitored by vacuum sensor 107; when vacuum pressure reaches a predetermined level between about 10 mm Hg and about 100 mm Hg the syringe movement is stopped, and an ablation interlock is removed allowing user actuated ablation; if the vacuum pressure decays to a level below the predetermined level, then the syringe actuator 106 is again moved to the right until the predetermined vacuum level is re-achieved. If the predetermined level cannot be achieved initially, or re-achieved within a syringe volume displacement between about 1 cc and about 20 cc then the ablation interlock remains in activation, or is reactivated, and the blood removed from the patient by the suction module is reinserted back into the patient. User interface 111 is configured to provide the user with an indication of the status of suction module 103, as well as the status of the ablation interlock. Once suction is established and the ablation interlock is removed the user may activate ablation using parameters selectable through the control module 110 user interface 111. Once the ablation is complete, the suction is removed. Catheter 92, and the carotid access sheath 1, are then withdrawn from the target area.

Control module 110 may be configured to supply electrode(s) 94 with neural stimulation energy, or neural blockade energy. The catheter may also be configured to work with a needle device used to access the periarterial space of the carotid bifurcation saddle 57 for the purposes of applying ablation energy, neural stimulation energy, neural blockade energy, neural stimulation chemicals, neural blockade chemical, or placement of a temperature sensor. The control module 110 may be configured to supply and control the function of said needle device(s).

Figure 40:
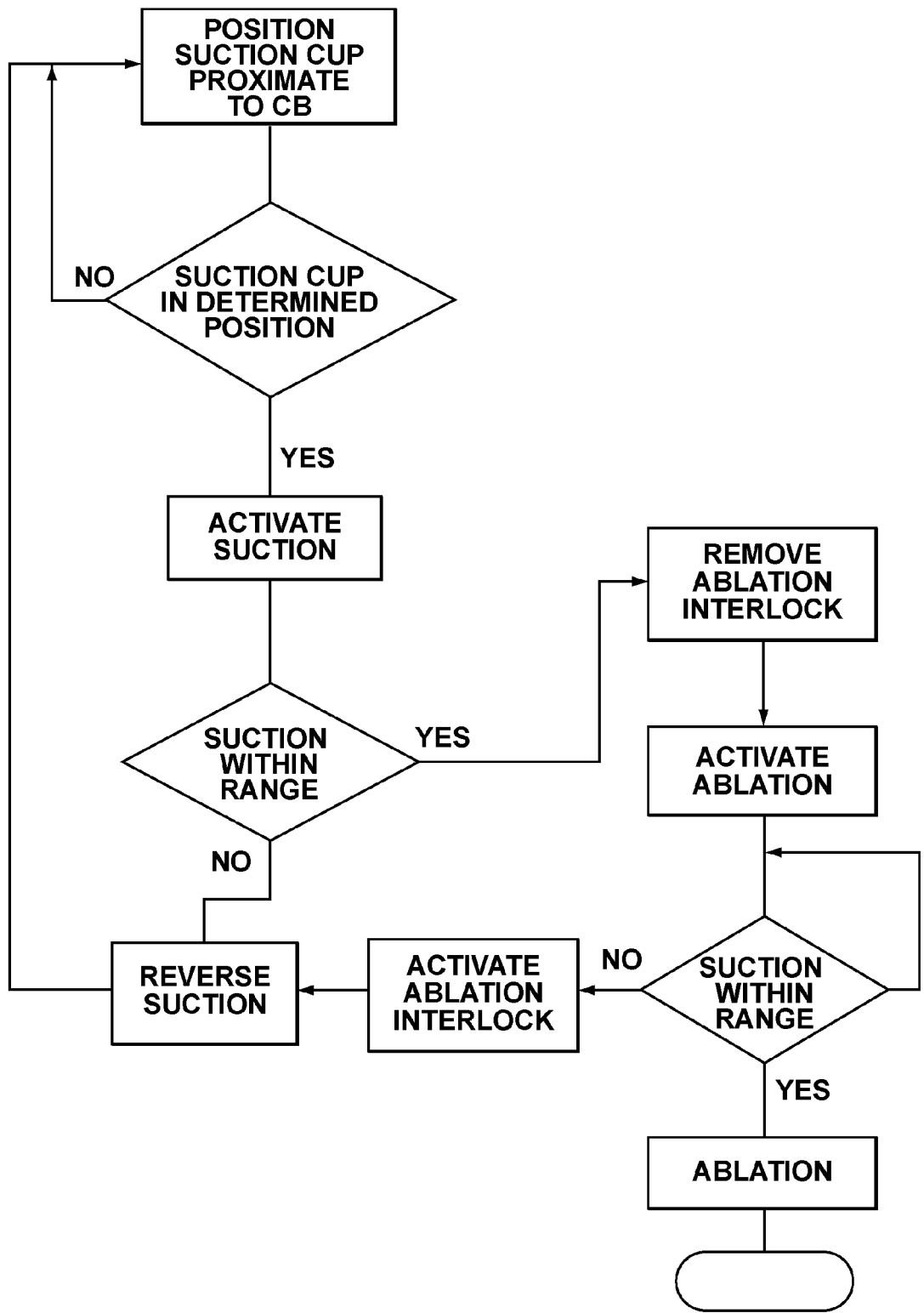
FIG. 40 is a flow chart of an algorithm for operating an endovascular ablation catheter having a suction element with a radiofrequency electrode.

FIG. 40 depicts a flow chart for the use of the system comprising an endovascular transmural ablation suction catheter.

Figure 41:
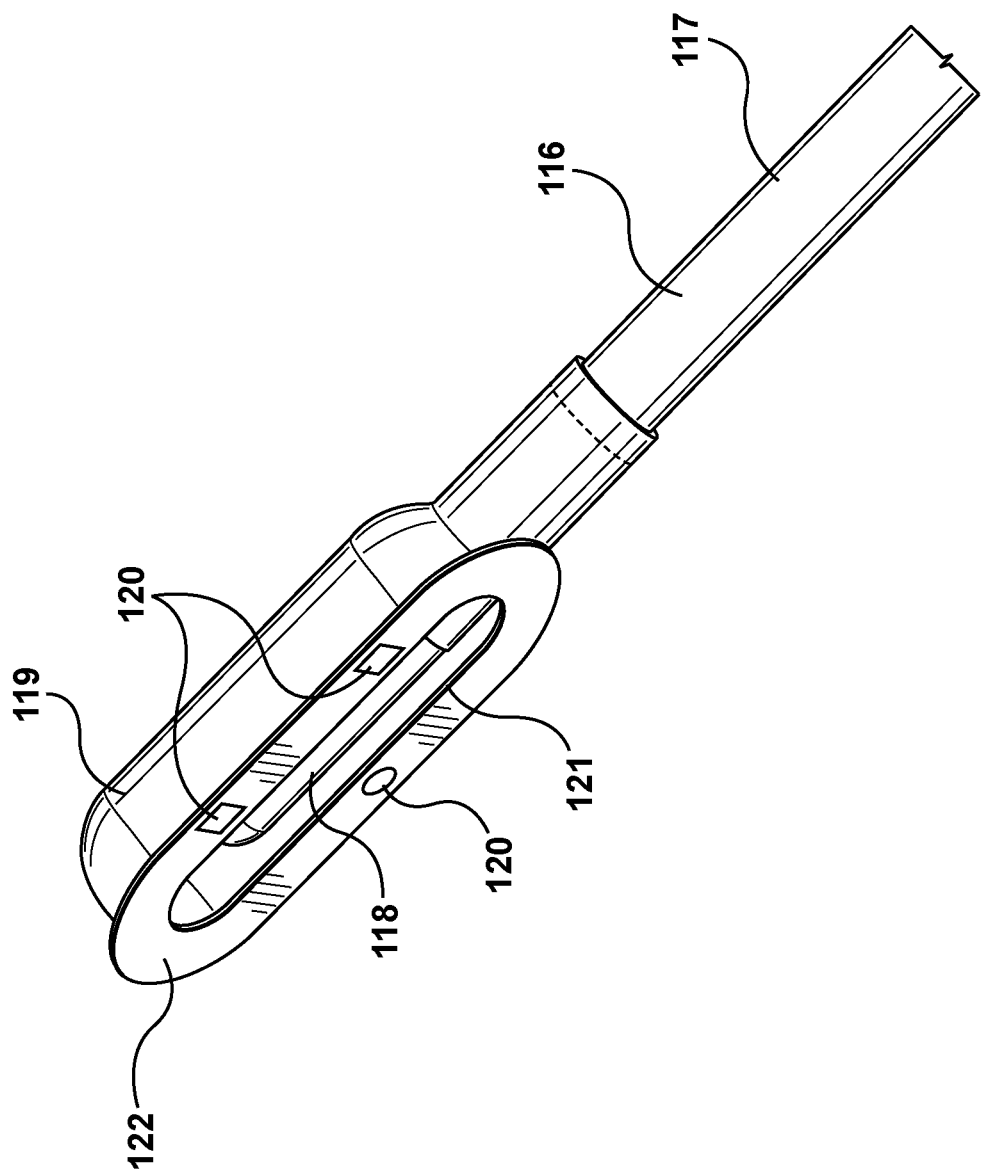
FIG. 41 is a schematic view of an endovascular ablation catheter having a side suction element with a radiofrequency electrode.

FIG. 41 depicts the distal end of an embodiment of an endovascular transmural ablation lateral suction catheter 116. Catheter 116 comprises a catheter shaft 117, an ablation element 118 mounted in the vicinity of the distal end of the catheter shaft 117, a lateral suction cup 119 also mounted in the vicinity of the distal end of the catheter shaft 117, and partially surrounding ablation element 118 as shown, a proximal terminal, not shown, comprising an ablation connector, and a suction connector. Catheter shaft 117 comprises a lumen in fluidic communication between the lateral suction cup 119 and the suction connector of the proximal terminal, and a conduit for an ablation agent in communication with ablation element 118 and the ablation connector of the proximal terminal. Catheter shaft 117 can be fabricated from a polymer suited for catheter construction such as Pebax or polyurethane, and may comprise a braided structure within its wall to provide torsional rigidity while maintaining axial flexibility to aid in directional positioning of lateral suction cup 119. Ablation element 118 may be configured for monopolar or bipolar RF ablation, cryo ablation, monopolar or bipolar neural stimulation, or monopolar or bipolar neural blockade. Lateral suction cup 119 is fabricated from an elastomer such as silicone rubber or polyurethane, and may have radiopaque markers 120 molded into a wall, or disposed upon a wall using an adhesive. The number of radiopaque markers 120, size, shape, and their positions provide the user with a substantially unambiguous indication of the position of lateral suction cup 119 within a carotid artery. Lateral suction cup 119 is bonded to the distal end of catheter shaft 117 with the ablation element 118 substantially surrounded by lateral suction cup 119 except for ablation aperture 121. Lateral suction cup 119 may comprise a suction flange 122 to facilitate suction fixation to the wall of a carotid artery during ablation. Catheter 116 is configured for use through a carotid access sheath 1 with a central lumen between 6 French and 12 French, not shown. The working length of the catheter may be about 100 cm to about 140 cm.

Figure 42:
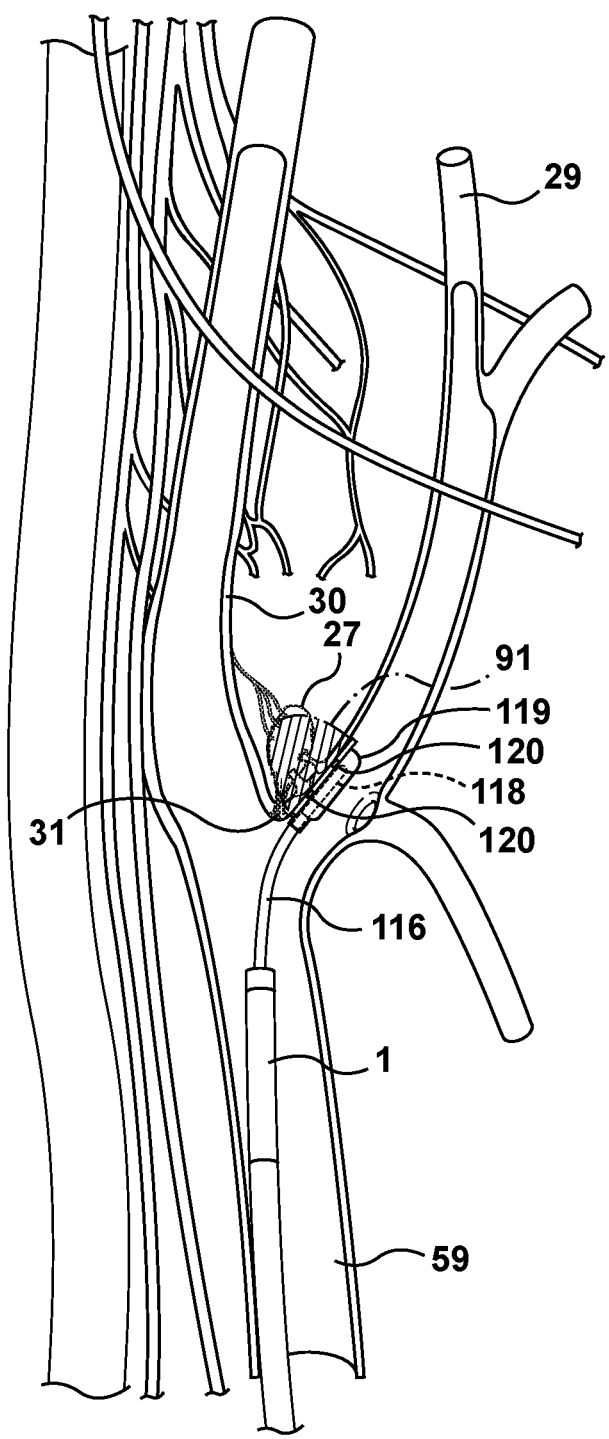
FIG. 42 is a cutaway illustration of a lateral view a patient's right carotid artery system with a schematic view of an endovascular ablation catheter having a side suction element with a radiofrequency electrode positioned in an external carotid artery for transmural ablation of a carotid body.

FIG. 42 depicts catheter 116 in position for ablation of a carotid body 27 immediately following an ablation. Suction cup 119 is shown in position against the wall of the external carotid artery proximate to carotid body 27 being held in place by suction applied to lateral suction cup 119 during ablation element activation. An exemplary system for the catheter use is depicted in FIGS. 39 and 40, and may further include a source for a cryo ablation agent and a means to control the cryo ablation agent.

Endovascular Transmural Ablation Balloon Catheter

Figure 43:
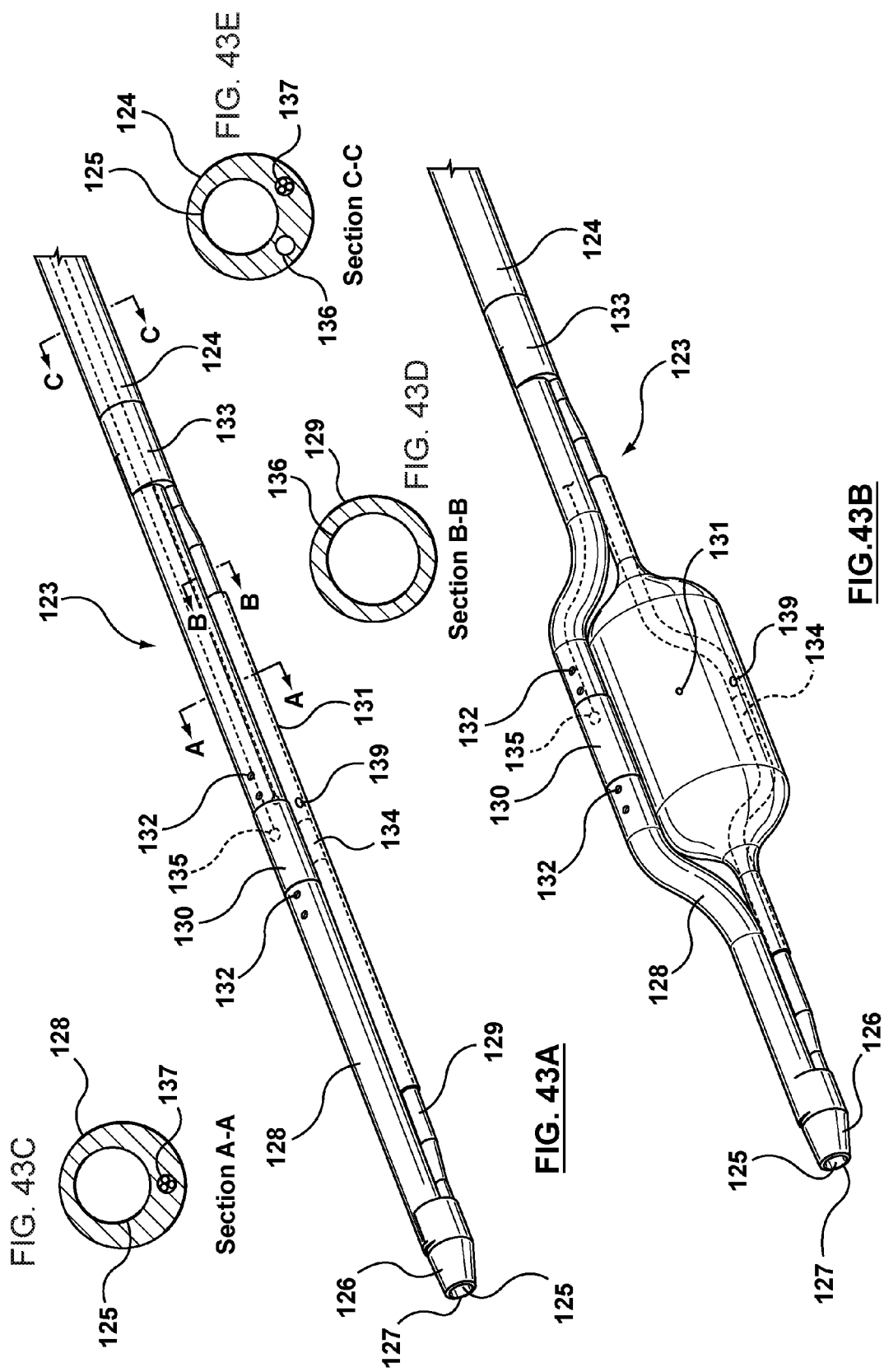
FIGS. 43A, 43C, 43D, and 43E illustrate an endovascular catheter having a deployable balloon and an ablation element, in an undeployed state.
FIG. 43B is a schematic view of an endovascular catheter having a deployable balloon and an ablation element, in a deployed state.

FIGS. 43A, 43B, 43C, 43D, and 43E depict an endovascular transmural ablation balloon catheter 123. Catheter 123 comprises catheter shaft 124, guide wire lumen 125, distal tip 126 comprising guide wire lumen valve 127, ablation electrode shaft 128, balloon shaft 129, ablation electrode 130, balloon 131, irrigation ports 132, proximal melt liner 133, radiopaque marker 134, and a proximal terminal, not shown, comprising a fluid connector in communication with guide wire lumen 125, a fluid connector for inflation of balloon 131, and an electrical connector for ablation electrode 130. Guide wire lumen 125 traverses the entire length of catheter 123 from distal tip 126, through electrode shaft 128, through melt liner 133, and through catheter shaft 124 to the fluid connector at the proximal terminal, not shown. Electrical wire lumen 137 runs from the distal end of electrode shaft through melt liner 133, Catheter shaft 124, to the electrical connector of the proximal terminal, not shown. Electrical wire lumen 137 contains wires to connect ablation electrode 130, and temperature sensor 135 with the electrical connector of the proximal terminal. Balloon inflation lumen 136 runs from the distal end of balloon shaft 129, through melt liner 133, catheter shaft 124 to the fluid connector configured for balloon inflation of the proximal terminal, not shown. Distal tip 126 forms a connection between electrode shaft 128 and balloon shaft 129, and comprises a valve 127, which functions as septum between the blood in the outer vicinity of distal tip 126 and guide wire lumen 125 in situ when a guide wire is absent from guide wire lumen 125, but allows for use of a guide wire in extension past distal tip 126 for catheter guidance. Guide wire lumen valve 127 causes irrigation fluid introduced into the guide wire lumen 125 under pressure from the fluid connector of the proximal terminal to exit through irrigation ports 132 which are in fluidic communication with guide wire lumen 125, that would otherwise, without guide wire lumen valve 127 substantially exit distal tip 126 through guide wire lumen 125, instead of through irrigation ports 132. Guide wire lumen valve 127 functions to direct irrigation fluid through irrigation ports 132 with a guide wire extended through guide wire lumen valve 127, and with a guide wire absent. Melt liner 133 connects electrode shaft 128 and balloon shaft 129 to catheter shaft 124 by thermal bonding technique, which preserves the continuity of guide wire lumen 125, electrical wire lumen 137, and balloon inflation lumen 136. Catheter shaft 124, distal tip 126, electrode shaft 128, balloon shaft 129, and melt liner 133 are fabricated from a thermoplastic material such as Pebax, or polyurethane. Ablation electrode 130 may be mounted in the vicinity of the center of ablation electrode shaft 128 as shown. Temperature sensor 135 may be mounted on the inner surface of ablation electrode 130. Wires connect ablation electrode 130 and temperature sensor 135 to the electrical connector of the proximal terminal as previously described. Balloon 131 is fabricated from an elastomer such as silicone rubber, and may be centrally mounted on balloon shaft 129 as shown using adhesive. The wall thickness of balloon 131 is between about 0.1 mm and about 0.4 mm when the balloon is un-inflated as depicted in FIG. 43A, and may be inflated to a diameter of 4 mm to 10 mm as depicted in FIG. 43B. Alternatively, balloon 131 may be fabricated from a non-elastomeric material such as PET. Radiopaque marker 134 is mounted centrally on balloon shaft 129 as shown. Balloon shaft 129 is configured to bend in the opposite direction of the bend in electrode shaft 128 as shown in FIG. 43B to provide the user with a substantially unambiguous fluoroscopic indication of the position of the ablation electrode within a carotid artery using the fluoroscopic spatial relationship between ablation electrode 130 and radiopaque marker 134.

In an alternative embodiment not shown but similar in concept to FIGS. 43A and 43B, an energy delivery element is a cryogenic applicator positioned on a shaft in a vicinity of a distal region of an endovascular catheter and an inflatable balloon is positioned next to the cryogenic applicator whereas in use the balloon may at least partially occlude a vessel and urge the cryogenic applicator into contact with an inner wall of a vessel proximate a target ablation site. The cryogenic applicator may be metallic and may comprise an expansion chamber within it. The expansion chamber maybe in fluid communication with a supply lumen used to deliver a cryogen such as substantially liquid $N_2O$ and an exhaust lumen. As the cryogen exits the supply lumen through an orifice or flow restrictor the cryogen expands into the expansion chamber due to a lower pressure and changes phase from substantially liquid to substantially gas. This phase change of the cryogen being an endothermic reaction removes thermal energy from the cryogenic applicator and tissue in thermal contact with it such as the vessel wall and target ablation site. The cryogen gas exits the expansion chamber through the exhaust lumen under lower pressure to a proximal region of the catheter where it is released or removed, for example to atmosphere or to a vacuum chamber. Cryogenic power and temperature may be controlled, for example by adjusting pressure in the expansion chamber via reducing out flow of gas from the exhaust lumen, or by controlling flow rate of cryogen through the supply lumen. Control of cryogenic power or temperature may be used to apply a reversible cryo-ablation, for example via slow cooling at a higher temperature, or a more permanent cryo-ablation. Reversible cryo-ablation may be used to confirm position before permanent cryo-ablation. Confirmation may comprise ensuring a vital nerve (e.g., vagus, sympathetic nerves, hypoglossal nerve) is not affected and that a target (e.g., carotid body or carotid body nerves) is affected. The balloon may be inflated with a gas such as $CO_2$. The balloon may occlude blood flow past the cryogenic applicator thus removing a variable that may influence thermodynamics of the creation of a cryo-ablation. Furthermore, by thermally insulating the cryogenic applicator from blood flow more cryogenic power may be directed toward the target ablation site allowing a deeper or colder ablation. Thus the balloon may improve predictability and efficacy of a cryogenic ablation. Following ablation the balloon may be deflated allowing blood flow to resume and warm the cryoapplicator and the catheter may be removed from the patient.

Figure 44:
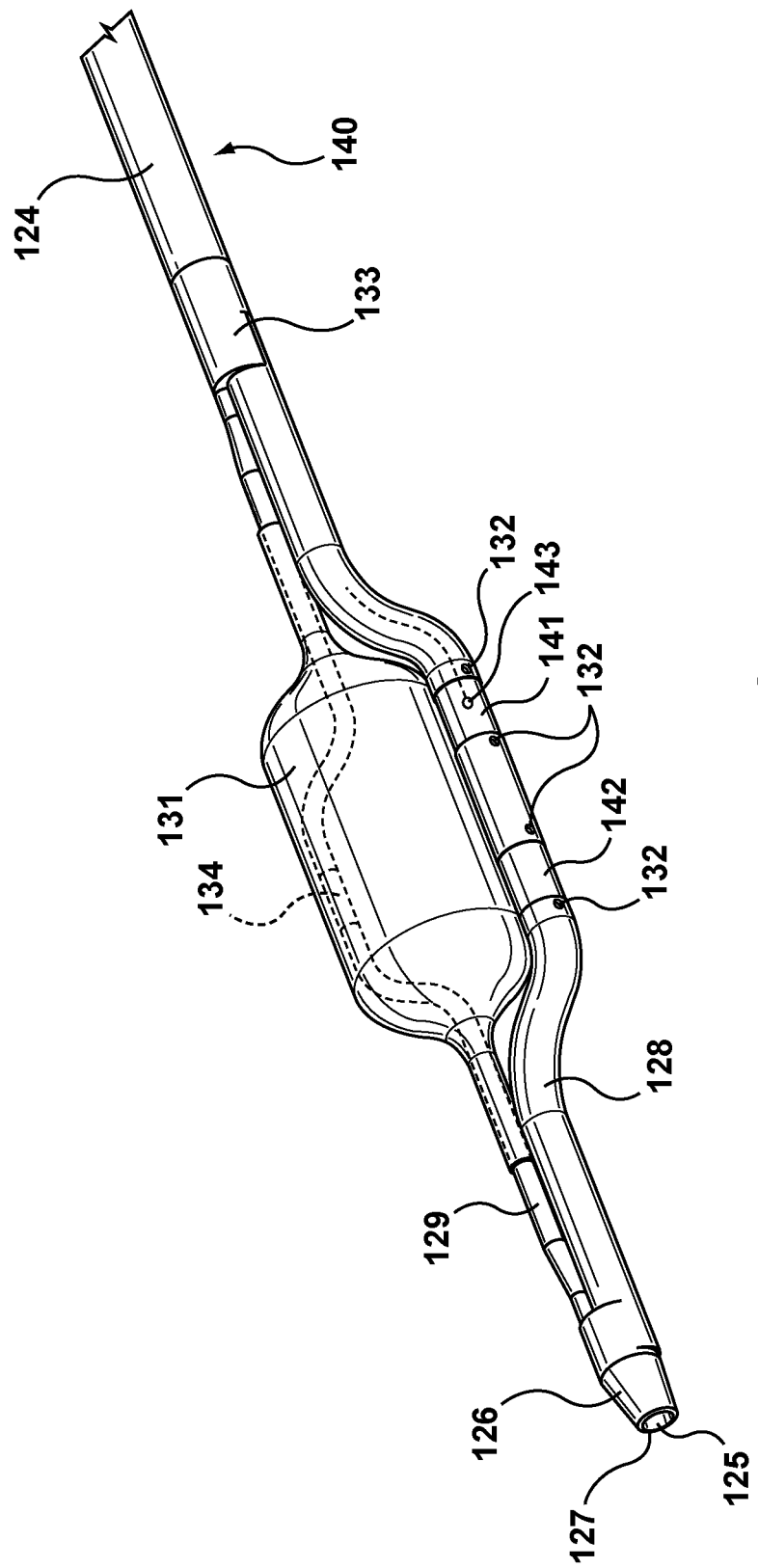
FIG. 44 is a schematic view of an endovascular catheter having a deployable balloon and bipolar radiofrequency electrodes, in a deployed state.

FIG. 44 depicts an alternate embodiment of catheter 140 of FIGS. 43A and 43B where there are two ablation electrodes 141, and 142 configured for bipolar RF ablation. As depicted, ablation electrode 141 is associated with temperature sensor 143, however, the bipolar catheter can be configured with a temperature sensor associated with each of the ablation electrodes 141 and 142. The electrical connector of the proximal terminal for this embodiment is configured for bipolar ablation, and may be configured for using two temperature sensors.

Figure 45:
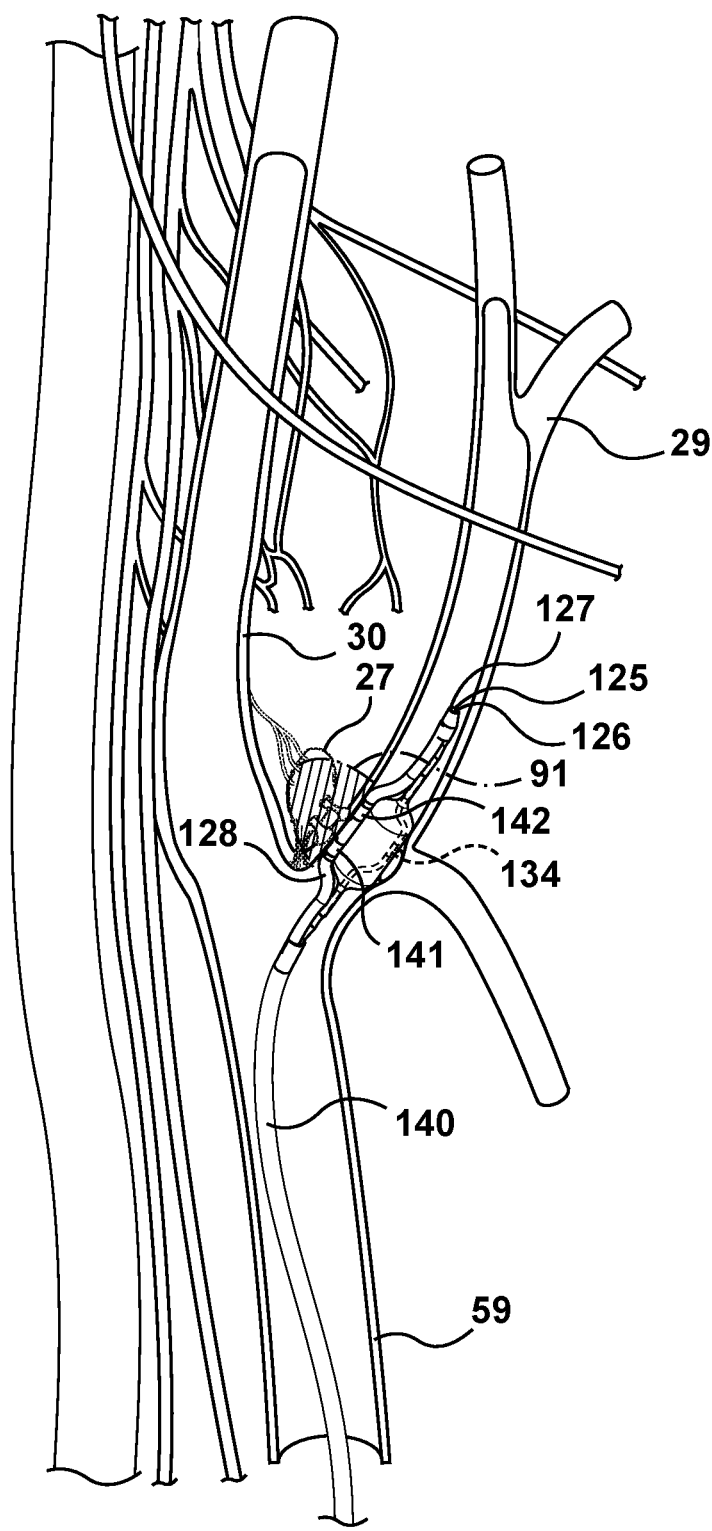
FIG. 45 is a cutaway illustration of a lateral view a patient's right carotid artery system with a schematic view of an endovascular ablation catheter having a deployable balloon with an ablation element positioned in the patient's external carotid artery for transmural ablation of a carotid body.
Figure 46:
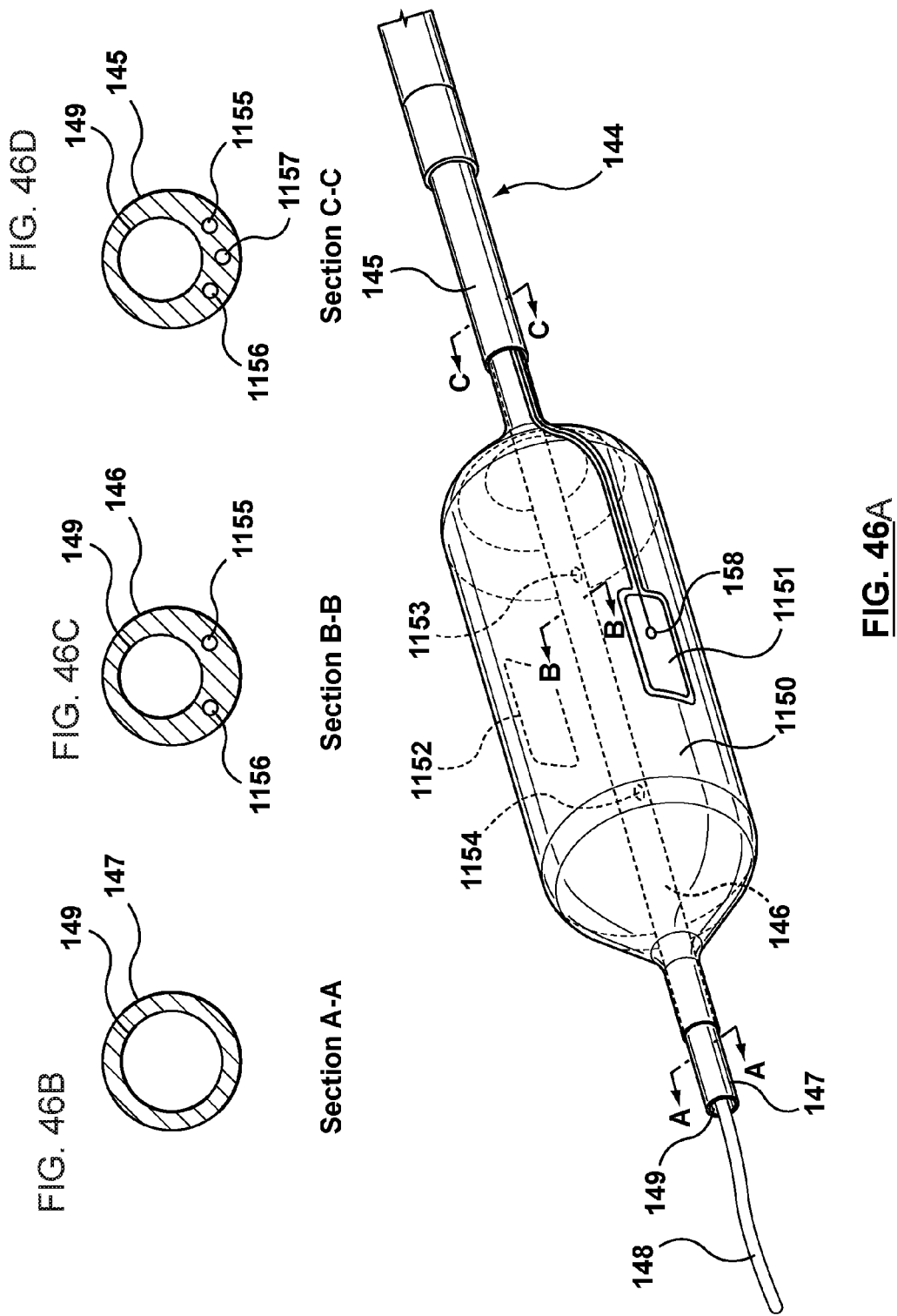
FIGS. 46A, 46B, 46C, and 46D show an endovascular catheter having a deployable balloon and an ablation element, in a deployed state.

FIG. 45 depicts bipolar catheter 140 in position for ablation of a carotid body 27 immediately following an ablation 91. As depicted, electrode shaft 128 and ablation electrodes 141 and 142 are pressed against the wall of the external carotid artery 29 by balloon 131 and proximate to carotid body 27. In this depiction, a guide wire is absent. In an exemplary method, ablation of carotid body 27 is accomplished using bipolar catheter 140 with the following steps. Optionally, the method includes determining a position and size of a target carotid body 27 within a patient. The distal end of bipolar catheter 140 is positioned into the external carotid artery 29 associated with carotid body 27 as shown using a guide wire and fluoroscopic imaging using electrodes 141 and 142, and radiopaque marker 134 as visual references. Balloon 131 is inflated using the fluid connector of the proximal terminal. The method then optionally fluoroscopically confirms the ablation electrodes are sufficiently proximate the determined position for ablation. The guide wire is then withdrawn. The ablation parameters are then selected. Irrigation is then initiated. Ablation is then performed. Irrigation is terminated. Balloon 131 is deflated, and catheter 140 is then withdrawn from the patient.

FIGS. 46A-46D depict a distal end of an exemplary embodiment of an endovascular transmural ablation balloon catheter 144 comprising balloon mounted ablation electrode (s) 1151. Catheter 144 comprises catheter shaft 145, guide wire lumen 149, distal tip 147, balloon shaft 146, ablation electrode(s) 151, and temperature sensor 158, balloon 1150, balloon inflation port 1153, balloon inflation port 1154, radiopaque marker 1152, and a proximal terminal, not shown, comprising a fluid connector in communication with guide wire lumen 149 a fluid connector in communication with fluid port 1153, a fluid connector in communication with fluid port 1154, and an electrical connector for ablation electrode 1151. Guide wire lumen 149 traverses the entire length of catheter 144 from distal tip 147, through balloon shaft 146, and through catheter shaft 145 to the fluid connector at the proximal terminal, not shown. Electrical wire lumen 157 runs from the distal end of catheter shaft 145, to the electrical connector of the proximal terminal, not shown. Electrical wire lumen 157 contains wires to connect ablation electrode 1151, and temperature sensor 158 with the electrical connector of the proximal terminal. Balloon inflation lumen 155 runs from the distal end of balloon shaft 146, through catheter shaft 145 to a fluid connector configured for balloon inflation of the proximal terminal, not shown. Balloon inflation lumen 156 runs from the distal end of balloon shaft 146, through catheter shaft 145 to a second fluid connector configured for balloon inflation of the proximal terminal, not shown. Balloon inflation port 1153 is in fluidic communication with balloon inflation lumen 155. Balloon inflation port 1154 is in fluidic communication with balloon inflation lumen 156. Catheter shaft 145, distal tip 147, and balloon shaft 146, are fabricated from a thermoplastic material such as Pebax, or polyurethane. Balloon 1150 is fabricated from a cross linked thermoplastic such as PET. Balloon 1150 is mounted on balloon shaft 146 as shown using adhesive. The wall thickness of balloon 131 is between about 0.05 mm and about 0.2 mm. Ablation electrode 1151 and temperature sensor 158 are centrally mounted on the surface of balloon 1150 as shown using an adhesive. Temperature sensor 158 is mounted on the inner surface of ablation electrode 1151. Wires connect ablation electrode 1151 and temperature sensor 158 to the electrical connector of the proximal terminal as previously described. Ablation electrode 1151 is between 2 mm and 6 mm wide in the radial direction, and between 2 mm and 10 mm in the axial direction. Ablation electrode 1151 is configured to be flexible to conform to balloon 1150. Radiopaque marker 1152 is mounted on the surface of the balloon in substantially diametric opposition to electrode 1151. Radiopaque marker 1152 is configured to be distinctly different in fluoroscopic appearance from electrode 1151 to provide the user with a substantially unambiguous indication of the location of electrode 1151 within a carotid artery using the fluoroscopic spatial relationship between ablation electrode 1151 and radiopaque marker 1152. Balloon 1150 inflation comprises circulation of fluid from inflation port 1153 through balloon 1150 and returning through fluid port 1154. Circulation of inflation fluid provides carotid artery wall with protective cooling. In an alternate embodiment, two or more electrodes may be disposed on the surface of balloon 1150 configured for bipolar RF ablation.

Figure 47:
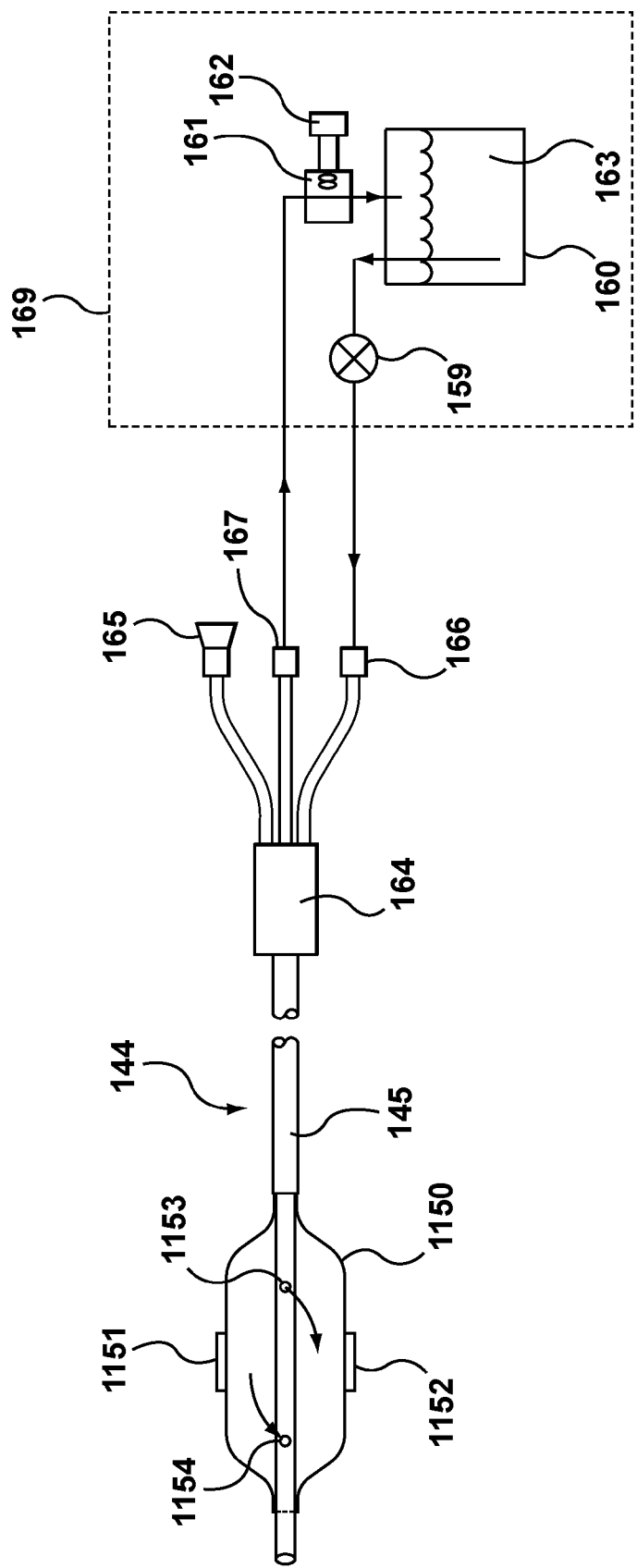
FIG. 47 is a schematic view of an endovascular catheter having a deployable balloon and an ablation element, in a deployed state.

FIG. 47 depicts the inflation means for catheter 144 in simplified schematic form. The pumping means comprises a pump 159, a liquid reservoir 160 comprising a sterile physiological liquid 163, a pressure relief valve 161, a means for setting a relief pressure 162, check valve, and a fluid umbilical. Pump 159 may be a positive displacement pump, such as a peristaltic roller pump. The fluid pumping rate of pump 159 is controllable, and the flow direction is reversible. Fluid reservoir 160 may be a container configured to hold about 0.5 liters to about 2 liters of sterile liquid, and to maintain sterility, and may be an IV bag. Sterile liquid is a physiological liquid 163 such as saline or ringers solution. The inflation means may be integrated into control console 169, or may be a separate module. Umbilical connects the inflation means to catheter 144. To inflate balloon 1150 liquid is pumped from reservoir 160 to a positive pressure by pump 159 to liquid connector 166 of catheter 144, through balloon 1150 from liquid port 1153 to liquid port 1154, then out of catheter 144 from liquid port 167, through check valve 171, pressure relief valve 161 and then back into reservoir 160. Pressure relief valve 161 provides a settable backpressure to cause balloon 1150 inflation, and to regulate balloon 1150 inflation pressure. To deflate balloon 1150 the direction of rotation of pump 159 is reversed, and check valve 171 closes causing a negative pressure in balloon 1150 resulting in deflation. The liquid pumping rate may be between about 10 ml to about 100 ml per minute.

Figure 48:
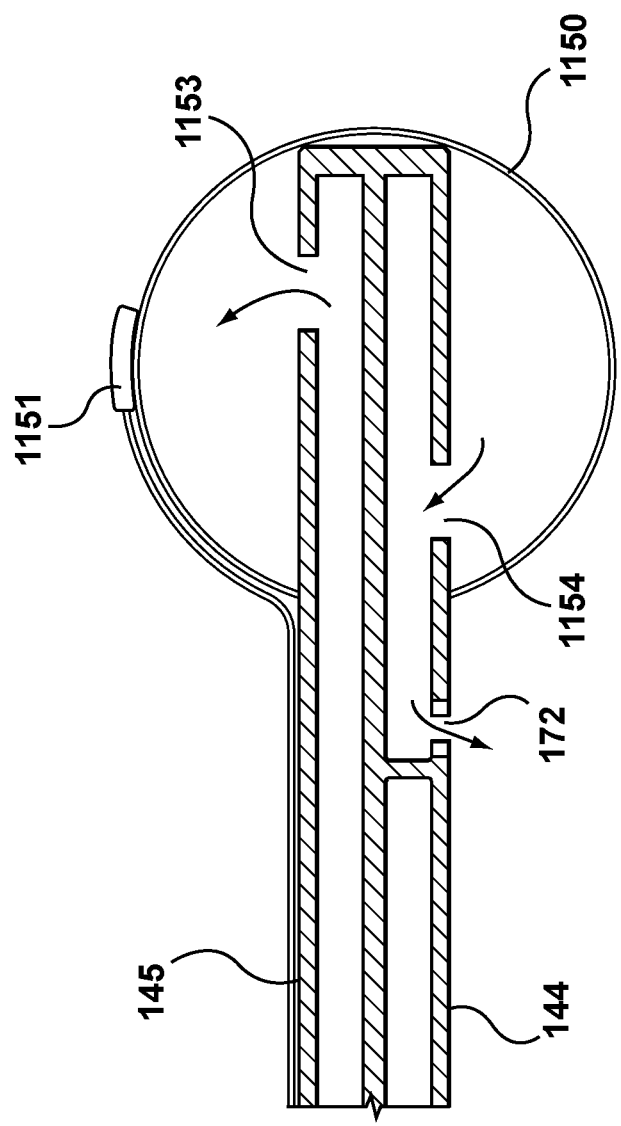
FIG. 48 is a schematic view of an endovascular catheter having a deployable balloon and an ablation element, in a deployed state.

FIG. 48 depicts in simplified schematic form an alternate embodiment of endovascular transmural ablation balloon catheter 144. In this embodiment, fluid is pumped under positive pressure through balloon 1150, from liquid port 1153 to liquid port 1154 and exits ETAB catheter 144 through orifice 172 proximal to balloon 1150 as shown. Orifice 172 is configured to provide a positive pressure within balloon 1150 when liquid is introduced into balloon 1150 through liquid port 1153 inflate balloon 1150, and to provide a negative pressure within balloon 1150 when liquid is withdrawn from balloon 1150 through liquid port 1153 to deflate balloon 1150.

Figure 49:
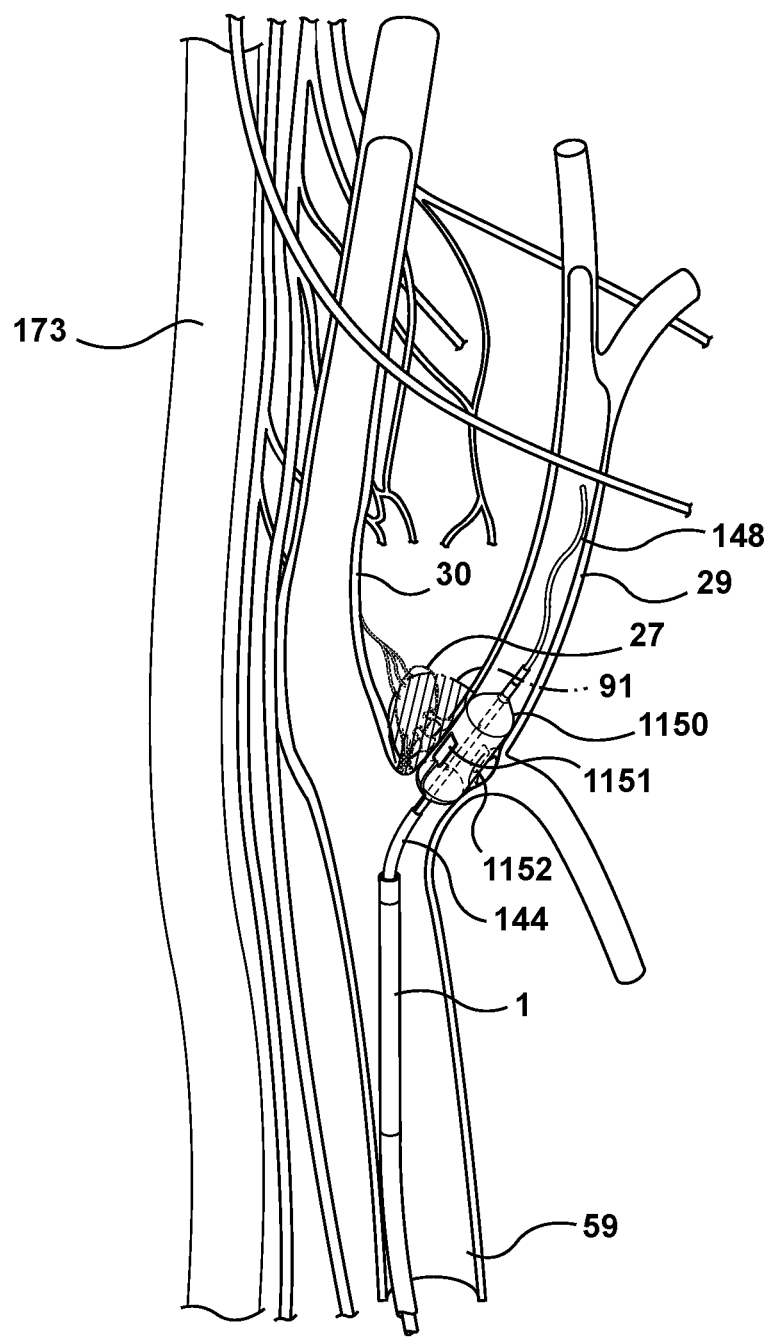
FIG. 49 is a cutaway illustration of a lateral view a patient's right carotid artery system with a schematic view of an endovascular ablation catheter having a cooled deployable balloon with an ablation element positioned in the patient's external carotid artery for transmural ablation of a carotid body.

FIG. 49 depicts catheter 144 in position for ablation of carotid body 27 immediately following formation of an ablation 91. As depicted electrode has been radially oriented in the direction of carotid body 27 by the user using fluoroscopic guidance with electrode 1151 and radiopaque marker 1152 serving as a visual reference to the location of electrode 1151 within external carotid artery 29 as shown. Catheter 144 may also be positioned within the internal carotid artery 30, and alternately the internal jugular vein 173 for transmural ablation of carotid body 27, similar to the approach shown in FIGS. 61A, 61B and 61C. Circulation of liquid within balloon 1150 may protect the wall of carotid artery 29 from collateral thermal injury, or may facilitate creation of a sufficiently sized ablation.

Figure 50B:
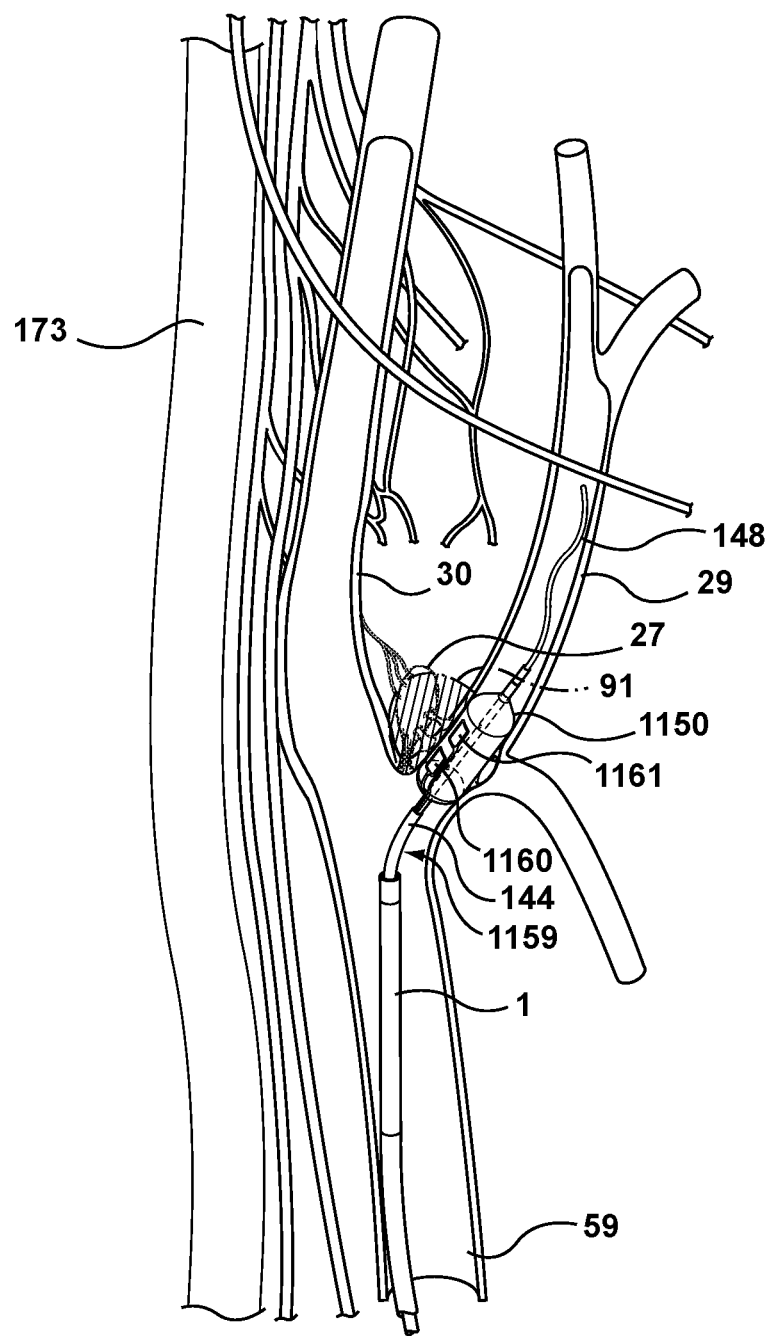
FIGS. 50Ai, 50Aii, 50Aiii, 50Aiv, 50B, and 50C illustrate an occluding balloon catheter mounted with electrodes adapted to operate in bipolar mode.
Figure 50C:
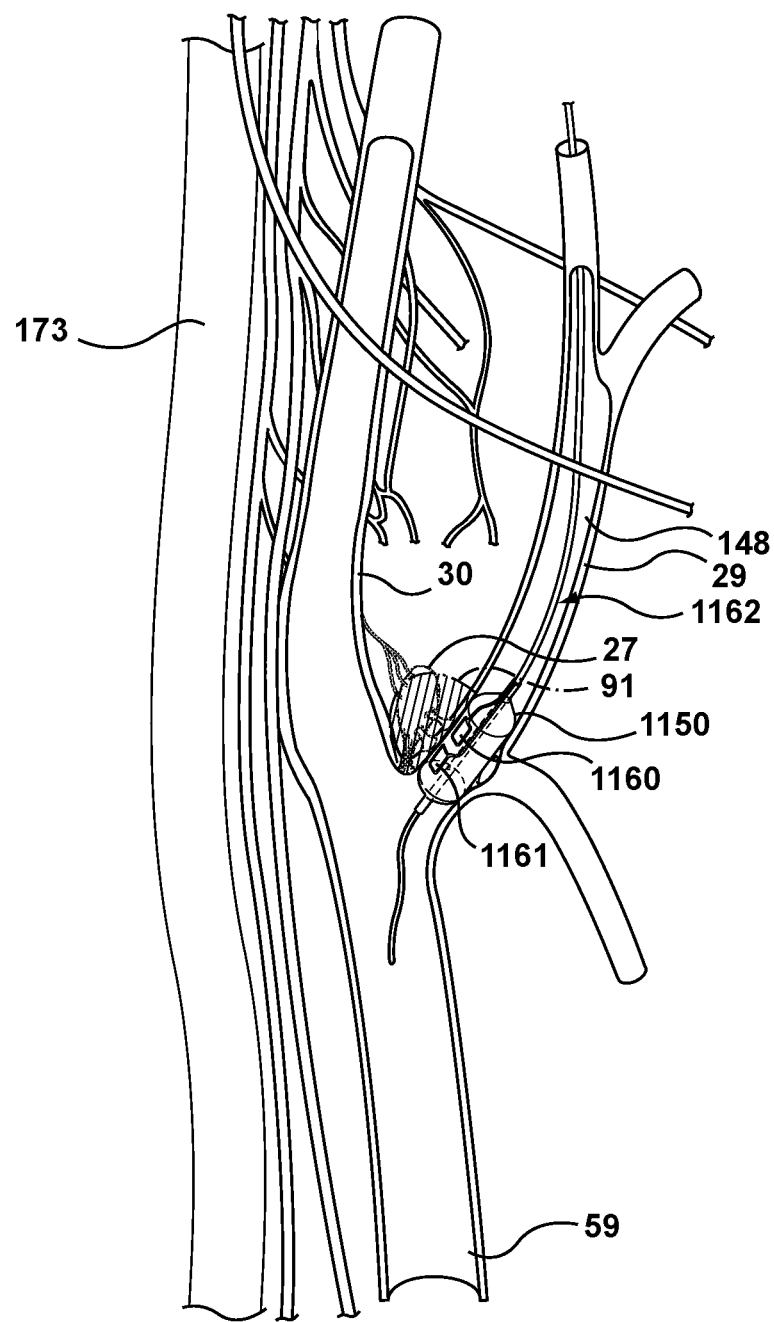

FIGS. 50Ai, 50Aii, 50Aiii, 50Aiv, illustrates an exemplary balloon catheter configured for bipolar RF ablation of a carotid body. The catheter may be designed similar to the catheter shown in FIG. 46, however at least one pair of electrodes 1160 and 1161 is mounted on balloon 1150. The pair of electrodes is aligned substantially parallel to the axis of the balloon. The pair of electrodes may be connected to a RF generator in bipolar mode, that is, so that electrode 1160 is a first pole and electrode 1161 is a second pole and RF current is passed from one electrode, through tissue, to the other electrode. The balloon is configured to occlude blood flow or at least inhibit blood flow from becoming a short circuit between the two electrodes. This arrangement allows RF energy to be directed into the vessel wall and periarterial tissue to ablate a carotid body or its nerves. The balloon 1150 may optionally be inflated with a circulating fluid that functions to remove heat from the electrodes so they can deliver greater energy to the tissue. FIG. 50B shows a bipolar RF balloon catheter 1159 being delivered from a common carotid artery 59 (e.g., via femoral artery access) to an external carotid artery 29. The balloon 1150 is inflated, causing electrodes 1160 and 1161 to come into contact with the vessel wall (e.g., on a carotid septum) substantially facing a carotid body. The electrodes may be radiopaque to facilitate radiographic visualization during placement. Contrast may be delivered to the common carotid artery during placement to visualize the arteries relative to the electrodes during placement and also to confirm that blood is not flowing past the electrodes. While a balloon is being positioned it may be in a deflated state and a user may rotate the balloon by torqueing the proximal end of the catheter until the electrode pair is sufficiently facing a target site. Optionally a balloon may be mounted with multiple pairs of RF electrodes spaced around the diameter of the balloon, e.g., 2, 3, 4, 5, or 6 pairs of electrodes, which may reduce or eliminate the need to rotate the balloon. A user may deliver the balloon to the carotid artery and inflate it and deliver RF energy only to the electrode pair that is positioned in the direction of the target site to be ablated. FIG. 50C shows a bipolar RF balloon catheter 1162 delivered retrograde, e.g., from a superficial temporal artery access to an external carotid artery. The catheter 1162 configured for superficial temporal artery delivery may be much shorter (e.g., about 10 to about 30 cm) and stiffer than catheter 1159 configured to be delivered from a femoral artery, and thus may be easier to rotate by rotating a proximal end of the catheter.

Endovascular Transmural Ablation Cage Catheter

FIGS. 51Ai, 51Aii, and 51B depict an endovascular transmural ablation cage catheter 174. Catheter 174 comprises cage 177, outer catheter shaft 175, inner catheter shaft 176, proximal terminal 185, and distal tip 178. Cage 177 comprises electrode 181 and associated temperature sensor 182, at least two cage wires 180, distal cage ring 183, and proximal cage ring 184. Outer catheter shaft 175 comprises central lumen 191, and electrical wire lumen 190. Outer catheter shaft 175 may comprise a braided wire structure within its outer wall to provide for torsional rigidity. Outer catheter shaft 175 may be fabricated from a polymer such as Pebax or polyurethane. Inner catheter shaft 176 comprises guide wire lumen 179 and is configured in a slidable relationship with central lumen 191 of outer catheter shaft 175. Proximal terminal 185 comprises handle 186, cage actuator 187, electrical connector 188, and guide wire lumen terminal 189. Distal cage ring 183 is bonded to the distal end of inner catheter shaft 176. Proximal cage ring 184 is bonded to the distal end of outer catheter shaft 175 as shown. Cage actuator 187 controls the distance between the distal end of inner catheter shaft 176 and distal end of outer catheter shaft 175. Cage 177 is configured such that when the actuator is positioned for maximum distance between the distal ends on inner catheter shaft 176 and outer catheter shaft 175 cage wires are in a substantially straight configuration as shown in FIG. 51A. Cage 177 is also configured such that when actuator is positioned to reduce the distance between inner catheter shaft 176 and outer catheter shaft 175, cage wires 180 expand in a radial direction as depicted in FIG. 51B. Electrode 181 may be disposed on cage 177 as shown by adhesive, solder or by welding. The outer surface 192 of electrode 177 is metallic. Temperature sensor 182 may be disposed on outer electrode surface 192, or be disposed beneath electrode surface 192. Wires, not shown, connect electrode 181 and temperature sensor 182 to electrical connector 188 of proximal terminal 185 through wire lumen 190. In an alternate embodiment at least one cage wire 180 may be configured as an electrode whereby the electrode surface is absent electrically isolative material, and remainder of cage 177 is coated with an electrically isolative material. Cage 177 may comprise any number of cage wires. Cage 177 may comprise cage wires that are axially oriented as shown, but may also comprise cage wire(s) in a spiral configuration, in a woven configuration, or a knitted configuration. Cage wires 180 may be metallic or may be non-metallic. Cage wires 180 may be dissimilar in size, material, geometry or radiopacity. Cage 177 may comprise more than one electrode surface, and catheter 174 may be configured for bipolar or monopolar RF ablation. Catheter 174 may be configured for monopolar or bipolar neural stimulation or neural blockade in addition to a configuration for transmural carotid body ablation.

Figure 52:
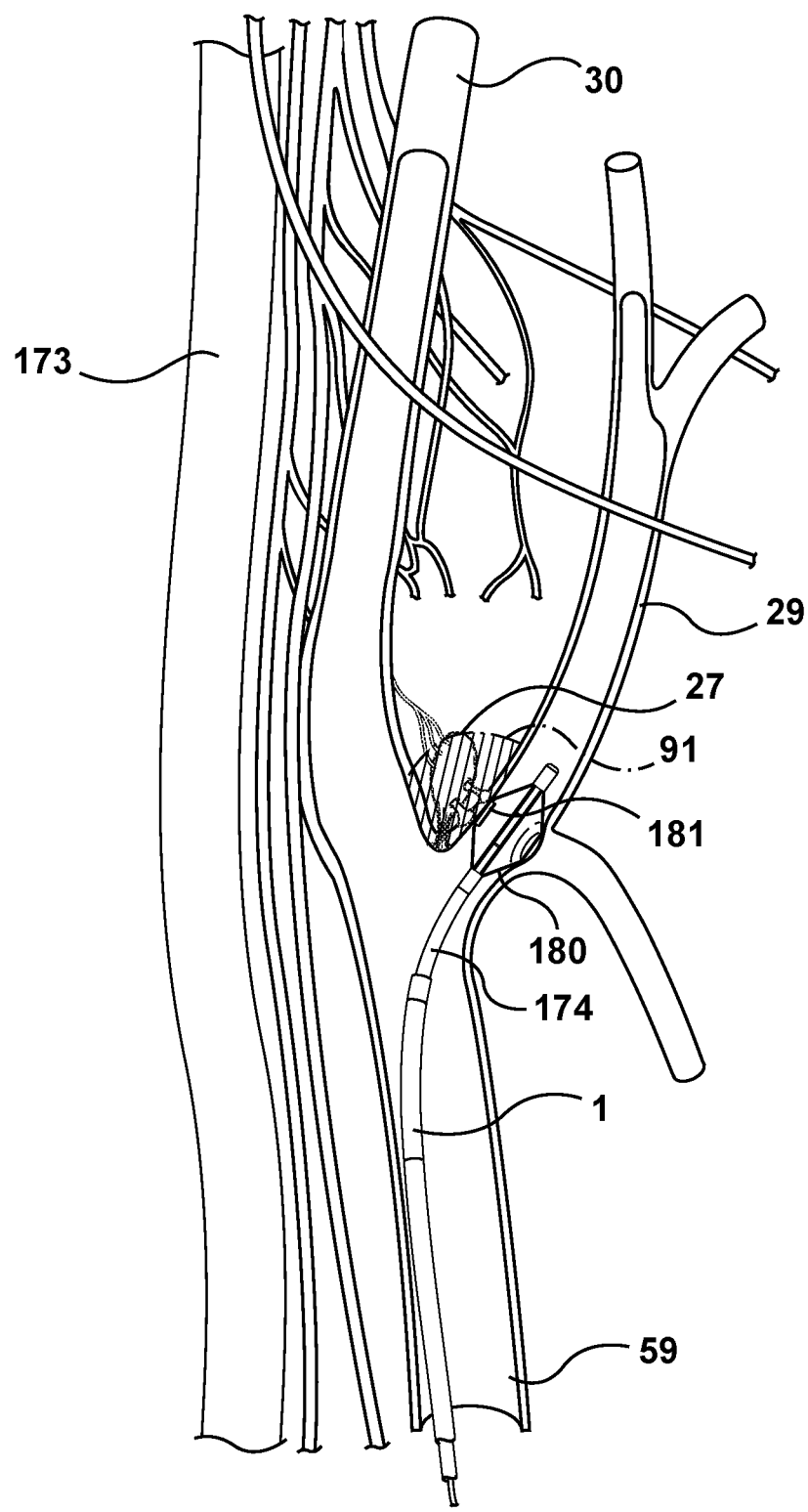
FIG. 52 is a cutaway illustration of a lateral view a patient's right carotid artery system with a schematic view of an endovascular catheter having a deployable wire basket in a deployed state, and having an ablation element positioned in the patient's external carotid artery for transmural ablation of a carotid body.

FIG. 52 depicts catheter 174 in position for ablation of carotid body 27 immediately following formation of an ablation 91. As depicted, electrode 181 has been radially oriented in the direction of carotid body 27 by the user using fluoroscopic guidance with electrode 1151 and opposing cage wires 180 which serve as radiopaque markers providing a visual reference to the location of electrode 181 within external carotid artery 29 as shown. Catheter 174 may also be positioned within the internal carotid artery 30, and alternately the internal jugular vein 173 for transmural ablation of carotid body 27, similar to the approach shown in FIGS. 61A, 61B and 61C. Cage wires 180 permit blood flow through the vessel from which it is used, providing protective cooling the vessel wall not in contact with electrode 181.

Rearward-Looking IVUS Catheter

Figure 53A:
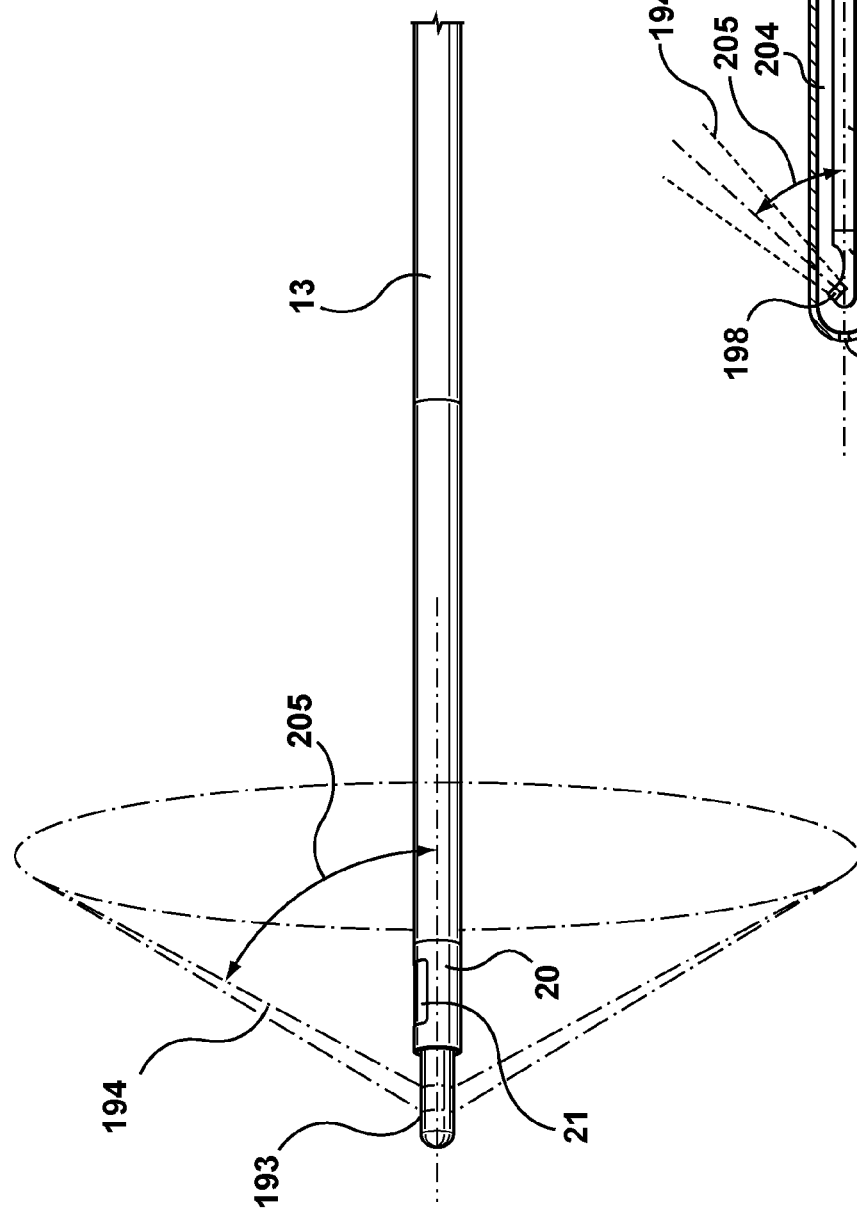
FIGS. 53A and 53B are schematic views of a back-looking intravascular ultrasound guidance catheter having an ablation element.
Figure 53B:
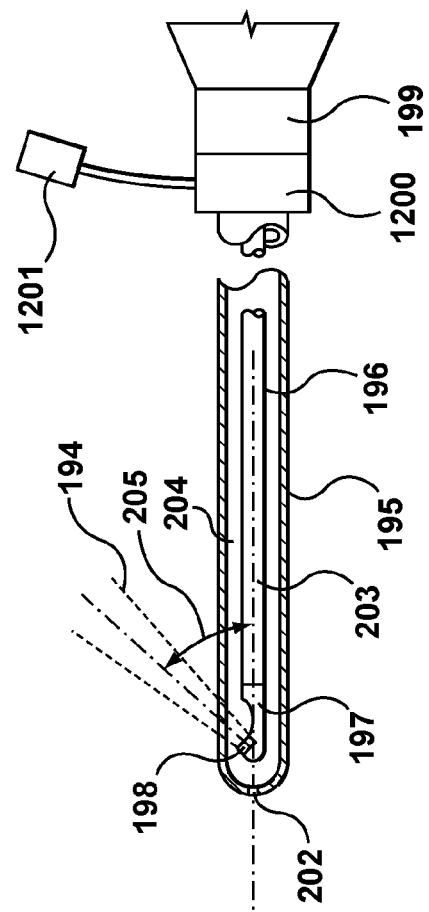

FIG. 53A depicts a rearward, or back, looking IVUS catheter 193 in configuration for use with carotid access sheath 13. FIG. 53B depicts catheter 193 in sectional view. Catheter 193 comprises sheath 195, imaging shaft 196, and proximal terminal 1200. Sheath 195 comprises a central lumen 204 with priming valve 202 in the vicinity of the distal tip, and proximal terminal 1200 in the vicinity of the proximal end. Fluid connector 1201 is in fluidic communication with central lumen 204. Imaging shaft 196 comprises a drive shaft 203 imaging crystal housing 197 at the distal end of drive shaft 203, a commutator coupling 199 mounted at the proximal end of drive shaft 203, and an electrical connection between imaging crystal housing 197 and commutator coupling 199. Commutator coupling 199 is configured for use with an IVUS imaging console, not shown. Imaging crystal housing 197 comprises a piezoelectric crystal 198 configured for imaging in a frequency range between 20 mHz and 100 mHz, (e.g., in the range 40 mHz to 50 mHZ). Crystal housing 197 is configured to orient piezoelectric crystal 198 at imaging angle 205. Imaging angle 205 is between 15 degrees and 50 degrees, (e.g., at an angle between 30 and 45 degrees). Prior to use, central lumen 204 is filled with a saline solution though fluid connector 1201 under pressure, forcing air to exit central lumen 204 through valve 202. The saline provides an acoustic coupling between piezoelectric crystal 198 and the wall of sheath 195. The techniques for constructing catheter 193 as depicted are familiar to those skilled in the art ultrasound imaging catheters, and therefore are not further elaborated.

Figure 54:
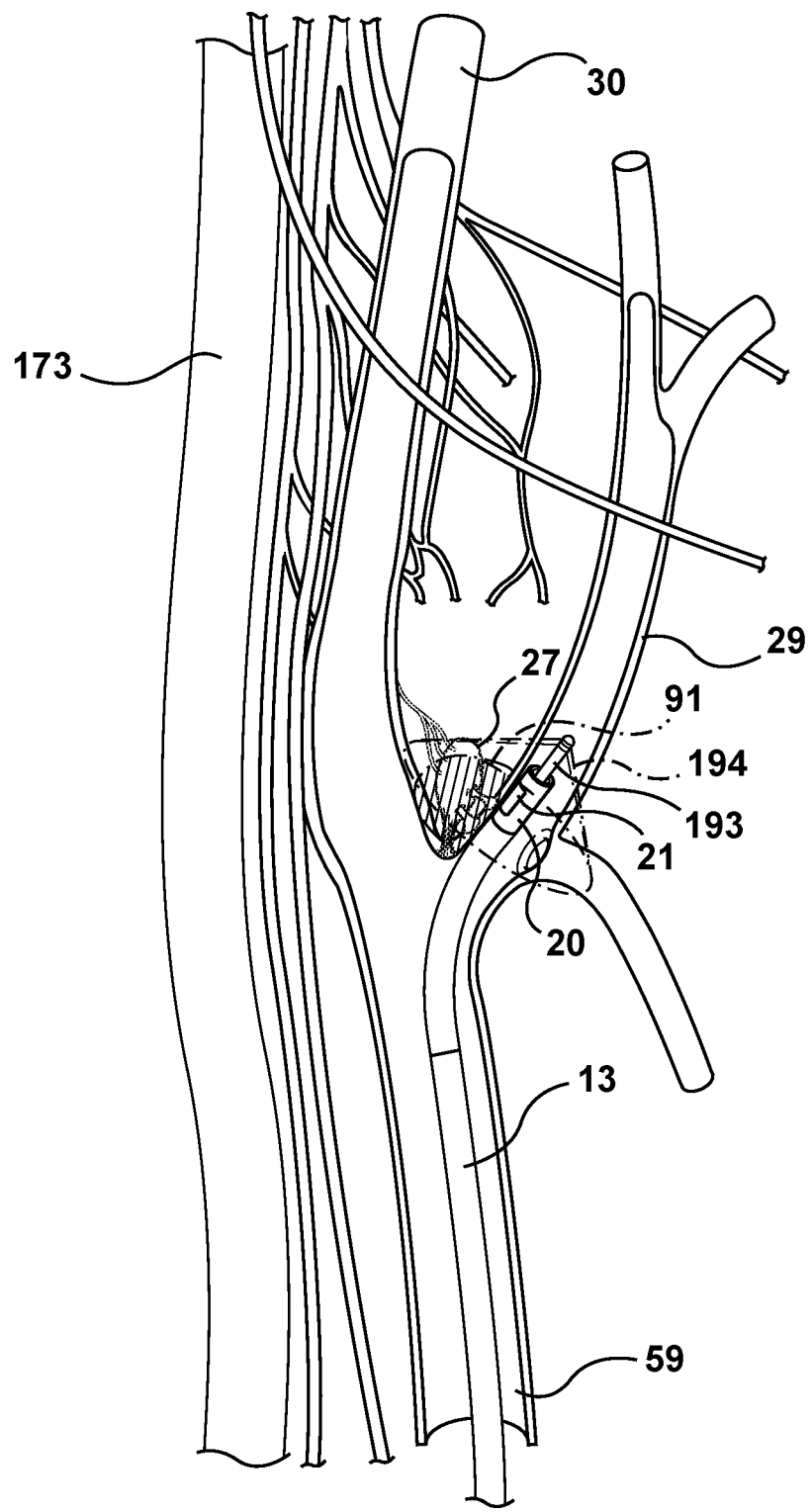
FIG. 54 is a cutaway illustration of a lateral view a patient's right carotid artery system with a schematic view of a back-looking intravascular ultrasound guidance catheter and having an ablation element positioned in the patient's external carotid artery for transmural ablation of a carotid body.

FIG. 54 depicts carotid access sheath 13 in position for ablation of carotid body 27 immediate following formation of an ablation 91, and catheter 193 in position for imaging ablation 91 in real time. Catheter 193 allows the user to image and identify anatomical structures associated with carotid body 27, the location of carotid body 27, and the size of carotid body 27. Catheter 193 may also allow the user to image and identify vital anatomical structures that are not associated with carotid body 27 whose function may be preserved. Catheter 193 further allows the user to image and monitor the formation of ablation lesion 91 in real time, which provides the user the ability to terminate ablation in the event of encroachment of the ablative lesion into the vicinity of vital anatomical structures not associated with carotid body 27. Information obtained by catheter imaging may be used to select ablation parameters. The ability of catheter 193 to image an ablation lesion is a function of the imaging frequency, and power, and the change in tissue characteristics due to ablation. Carotid access sheath 13 and catheter 193 may also be positioned within the internal carotid artery 30, and alternately the internal jugular vein 173 for transmural ablation of carotid body 27, similar to the approach shown in FIGS. 61A, 61B and 61C.

Endovascular Transmural Ablation Cooled Tip Catheter

Figure 55A:
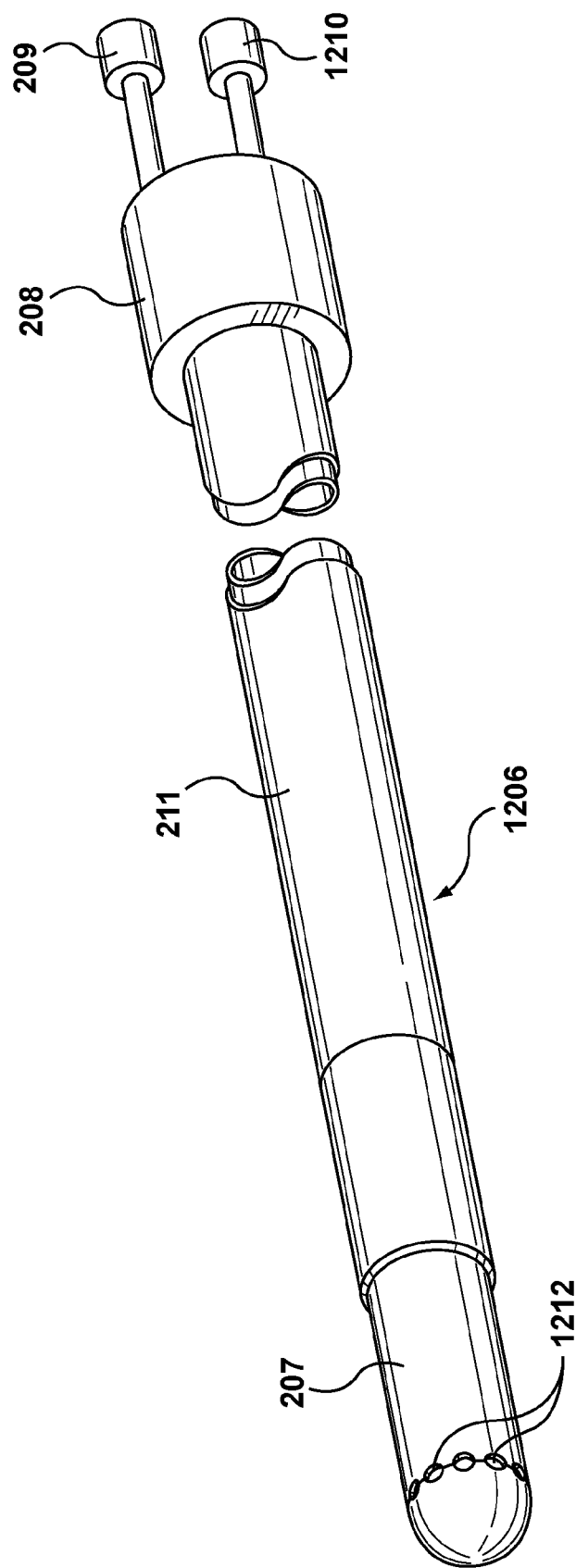
FIG. 55A is a schematic view of an endovascular ablation catheter configured for transmural cooled radiofrequency ablation of a carotid body.
Figure 55B:
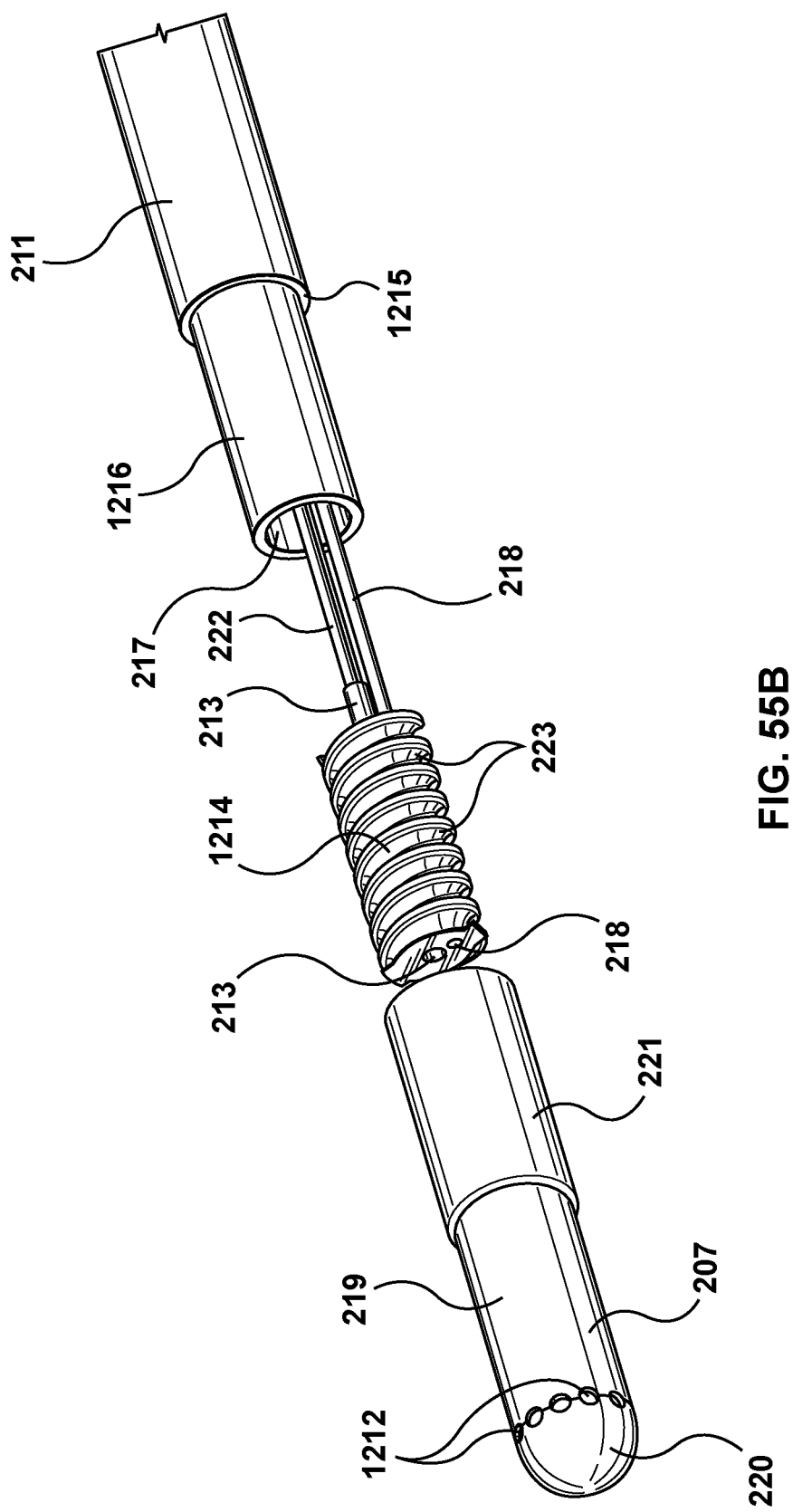
FIG. 55B is an exploded view of an endovascular ablation catheter configured for transmural cooled radiofrequency ablation of a carotid body.

FIG. 55A depicts an endovascular transmural ablation cooled tip catheter 1206. FIG. 55B depicts the distal end of catheter 1206 in exploded view. Catheter 1206 comprises ablation electrode 207, catheter shaft 206, and proximal terminal 208. Ablation electrode 207 comprises electrode cap 219, heat exchanger 1214, temperature sensor 213 mounted in heat exchanger 1214, electrical conductor 218 in electrical communication with heat exchanger 1214 and electrode coupling sleeve 221. Catheter shaft 211 comprises a central lumen, a core extrusion 1216, and a braided overlay 1215. Proximal terminal 208 comprises electrical connector 209, and fluid connector 1210. Temperature sensor wires 222 and electrical conductor 218 connect ablation electrode 207 to electrical connector 209. Electrode cap 219 is in electrical communication with heat exchanger 1214. Fluid ports 1212 depicted in the vicinity of ablation electrode 207 distal tip 220 is in fluidic communication with heat exchanger 1214, central lumen 217, and fluid connector 1210. Catheter 1206 is configured for active cooling of ablation electrode 207 during ablation to prevent tissue in contact with ablation electrode 207 from overheating to allow for a higher ablation power, and therefore a larger ablation lesion than is possible without said cooling. As depicted a physiological liquid such as saline liquid is pumped through catheter from fluid connector 1210 to fluid ports 1212 at a rate of between about 5 ml per minute to about 100 ml per minute by a pump, not shown, or by a syringe. The heat exchanger 1214 is configured transfer heat from electrode cap 219 into the physiological liquid in an efficient manner using spiral flow channels 223. As an alternate configuration fluid ports 1212 could be replaced by having electrode cap 219 as a porous structure where the liquid exiting ablation electrode 207 is substantially distributed over the surface of ablation electrode 207 surface. Heat exchanger 1214 and electrode cap 219 are fabricated from metallic material. Catheter shaft 211 is substantially fabricated from a polymeric material such as Pebax, or polyurethane. Catheter 1206 can be configured to work through a steerable carotid assess sheath, or may incorporate steerable capabilities.

Figure 56:
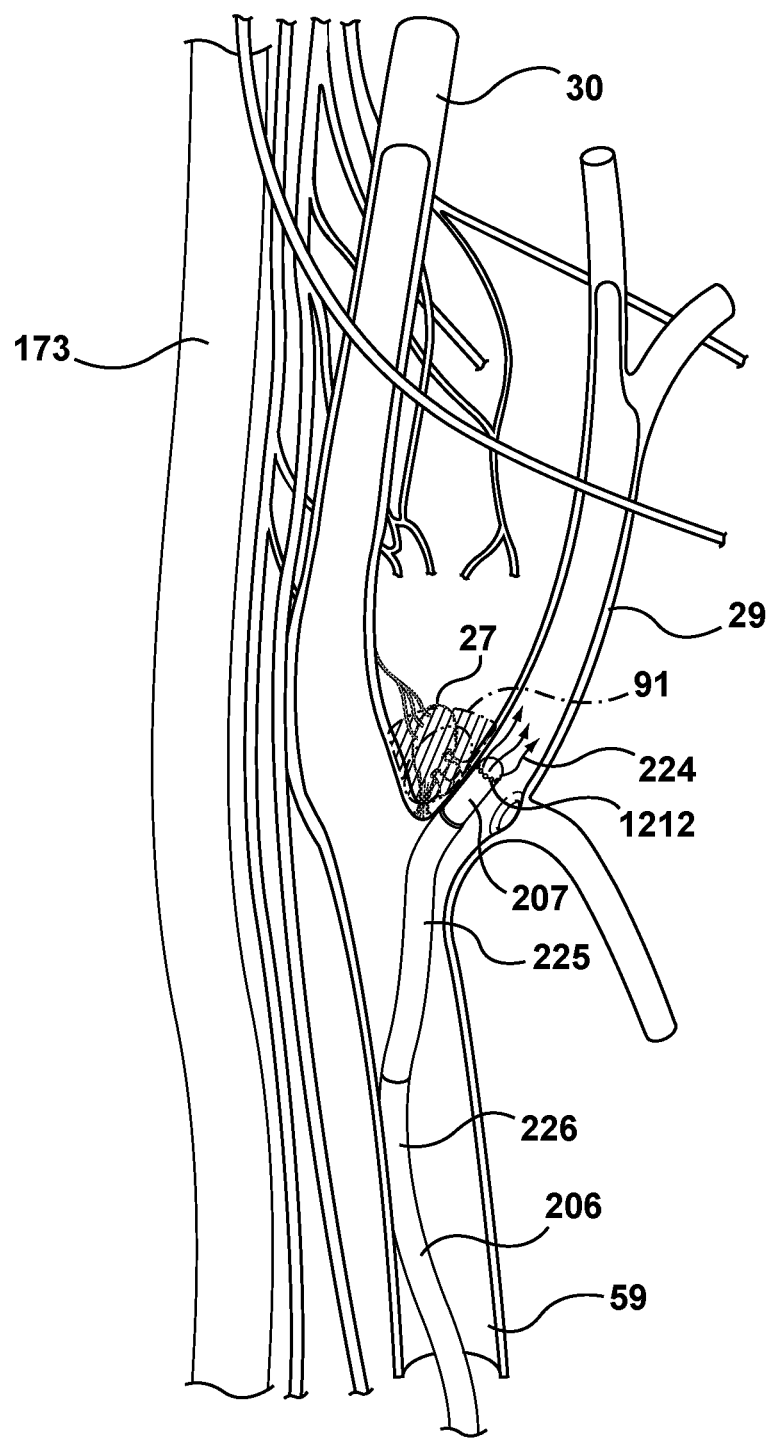
FIG. 56 is a cutaway illustration of a lateral view a patient's right carotid artery system with a schematic view of a steerable endovascular ablation catheter configured for transmural cooled radiofrequency ablation of a carotid body.

FIG. 56 depicts a steerable configuration of catheter 206 in position for ablation of carotid body 27 immediate following an ablation 91. As depicted electrode 207 has been positioned against the wall of carotid artery 29 immediately adjacent to carotid body 27 by the user using fluoroscopic guidance and the steering capability of catheter 206 comprising deflectable distal segment 225, and non-deflectable segment 226. Cooling saline 224 is depicted exiting liquid ports 1212. Catheter 1206 may also be positioned within the internal carotid artery 30, and alternately the internal jugular vein 173 for transmural ablation of carotid body 27, similar to the approach shown in FIGS. 61A, 61B and 61C.

Endovascular Transmural Cryo Ablation Catheter

FIG. 57A depicts in simplified schematic form an endovascular transmural cryo ablation catheter 227. FIG. 57B depicts in cross section view a catheter 227. Catheter 227 comprises cryo-ablation element 228, catheter shaft 229, proximal terminal 230, and optional neural modulation electrodes 233. Proximal terminal 230 comprises electrical connector 231, cryogen connector 232, and gas exhaust port 242. Cryo-ablation element 228 comprises cryo cap 234, heat exchanger 236, capillary tube 237, and temperature sensor 238. Cryo cap 234 is a thin walled metallic structure with high thermal conductivity. Heat exchanger 236 is a porous metallic structure with high thermal conductivity and is disposed within cryo cap 234 in an intimate heat transfer relationship. Heat exchanger 236 may be fabricated using a sintering process of a metal with high thermal conductivity such as copper. Capillary tube 237 is configured to meter the flow of cryogen from cryogen supply tube 240 into expansion chamber 235 at a predetermined rate. Capillary tube 237 may be fabricated from a stainless steel hypodermic tube. Temperature sensor 238 is disposed in the vicinity of heat exchanger 236. Cryogen supply tube 240 is bonded by adhesive to capillary tube 238 as shown. Ablation element 228 is bonded to the distal end of catheter shaft 229. Catheter shaft 229 comprises a central lumen 241, and may be fabricated from a polymer such as Pebax or polyurethane, with an outer diameter between 5 French and 12 French. The working length of catheter 227 is between 90 cm and 140 cm. Cryogen supply tube 240 is configured for delivery of a cryogen under high pressure on the order of about 500 psi to about 2000 psi. Cryogen supply tube may be fabricated from a polymer, or from a super elastic metal alloy such as Nitinol. Cryogen supply tube 240 is in fluidic communication with cryogen connector 232. Central lumen 241 is in fluidic communication with exhaust port 242. Electrical cable 239 connects temperature sensor 238, and neural modulation electrodes 233 to electrical connector 231.

FIG. 58A depicts the distal end of catheter 227 in working configuration with steerable carotid access sheath 1. FIG. 58B depicts an alternate embodiment of catheter 243 with steering capability comprising a user deflectable segment 245 and a non-deflectable segment 246 proximal to deflectable segment 245. Deflectable segment 245 is actuated by a pull wire, and a deflection actuator disposed on a handle of proximal terminal, not shown. An ice ball 244 is depicted to represent a cryo-ablation functional modality.

Figure 59:
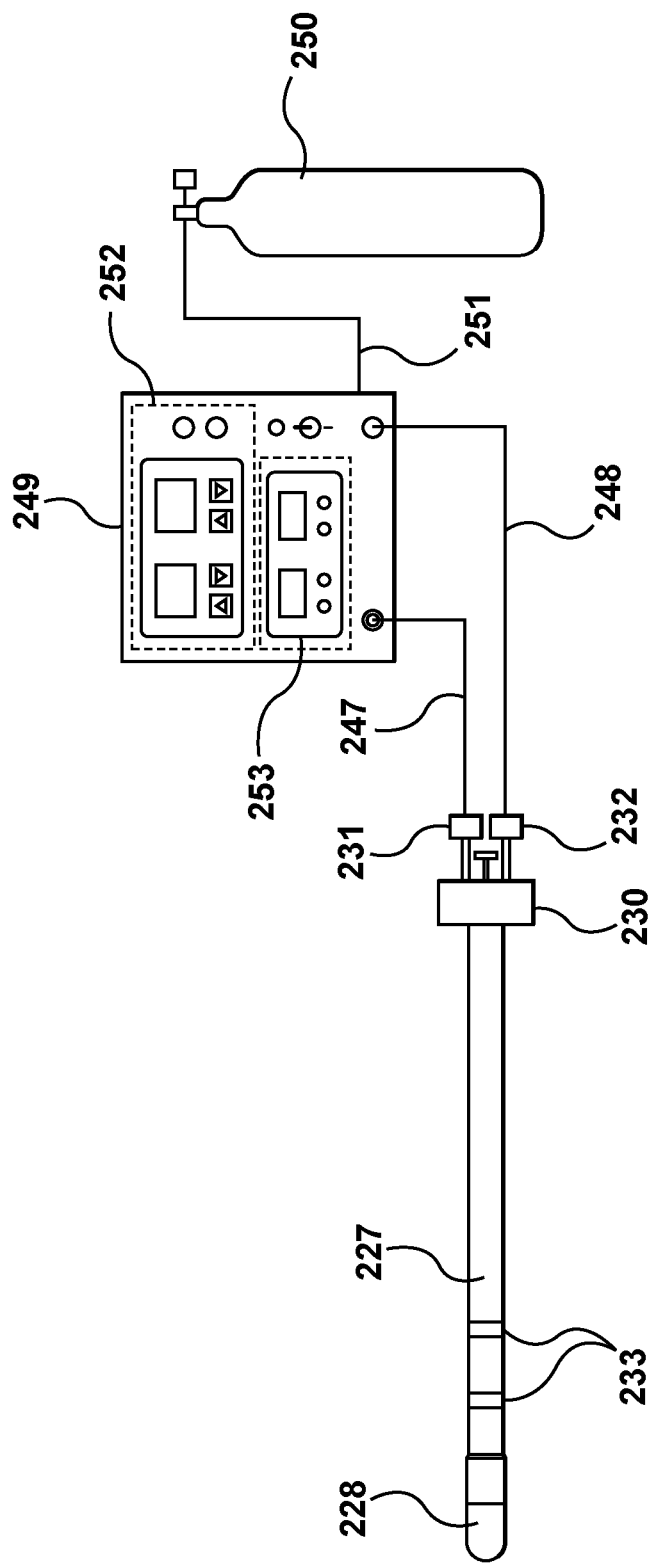
FIG. 59 is a schematic view of an endovascular ablation catheter having a point-ablate cryogenic ablation element.

FIG. 59 depicts in simplified schematic form an exemplary endovascular transmural cryo ablation system. The system comprises catheter 227, control console 249, cryogen source 250, electrical umbilical 247, cryogen umbilical 248, and cryogen supply line 251. Control console 249 has a user interface 252 that provides the user with a means to select cryo-ablation parameters, activate and deactivate a cryo-ablation, and to monitor the progress of a cryo-ablation. In addition, control console 249 may have second user interface 253 that allows the user to select electrical neuro-modulation parameters, activate neuro-modulation, deactivate neuro-modulation, and to monitor neuro-modulation. Control console 249 comprises a means to control flow of cryogen from cryogen source 250 to catheter 227 according to user settings of user interface 252.

In an exemplary method of use (with reference to FIGS. 57A, 57B, and 59), ablation element 228 receives cryogen under high pressure from control console 249, cryogen umbilical 248, cryogen connector 232, and cryogen supply tube 240. Cryogen under high pressure enters low pressure expansion chamber 235 resulting in a drop in temperature dependent on the cryogen used, the pressure of the cryogen prior to expansion, and the expanded pressure. The expanded cryogen flows through heat exchanger 236, which transfers heat from ablation cap surface into the cryogen flowing through heat exchanger 236. Temperature sensor 238 is used by the control console to control the flow the cryogen from the control console 249 to catheter 227 by means of flow or pressure modulation. The cryogen exits heat exchanger 236 into central lumen 241 and out exhaust port 242. Cryogen may be supplied to cryo-ablation element 228 in the form of a liquid such liquid nitrogen, or liquid carbon dioxide resulting in part in an evaporative cooling process, or the cryogen may be supplied to 228 in the form of a gas such as argon, nitrogen, or carbon dioxide where the cooling process is by Joule-Thompson effect (adiabatic expansion). The surface temperature of a cryo-ablation element may be controlled by control console 249 at a temperature between −20 degrees centigrade and −120 degrees centigrade during ablation by controlling the flow rate, or pressure of the cryogen.

Figure 60:
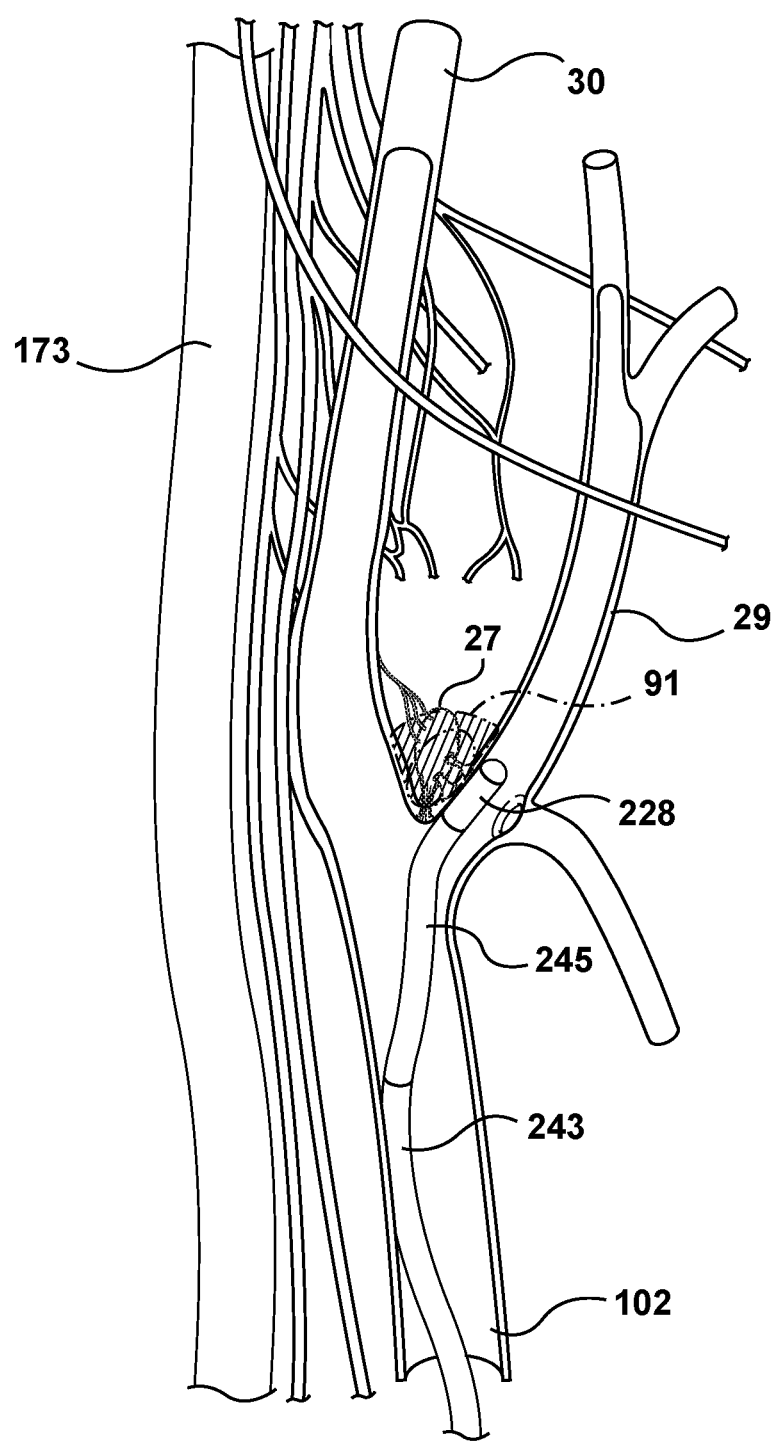
FIG. 60 is a cutaway illustration of a lateral view a patient's right carotid artery system with a schematic view of an endovascular ablation catheter having a point-ablate cryogenic ablation element, contained in a sheath, showing an ice ball formed around the cryogenic ablation element.

FIG. 60 depicts a steerable configuration of catheter 243 in position for cryo-ablation of carotid body 27 immediately following an ablation 91. As depicted cryo-ablation element 228 has been placed against the wall of external carotid artery 29 adjacent to carotid body 27 by the user using fluoroscopic guidance and the steering capability of catheter 243 comprising deflectable distal segment 245, and non-deflectable segment 246. Catheter 243 may alternatively be positioned within the internal carotid artery 30, or the internal jugular vein 173 for transmural cryo-ablation of carotid body 27, similar to the approach shown in FIGS. 61A, 61B and 61C.

Figures 61A, 61B, 61C:
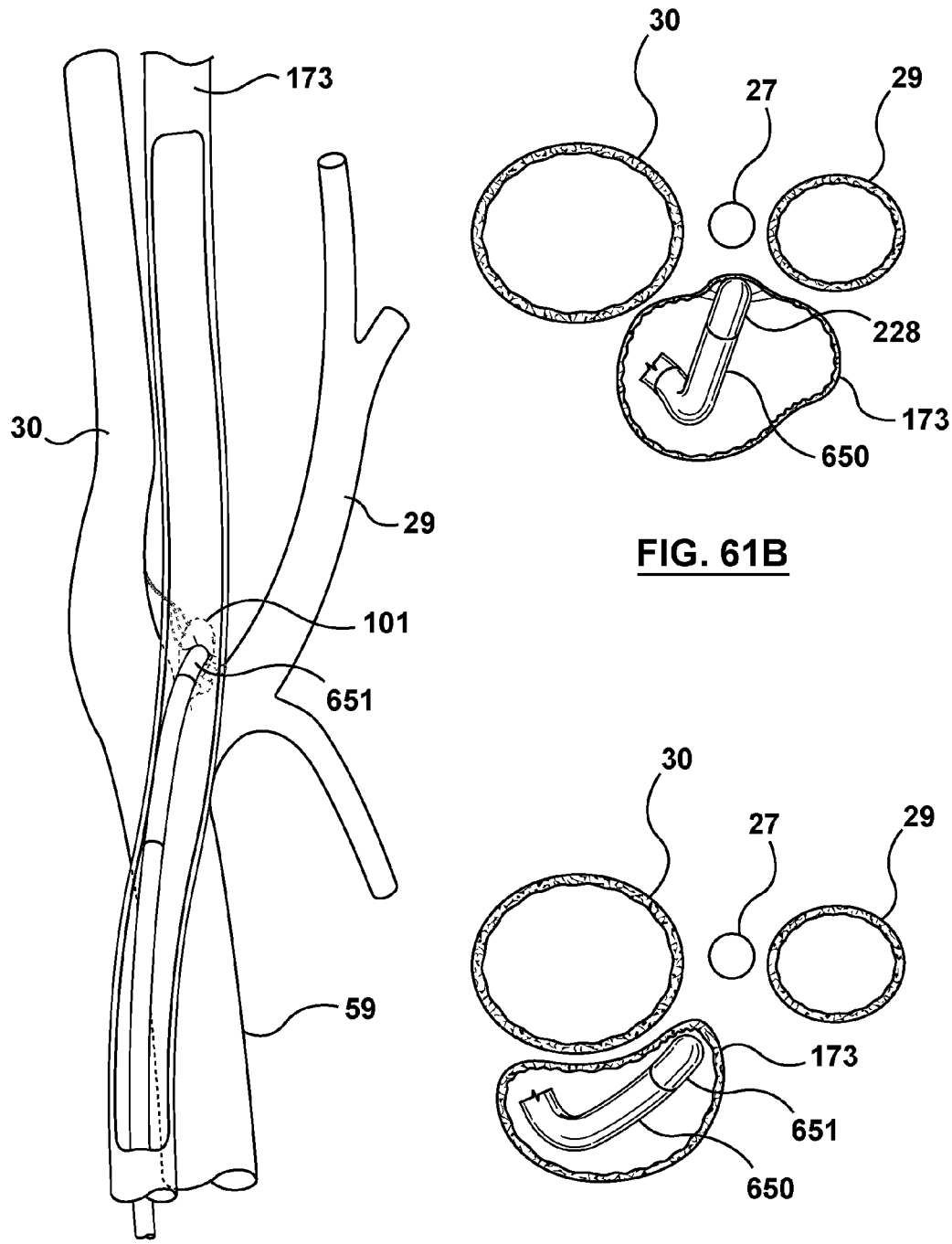
FIG. 61A is a cutaway illustration of a lateral view of a patient's right internal jugular vein with a schematic view of an endovascular ablation catheter positioned for transmural ablation of a carotid body from within the jugular vein.
FIGS. 61B and 61C are cross sectional views of a patient's internal and external carotid arteries, carotid body and internal jugular vein with an endovascular ablation catheter positioned for transmural ablation of a carotid body from within the jugular vein.

FIG. 61A depicts in simplified schematic form the placement of a carotid body ablation catheter 650 into a patient via an endovascular approach with a femoral vein puncture. The distal end of the catheter 651 is depicted in the left internal jugular vein 173 at the level of a carotid septum containing a target carotid body 101, positioned to deliver ablative energy to a carotid body or its nerves. As depicted the catheter 650 is inserted into the patient at an insertion site in the vicinity of the groin into a femoral vein and advanced through the inferior vena cava, superior vena cava, left common jugular vein and into the left internal jugular vein 173. Alternatively, the insertion site may be selected to gain venous access through a brachial vein, a sub-clavian vein, a common jugular vein 53, or any suitable peripheral vein. Furthermore, the distal end of the catheter 650 may be positioned for carotid body ablation in a different vein that proximate to a target ablation site, such as a facial vein (not shown) depending on the particular vascular and neural anatomy of the patient.

In some patients an internal jugular vein 173 is positioned touching or within about 5 mm of a target carotid body 27 as shown in FIG. 61B. In such a scenario a carotid body ablation catheter 650 may be advanced into the internal jugular vein 173 and an ablation element 228 may be placed to deliver ablation energy to the target carotid body 27.

In some patients an internal jugular vein 173 is positioned greater than about 5 mm from a target carotid body 27 as shown in FIG. 61C. In such a scenario the internal jugular vein 173, which is relatively pliable, may be maneuvered closer to the target carotid body 27 by applying a deflection force to a catheter 650 in the vein. Once close enough to the target site an ablation element 651 on a distal end of the catheter 650 may deliver ablative energy.

An angiographic catheter may be positioned in a common carotid artery 59 for the purpose creating an arterial angiographic image of the region of the carotid arteries 59, 30 and 29 for the purpose of guiding a trans-venous ablation catheter. An angiographic catheter may be inserted into a femoral artery through an insertion site in the groin, then advanced through the abdominal aorta, the aortic arch, and into the left common carotid artery 59 using standard angiographic techniques. It would be understood to those skilled in the art of endovascular interventions that means other than carotid artery angiography can be used to guide trans-venous carotid body ablation. For example, extracorporeal ultrasonic imaging of the neck may be used, as well as intra-vascular ultrasound, computed tomography angiography, and other known modalities alone or in combination.

Deployable Helical Structure

Figure 62:
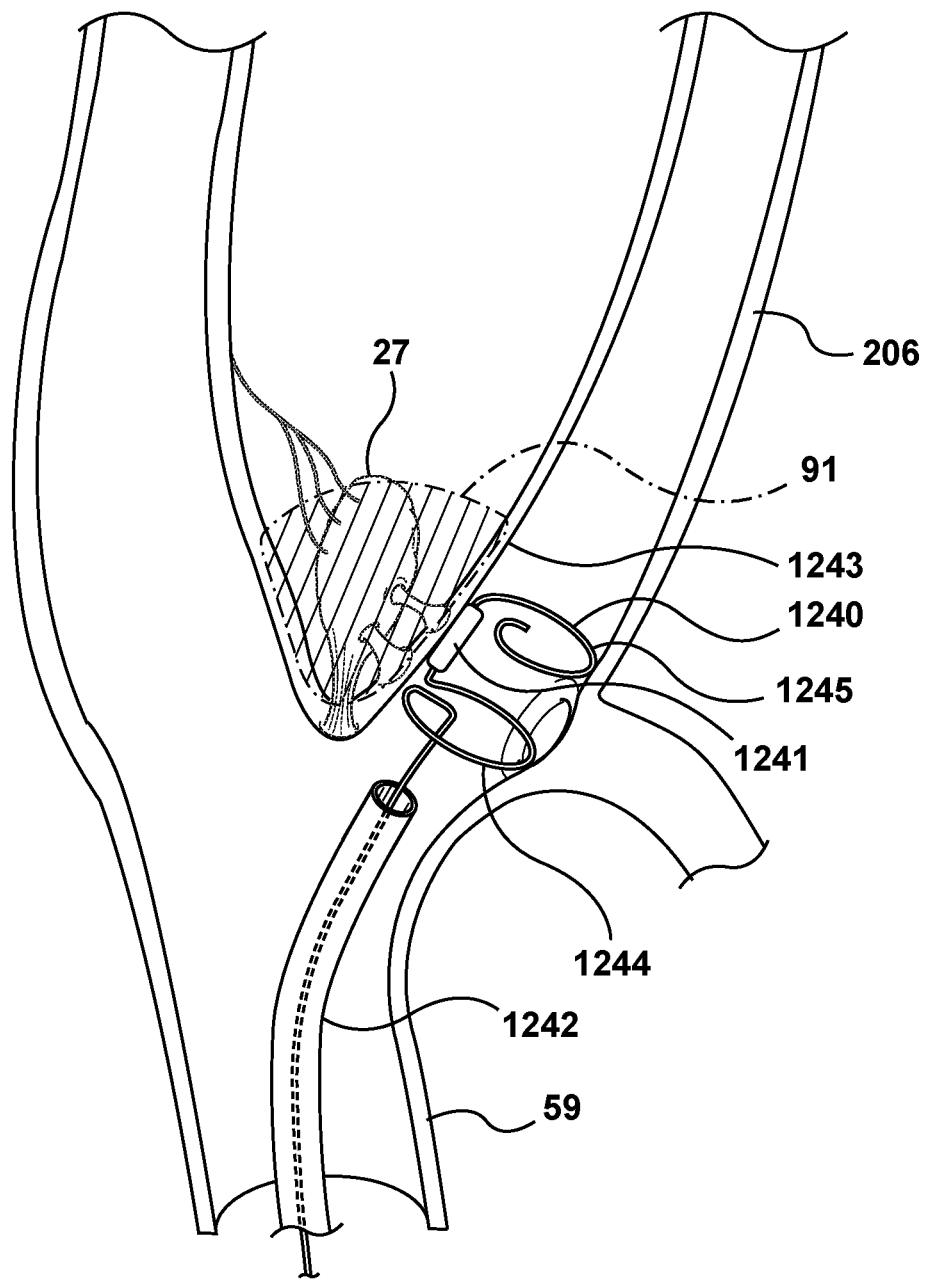
FIG. 62 is a schematic illustration of a carotid body ablation catheter having a deployable helix.

As shown in FIG. 62, a carotid body ablation catheter may comprise a deployable helical structure 1240 with at least one ablation electrode 1241 mounted to the helix. The helix may comprise an elastic or superelastic structural member such as Nitinol that allows the helix to resiliently conform to an undeployed state when contained in a delivery sheath 1242 and deploy to a helical configuration when advanced from the sheath 1242. The helical structure functions to provide stability and contact force of the electrode 1241 with the vessel wall 1243. The helical structure 1240 may have a preformed shape with a diameter of about 6 mm, which may allow it to expand in vessel such as an external carotid artery 206 having a diameter of about 4 to 6 mm and apply an outward force on the vessel wall 1243. The preformed shape may comprise a first helix 12111 proximal the electrode and a second helix 1245 distal the electrode with an electrode mounting section that is substantially parallel to the axis of the helical structure, or the axis of the vessel. The electrode mounting section may be about 4 to about 8 mm long for mounting an about 4 to about 8 mm long cylindrical electrode with a diameter between about 1 and about 3 mm. Alternatively, the preformed shape may comprise a single helix and an electrode may have a substantially spherical shape with a diameter of about 1 to about 3 mm. The catheter may comprise a single electrode, in which case the helical structure may require rotation to align the electrode with the target ablation site. Alternatively, the catheter may comprise multiple electrodes (e.g., 2, 3, 4, 5, or more, electrodes) and the electrode that is best aligned with a target ablation site may be activated.

Figure 63:
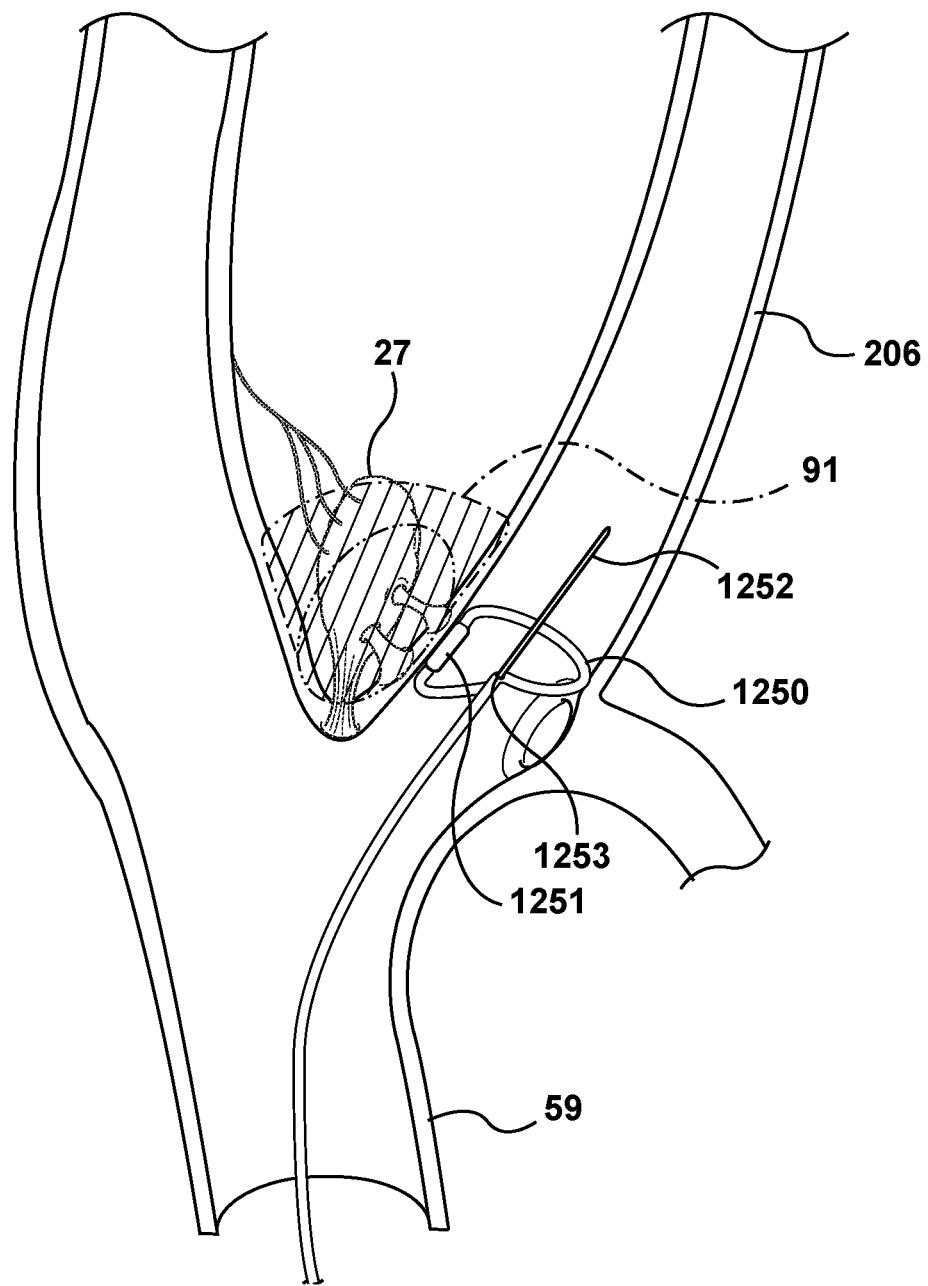
FIG. 63 is a schematic illustration of a carotid body ablation catheter having a deployable loop.

FIG. 63 illustrates an embodiment of a carotid body ablation catheter that comprises an expandable loop 1250 with an electrode 1251 mounted to the loop. The loop may have an adjustable radius that is controlled by a pull wire connected to an actuator in a handle (not shown). Alternatively, the loop may be self-expanding, comprising an elastic member such as Nitinol that is adapted to deploy when advanced distally from a sheath. The loop functions to stabilize and provide contact force of an electrode 1251 mounted to the loop, with a wall of an external carotid artery 206. The loop may be configured to expand to a diameter of about 6 mm. The electrode 1251 may be cylindrical, for example, having a length of about 4 to about 8 mm and a diameter of about 1 to about 3 mm. Alternatively, the electrode may be spherical with a diameter of about 1 to about 3 mm. A user-controlled loop radius may beneficially allow the user to deploy the loop to a diameter less than the vessel diameter, rotate the loop to align the electrode with a target ablation site, then further expand the loop to apply contact force between the electrode and vessel wall. The catheter may optionally comprise a lumen 1253 in which a guide wire can be positioned such that the catheter can be delivered over a guide wire 1252.

Methods of Therapy:

In some embodiments an embolism protection device or system is also positioned within the patient's vasculature. There may be danger of creating a brain embolism while performing an endovascular procedure in a patient's carotid artery, for example, a thrombus may be created by delivering ablation energy such as on a radiofrequency electrode, or a piece of atheromatous plaque may be dislodged by catheter movement. In addition to a carotid body ablation catheter, an endovascular catheter may be used to place a brain embolism protection device in a patient's internal carotid artery during a carotid body ablation procedure. The treatment may include occluding a patient's internal carotid artery. Blood flowing from a common carotid artery 102 would not flow through a connecting internal carotid artery 201, which feeds the brain, but instead would flow through the external carotid artery, which feeds other structures of the head that are much more capable of safely receiving an embolism. For example, a brain embolism protection device 610 in the form of an inflatable balloon is placed in an internal carotid artery 201. The balloon may be made from a soft, stretchable, compliant balloon material such as silicone and may be inflated with a fluid (e.g., saline or contrast agent) through an inflation lumen. The inflation fluid may be injected into an inlet port by a syringe or by a computer controlled pump system. The balloon may be placed, using a delivery sheath, in an internal carotid artery (e.g., up to about 10 cm from a carotid bifurcation). Contrast solution may be injected into the common carotid artery 102, for example through the delivery sheath to allow radiographic visualization of the common 102, internal 201 and external 206 carotid arteries, which may assist a physician to position a brain embolism protection device 610. An endovascular ablation catheter may place an energy delivery element proximate a carotid body, for example in a carotid body. It is expected that blood flow would carry any debris into the external carotid artery where it is harmless. Occlusion of an internal carotid artery may be done for a period of time that allows an ablation procedure and that is safe for the brain (e.g., less than or equal to about 3 minutes, or between about 1 to 2 minutes). After the carotid body is ablated the brain embolism protection device may be deployed and removed from the patient or positioned on the patient's contralateral side in the event of ablating the contralateral carotid body.

In another embodiment a brain embolism protection device may be a blood-permeable filter deployed in a patient's internal carotid artery. A filter may be a fine mesh or net connected to a deployable frame that expands to envelop a cross-section of an internal carotid artery distal to a bifurcation. Other embodiments of a blood-permeable filter may include wire-type expandable devices such as baskets or umbrellas. Such a filter may allow antegrade blood flow to continue to the brain while trapping and retrieving debris in the blood, preventing a brain embolism. Such a device may be deployed in an internal carotid artery prior to the placement of ablation catheter and retrieved following ablation.

A method in accordance with a particular embodiment includes ablating at least one of a patient's carotid bodies based at least in part on identifying the patient as having a sympathetically mediated disease such as cardiac, metabolic, or pulmonary disease such as hypertension, pulmonary hypertension (e.g., refractory hypertension), congestive heart failure (CHF), or dyspnea.

A procedure may include diagnosis, selection based on diagnosis, further screening (e.g., baseline assessment of chemosensitivity), treating a patient based at least in part on diagnosis or further screening via a chemoreceptor (e.g., carotid body) ablation procedure such as one of the embodiments disclosed. Additionally, following ablation a method of therapy may involve conducting a post-ablation assessment to compare with the baseline assessment and making decisions based on the assessment (e.g., adjustment of drug therapy, re-treat in new position or with different parameters, or ablate a second chemoreceptor if only one was previously ablated).

In some embodiments carotid body ablation procedure may comprise the following steps or a combination thereof: patient sedation, locating a target peripheral chemoreceptor, visualizing a target peripheral chemoreceptor (e.g., carotid body), confirming a target ablation site is or is proximate a peripheral chemoreceptor, confirming a target ablation site is safely distant from vital structures that are preferably protected (e.g., hypoglossal and vagus nerves), providing stimulation (e.g., electrical, mechanical, chemical) to a target site or target peripheral chemoreceptor prior to, during or following an ablation step, monitoring physiological responses to said stimulation, anesthetizing a target site, protecting the brain from potential embolism, thermally protecting an arterial or venous wall (e.g., carotid artery, jugular vein), ablating a target site or peripheral chemoreceptor, monitoring ablation parameters (e.g., temperature, impedance, blood flow in a carotid artery), confirming a reduction of chemoreceptor activity (e.g., chemosensitivity, HR, blood pressure, ventilation, sympathetic nerve activity) during or following an ablation step, removing an ablation device, conducting a post-ablation assessment, repeating any steps of the chemoreceptor ablation procedure on another peripheral chemoreceptor in the patient.

Patient screening, as well as post-ablation assessment may include physiological tests or gathering of information, for example, chemoreflex sensitivity, central sympathetic nerve activity, heart rate, heart rate variability, blood pressure, ventilation, production of hormones, peripheral vascular resistance, blood pH, blood $PCO_2$, degree of hyperventilation, peak $VO_2$, $VE/VCO_2$ slope. Directly measured maximum oxygen uptake (more correctly $pVO_2$ in heart failure patients) and index of respiratory efficiency $VE/VCO_2$ slope has been shown to be a reproducible marker of exercise tolerance in heart failure and provide objective and additional information regarding a patient's clinical status and prognosis.

A method of therapy may include electrical stimulation of a target region, using a stimulation electrode, to confirm proximity to a carotid body. For example, a stimulation signal having a 1-10 milliamps (mA) pulse train at about 20 to 40 Hz with a pulse duration of 50 to 500 microseconds (µs) that produces a positive carotid body stimulation effect may indicate that the stimulation electrode is within sufficient proximity to the carotid body or nerves of the carotid body to effectively ablate it. A positive carotid body stimulation effect could be increased blood pressure, heart rate, or ventilation concomitant with application of the stimulation. These variables could be monitored, recorded, or displayed to help assess confirmation of proximity to a carotid body. A catheter-based technique, for example, may have a stimulation electrode proximal to the energy delivery element used for ablation. Alternatively, the energy delivery element itself may also be used as a stimulation electrode. Alternatively, an energy delivery element that delivers a form of ablative energy that is not electrical, such as a cryogenic ablation applicator, may be configured to also deliver an electrical stimulation signal as described earlier. Yet another alternative embodiment comprises a stimulation electrode that is distinct from an ablation element. For example, during a surgical procedure a stimulation probe can be touched to a suspected carotid body that is surgically exposed. A positive carotid body stimulation effect could confirm that the suspected structure is a carotid body and ablation can commence. Physiological monitors (e.g., heart rate monitor, blood pressure monitor, blood flow monitor, MSNA monitor) may communicate with a computerized stimulation generator, which may also be an ablation generator, to provide feedback information in response to stimulation. If a physiological response correlates to a given stimulation the computerized generator may provide an indication of a positive confirmation.

Alternatively or in addition a drug known to excite the chemo sensitive cells of the carotid body can be injected directly into the carotid artery or given systemically into a patient's vein or artery in order to elicit hemodynamic or respiratory response. Examples of drugs that may excite a chemoreceptor include nicotine, atropine, Doxapram, Almitrine, hyperkalemia, Theophylline, adenosine, sulfides, Lobeline, Acetylcholine, ammonium chloride, methylamine, potassium chloride, anabasine, coniine, cytosine, acetaldehyde, acetyl ester and the ethyl ether of i-methylcholine, Succinylcholine, Piperidine, monophenol ester of homo-isomuscarine and acetylsalicylamides, alkaloids of veratrum, sodium citrate, adenosinetriphosphate, dinitrophenol, caffeine, theobromine, ethyl alcohol, ether, chloroform, phenyldiguanide, sparteine, coramine (nikethamide), metrazol (pentylenetetrazol), iodomethylate of dimethylaminomethylenedioxypropane, ethyltrimethylammoniumpropane, trimethylammonium, hydroxytryptamine, papaverine, neostigmine, acidity.

A method of therapy may further comprise applying electrical or chemical stimulation to the target area or systemically following ablation to confirm a successful ablation. Heart rate, blood pressure or ventilation may be monitored for change or compared to the reaction to stimulation prior to ablation to assess if the targeted carotid body was ablated. Post-ablation stimulation may be done with the same apparatus used to conduct the pre-ablation stimulation. Physiological monitors (e.g., heart rate monitor, blood pressure monitor, blood flow monitor, MSNA monitor) may communicate with a computerized stimulation generator, which may also be an ablation generator, to provide feedback information in response to stimulation. If a physiological response correlated to a given stimulation is reduced following an ablation compared to a physiological response prior to the ablation, the computerized generator may provide an indication ablation efficacy or possible procedural suggestions such as repeating an ablation, adjusting ablation parameters, changing position, ablating another carotid body or chemosensor, or concluding the procedure.

Visualization:

An optional step of visualizing internal structures (e.g., carotid body or surrounding structures) may be accomplished using one or more non-invasive imaging modalities, for example fluoroscopy, radiography, arteriography, computer tomography (CT), computer tomography angiography with contrast (CTA), magnetic resonance imaging (MRI), or sonography, or minimally invasive techniques (e.g., IVUS, endoscopy, optical coherence tomography). A visualization step may be performed as part of a patient assessment, prior to an ablation procedure to assess risks and location of anatomical structures, during an ablation procedure to help guide an ablation device, or following an ablation procedure to assess outcome (e.g., efficacy of the ablation). Visualization may be used to: (a) locate a carotid body, (b) locate vital structures that may be adversely affected, or (c) locate, identify and measure arterial plaque.

Endovascular (for example transfemoral) arteriography of the common carotid and then selective arteriography of the internal and external carotids may be used to determine a position of a catheter tip at a carotid bifurcation. Additionally, ostia of glomic arteries (these arteries may be up to 4 mm long and arise directly from the main parent artery) can be identified by dragging the dye injection catheter and releasing small amounts ("puffs") of dye. If a glomic artery is identified it can be cannulated by a guide wire and possibly further cannulated by small caliber catheter. Direct injection of dye into glomic arteries can further assist the interventionalist in the ablation procedure. It is appreciated that the feeding glomic arteries are small and microcatheters may be needed to cannulate them.

Alternatively, ultrasound visualization may allow a physician to see the carotid arteries and even the carotid body. Another method for visualization may consist of inserting a small needle (e.g., 22 Gauge) with sonography or computer tomography (CT) guidance into or toward the carotid body. A wire or needle can be left in place as a fiducial guide, or contrast can be injected into the carotid body. Runoff of contrast to the jugular vein may confirm that the target is achieved.

Computer Tomography (CT) and computer tomography angiography (CTA) may also be used to aid in identifying a carotid body. Such imaging could be used to help guide an ablation device to a carotid body.

Ultrasound visualization (e.g., sonography) is an ultrasound-based imaging technique used for visualizing subcutaneous body structures including blood vessels and surrounding tissues. Doppler ultrasound uses reflected ultrasound waves to identify and display blood flow through a vessel. Operators typically use a hand-held transducer/transceiver placed directly on a patient's skin and aimed inward directing ultrasound waves through the patient's tissue. Ultrasound may be used to visualize a patient's carotid body to help guide an ablation device.

Visualization and navigation steps may comprise multiple imaging modalities (e.g., CT, fluoroscopy, ultrasound) superimposed digitally to use as a map for instrument positioning. Superimposing borders of great vessels such as carotid arteries can be done to combine images.

Responses to stimulation at different coordinate points can be stored digitally as a 3-dimensional or 2-dimensional orthogonal plane map. Such an electric map of the carotid bifurcation showing points, or point coordinates that are electrically excitable such as baroreceptors, baroreceptor nerves, chemoreceptors and chemoreceptor nerves can be superimposed with an image (e.g., CT, fluoroscopy, ultrasound) of vessels. This can be used to guide the procedure, and identify target areas and areas to avoid.

In addition, as noted above, it should be understood that a device providing therapy can also be used to locate a carotid body as well as to provide various stimuli (electrical, chemical, other) to test a baseline response of the carotid body chemoreflex (CBC) or carotid sinus baroreflex (CSB) and measure changes in these responses after therapy or a need for additional therapy to achieve the desired physiological and clinical effects.

Patient Selection and Assessment:

In an embodiment, a procedure may comprise assessing a patient to be a plausible candidate for carotid body ablation. Such assessment may involve diagnosing a patient with a sympathetically mediated disease (e.g., MSNA microneurography, measure of cataclomines in blood or urine, heart rate, or low/high frequency analysis of heart rate variability may be used to assess sympathetic tone). Patient assessment may further comprise other patient selection criteria, for example indices of high carotid body activity (i.e., carotid body hypersensitivity or hyperactivity) such as a combination of hyperventilation and hypocarbia at rest, high carotid body nerve activity (e.g., measured directly), incidence of periodic breathing, dyspnea, central sleep apnea elevated brain natriuretic peptide, low exercise capacity, having cardiac resynchronization therapy, atrial fibrillation, ejection fraction of the left ventricle, using beta blockers or ACE inhibitors.

Patient assessment may further involve selecting patients with high peripheral chemosensitivity (e.g., a respiratory response to hypoxia normalized to the desaturation of oxygen greater than or equal to about 0.7 l/min/min $SpO_2$), which may involve characterizing a patient's chemoreceptor sensitivity, reaction to temporarily blocking carotid body chemoreflex, or a combination thereof.

Although there are many ways to measure chemosensitivity they can be divided into (a) active provoked response and (b) passive monitoring. Active tests can be done by inducing intermittent hypoxia (such as by taking breaths of nitrogen or $CO_2$ or combination of gases) or by rebreathing air into and from a 4 to 10 liter bag. For example: a hypersensitive response to a short period of hypoxia measured by increase of respiration or heart rate may provide an indication for therapy. Ablation or significant reduction of such response could be indicative of a successful procedure. Also, electrical stimulation, drugs and chemicals (e.g., dopamine, lidocane) exist that can block or excite a carotid body when applied locally or intravenously.

The location and baseline function of the desired area of therapy (including the carotid and aortic chemoreceptors and baroreceptors and corresponding nerves) may be determined prior to therapy by application of stimuli to the carotid body or other organs that would result in an expected change in a physiological or clinical event such as an increase or decrease in SNS activity, heart rate or blood pressure. These stimuli may also be applied after the therapy to determine the effect of the therapy or to indicate the need for repeated application of therapy to achieve the desired physiological or clinical effect(s). The stimuli can be either electrical or chemical in nature and can be delivered via the same or another catheter or can be delivered separately (such as injection of a substance through a peripheral IV to affect the CBC that would be expected to cause a predicted physiological or clinical effect).

A baseline stimulation test may be performed to select patients that may benefit from a carotid body ablation procedure. For example, patients with a high peripheral chemosensitivity gain (e.g., greater than or equal to about two standard deviations above an age matched general population chemosensitivity, or alternatively above a threshold peripheral chemosensitivity to hypoxia of 0.5 or 0.7 ml/min/% $O_2$) may be selected for a carotid body ablation procedure. A prospective patient suffering from a cardiac, metabolic, or pulmonary disease (e.g., hypertension, CHF, diabetes) may be selected 700. The patient may then be tested to assess a baseline peripheral chemoreceptor sensitivity (e.g., minute ventilation, tidal volume, ventilator rate, heart rate, or other response to hypoxic or hypercapnic stimulus) 702. Baseline peripheral chemosensitivity may be assessed using tests known in the art which involve inhalation of a gas mixture having reduced $O_2$ content (e.g., pure nitrogen, $CO_2$, helium, or breathable gas mixture with reduced amounts of $O_2$ and increased amounts of $CO_2$) or rebreathing of gas into a bag. Concurrently, the patient's minute ventilation or initial sympathetically mediated physiologic parameter such as minute ventilation or HR may be measured and compared to the $O_2$ level in the gas mixture. Tests like this may elucidate indices called chemoreceptor set-point and gain. These indices are indicative of chemoreceptor sensitivity. If the patient's chemosensitivity is not assessed to be high (e.g., less than about two standard deviations of an age matched general population chemosensitivity, or other relevant numeric threshold) then the patient may not be a suitable candidate for a carotid body ablation procedure 704. Conversely, a patient with chemoreceptor hypersensitivity (e.g., greater than or equal to about two standard deviations above normal) may proceed to have a carotid body ablation procedure 706. Following a carotid body ablation procedure the patient's chemosensitivity may optionally be tested again 708 and compared to the results of the baseline test 702. The second test 708 or the comparison of the second test to the baseline test may provide an indication of treatment success 710 or suggest further intervention 712 such as possible adjustment of drug therapy, repeating the carotid body ablation procedure with adjusted parameters or location, or performing another carotid body ablation procedure on a second carotid body if the first procedure only targeted one carotid body. It may be expected that a patient having chemoreceptor hypersensitivity or hyperactivity may return to about a normal sensitivity or activity following a successful carotid body ablation procedure.

In an alternative protocol for selecting a patient for a carotid body ablation, patients with high peripheral chemosensitivity or carotid body activity (e.g., ≥about 2 standard deviations above normal) alone or in combination with other clinical and physiologic parameters may be particularly good candidates for carotid body ablation therapy if they further respond positively to temporary blocking of carotid body activity. A prospective patient suffering from a cardiac, metabolic, or pulmonary disease may be selected 700 to be tested to assess the baseline peripheral chemoreceptor sensitivity 702. A patient without high chemosensitivity may not be a plausible candidate 704 for a carotid body ablation procedure. A patient with a high chemosensitivity may be given a further assessment that temporarily blocks a carotid body chemoreflex 714. For example a temporary block may be done chemically, for example using a chemical such as intravascular dopamine or dopamine-like substances, intravascular alpha-2 adrenergic agonists, oxygen, in general alkalinity, or local or topical application of atropine externally to the carotid body. A patient having a negative response to the temporary carotid body block test (e.g., sympathetic activity index such as respiration, HR, heart rate variability, MSNA, vasculature resistance, etc. is not significantly altered) may be a less plausible candidate 704 for a carotid body ablation procedure. Conversely, a patient with a positive response to the temporary carotid body block test (e.g., respiration or index of sympathetic activity is altered significantly) may be a more plausible candidate for a carotid body ablation procedure 716.

There are a number of potential ways to conduct a temporary carotid body block test 714. Hyperoxia (e.g., higher than normal levels of $PO_2$) for example, is known to partially block (about a 50%) or reduce afferent sympathetic response of the carotid body. Thus, if a patient's sympathetic activity indexes (e.g., respiration, HR, HRV, MSNA) are reduced by hyperoxia (e.g., inhalation of higher than normal levels of $O_2$) for 3-5 minutes, the patient may be a particularly plausible candidate for carotid body ablation therapy. A sympathetic response to hyperoxia may be achieved by monitoring minute ventilation (e.g., reduction of more than 20-30% may indicate that a patient has carotid body hyperactivity). To evoke a carotid body response, or compare it to carotid body response in normoxic conditions, $CO_2$ above 3-4% may be mixed into the gas inspired by the patient (nitrogen content will be reduced) or another pharmacological agent can be used to invoke a carotid body response to a change of $CO_2$, pH or glucose concentration. Alternatively, "withdrawal of hypoxic drive" to rest state respiration in response to breathing a high concentration $O_2$ gas mix may be used for a simpler test.

An alternative temporary carotid body block test involves administering a sub-anesthetic amount of anesthetic gas halothane, which is known to temporarily suppress carotid body activity. Furthermore, there are injectable substances such as dopamine that are known to reversibly inhibit the carotid body. However, any substance, whether inhaled, injected or delivered by another manner to the carotid body that affects carotid body function in the desired fashion may be used.

Another alternative temporary carotid body block test involves application of cryogenic energy to a carotid body (i.e., removal of heat). For example, a carotid body or its nerves may be cooled to a temperature range between about −15° C. to 0° C. to temporarily reduce nerve activity or blood flow to and from a carotid body thus reducing or inhibiting carotid body activity.

An alternative method of assessing a temporary carotid body block test may involve measuring pulse pressure. Noninvasive pulse pressure devices such as Nexfin (made by BMEYE, based in Amsterdam, The Netherlands) can be used to track beat-to-beat changes in peripheral vascular resistance. Patients with hypertension or CHF may be sensitive to temporary carotid body blocking with oxygen or injection of a blocking drug. The peripheral vascular resistance of such patients may be expected to reduce substantially in response to carotid body blocking. Such patients may be good candidates for carotid body ablation therapy.

Yet another index that may be used to assess if a patient may be a good candidate for carotid body ablation therapy is increase of baroreflex, or baroreceptor sensitivity, in response to carotid body blocking. It is known that hyperactive chemosensitivity suppresses baroreflex. If carotid body activity is temporarily reduced the carotid sinus baroreflex (baroreflex sensitivity (BRS) or baroreflex gain) may be expected to increase. Baroreflex contributes a beneficial parasympathetic component to autonomic drive. Depressed BRS is often associated with an increased incidence of death and malignant ventricular arrhythmias. Baroreflex is measurable using standard non-invasive methods. One example is spectral analysis of RR interval of ECG and systolic blood pressure variability in both the high- and low-frequency bands. An increase of baroreflex gain in response to temporary blockade of carotid body can be a good indication for permanent therapy. Baroreflex sensitivity can also be measured by heart rate response to a transient rise in blood pressure induced by injection of phenylephrine.

An alternative method involves using an index of glucose tolerance to select patients and determine the results of carotid body blocking or removal in diabetic patients. There is evidence that carotid body hyperactivity contributes to progression and severity of metabolic disease.

In general, a beneficial response can be seen as an increase of parasympathetic or decrease of sympathetic tone in the overall autonomic balance. For example, Power Spectral Density (PSD) curves of respiration or FIR can be calculated using nonparametric Fast Fourier Transform algorithm (FFT). FFT parameters can be set to 256-64 k buffer size, Hamming window, 50% overlap, 0 to 0.5 or 0.1 to 1.0 Hz range. HR and respiratory signals can be analyzed for the same periods of time corresponding to (1) normal unblocked carotid body breathing and (2) breathing with blocked carotid body.

Power can be calculated for three bands: the very low frequency (VLF) between 0 and 0.04 Hz, the low frequency band (LF) between 0.04-0.15 Hz and the high frequency band (HF) between 0.15-0.4 Hz. Cumulative spectral power in LF and HF bands may also be calculated; normalized to total power between 0.04 and 0.4 Hz (TF=HF+LF) and expressed as % of total. Natural breathing rate of CHF patient, for example, can be rather high, in the 0.3-0.4 Hz range.

The VLF band may be assumed to reflect periodic breathing frequency (typically 0.016 Hz) that can be present in CHF patients. It can be excluded from the HF/LF power ratio calculations.

The powers of the LF and HF oscillations characterizing heart rate variability (HRV) appear to reflect, in their reciprocal relationship, changes in the state of the sympathovagal (sympathetic to parasympathetic) balance occurring during numerous physiological and pathophysiological conditions. Thus, increase of HF contribution in particular can be considered a positive response to carotid body blocking.

Another alternative method of assessing carotid body activity comprises nuclear medicine scanning, for example with ocretide, somatostatin analogues, or other substances produced or bound by the carotid body.

Furthermore, artificially increasing blood flow may reduce carotid body activation. Conversely artificially reducing blood flow may stimulate carotid body activation. This may be achieved with drugs know in the art to alter blood flow.

There is a considerable amount of scientific evidence to demonstrate that hypertrophy of a carotid body often accompanies disease. A hypertrophied (i.e. enlarged) carotid body may further contribute to the disease. Thus identification of patients with enlarged carotid bodies may be instrumental in determining candidates for therapy. Imaging of a carotid body may be accomplished by angiography performed with radiographic, computer tomography, or magnetic resonance imaging.

It should be understood that the available measurements are not limited to those described above. It may be possible to use any single or a combination of measurements that reflect any clinical or physiological parameter effected or changed by either increases or decreases in carotid body function to evaluate the baseline state, or change in state, of a patient's chemosensitivity.

There is a considerable amount of scientific evidence to demonstrate that hypertrophy of a carotid body often accompanies disease. A hypertrophied or enlarged carotid body may further contribute to the disease. Thus identification of patients with enlarged carotid bodies may be instrumental in determining candidates for therapy.

Further, it is possible that although patients do not meet a preselected clinical or physiological definition of high peripheral chemosensitivity (e.g., greater than or equal to about two standard deviations above normal), administration of a substance that suppresses peripheral chemosensitivity may be an alternative method of identifying a patient who is a candidate for the proposed therapy. These patients may have a different physiology or co-morbid disease state that, in concert with a higher than normal peripheral chemosensitivity (e.g., greater than or equal to normal and less than or equal to about 2 standard deviations above normal), may still allow the patient to benefit from carotid body ablation. The proposed therapy may be at least in part based on an objective that carotid body ablation will result in a clinically significant or clinically beneficial change in the patient's physiological or clinical course. It is reasonable to believe that if the desired clinical or physiological changes occur even in the absence of meeting the predefined screening criteria, then therapy could be performed.

It is to be understood that the disclosure is not to be limited to the disclosed embodiment(s). The disclosure also covers various modifications and equivalent arrangements included within the spirit and scope of the disclosure.

Exemplary Methods of Therapy:

Patients having CHF or hypertension concurrent with heightened peripheral chemoreflex activity and sensitivity often react as if their system was hypercapnic even if it is not. The reaction is to hyperventilate, a maladaptive attempt to rid the system of $CO_2$, thus overcompensating and creating a hypocapnic and alkalotic system. Some researchers attribute this hypersensitivity/hyperactivity of the carotid body to the direct effect of catecholamines, hormones circulating in excessive quantities in the blood stream of CHF patients. The procedure may be particularly useful to treat such patients who are hypocapnic and possibly alkalotic resulting from high tonic output from carotid bodies. Such patients are particularly predisposed to periodic breathing and central apnea hypopnea type events that cause arousal, disrupt sleep, cause intermittent hypoxia and are by themselves detrimental and difficult to treat.

It is appreciated that periodic breathing of Cheyne Stokes pattern occurs in patients during sleep, exercise and even at rest as a combination of central hypersensitivity to $CO_2$, peripheral chemosensitivity to $O_2$ and $CO_2$ and prolonged circulatory delay. All these parameters are often present in CHF patients that are at high risk of death. Thus, patients with hypocapnea, CHF, high chemosensitivity and prolonged circulatory delay, and specifically ones that exhibit periodic breathing at rest or during exercise or induced by hypoxia are likely beneficiaries of the proposed therapy.

Hyperventilation is defined as breathing in excess of a person's metabolic need at a given time and level of activity. Hyperventilation is more specifically defined as minute ventilation in excess of that needed to remove $CO_2$ from blood in order to maintain blood $CO_2$ in the normal range (e.g., around 40 mmHg partial pressure). For example, patients with arterial blood $PCO_2$ in the range of 32-37 mmHg can be considered hypocapnic and in hyperventilation.

For the purpose of this disclosure hyperventilation is equivalent to abnormally low levels of carbon dioxide in the blood (e.g., hypocapnia, hypocapnea, or hypocarbia) caused by overbreathing. Hyperventilation is the opposite of hypoventilation (e.g., underventilation) that often occurs in patients with lung disease and results in high levels of carbon dioxide in the blood (e.g., hypercapnia or hypercarbia).

A low partial pressure of carbon dioxide in the blood causes alkalosis, because $CO_2$ is acidic in solution and reduced $CO_2$ makes blood pH more basic, leading to lowered plasma calcium ions and nerve and muscle excitability. This condition is undesirable in cardiac patients since it can increase probability of cardiac arrhythmias.

Alkalemia may be defined as abnormal alkalinity, or increased pH of the blood. Respiratory alkalosis is a state due to excess loss of carbon dioxide from the body, usually as a result of hyperventilation. Compensated alkalosis is a form in which compensatory mechanisms have returned the pH toward normal. For example, compensation can be achieved by increased excretion of bicarbonate by the kidneys.

Compensated alkalosis at rest can become uncompensated during exercise or as a result of other changes of metabolic balance. Thus the invented method is applicable to treatment of both uncompensated and compensated respiratory alkalosis.

Tachypnea means rapid breathing. For the purpose of this disclosure a breathing rate of about 6 to 16 breaths per minute at rest is considered normal but there is a known benefit to lower rate of breathing in cardiac patients. Reduction of tachypnea can be expected to reduce respiratory dead space, increase breathing efficiency, and increase parasympathetic tone.

Therapy Example: Role of Chemoreflex and Central Sympathetic Nerve Activity in CHF Chronic elevation in sympathetic nerve activity (SNA) is associated with the development and progression of certain types of hypertension and contributes to the progression of congestive heart failure (CHF). It is also known that sympathetic excitatory cardiac, somatic, and central/peripheral chemoreceptor reflexes are abnormally enhanced in CHF and hypertension (Ponikowski, 2011 and Giannoni, 2008 and 2009).

Arterial chemoreceptors serve an important regulatory role in the control of alveolar ventilation. They also exert a powerful influence on cardiovascular function.

Delivery of Oxygen ($O_2$) and removal of Carbon Dioxide ($CO_2$) in the human body is regulated by two control systems, behavioral control and metabolic control. The metabolic ventilatory control system drives our breathing at rest and ensures optimal cellular homeostasis with respect to pH, partial pressure of carbon dioxide ($PCO_2$), and partial pressure of oxygen ($PO_2$). Metabolic control uses two sets of chemoreceptors that provide a fine-tuning function: the central chemoreceptors located in the ventral medulla of the brain and the peripheral chemoreceptors such as the aortic chemoreceptors and the carotid body chemoreceptors. As shown in FIG. 4, the carotid body 101, a small, ovoid-shaped (often described as a grain of rice), and highly vascularized organ is situated in or near the carotid bifurcation 200, where the common carotid artery 102 branches in to an internal carotid artery (IC) 201 and external carotid artery (EC) 206. The central chemoreceptors are sensitive to hypercapnia (high $PCO_2$), and the peripheral chemoreceptors are sensitive to hypercapnia and hypoxia (low blood $PO_2$). Under normal conditions activation of the sensors by their respective stimuli results in quick ventilatory responses aimed at the restoration of cellular homeostasis.

As early as 1868, Pflüger recognized that hypoxia stimulated ventilation, which spurred a search for the location of oxygen-sensitive receptors both within the brain and at various sites in the peripheral circulation. When Corneille Heymans and his colleagues observed that ventilation increased when the oxygen content of the blood flowing through the bifurcation of the common carotid artery was reduced (winning him the Nobel Prize in 1938), the search for the oxygen chemosensor responsible for the ventilatory response to hypoxia was largely considered accomplished.

The persistence of stimulatory effects of hypoxia in the absence (after surgical removal) of the carotid chemoreceptors (e.g., the carotid bodies) led other investigators, among them Julius Comroe, to ascribe hypoxic chemosensitivity to other sites, including both peripheral sites (e.g., aortic bodies) and central brain sites (e.g., hypothalamus, pons and rostral ventrolateral medulla). The aortic chemoreceptor, located in the aortic body, may also be an important chemoreceptor in humans with significant influence on vascular tone and cardiac function.

The carotid body exhibits great sensitivity to hypoxia (low threshold and high gain). In chronic Congestive Heart Failure (CHF), the sympathetic nervous system activation that is directed to attenuate systemic hypoperfusion at the initial phases of CHF may ultimately exacerbate the progression of cardiac dysfunction that subsequently increases the extra-cardiac abnormalities, a positive feedback cycle of progressive deterioration, a vicious cycle with ominous consequences. It was thought that much of the increase in the sympathetic nerve activity (SNA) in CHF was based on an increase of sympathetic flow at a level of the CNS and on the depression of arterial baroreflex function. In the past several years, it has been demonstrated that an increase in the activity and sensitivity of peripheral chemoreceptors (heightened chemoreflex function) also plays an important role in the enhanced SNA that occurs in CHF.

Role of Altered Chemoreflex in CHF:

As often happens in chronic disease states, chemoreflexes that are dedicated under normal conditions to maintaining homeostasis and correcting hypoxia contribute to increase the sympathetic tone in patients with CHF, even under normoxic conditions. The understanding of how abnormally enhanced sensitivity of the peripheral chemosensors, particularly the carotid body, contributes to the tonic elevation in SNA in patients with CHF has come from several studies in animals. According to one theory, the local angiotensin receptor system plays a fundamental role in the enhanced carotid body chemoreceptor sensitivity in CHF. In addition, evidence in both CHF patients and animal models of CHF has clearly established that the carotid body chemoreflex is often hypersensitive in CHF patients and contributes to the tonic elevation in sympathetic function. This derangement derives from altered function at the level of both the afferent and central pathways of the reflex arc. The mechanisms responsible for elevated afferent activity from the carotid body in CHF are not yet fully understood.

Regardless of the exact mechanism behind the carotid body hypersensitivity, the chronic sympathetic activation driven from the carotid body and other autonomic pathways leads to further deterioration of cardiac function in a positive feedback cycle. As CHF ensues, the increasing severity of cardiac dysfunction leads to progressive escalation of these alterations in carotid body chemoreflex function to further elevate sympathetic activity and cardiac deterioration. The trigger or causative factors that occur in the development of CHF that sets this cascade of events in motion and the time course over which they occur remain obscure. Ultimately, however, causative factors are tied to the cardiac pump failure and reduced cardiac output. According to one theory, within the carotid body, a progressive and chronic reduction in blood flow may be the key to initiating the maladaptive changes that occur in carotid body chemoreflex function in CHF.

There is sufficient evidence that there is increased peripheral and central chemoreflex sensitivity in heart failure, which is likely to be correlated with the severity of the disease. There is also some evidence that the central chemoreflex is modulated by the peripheral chemoreflex. According to current theories, the carotid body is the predominant contributor to the peripheral chemoreflex in humans; the aortic body having a minor contribution.

Although the mechanisms responsible for altered central chemoreflex sensitivity remain obscure, the enhanced peripheral chemoreflex sensitivity can be linked to a depression of nitric oxide production in the carotid body affecting afferent sensitivity, and an elevation of central angiotensin II affecting central integration of chemoreceptor input. The enhanced chemoreflex may be responsible, in part, for the enhanced ventilatory response to exercise, dyspnea, Cheyne-Stokes breathing, and sympathetic activation observed in chronic heart failure patients. The enhanced chemoreflex may be also responsible for hyperventilation and tachypnea (e.g., fast breathing) at rest and exercise, periodic breathing during exercise, rest and sleep, hypocapnia, vasoconstriction, reduced peripheral organ perfusion and hypertension.

Dyspnea:

Shortness of breath, or dyspnea, is a feeling of difficult or labored breathing that is out of proportion to the patient's level of physical activity. It is a symptom of a variety of different diseases or disorders and may be either acute or chronic. Dyspnea is the most common complaint of patients with cardiopulmonary diseases.

Dyspnea is believed to result from complex interactions between neural signaling, the mechanics of breathing, and the related response of the central nervous system. A specific area has been identified in the mid-brain that may influence the perception of breathing difficulties.

The experience of dyspnea depends on its severity and underlying causes. The feeling itself results from a combination of impulses relayed to the brain from nerve endings in the lungs, rib cage, chest muscles, or diaphragm, combined with the perception and interpretation of the sensation by the patient. In some cases, the patient's sensation of breathlessness is intensified by anxiety about its cause. Patients describe dyspnea variously as unpleasant shortness of breath, a feeling of increased effort or tiredness in moving the chest muscles, a panicky feeling of being smothered, or a sense of tightness or cramping in the chest wall.

The four generally accepted categories of dyspnea are based on its causes: cardiac, pulmonary, mixed cardiac or pulmonary, and non-cardiac or non-pulmonary. The most common heart and lung diseases that produce dyspnea are asthma, pneumonia, COPD, and myocardial ischemia or heart attack (myocardial infarction). Foreign body inhalation, toxic damage to the airway, pulmonary embolism, congestive heart failure (CHF), anxiety with hyperventilation (panic disorder), anemia, and physical deconditioning because of sedentary lifestyle or obesity can produce dyspnea. In most cases, dyspnea occurs with exacerbation of the underlying disease. Dyspnea also can result from weakness or injury to the chest wall or chest muscles, decreased lung elasticity, obstruction of the airway, increased oxygen demand, or poor pumping action of the heart that results in increased pressure and fluid in the lungs, such as in CHF.

Acute dyspnea with sudden onset is a frequent cause of emergency room visits. Most cases of acute dyspnea involve pulmonary (lung and breathing) disorders, cardiovascular disease, or chest trauma. Sudden onset of dyspnea (acute dyspnea) is most typically associated with narrowing of the airways or airflow obstruction (bronchospasm), blockage of one of the arteries of the lung (pulmonary embolism), acute heart failure or myocardial infarction, pneumonia, or panic disorder.

Chronic dyspnea is different. Long-standing dyspnea (chronic dyspnea) is most often a manifestation of chronic or progressive diseases of the lung or heart, such as COPD, which includes chronic bronchitis and emphysema. The treatment of chronic dyspnea depends on the underlying disorder. Asthma can often be managed with a combination of medications to reduce airway spasms and removal of allergens from the patient's environment. COPD requires medication, lifestyle changes, and long-term physical rehabilitation. Anxiety disorders are usually treated with a combination of medication and psychotherapy.

Although the exact mechanism of dyspnea in different disease states is debated, there is no doubt that the CBC plays some role in most manifestations of this symptom. Dyspnea seems to occur most commonly when afferent input from peripheral receptors is enhanced or when cortical perception of respiratory work is excessive.

Surgical Removal of the Glomus and Resection of Carotid Body Nerves:

A surgical treatment for asthma, removal of the carotid body or glomus (glomectomy), was described by Japanese surgeon Komei Nakayama in 1940s. According to Nakayama in his study of 4,000 patients with asthma, approximately 80% were cured or improved six months after surgery and 58% allegedly maintained good results after five years. Komei Nakayama performed most of his surgeries while at the Chiba University during World War II. Later in the 1950's, a U.S. surgeon, Dr. Overholt, performed the Nakayama operation on 160 U.S. patients. He felt it necessary to remove both carotid bodies in only three cases. He reported that some patients feel relief the instant when the carotid body is removed, or even earlier, when it is inactivated by an injection of procaine (Novocain).

Overholt, in his paper Glomectomy for Asthma published in Chest in 1961, described surgical glomectomy the following way: "A two-inch incision is placed in a crease line in the neck, one-third of the distance between the angle of the mandible and clavicle. The platysma muscle is divided and the sternocleidomastoid retracted laterally. The dissection is carried down to the carotid sheath exposing the bifurcation. The superior thyroid artery is ligated and divided near its take-off in order to facilitate rotation of the carotid bulb and expose the medial aspect of the bifurcation. The carotid body is about the size of a grain of rice and is hidden within the adventitia of the vessel and is of the same color. The perivascular adventitia is removed from one centimeter above to one centimeter below the bifurcation. This severs connections of the nerve plexus which surrounds the carotid body. The dissection of the adventitia is necessary in order to locate and identify the body. It is usually located exactly at the point of bifurcation on its medial aspect. Rarely, it may be found either in the center of the crotch or on the lateral wall. The small artery entering the carotid body is clamped, divided, and ligated. The upper stalk of tissue above the carotid body is then clamped, divided, and ligated."

In January, 1965, the New England Journal of Medicine published a report of 15 cases in which there had been unilateral removal of the cervical glomus (carotid body) for the treatment of bronchial asthma, with no objective beneficial effect. This effectively stopped the practice of glomectomy to treat asthma in the U.S.

Winter developed a technique for separating nerves that contribute to the carotid sinus nerves into two bundles, carotid sinus (baroreflex) and carotid body (chemoreflex), and selectively cutting out the latter. The Winter technique is based on his discovery that carotid sinus (baroreflex) nerves are predominantly on the lateral side of the carotid bifurcation and carotid body (chemoreflex) nerves are predominantly on the medial side.

Neuromodulation of the Carotid Body Chemoreflex:

Hlavaka in U.S. Patent Application Publication 2010/0070004 filed Aug. 7, 2009, describes implanting an electrical stimulator to apply electrical signals, which block or inhibit chemoreceptor signals in a patient suffering dyspnea. Hlavaka teaches that "some patients may benefit from the ability to reactivate or modulate chemoreceptor functioning." Hlavaka focuses on neuromodulation of the chemoreflex by selectively blocking conduction of nerves that connect the carotid body to the CNS. Hlavaka describes a traditional approach of neuromodulation with an implantable electric pulse generator that does not modify or alter tissue of the carotid body or chemoreceptors.

The central chemoreceptors are located in the brain and are difficult to access. The peripheral chemoreflex is modulated primarily by carotid bodies that are more accessible. Previous clinical practice had very limited clinical success with the surgical removal of carotid bodies to treat asthma in 1940s and 1960s.

Additional Exemplary Embodiments

Any of the embodiments herein can include a forceps structure that includes means for pressing the ablation element against a wall of a carotid artery at a specific location adjacent the carotid septum.

Any of the embodiments herein can include first and second arms that are configured so that a force of contact distends the ablation element about 1 mm to 3 mm into a wall of a carotid artery.

Any of the embodiments herein can include a forceps structure that includes means for pressing the ablation element against a wall of a carotid artery.

Any of the embodiments herein can include an ablation element that is positioned on the arm such that it engages a wall of the internal or external carotid artery delimiting a carotid septum.

Any of the embodiments herein can include an ablation element that comprises a surface adapted to contact a vessel wall adjacent the carotid septum.

Any of the embodiments herein can include an ablation element that is an electrode disposed on the first or the second arm.

Any of the embodiments herein can include first and second arms that are adapted to compress the carotid septum.

Any of the embodiments herein can include an arm actuator adapted to move the first and second arms towards each other.

Any of the embodiments herein can include first and second arms that are further adapted to move away from each other toward a preset position.

Any of the embodiments herein can include an ablation element that comprises a first electrode disposed on the first arm and a second electrode disposed on the second arm.

Any of the embodiments herein can include first and second arms that are adapted to move from an undeployed configuration to a deployed configuration in which the first and second arms are further apart than in the undeployed configuration.

Any of the embodiments herein can include a sheath adapted to contain first and second arms during endovascular advancement.

Any of the embodiments herein can include a functional sheath diameter between 3 French and 12 French.

Any of the embodiments herein can include first and second arms that are adapted to move toward the deployed configuration as they emerge from a sheath.

Any of the embodiments herein can include a sheath that is adapted to be advanced toward first and second arms to move the first and second arms toward each other.

Any of the embodiments herein can include an ablation element that is configured to heat the target tissue to a temperature above 37° C. or above 45° C.

Any of the embodiments herein can include one or more temperature sensors positioned at the first and/or second arms.

Any of the embodiments herein can include a catheter that is configured to be positioned against the carotid bifurcation saddle to position the ablation element at a predetermined distance distal of the carotid bifurcation saddle.

Any of the embodiments herein can include a catheter that is configured to place the ablation element against the wall of a carotid artery at a position no more than 15 mm distal to the carotid bifurcation saddle.

Any of the embodiments herein can include an ablation catheter and an ablation source operably connected to the ablation element of the ablation catheter, and a user control comprising an ablation actuator operative to deliver an ablation agent from the ablation source to the ablation element to ablate the target tissue.

Any of the embodiments herein can include an ablation source that comprises an RF generator.

Any of the embodiments herein can include an ablation element comprises a first electrode disposed on the first arm and a second electrode disposed on the second arm, and wherein the first and second electrodes are connected to opposite poles of an RF generator.

Any of the embodiments herein can include an ablation element that comprises a first electrode disposed on the first arm and a second electrode disposed on the second arm, and wherein the first and second electrodes are connected to the same poles of the RF generator.

Any of the embodiments herein can include a user control that is configured to specify or calculate treatment parameters to control a desired ablation.

Any of the embodiments herein can include first and second arms that are adapted to position the ablation element into contact with the vessel wall at a bifurcation between the external carotid artery and the internal carotid artery.

Any of the embodiments herein can include an ablation element that comprises a sharp distal point adapted to penetrate through the vessel wall into the carotid septum.

Any of the embodiments herein can include contacting an ablation element with a vessel wall no more than 15 mm distal to a carotid bifurcation saddle.

Any of the embodiments herein can include inserting an ablation element into the carotid septum.

Any of the embodiments herein can include grasping the carotid septum with first and second arms.

Any of the embodiments herein can include compressing the carotid septum with first and second arms.

Any of the embodiments herein can include moving the first and second arms away from each other.

Any of the embodiments herein can include permitting the first and second arms to return toward a preset position.

Any of the embodiments herein can include moving first and second arms toward each other.

Any of the embodiments herein can include operating an arm actuator.

Any of the embodiments herein can include actuating an ablation element to ablate the target tissue while first and second arms are engaged with the artery walls.

Any of the embodiments herein can include using first and second electrodes to ablate the target tissue with RF energy.

Any of the embodiments herein can include heating the target tissue to a temperature above 37° C.

Any of the embodiments herein can include heating the target tissue to a temperature above 45° C.

Any of the embodiments herein can include delivering ablation energy from the ablation element to the target tissue for 30-120 seconds.

What is claimed is:

1. An ablation method for ablating target tissue within a carotid septum of a patient, the method comprising:

endovascularly positioning a distal region of an ablation catheter proximate a carotid septum;

deploying an ablation needle from an ablation catheter, piercing tissue with the needle, and positioning the needle into the carotid septum; and delivering an ablation agent through the ablation needle and into the carotid septum, to ablate tissue within the carotid septum and treat at least one of hypertension, heart failure, and central sleep apnea.

2. The ablation method of claim 1, wherein the endovascularly positioning step comprises endovascularly positioning the distal region of the ablation catheter in a common carotid artery, internal carotid artery, or external carotid artery.

3. The ablation method of claim 1, wherein the endovascularly positioning step comprises endovascularly positioning the distal region of the ablation catheter proximate a carotid bifurcation.

4. The ablation method of claim 1, wherein the deploying step comprises deploying the ablation needle from a distal end of the distal region of the ablation catheter.

5. The ablation method of claim 1, wherein the delivering step comprises delivering guanethidine through the ablation needle and into the carotid septum.

6. The ablation method of claim 1, further comprising injecting a chemical to temporarily block or stimulate nerves in or near the carotid septum, at least one of before or after ablating the tissue, as part of an ablation assessment.

7. The ablation method of claim 1, further comprising, stabilizing the ablation catheter within a lumen.

8. The ablation method of claim 1, wherein piercing tissue with the needle comprises piercing the ablation needle through a carotid bifurcation and into the carotid septum.

9. The ablation method of claim 8, further comprising positioning a first au into an external carotid artery and positioning a second arm into an internal carotid artery, wherein positioning the first and second arms in the respective carotid arteries assists in positioning a distal end of the catheter at the carotid bifurcation and adds stability to the catheter, and wherein the deploying step comprises deploying the ablation needle from the distal end of the catheter.

10. The ablation method of claim 1, wherein deploying the ablation needle comprises deploying an ablation needle that comprises a curved portion.

* * * * *